US009617549B2

(12) United States Patent
Ferrari et al.

(10) Patent No.: US 9,617,549 B2
(45) Date of Patent: *Apr. 11, 2017

(54) ENHANCED PROTEIN EXPRESSION IN *BACILLUS*

(71) Applicant: Danisco US Inc., Palo Alto, CA (US)

(72) Inventors: Eugenio Ferrari, Reggiolo (IT); Carole Harbison, Ithaca, NY (US); M. Harunur Rashid, Sunnyvale, CA (US); Walter Weyler, San Francisco, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/857,343

(22) Filed: Sep. 17, 2015

(65) Prior Publication Data

US 2016/0168582 A1 Jun. 16, 2016

Related U.S. Application Data

(63) Continuation of application No. 13/745,630, filed on Jan. 18, 2013, now Pat. No. 9,175,294, which is a continuation of application No. 13/356,572, filed on Jan. 23, 2012, now Pat. No. 8,383,366, which is a continuation of application No. 10/507,720, filed as application No. PCT/US03/09585 on Mar. 28, 2003, now Pat. No. 8,124,399.

(60) Provisional application No. 60/368,949, filed on Mar. 29, 2002, provisional application No. 60/368,858, filed on Mar. 29, 2002, provisional application No. 60/376,343, filed on Apr. 29, 2002.

(51) Int. Cl.

| | |
|---|---|
| ***C12P 21/04*** | (2006.01) |
| ***C12P 21/06*** | (2006.01) |
| ***C12N 15/75*** | (2006.01) |
| ***C07K 14/32*** | (2006.01) |
| ***C12N 9/54*** | (2006.01) |
| ***C12P 21/02*** | (2006.01) |
| ***C12R 1/125*** | (2006.01) |

(52) U.S. Cl.

CPC .............. *C12N 15/75* (2013.01); *C07K 14/32* (2013.01); *C12N 9/54* (2013.01); *C12P 21/02* (2013.01); *C12R 1/125* (2013.01); *C12Y 304/00* (2013.01)

(58) Field of Classification Search

CPC ...................................................... C12N 15/75

See application file for complete search history.

(56) References Cited

U.S. PATENT DOCUMENTS 8,124,399 B2 * 2/2012 Ferrari .................. C07K 14/32 435/252.3

* cited by examiner

*Primary Examiner* — Albert Navarro

(74) *Attorney, Agent, or Firm* — Danisco US Inc.

(57) ABSTRACT

The present invention provides cells that have been genetically manipulated to have an altered capacity to produce expressed proteins. In particular, the present invention relates to Gram-positive microorganisms, such as *Bacillus* species having enhanced expression of a protein of interest, wherein one or more chromosomal genes have been inactivated, and preferably wherein one or more chromosomal genes have been deleted from the *Bacillus* chromosome. In some further embodiments, one or more indigenous chromosomal regions have been deleted from a corresponding wild-type *Bacillus* host chromosome.

15 Claims, 5 Drawing Sheets

SEQUENCE LISTING

```
<160> NUMBER OF SEQ ID NOS: 205

<210> SEQ ID NO 1
<211> LENGTH: 129
<212> TYPE: DNA
<213> ORGANISM: Bacillus subtilis

<400> SEQUENCE: 1

atgaaaaaag ctgtcattgt agaaaacaaa ggttgtgcaa catgctcgat cggagccgct      60

tgtctagtgg acggtcctat ccctgatttt gaaattgccg gtgcaacagg tctattcggt     120

ctatgggg                                                              129


<210> SEQ ID NO 2
<211> LENGTH: 43
<212> TYPE: PRT
<213> ORGANISM: Bacillus subtilis
```

<400> SEQUENCE: 2

```
Met Lys Lys Ala Val Ile Val Glu Asn Lys Gly Cys Ala Thr Cys Ser
 1               5                  10                  15

Ile Gly Ala Ala Cys Leu Val Asp Gly Pro Ile Pro Asp Phe Glu Ile
            20                  25                  30

Ala Gly Ala Thr Gly Leu Phe Gly Leu Trp Gly
        35                  40
```

<210> SEQ ID NO 3
<211> LENGTH: 456
<212> TYPE: DNA
<213> ORGANISM: Bacillus subtilis

<400> SEQUENCE: 3

```
atgattggaa gaattatccg tttgtaccgt aaaagaaaag gctattctat taatcagctg     60

gctgttgagt caggcgtatc caaatcctat ttaagcaaga ttgaaagagg cgttcacacg    120

aatccgtccg ttcaattttt aaaaaaagtt tctgccacac tggaagttga attaacagaa    180

ttatttgacg cagaaacaat gatgtatgaa aaaatcagcg gcggtgaaga agaatggcgc    240

gtacatttag tgcaagccgt acaagccggg atggaaaagg aagaattgtt cacttttacg    300

aacagactca agaaagaaca gcctgaaact gcctcttacc gcaaccgcaa actgacggaa    360

tccaatatag aagaatggaa agcgctgatg gcggaggcaa gagaaatcgg cttgtctgtc    420

catgaagtca aatccttttt aaaaacaaag ggaaga                             456
```

<210> SEQ ID NO 4
<211> LENGTH: 152
<212> TYPE: PRT
<213> ORGANISM: Bacillus subtilis

<400> SEQUENCE: 4

```
Met Ile Gly Arg Ile Ile Arg Leu Tyr Arg Lys Arg Lys Gly Tyr Ser
 1               5                  10                  15

Ile Asn Gln Leu Ala Val Glu Ser Gly Val Ser Lys Ser Tyr Leu Ser
            20                  25                  30

Lys Ile Glu Arg Gly Val His Thr Asn Pro Ser Val Gln Phe Leu Lys
        35                  40                  45

Lys Val Ser Ala Thr Leu Glu Val Glu Leu Thr Glu Leu Phe Asp Ala
    50                  55                  60

Glu Thr Met Met Tyr Glu Lys Ile Ser Gly Gly Glu Glu Glu Trp Arg
65                  70                  75                  80

Val His Leu Val Gln Ala Val Gln Ala Gly Met Glu Lys Glu Glu Leu
                85                  90                  95

Phe Thr Phe Thr Asn Arg Leu Lys Lys Glu Gln Pro Glu Thr Ala Ser
            100                 105                 110

Tyr Arg Asn Arg Lys Leu Thr Glu Ser Asn Ile Glu Glu Trp Lys Ala
        115                 120                 125

Leu Met Ala Glu Ala Arg Glu Ile Gly Leu Ser Val His Glu Val Lys
    130                 135                 140

Ser Phe Leu Lys Thr Lys Gly Arg
145                 150
```

<210> SEQ ID NO 5
<211> LENGTH: 165
<212> TYPE: DNA
<213> ORGANISM: Bacillus subtilis

<400> SEQUENCE: 5

```
atgaaaagaa accaaaaaga atgggaatct gtgagtaaaa aaggacttat gaagccggga     60

ggtacttcga ttgtgaaagc tgctggctgc atgggctgtt gggcctcgaa gagtattgct    120

atgacacgtg tttgtgcact tccgcatcct gctatgagag ctatt                    165
```

<210> SEQ ID NO 6
<211> LENGTH: 55
<212> TYPE: PRT
<213> ORGANISM: Bacillus subtilis

<400> SEQUENCE: 6

```
Met Lys Arg Asn Gln Lys Glu Trp Glu Ser Val Ser Lys Lys Gly Leu
1               5                   10                  15

Met Lys Pro Gly Gly Thr Ser Ile Val Lys Ala Ala Gly Cys Met Gly
            20                  25                  30

Cys Trp Ala Ser Lys Ser Ile Ala Met Thr Arg Val Cys Ala Leu Pro
        35                  40                  45

His Pro Ala Met Arg Ala Ile
    50                  55
```

<210> SEQ ID NO 7
<211> LENGTH: 831
<212> TYPE: DNA
<213> ORGANISM: Bacillus subtilis

<400> SEQUENCE: 7

```
atgaaaatca gtatgcaaaa agcagatttt tggaaaaaag cagcgatctc attacttgtt     60

ttcaccatgt tttttaccct gatgatgagc gaaacggttt ttgcggcggg actgaataaa    120

gatcaaaagc gccgggcgga acagctgaca agtatctttg aaaacggcac aacggagatc    180

caatatggat atgtagagcg attggatgac gggcgaggct atacatgcgg acgggcaggc    240

tttacaacgg ctaccgggga tgcattggaa gtagtggaag tatacacaaa ggcagttccg    300

aataacaaac tgaaaaagta tctgcctgaa ttgcgccgtc tggccaagga agaaagcgat    360

gatacaagca atctcaaggg attcgcttct gcctggaagt cgcttgcaaa tgataaggaa    420

tttcgcgccg ctcaagacaa agtaaatgac catttgtatt atcagcctgc catgaaacga    480

tcggataatg ccggactaaa aacagcattg gcaagagctg tgatgtacga tacggttatt    540

cagcatggcg atggtgatga ccctgactct tttatgcct tgattaaacg tacgaacaaa    600

aaagcgggcg gatcacctaa agacggaata gacgagaaga agtggttgaa taaattcttg    660

gacgtacgct atgacgatct gatgaatccg gccaatcatg acacccgtga cgaatggaga    720

gaatcagttg cccgtgtgga cgtgcttcgc tctatcgcca aggagaacaa ctataatcta    780

aacggaccga ttcatgttcg ttcaaacgag tacggtaatt ttgtaatcaa a             831
```

<210> SEQ ID NO 8
<211> LENGTH: 277
<212> TYPE: PRT
<213> ORGANISM: Bacillus subtilis

<400> SEQUENCE: 8

```
Met Lys Ile Ser Met Gln Lys Ala Asp Phe Trp Lys Lys Ala Ala Ile
1               5                   10                  15

Ser Leu Leu Val Phe Thr Met Phe Phe Thr Leu Met Met Ser Glu Thr
            20                  25                  30
```

```
Val Phe Ala Ala Gly Leu Asn Lys Asp Gln Lys Arg Arg Ala Glu Gln
        35                  40                  45

Leu Thr Ser Ile Phe Glu Asn Gly Thr Thr Glu Ile Gln Tyr Gly Tyr
    50                  55                  60

Val Glu Arg Leu Asp Asp Gly Arg Gly Tyr Thr Cys Gly Arg Ala Gly
65                  70                  75                  80

Phe Thr Thr Ala Thr Gly Asp Ala Leu Glu Val Val Glu Val Tyr Thr
                85                  90                  95

Lys Ala Val Pro Asn Asn Lys Leu Lys Lys Tyr Leu Pro Glu Leu Arg
            100                 105                 110

Arg Leu Ala Lys Glu Glu Ser Asp Asp Thr Ser Asn Leu Lys Gly Phe
        115                 120                 125

Ala Ser Ala Trp Lys Ser Leu Ala Asn Asp Lys Glu Phe Arg Ala Ala
    130                 135                 140

Gln Asp Lys Val Asn Asp His Leu Tyr Tyr Gln Pro Ala Met Lys Arg
145                 150                 155                 160

Ser Asp Asn Ala Gly Leu Lys Thr Ala Leu Ala Arg Ala Val Met Tyr
                165                 170                 175

Asp Thr Val Ile Gln His Gly Asp Gly Asp Asp Pro Asp Ser Phe Tyr
            180                 185                 190

Ala Leu Ile Lys Arg Thr Asn Lys Lys Ala Gly Gly Ser Pro Lys Asp
        195                 200                 205

Gly Ile Asp Glu Lys Lys Trp Leu Asn Lys Phe Leu Asp Val Arg Tyr
    210                 215                 220

Asp Asp Leu Met Asn Pro Ala Asn His Asp Thr Arg Asp Glu Trp Arg
225                 230                 235                 240

Glu Ser Val Ala Arg Val Asp Val Leu Arg Ser Ile Ala Lys Glu Asn
                245                 250                 255

Asn Tyr Asn Leu Asn Gly Pro Ile His Val Arg Ser Asn Glu Tyr Gly
            260                 265                 270

Asn Phe Val Ile Lys
        275
```

<210> SEQ ID NO 9
<211> LENGTH: 792
<212> TYPE: DNA
<213> ORGANISM: Bacillus subtilis

<400> SEQUENCE: 9

```
ttgatcatga cacaaccatc aaaaactacg aaactaacta aagatgaagt cgatcggctc     60

ataagcgatt accaaacaaa gcaagatgaa caagcgcagg aaacgcttgt gcgggtgtat    120

acaaatctgg ttgacatgct tgcgaaaaaa tactcaaaag gcaaaagctt ccacgaggat    180

ctccgccagg tcggcatgat cgggctgcta ggcgcgatta agcgatacga tcctgttgtc    240

ggcaaatcgt ttgaagcttt tgcaatcccg acaatcatcg gtgaaattaa acgtttcctc    300

agagataaaa catggagcgt tcatgtgccg agacgaatta aagaactcgg tccaagaatc    360

aaaatggcgg ttgatcagct gaccactgaa acacaaagat cgccgaaagt cgaagagatt    420

gccgaattcc tcgatgtttc tgaagaagag gttcttgaaa cgatggaaat gggcaaaagc    480

tatcaagcct tatccgttga ccacagcatt gaagcggatt cggacggaag cactgtcacg    540

attcttgata tcgtcggatc acaggaggac ggatatgagc gggtcaacca gcaattgatg    600

ctgcaaagcg tgcttcatgt cctttcagac cgtgagaaac aaatcataga ccttacgtat    660

attcaaaaca aaagccaaaa agaaactggg gacattctcg gtatatctca aatgcacgtc    720
```

```
tcgcgcttgc aacgcaaagc tgtgaagaag ctcagagagg ccttgattga agatccctcg    780

atggagttaa tg                                                        792


<210> SEQ ID NO 10
<211> LENGTH: 264
<212> TYPE: PRT
<213> ORGANISM: Bacillus subtilis

<400> SEQUENCE: 10

Met Ile Met Thr Gln Pro Ser Lys Thr Thr Lys Leu Thr Lys Asp Glu
1               5                   10                  15

Val Asp Arg Leu Ile Ser Asp Tyr Gln Thr Lys Gln Asp Glu Gln Ala
            20                  25                  30

Gln Glu Thr Leu Val Arg Val Tyr Thr Asn Leu Val Asp Met Leu Ala
        35                  40                  45

Lys Lys Tyr Ser Lys Gly Lys Ser Phe His Glu Asp Leu Arg Gln Val
    50                  55                  60

Gly Met Ile Gly Leu Leu Gly Ala Ile Lys Arg Tyr Asp Pro Val Val
65                  70                  75                  80

Gly Lys Ser Phe Glu Ala Phe Ala Ile Pro Thr Ile Ile Gly Glu Ile
                85                  90                  95

Lys Arg Phe Leu Arg Asp Lys Thr Trp Ser Val His Val Pro Arg Arg
            100                 105                 110

Ile Lys Glu Leu Gly Pro Arg Ile Lys Met Ala Val Asp Gln Leu Thr
        115                 120                 125

Thr Glu Thr Gln Arg Ser Pro Lys Val Glu Glu Ile Ala Glu Phe Leu
    130                 135                 140

Asp Val Ser Glu Glu Glu Val Leu Glu Thr Met Glu Met Gly Lys Ser
145                 150                 155                 160

Tyr Gln Ala Leu Ser Val Asp His Ser Ile Glu Ala Asp Ser Asp Gly
                165                 170                 175

Ser Thr Val Thr Ile Leu Asp Ile Val Gly Ser Gln Glu Asp Gly Tyr
            180                 185                 190

Glu Arg Val Asn Gln Gln Leu Met Leu Gln Ser Val Leu His Val Leu
        195                 200                 205

Ser Asp Arg Glu Lys Gln Ile Ile Asp Leu Thr Tyr Ile Gln Asn Lys
    210                 215                 220

Ser Gln Lys Glu Thr Gly Asp Ile Leu Gly Ile Ser Gln Met His Val
225                 230                 235                 240

Ser Arg Leu Gln Arg Lys Ala Val Lys Lys Leu Arg Glu Ala Leu Ile
                245                 250                 255

Glu Asp Pro Ser Met Glu Leu Met
            260


<210> SEQ ID NO 11
<211> LENGTH: 744
<212> TYPE: DNA
<213> ORGANISM: Bacillus subtilis

<400> SEQUENCE: 11

atggttttat tctttcagat catggtctgg tgcatcgtgg ccggactggg gttatacgtg     60

tatgccacgt ggcgtttcga agcgaaggtc aaagaaaaaa tgtccgccat tcggaaaact    120

tggtatttgc tgtttgttct gggcgctatg gtatactgga catatgagcc cacttcccta    180

tttacccact gggaacggta tctcattgtc gcagtcagtt ttgctttgat tgatgctttt    240
```

```
atcttcttaa gtgcatatgt caaaaaactg gccggcagcg agcttgaaac agacacaaga    300

gaaattcttg aagaaaacaa cgaaatgctc cacatgtatc tcaatcggct gaaaacatac    360

caatacctat tgaaaaacga accgatccat gtttattatg gaagtataga tgcttatgct    420

gaaggtattg ataagctgct gaaaacctat gctgataaaa tgaacttaac ggcttctctt    480

tgccactatt cgacacaggc tgataaagac cggttaaccg agcatatgga tgatccggca    540

gatgtacaaa cacggctcga tcgaaaggat gtttattacg accaatacgg aaaagtggtt    600

ctcatccctt ttaccatcga gacacagaac tatgtcatca agctgacgtc tgacagcatt    660

gtcacggaat ttgattattt gctatttacg tcattaacga gcatatatga tttggtgctg    720

ccaattgagg aggaaggtga agga                                            744
```

```
<210> SEQ ID NO 12
<211> LENGTH: 248
<212> TYPE: PRT
<213> ORGANISM: Bacillus subtilis

<400> SEQUENCE: 12

Met Val Leu Phe Phe Gln Ile Met Val Trp Cys Ile Val Ala Gly Leu
1               5                   10                  15

Gly Leu Tyr Val Tyr Ala Thr Trp Arg Phe Glu Ala Lys Val Lys Glu
            20                  25                  30

Lys Met Ser Ala Ile Arg Lys Thr Trp Tyr Leu Leu Phe Val Leu Gly
        35                  40                  45

Ala Met Val Tyr Trp Thr Tyr Glu Pro Thr Ser Leu Phe Thr His Trp
    50                  55                  60

Glu Arg Tyr Leu Ile Val Ala Val Ser Phe Ala Leu Ile Asp Ala Phe
65                  70                  75                  80

Ile Phe Leu Ser Ala Tyr Val Lys Lys Leu Ala Gly Ser Glu Leu Glu
                85                  90                  95

Thr Asp Thr Arg Glu Ile Leu Glu Glu Asn Asn Glu Met Leu His Met
            100                 105                 110

Tyr Leu Asn Arg Leu Lys Thr Tyr Gln Tyr Leu Leu Lys Asn Glu Pro
        115                 120                 125

Ile His Val Tyr Tyr Gly Ser Ile Asp Ala Tyr Ala Glu Gly Ile Asp
    130                 135                 140

Lys Leu Leu Lys Thr Tyr Ala Asp Lys Met Asn Leu Thr Ala Ser Leu
145                 150                 155                 160

Cys His Tyr Ser Thr Gln Ala Asp Lys Asp Arg Leu Thr Glu His Met
                165                 170                 175

Asp Asp Pro Ala Asp Val Gln Thr Arg Leu Asp Arg Lys Asp Val Tyr
            180                 185                 190

Tyr Asp Gln Tyr Gly Lys Val Val Leu Ile Pro Phe Thr Ile Glu Thr
        195                 200                 205

Gln Asn Tyr Val Ile Lys Leu Thr Ser Asp Ser Ile Val Thr Glu Phe
    210                 215                 220

Asp Tyr Leu Leu Phe Thr Ser Leu Thr Ser Ile Tyr Asp Leu Val Leu
225                 230                 235                 240

Pro Ile Glu Glu Glu Gly Glu Gly
                245


<210> SEQ ID NO 13
<211> LENGTH: 120
<212> TYPE: DNA
```

<213> ORGANISM: Bacillus subtilis

<400> SEQUENCE: 13

```
atgaaattga aatctaagtt gtttgttatt tgtttggccg cagccgcgat ttttacagcg     60

gctggcgttt ctgctaatgc ggaagcactc gactttcatg tgacagaaag aggaatgacg    120
```

<210> SEQ ID NO 14
<211> LENGTH: 40
<212> TYPE: PRT
<213> ORGANISM: Bacillus subtilis

<400> SEQUENCE: 14

```
Met Lys Leu Lys Ser Lys Leu Phe Val Ile Cys Leu Ala Ala Ala Ala
 1               5                  10                  15

Ile Phe Thr Ala Ala Gly Val Ser Ala Asn Ala Glu Ala Leu Asp Phe
            20                  25                  30

His Val Thr Glu Arg Gly Met Thr
        35                  40
```

<210> SEQ ID NO 15
<211> LENGTH: 1134
<212> TYPE: DNA
<213> ORGANISM: Bacillus subtilis

<400> SEQUENCE: 15

```
ttgaggatga agcagacgat tccgtcctct tatgtcgggc ttaaaattaa tgaatggtat     60

actcatatcc ggcagttcca cgtcgctgaa gccgaacggg tcaagctcga agtagaaaga    120

gaaattgagg atatggaaga agaccaagat ttgctgctgt attattcttt aatggagttc    180

aggcaccgtg tcatgctgga ttacattaag ccttttggag aggacacgtc gcagctagag    240

ttttcagaat tgttagaaga catcgaaggg aatcagtaca agctgacagg gcttctcgaa    300

tattacttta attttttcg aggaatgtat gaatttaagc agaagatgtt tgtcagtgcc    360

atgatgtatt ataaacgggc agaaaagaat cttgccctcg tctcggatga tattgagaaa    420

gcagagtttg cttttaaaat ggctgagatt ttttacaatt taaaacaaac ctatgtttcg    480

atgagctacg ccgttcaggc attagaaaca taccaaatgt atgaaacgta caccgtccgc    540

agaatccaat gtgaattcgt tattgcaggt aattatgatg atatgcagta tccagaaaga    600

gcattgcccc acttagaact ggctttagat cttgcaaaga aagaaggcaa tccccgcctg    660

atcagttctg ccctatataa tctcggaaac tgctatgaga aaatgggtga actgcaaaag    720

gcagccgaat actttgggaa atctgtttct atttgcaagt cggaaaagtt cgataatctt    780

ccgcattcta tctactcttt aacacaagtt ctgtataaac aaaaaaatga cgccgaagcg    840

caaaaaaagt atcgtgaagg attggaaatc gcccgtcaat acagtgatga attatttgtg    900

gagcttttc aatttttaca tgcgttatac ggaaaaaaca ttgacacaga atcagtctca    960

cacacctttc aatttcttga agaacatatg ctgtatcctt atattgaaga gctggcgcat   1020

gatgctgccc aattctatat agaaaacgga cagcccgaaa aagcactttc attttatgag   1080

aaaatggtgc acgcacaaaa acaaatccag agaggagatt gtttatatga aatc         1134
```

<210> SEQ ID NO 16
<211> LENGTH: 378
<212> TYPE: PRT
<213> ORGANISM: Bacillus subtilis

<400> SEQUENCE: 16

```
Met Arg Met Lys Gln Thr Ile Pro Ser Ser Tyr Val Gly Leu Lys Ile
 1               5                   10                  15

Asn Glu Trp Tyr Thr His Ile Arg Gln Phe His Val Ala Glu Ala Glu
            20                  25                  30

Arg Val Lys Leu Glu Val Glu Arg Glu Ile Glu Asp Met Glu Glu Asp
        35                  40                  45

Gln Asp Leu Leu Leu Tyr Tyr Ser Leu Met Glu Phe Arg His Arg Val
    50                  55                  60

Met Leu Asp Tyr Ile Lys Pro Phe Gly Glu Asp Thr Ser Gln Leu Glu
65                  70                  75                  80

Phe Ser Glu Leu Leu Glu Asp Ile Glu Gly Asn Gln Tyr Lys Leu Thr
                85                  90                  95

Gly Leu Leu Glu Tyr Tyr Phe Asn Phe Phe Arg Gly Met Tyr Glu Phe
            100                 105                 110

Lys Gln Lys Met Phe Val Ser Ala Met Met Tyr Tyr Lys Arg Ala Glu
        115                 120                 125

Lys Asn Leu Ala Leu Val Ser Asp Asp Ile Glu Lys Ala Glu Phe Ala
    130                 135                 140

Phe Lys Met Ala Glu Ile Phe Tyr Asn Leu Lys Gln Thr Tyr Val Ser
145                 150                 155                 160

Met Ser Tyr Ala Val Gln Ala Leu Glu Thr Tyr Gln Met Tyr Glu Thr
                165                 170                 175

Tyr Thr Val Arg Arg Ile Gln Cys Glu Phe Val Ile Ala Gly Asn Tyr
            180                 185                 190

Asp Asp Met Gln Tyr Pro Glu Arg Ala Leu Pro His Leu Glu Leu Ala
        195                 200                 205

Leu Asp Leu Ala Lys Lys Glu Gly Asn Pro Arg Leu Ile Ser Ser Ala
    210                 215                 220

Leu Tyr Asn Leu Gly Asn Cys Tyr Glu Lys Met Gly Glu Leu Gln Lys
225                 230                 235                 240

Ala Ala Glu Tyr Phe Gly Lys Ser Val Ser Ile Cys Lys Ser Glu Lys
                245                 250                 255

Phe Asp Asn Leu Pro His Ser Ile Tyr Ser Leu Thr Gln Val Leu Tyr
            260                 265                 270

Lys Gln Lys Asn Asp Ala Glu Ala Gln Lys Lys Tyr Arg Glu Gly Leu
        275                 280                 285

Glu Ile Ala Arg Gln Tyr Ser Asp Glu Leu Phe Val Glu Leu Phe Gln
    290                 295                 300

Phe Leu His Ala Leu Tyr Gly Lys Asn Ile Asp Thr Glu Ser Val Ser
305                 310                 315                 320

His Thr Phe Gln Phe Leu Glu Glu His Met Leu Tyr Pro Tyr Ile Glu
                325                 330                 335

Glu Leu Ala His Asp Ala Ala Gln Phe Tyr Ile Glu Asn Gly Gln Pro
            340                 345                 350

Glu Lys Ala Leu Ser Phe Tyr Glu Lys Met Val His Ala Gln Lys Gln
        355                 360                 365

Ile Gln Arg Gly Asp Cys Leu Tyr Glu Ile
    370                 375
```

<210> SEQ ID NO 17
<211> LENGTH: 1353
<212> TYPE: DNA
<213> ORGANISM: Bacillus subtilis

<400> SEQUENCE: 17

```
atgaaaaaca agccgctcgc gtttcagata tgggttgtca tatccggcat cctgttagcg     60
atatcgattt tactgcttgt gttattttca aacacgctgc gagatttttt cactaatgaa    120
acgtatacga cgattgaaaa tgagcagcat gttctgacag agtaccgcct gccaggttcg    180
attgaaaggc gctattacag cgaggaagcg acggcgccga caactgtccg ctccgtacag    240
cacgtgctcc ttcctgaaaa tgaagaggct tcttcagaca aggatttaag cattctgtca    300
tcttcattta tccacaaggt gtacaagctg gctgataagc aggaagctaa aaagaaacgt    360
tacagcgccg acgtcaatgg agagaaagtg tttttgtca ttaaaaaggg actttccgtc     420
aatggacaat cagcgatgat gctctcttac gcgcttgatt cttatcggga cgatttggcc    480
tataccttgt tcaaacagct tctgtttatt atagctgtcg tcattttatt aagctggatt    540
ccggctattt ggcttgcaaa gtatttatca aggcctcttg tatcatttga aaaacacgtc    600
aaacggattt ctgaacagga ttgggatgac ccagtaaaag tggaccggaa agatgaaatc    660
ggcaaattgg gccataccat cgaagagatg cgccaaaagc ttgtgcaaaa ggatgaaaca    720
gaaagaactc tattgcaaaa tatctctcat gatttaaaaa cgccggtcat ggtcatcaga    780
ggctatacac aatcaattaa agacgggatt tttcctaaag gagaccttga aaacactgta    840
gatgttattg aatgcgaagc tcttaagctg gagaaaaaaa taaaggattt attatattta    900
acgaagctgg attatttagc gaagcaaaaa gtgcagcacg acatgttcag tattgtggaa    960
gtgacagaag aagtcatcga acgattgaag tgggcgcgga aagaactatc gtgggaaatt   1020
gatgtagaag aggatatttt gatgccgggc gatccggagc aatggaacaa actcctcgaa   1080
aacattttgg aaaatcaaat ccgctatgct gagacaaaaa tagaaatcag catgaaacaa   1140
gatgatcgaa atatcgtgat caccattaaa aatgacggtc cgcatattga agatgagatg   1200
ctctccagcc tctatgagcc ttttaataaa gggaagaaag gcgaattcgg cattggtcta   1260
agcatcgtaa aacgaatttt aactcttcat aaggcatcta tctcaattga aaatgacaaa   1320
acgggtgtat catacc gcat agcagtgcca aaa                                1353
```

```
<210> SEQ ID NO 18
<211> LENGTH: 450
<212> TYPE: PRT
<213> ORGANISM: Bacillus subtilis

<400> SEQUENCE: 18

Met Lys Asn Lys Pro Leu Ala Phe Gln Ile Trp Val Val Ile Ser Gly
1               5                   10                  15

Ile Leu Leu Ala Ile Ser Ile Leu Leu Leu Val Leu Phe Ser Asn Thr
            20                  25                  30

Leu Arg Asp Phe Phe Thr Asn Glu Thr Tyr Thr Thr Ile Glu Asn Glu
        35                  40                  45

Gln His Val Leu Thr Glu Tyr Arg Leu Pro Gly Ser Ile Glu Arg Arg
    50                  55                  60

Tyr Tyr Ser Glu Glu Ala Thr Ala Pro Thr Thr Val Arg Ser Val Gln
65                  70                  75                  80

His Val Leu Leu Pro Glu Asn Glu Glu Ala Ser Ser Asp Lys Asp Leu
                85                  90                  95

Ser Ile Leu Ser Ser Ser Phe Ile His Lys Val Tyr Lys Leu Ala Asp
            100                 105                 110

Lys Gln Glu Ala Lys Lys Lys Arg Tyr Ser Ala Asp Val Asn Gly Glu
        115                 120                 125
```

```
Lys Val Phe Phe Val Ile Lys Lys Gly Leu Ser Val Asn Gly Gln Ser
    130                 135                 140

Ala Met Met Leu Ser Tyr Ala Leu Asp Ser Tyr Arg Asp Asp Leu Ala
145                 150                 155                 160

Tyr Thr Leu Phe Lys Gln Leu Leu Phe Ile Ile Ala Val Val Ile Leu
                165                 170                 175

Leu Ser Trp Ile Pro Ala Ile Trp Leu Ala Lys Tyr Leu Ser Arg Pro
            180                 185                 190

Leu Val Ser Phe Glu Lys His Val Lys Arg Ile Ser Glu Gln Asp Trp
        195                 200                 205

Asp Asp Pro Val Lys Val Asp Arg Lys Asp Glu Ile Gly Lys Leu Gly
    210                 215                 220

His Thr Ile Glu Glu Met Arg Gln Lys Leu Val Gln Lys Asp Glu Thr
225                 230                 235                 240

Glu Arg Thr Leu Leu Gln Asn Ile Ser His Asp Leu Lys Thr Pro Val
                245                 250                 255

Met Val Ile Arg Gly Tyr Thr Gln Ser Ile Lys Asp Gly Ile Phe Pro
            260                 265                 270

Lys Gly Asp Leu Glu Asn Thr Val Asp Val Ile Glu Cys Glu Ala Leu
        275                 280                 285

Lys Leu Glu Lys Lys Ile Lys Asp Leu Leu Tyr Leu Thr Lys Leu Asp
    290                 295                 300

Tyr Leu Ala Lys Gln Lys Val Gln His Asp Met Phe Ser Ile Val Glu
305                 310                 315                 320

Val Thr Glu Glu Val Ile Glu Arg Leu Lys Trp Ala Arg Lys Glu Leu
                325                 330                 335

Ser Trp Glu Ile Val Glu Glu Asp Ile Leu Met Pro Gly Asp Pro Glu
            340                 345                 350

Gln Trp Asn Lys Leu Leu Glu Asn Ile Leu Glu Asn Gln Ile Arg Tyr
        355                 360                 365

Ala Glu Thr Lys Ile Glu Ile Ser Met Lys Gln Asp Asp Arg Asn Ile
    370                 375                 380

Val Ile Thr Ile Lys Asn Asp Gly Pro His Ile Glu Asp Glu Met Leu
385                 390                 395                 400

Ser Ser Leu Tyr Glu Pro Phe Asn Lys Gly Lys Lys Gly Glu Phe Gly
                405                 410                 415

Ile Gly Leu Ser Ile Val Lys Arg Ile Leu Thr Leu His Lys Ala Ser
            420                 425                 430

Ile Ser Ile Glu Asn Asp Lys Thr Gly Val Ser Tyr Arg Ile Ala Val
        435                 440                 445

Pro Lys
    450
```

<210> SEQ ID NO 19
<211> LENGTH: 2013
<212> TYPE: DNA
<213> ORGANISM: Bacillus subtilis

<400> SEQUENCE: 19

```
atgtttaaaa ataatgtcat acttttaaat tcaccttatc atgcacatgc tcataaagag      60

gggtttattc taaaaagggg atggacggtt ttggaaagca agtacctaga tctactcgca     120

caaaaatacg attgtgaaga aaaagtggta acagaaatca tcaatttgaa agcgatattg     180

aacctgccaa aaggcaccga gcattttgtc agtgatctgc acggagagta tcaggcattc     240
```

```
cagcacgtgt tgcgcaatgg ttcaggacga gtcaaagaga agatacgcga catcttcagc    300
ggtgtcattt acgatagaga aattgatgaa ttagcagcat tggtctatta tccggaagac    360
aaactgaaat taatcaaaca tgactttgat gcgaaagaag cgttaaacga gtggtataaa    420
gaaacgattc atcgaatgat taagctcgtt tcatattgct cctctaagta tacccgctcc    480
aaattacgca aagcactgcc tgcccaattt gcttatatta cggaggagct gttatacaaa    540
acagaacaag ctggcaacaa ggagcaatat tactccgaaa tcattgatca gatcattgaa    600
cttggccaag ccgataagct gatcaccggc cttgcttaca gcgttcagcg attggtggtc    660
gaccatctgc atgtggtcgg cgatatttat gaccgcggcc cgcagccgga tagaattatg    720
gaagaactga tcaactatca ttctgtcgat attcagtggg gaaatcacga tgtcctttgg    780
atcggcgcct attccggttc caaagtgtgc ctggccaata ttatccgcat ctgtgcccgc    840
tacgacaacc tggatattat tgaggacgtg tacggcatca acctgagacc gctgctgaac    900
ctggccgaaa aatattatga tgataatcca gcgttccgtc caaaagcaga cgaaaacagg    960
ccagaggatg agattaagca aatcacaaaa atccatcaag cgattgccat gatccaattc   1020
aagcttgaga gcccgattat caagagacgg ccgaacttta atatggaaga gcggctgtta   1080
ttagagaaaa tagactatga caaaaatgaa atcacgctga acggaaaaac atatcaactg   1140
gaaaacacct gctttgcgac gattaatccg gagcagccag atcagctatt agaagaagaa   1200
gcagaagtca tagacaagct gctattctct gtccagcatt ccgaaaagct gggccgccat   1260
atgaatttta tgatgaaaaa aggcagcctt tatttaaaat ataacggcaa cctgttgatt   1320
cacggctgta ttccagttga tgaaaacggc aatatggaaa cgatgatgat tgaggataaa   1380
ccgtatgcgg gccgtgagct gctcgatgta tttgaacgat tcttgcggga agcctttgcc   1440
cacccggaag aaaccgatga cctggcgaca gatatggctt ggtatttatg gacaggcgaa   1500
tactcctccc tcttcggaaa acgcgccatg acgacatttg agcgctattt catcaaagag   1560
aaggaaacgc ataaagagaa gaaaaacccg tattattatt tacgagaaga cgaggcaacc   1620
tgccgaaaca tcctggcaga attcggcctc aatccagatc acggccatat catcaacggc   1680
catacacctg taaaagaaat cgaaggagaa gacccaatca aagcaaacgg aaaaatgatc   1740
gtcatcgacg gcggcttctc caaagcctac caatccacaa caggcatcgc cggctacacg   1800
ctgctataca actcctacgg catgcagctc gtcgcccata aacacttcaa ttccaaggca   1860
gaagtcctaa gcaccggaac cgacgtctta acggtcaaac gattagtgga caaagagctt   1920
gagcggaaga aagtgaagga aacgaatgtg ggtgaggaat tgttgcagga agttgcgatt   1980
ttagagagtt tgcgggagta tcggtatatg aag                                2013
```

<210> SEQ ID NO 20
<211> LENGTH: 671
<212> TYPE: PRT
<213> ORGANISM: Bacillus subtilis

<400> SEQUENCE: 20

```
Met Phe Lys Asn Asn Val Ile Leu Leu Asn Ser Pro Tyr His Ala His
1               5                   10                  15

Ala His Lys Glu Gly Phe Ile Leu Lys Arg Gly Trp Thr Val Leu Glu
            20                  25                  30

Ser Lys Tyr Leu Asp Leu Leu Ala Gln Lys Tyr Asp Cys Glu Glu Lys
        35                  40                  45

Val Val Thr Glu Ile Ile Asn Leu Lys Ala Ile Leu Asn Leu Pro Lys
    50                  55                  60
```

```
Gly Thr Glu His Phe Val Ser Asp Leu His Gly Glu Tyr Gln Ala Phe
65                  70                  75                  80

Gln His Val Leu Arg Asn Gly Ser Gly Arg Val Lys Glu Lys Ile Arg
                85                  90                  95

Asp Ile Phe Ser Gly Val Ile Tyr Asp Arg Glu Ile Asp Glu Leu Ala
            100                 105                 110

Ala Leu Val Tyr Tyr Pro Glu Asp Lys Leu Lys Leu Ile Lys His Asp
        115                 120                 125

Phe Asp Ala Lys Glu Ala Leu Asn Glu Trp Tyr Lys Glu Thr Ile His
    130                 135                 140

Arg Met Ile Lys Leu Val Ser Tyr Cys Ser Ser Lys Tyr Thr Arg Ser
145                 150                 155                 160

Lys Leu Arg Lys Ala Leu Pro Ala Gln Phe Ala Tyr Ile Thr Glu Glu
                165                 170                 175

Leu Leu Tyr Lys Thr Glu Gln Ala Gly Asn Lys Glu Gln Tyr Tyr Ser
            180                 185                 190

Glu Ile Ile Asp Gln Ile Ile Glu Leu Gly Gln Ala Asp Lys Leu Ile
        195                 200                 205

Thr Gly Leu Ala Tyr Ser Val Gln Arg Leu Val Val Asp His Leu His
    210                 215                 220

Val Val Gly Asp Ile Tyr Asp Arg Gly Pro Gln Pro Asp Arg Ile Met
225                 230                 235                 240

Glu Glu Leu Ile Asn Tyr His Ser Val Asp Ile Gln Trp Gly Asn His
                245                 250                 255

Asp Val Leu Trp Ile Gly Ala Tyr Ser Gly Ser Lys Val Cys Leu Ala
            260                 265                 270

Asn Ile Ile Arg Ile Cys Ala Arg Tyr Asp Asn Leu Asp Ile Ile Glu
        275                 280                 285

Asp Val Tyr Gly Ile Asn Leu Arg Pro Leu Leu Asn Leu Ala Glu Lys
    290                 295                 300

Tyr Tyr Asp Asp Asn Pro Ala Phe Arg Pro Lys Ala Asp Glu Asn Arg
305                 310                 315                 320

Pro Glu Asp Glu Ile Lys Gln Ile Thr Lys Ile His Gln Ala Ile Ala
                325                 330                 335

Met Ile Gln Phe Lys Leu Glu Ser Pro Ile Ile Lys Arg Arg Pro Asn
            340                 345                 350

Phe Asn Met Glu Glu Arg Leu Leu Leu Glu Lys Ile Asp Tyr Asp Lys
        355                 360                 365

Asn Glu Ile Thr Leu Asn Gly Lys Thr Tyr Gln Leu Glu Asn Thr Cys
    370                 375                 380

Phe Ala Thr Ile Asn Pro Glu Gln Pro Asp Gln Leu Leu Glu Glu Glu
385                 390                 395                 400

Ala Glu Val Ile Asp Lys Leu Leu Phe Ser Val Gln His Ser Glu Lys
                405                 410                 415

Leu Gly Arg His Met Asn Phe Met Met Lys Lys Gly Ser Leu Tyr Leu
            420                 425                 430

Lys Tyr Asn Gly Asn Leu Leu Ile His Gly Cys Ile Pro Val Asp Glu
        435                 440                 445

Asn Gly Asn Met Glu Thr Met Met Ile Glu Asp Lys Pro Tyr Ala Gly
    450                 455                 460

Arg Glu Leu Leu Asp Val Phe Glu Arg Phe Leu Arg Glu Ala Phe Ala
465                 470                 475                 480
```

```
His Pro Glu Glu Thr Asp Asp Leu Ala Thr Asp Met Ala Trp Tyr Leu
                485                 490                 495

Trp Thr Gly Glu Tyr Ser Ser Leu Phe Gly Lys Arg Ala Met Thr Thr
            500                 505                 510

Phe Glu Arg Tyr Phe Ile Lys Glu Lys Glu Thr His Lys Glu Lys Lys
        515                 520                 525

Asn Pro Tyr Tyr Tyr Leu Arg Glu Asp Glu Ala Thr Cys Arg Asn Ile
    530                 535                 540

Leu Ala Glu Phe Gly Leu Asn Pro Asp His Gly His Ile Ile Asn Gly
545                 550                 555                 560

His Thr Pro Val Lys Glu Ile Glu Gly Glu Asp Pro Ile Lys Ala Asn
                565                 570                 575

Gly Lys Met Ile Val Ile Asp Gly Gly Phe Ser Lys Ala Tyr Gln Ser
            580                 585                 590

Thr Thr Gly Ile Ala Gly Tyr Thr Leu Leu Tyr Asn Ser Tyr Gly Met
        595                 600                 605

Gln Leu Val Ala His Lys His Phe Asn Ser Lys Ala Glu Val Leu Ser
    610                 615                 620

Thr Gly Thr Asp Val Leu Thr Val Lys Arg Leu Val Asp Lys Glu Leu
625                 630                 635                 640

Glu Arg Lys Lys Val Lys Glu Thr Asn Val Gly Glu Glu Leu Leu Gln
                645                 650                 655

Glu Val Ala Ile Leu Glu Ser Leu Arg Glu Tyr Arg Tyr Met Lys
            660                 665                 670


<210> SEQ ID NO 21
<211> LENGTH: 765
<212> TYPE: DNA
<213> ORGANISM: Bacillus subtilis

<400> SEQUENCE: 21

atgaaacgag aaagcaacat tcaagtgctc agccgtggtc aaaaagatca gcctgtgagc      60

cagatttatc aagtatcaac aatgacttct ctattagacg gagtatatga cggagatttt     120

gaactgtcag agattccgaa atatggagac ttcggtatcg gaacctttaa caagcttgac     180

ggagagctga ttgggtttga cggcgaattt taccgtcttc gctcagacgg aaccgcgaca     240

ccggtccaaa atggagaccg ttcaccgttc tgttcattta cgttctttac accggacatg     300

acgcacaaaa ttgatgcgaa aatgacacgc gaagactttg aaaaagagat caacagcatg     360

ctgccaagca gaaacttatt ttatgcaatt cgcattgacg gattgtttaa aaaggtgcag     420

acaagaacag tagaacttca agaaaaacct tacgtgccaa tggttgaagc ggtcaaaaca     480

cagccgattt tcaacttcga caacgtgaga ggaacgattg taggtttctt gacaccagct     540

tatgcaaacg gaatcgccgt ttctggctat cacctgcact tcattgacga aggacgcaat     600

tcaggcggac acgtttttga ctatgtgctt gaggattgca cggttacgat ttctcaaaaa     660

atgaacatga atctcagact tccgaacaca gcggatttct ttaatgcgaa tctggataac     720

cctgattttg cgaaagatat cgaaacaact gaaggaagcc ctgaa                     765


<210> SEQ ID NO 22
<211> LENGTH: 255
<212> TYPE: PRT
<213> ORGANISM: Bacillus subtilis

<400> SEQUENCE: 22

Met Lys Arg Glu Ser Asn Ile Gln Val Leu Ser Arg Gly Gln Lys Asp
```

-continued

```
 1               5                   10                  15

Gln Pro Val Ser Gln Ile Tyr Gln Val Ser Thr Met Thr Ser Leu Leu
            20                  25                  30

Asp Gly Val Tyr Asp Gly Asp Phe Glu Leu Ser Glu Ile Pro Lys Tyr
        35                  40                  45

Gly Asp Phe Gly Ile Gly Thr Phe Asn Lys Leu Asp Gly Glu Leu Ile
    50                  55                  60

Gly Phe Asp Gly Glu Phe Tyr Arg Leu Arg Ser Asp Gly Thr Ala Thr
65                  70                  75                  80

Pro Val Gln Asn Gly Asp Arg Ser Pro Phe Cys Ser Phe Thr Phe Phe
                85                  90                  95

Thr Pro Asp Met Thr His Lys Ile Asp Ala Lys Met Thr Arg Glu Asp
            100                 105                 110

Phe Glu Lys Glu Ile Asn Ser Met Leu Pro Ser Arg Asn Leu Phe Tyr
        115                 120                 125

Ala Ile Arg Ile Asp Gly Leu Phe Lys Lys Val Gln Thr Arg Thr Val
    130                 135                 140

Glu Leu Gln Glu Lys Pro Tyr Val Pro Met Val Glu Ala Val Lys Thr
145                 150                 155                 160

Gln Pro Ile Phe Asn Phe Asp Asn Val Arg Gly Thr Ile Val Gly Phe
                165                 170                 175

Leu Thr Pro Ala Tyr Ala Asn Gly Ile Ala Val Ser Gly Tyr His Leu
            180                 185                 190

His Phe Ile Asp Glu Gly Arg Asn Ser Gly Gly His Val Phe Asp Tyr
        195                 200                 205

Val Leu Glu Asp Cys Thr Val Thr Ile Ser Gln Lys Met Asn Met Asn
    210                 215                 220

Leu Arg Leu Pro Asn Thr Ala Asp Phe Phe Asn Ala Asn Leu Asp Asn
225                 230                 235                 240

Pro Asp Phe Ala Lys Asp Ile Glu Thr Thr Glu Gly Ser Pro Glu
                245                 250                 255


<210> SEQ ID NO 23
<211> LENGTH: 1020
<212> TYPE: DNA
<213> ORGANISM: Bacillus subtilis

<400> SEQUENCE: 23

atgaaggtaa aagtagcgat caacgggttt ggaagaatcg gaagaatggt ttttagaaaa     60

gcgatgttag acgatcaaat tcaagtagtg gccattaacg ccagctattc cgcagaaacg    120

ctggctcatt taataaagta tgacacaatt cacggcagat acgacaaaga ggttgtggct    180

ggtgaagata gcctgatcgt aaatggaaag aaagtgcttt tgttaaacag ccgtgatcca    240

aaacagctgc cttggcggga atatgatatt gacatagtcg tcgaagcaac agggaagttt    300

aatgctaaag ataaagcgat gggccatata gaagcaggtg caaaaaaagt gattttgacc    360

gctccgggaa aaaatgaaga cgttaccatt gtgatgggcg taaatgagga ccaattcgac    420

gctgagcgcc atgtcattat ttcaaatgcg tcatgcacga caaattgcct tgcgcctgtt    480

gtaaaagtgc tggatgaaga gtttggcatt gagagcggtc tgatgactac agttcatgcg    540

tatacgaatg accaaaaaaa tattgataac ccgcacaaag atttgcgccg ggcgcgggct    600

tgcggtgaat ccatcattcc aacaacaaca ggagcggcaa aggcgctttc gcttgtgctg    660

ccgcatctga aaggaaaact tcacggcctc gccttgcgtg tccctgttcc gaacgtctca    720
```

```
ttggttgatc tcgttgttga tctgaaaacg gatgttacgg ctgaagaagt aaacgaggca    780

tttaaacgcg ctgccaaaac gtcgatgtac ggtgtacttg attactcaga tgaaccgctc    840

gtttcgactg attataatac gaatccgcat tcagcggtca ttgacgggct tacaacaatg    900

gtaatggaag acaggaaagt aaaggtgctg gcgtggtatg acaacgaatg ggctactcc     960

tgcagagttg ttgatctaat ccgccatgta gcggcacgaa tgaaacatcc gtctgctgta   1020


<210> SEQ ID NO 24
<211> LENGTH: 340
<212> TYPE: PRT
<213> ORGANISM: Bacillus subtilis

<400> SEQUENCE: 24

Met Lys Val Lys Val Ala Ile Asn Gly Phe Gly Arg Ile Gly Arg Met
 1               5                  10                  15

Val Phe Arg Lys Ala Met Leu Asp Asp Gln Ile Gln Val Val Ala Ile
            20                  25                  30

Asn Ala Ser Tyr Ser Ala Glu Thr Leu Ala His Leu Ile Lys Tyr Asp
        35                  40                  45

Thr Ile His Gly Arg Tyr Asp Lys Glu Val Val Ala Gly Glu Asp Ser
    50                  55                  60

Leu Ile Val Asn Gly Lys Lys Val Leu Leu Leu Asn Ser Arg Asp Pro
65                  70                  75                  80

Lys Gln Leu Pro Trp Arg Glu Tyr Asp Ile Asp Ile Val Val Glu Ala
                85                  90                  95

Thr Gly Lys Phe Asn Ala Lys Asp Lys Ala Met Gly His Ile Glu Ala
            100                 105                 110

Gly Ala Lys Lys Val Ile Leu Thr Ala Pro Gly Lys Asn Glu Asp Val
        115                 120                 125

Thr Ile Val Met Gly Val Asn Glu Asp Gln Phe Asp Ala Glu Arg His
    130                 135                 140

Val Ile Ile Ser Asn Ala Ser Cys Thr Thr Asn Cys Leu Ala Pro Val
145                 150                 155                 160

Val Lys Val Leu Asp Glu Glu Phe Gly Ile Glu Ser Gly Leu Met Thr
                165                 170                 175

Thr Val His Ala Tyr Thr Asn Asp Gln Lys Asn Ile Asp Asn Pro His
            180                 185                 190

Lys Asp Leu Arg Arg Ala Arg Ala Cys Gly Glu Ser Ile Ile Pro Thr
        195                 200                 205

Thr Thr Gly Ala Ala Lys Ala Leu Ser Leu Val Leu Pro His Leu Lys
    210                 215                 220

Gly Lys Leu His Gly Leu Ala Leu Arg Val Pro Val Pro Asn Val Ser
225                 230                 235                 240

Leu Val Asp Leu Val Val Asp Leu Lys Thr Asp Val Thr Ala Glu Glu
                245                 250                 255

Val Asn Glu Ala Phe Lys Arg Ala Ala Lys Thr Ser Met Tyr Gly Val
            260                 265                 270

Leu Asp Tyr Ser Asp Glu Pro Leu Val Ser Thr Asp Tyr Asn Thr Asn
        275                 280                 285

Pro His Ser Ala Val Ile Asp Gly Leu Thr Thr Met Val Met Glu Asp
    290                 295                 300

Arg Lys Val Lys Val Leu Ala Trp Tyr Asp Asn Glu Trp Gly Tyr Ser
305                 310                 315                 320

Cys Arg Val Val Asp Leu Ile Arg His Val Ala Ala Arg Met Lys His
```

```
            325                 330                 335

Pro Ser Ala Val
            340


<210> SEQ ID NO 25
<211> LENGTH: 1176
<212> TYPE: DNA
<213> ORGANISM: Bacillus subtilis

<400> SEQUENCE: 25

atgacgaagg aatttgagtt tttaaaagca gagcttaata gtatgaaaga aaaccataca      60

tggcaagaca taaaacagct tgaatctatg cagggcccat ctgtcacagt gaatcaccaa     120

aaagtcattc agctatcttc taataattac ctcggattca cttcacatcc tagactcatc     180

aacgccgcac aggaggccgt tcagcagtat ggagccggca ccggatcagt gagaacgatt     240

gcgggtacat ttacaatgca tcaagagctt gagaaaaagc tggcagcctt taaaaaaacg     300

gaggcggcac ttgtattcca atcaggcttc acaacaaacc aaggcgtact ttcaagtatt     360

ctatcaaaag aggacattgt catctcagat gaattgaacc atgcctctat tattgacgga     420

attcgactga caaaggcgga taaaaaggtg tatcagcacg tcaatatgag tgatttagag     480

cgggtgctga gaaagtcaat gaattatcgg atgcgtctga ttgtgacaga cggcgtattt     540

tccatggatg gcaacatagc tcctctgcct gatattgtag agctcgctga gaaatatgac     600

gcatttgtga tggtggatga cgcccatgca tccggagtac ttggcgaaaa cggcagggga     660

acggtgaatc acttcggtct tgacggcaga gtgcatattc aggtcggaac attaagcaag     720

gcaatcggag tgctcggcgg ctacgctgca ggttcaaagg tgctgatcga ttatttgcgc     780

cataaaggcc gtccattttt attcagcaca tctcatccgc cggcagtcac tgcagcttgt     840

atggaagcga ttgatgtctt gcttgaagag ccggagcata tggagcgctt gtgggagaat     900

actgcctatt ttaaagcaat gcttgtgaaa atgggtctga ctctcacgaa gagtgaaacg     960

ccgattcttc ctattttaat aggtgatgaa ggtgtggcaa agcaattttc agatcagctc    1020

ctttctcgcg gtgtttttgc ccaaagtatc gttttcccga ctgtagcaaa gggaaaagcc    1080

agaattcgca cgattataac agcagagcac accaaagatg aactggatca ggcgcttgat    1140

gtcatcgaaa agacggcaaa ggagctccag ctattg                              1176


<210> SEQ ID NO 26
<211> LENGTH: 392
<212> TYPE: PRT
<213> ORGANISM: Bacillus subtilis

<400> SEQUENCE: 26

Met Thr Lys Glu Phe Glu Phe Leu Lys Ala Glu Leu Asn Ser Met Lys
 1               5                   10                  15

Glu Asn His Thr Trp Gln Asp Ile Lys Gln Leu Glu Ser Met Gln Gly
            20                  25                  30

Pro Ser Val Thr Val Asn His Gln Lys Val Ile Gln Leu Ser Ser Asn
        35                  40                  45

Asn Tyr Leu Gly Phe Thr Ser His Pro Arg Leu Ile Asn Ala Ala Gln
    50                  55                  60

Glu Ala Val Gln Gln Tyr Gly Ala Gly Thr Gly Ser Val Arg Thr Ile
65                  70                  75                  80

Ala Gly Thr Phe Thr Met His Gln Glu Leu Glu Lys Lys Leu Ala Ala
                85                  90                  95
```

```
Phe Lys Lys Thr Glu Ala Ala Leu Val Phe Gln Ser Gly Phe Thr Thr
            100                 105                 110

Asn Gln Gly Val Leu Ser Ser Ile Leu Ser Lys Glu Asp Ile Val Ile
        115                 120                 125

Ser Asp Glu Leu Asn His Ala Ser Ile Ile Asp Gly Ile Arg Leu Thr
    130                 135                 140

Lys Ala Asp Lys Lys Val Tyr Gln His Val Asn Met Ser Asp Leu Glu
145                 150                 155                 160

Arg Val Leu Arg Lys Ser Met Asn Tyr Arg Met Arg Leu Ile Val Thr
                165                 170                 175

Asp Gly Val Phe Ser Met Asp Gly Asn Ile Ala Pro Leu Pro Asp Ile
            180                 185                 190

Val Glu Leu Ala Glu Lys Tyr Asp Ala Phe Val Met Val Asp Asp Ala
        195                 200                 205

His Ala Ser Gly Val Leu Gly Glu Asn Gly Arg Gly Thr Val Asn His
    210                 215                 220

Phe Gly Leu Asp Gly Arg Val His Ile Gln Val Gly Thr Leu Ser Lys
225                 230                 235                 240

Ala Ile Gly Val Leu Gly Gly Tyr Ala Ala Gly Ser Lys Val Leu Ile
                245                 250                 255

Asp Tyr Leu Arg His Lys Gly Arg Pro Phe Leu Phe Ser Thr Ser His
            260                 265                 270

Pro Pro Ala Val Thr Ala Ala Cys Met Glu Ala Ile Asp Val Leu Leu
        275                 280                 285

Glu Glu Pro Glu His Met Glu Arg Leu Trp Glu Asn Thr Ala Tyr Phe
    290                 295                 300

Lys Ala Met Leu Val Lys Met Gly Leu Thr Leu Thr Lys Ser Glu Thr
305                 310                 315                 320

Pro Ile Leu Pro Ile Leu Ile Gly Asp Glu Gly Val Ala Lys Gln Phe
                325                 330                 335

Ser Asp Gln Leu Leu Ser Arg Gly Val Phe Ala Gln Ser Ile Val Phe
            340                 345                 350

Pro Thr Val Ala Lys Gly Lys Ala Arg Ile Arg Thr Ile Ile Thr Ala
        355                 360                 365

Glu His Thr Lys Asp Glu Leu Asp Gln Ala Leu Asp Val Ile Glu Lys
    370                 375                 380

Thr Ala Lys Glu Leu Gln Leu Leu
385                 390


<210> SEQ ID NO 27
<211> LENGTH: 1581
<212> TYPE: DNA
<213> ORGANISM: Bacillus subtilis

<400> SEQUENCE: 27

atgaactcag ttgatttgac cgctgattta caagccttat taacatgtcc aaatgtgcgt      60

cataatttat cagcagcaca gctaacagaa aaagtcctct cccgaaacga aggcatttta     120

acatccacag gtgctgttcg cgcgacaaca ggcgcttaca caggacgctc acctaaagat     180

aaattcatcg tggaggaaga aagcacgaaa aataagatcg attggggccc ggtgaatcag     240

ccgatttcag aagaagcgtt tgagcggctg tacacgaaag ttgtcagcta tttaaaggag     300

cgagatgaac tgtttgtttt cgaaggattt gccggagcag acgagaaata caggctgccg     360

atcactgtcg taaatgagtt cgcatggcac aatttatttg cgcggcagct gtttatccgt     420
```

```
ccggaaggaa atgataagaa aacagttgag cagccgttca ccattctttc tgctccgcat    480

ttcaaagcgg atccaaaaac agacggcact cattccgaaa cgtttattat tgtctctttc    540

gaaaagcgga caattttaat cggcggaact gagtatgccg gtgaaatgaa gaagtccatt    600

ttctccatta tgaatttcct gctgcctgaa agagatattt tatctatgca ctgctccgcc    660

aatgtcggtg aaaaaggcga tgtcgccctt ttcttcggac tgtcaggaac aggaaagacc    720

accctgtcgg cagatgctga ccgcaagctg atcggtgacg atgaacatgg ctggtctgat    780

acaggcgtct ttaatattga aggcggatgc tacgctaagt gtattcattt aagcgaggaa    840

aaggagccgc aaatctttaa cgcgatccgc ttcgggtctg ttctcgaaaa tgtcgttgtg    900

gatgaagata cacgcgaagc caattatgat gattccttct atactgaaaa cacgcgggca    960

gcttacccga ttcatatgat taataacatc gtgactccaa gcatggccgg ccatccgtca   1020

gccattgtat ttttgacggc tgatgccttc ggagtcctgc cgccgatcag caaactaacg   1080

aaggagcagg tgatgtacca tttttgagc ggttacacga gtaagcttgc cggaaccgaa   1140

cgtggtgtca cgtctcctga aacgacgttt tctacatgct tcggctcacc gttcctgccg   1200

cttcctgctc acgtctatgc tgaaatgctc ggcaaaaaga tcgatgaaca cggcgcagac   1260

gttttcttag tcaataccgg atggaccggg ggcggctacg gcacaggcga acgaatgaag   1320

ctttcttaca ctagagcaat ggtcaaagca gcgattgaag gcaaattaga ggatgctgaa   1380

atgataactg acgatatttt cggcctgcac attccggccc atgttcctgg cgttcctgat   1440

catatccttc agcctgaaaa cacgtggacc aacaaggaag aatacaaaga aaaagcagtc   1500

taccttgcaa atgaattcaa agagaacttt aaaaagttcg cacataccga tgccatcgcc   1560

caggcaggcg gccctctcgt a                                             1581
```

<210> SEQ ID NO 28
<211> LENGTH: 527
<212> TYPE: PRT
<213> ORGANISM: Bacillus subtilis

<400> SEQUENCE: 28

```
Met Asn Ser Val Asp Leu Thr Ala Asp Leu Gln Ala Leu Leu Thr Cys
1               5                   10                  15

Pro Asn Val Arg His Asn Leu Ser Ala Ala Gln Leu Thr Glu Lys Val
            20                  25                  30

Leu Ser Arg Asn Glu Gly Ile Leu Thr Ser Thr Gly Ala Val Arg Ala
        35                  40                  45

Thr Thr Gly Ala Tyr Thr Gly Arg Ser Pro Lys Asp Lys Phe Ile Val
    50                  55                  60

Glu Glu Glu Ser Thr Lys Asn Lys Ile Asp Trp Gly Pro Val Asn Gln
65                  70                  75                  80

Pro Ile Ser Glu Glu Ala Phe Glu Arg Leu Tyr Thr Lys Val Val Ser
                85                  90                  95

Tyr Leu Lys Glu Arg Asp Glu Leu Phe Val Phe Glu Gly Phe Ala Gly
            100                 105                 110

Ala Asp Glu Lys Tyr Arg Leu Pro Ile Thr Val Val Asn Glu Phe Ala
        115                 120                 125

Trp His Asn Leu Phe Ala Arg Gln Leu Phe Ile Arg Pro Glu Gly Asn
    130                 135                 140

Asp Lys Lys Thr Val Glu Gln Pro Phe Thr Ile Leu Ser Ala Pro His
145                 150                 155                 160

Phe Lys Ala Asp Pro Lys Thr Asp Gly Thr His Ser Glu Thr Phe Ile
```

```
                165                 170                 175

Ile Val Ser Phe Glu Lys Arg Thr Ile Leu Ile Gly Gly Thr Glu Tyr
            180                 185                 190

Ala Gly Glu Met Lys Lys Ser Ile Phe Ser Ile Met Asn Phe Leu Leu
        195                 200                 205

Pro Glu Arg Asp Ile Leu Ser Met His Cys Ser Ala Asn Val Gly Glu
    210                 215                 220

Lys Gly Asp Val Ala Leu Phe Phe Gly Leu Ser Gly Thr Gly Lys Thr
225                 230                 235                 240

Thr Leu Ser Ala Asp Ala Asp Arg Lys Leu Ile Gly Asp Asp Glu His
                245                 250                 255

Gly Trp Ser Asp Thr Gly Val Phe Asn Ile Glu Gly Gly Cys Tyr Ala
            260                 265                 270

Lys Cys Ile His Leu Ser Glu Glu Lys Glu Pro Gln Ile Phe Asn Ala
        275                 280                 285

Ile Arg Phe Gly Ser Val Leu Glu Asn Val Val Val Asp Glu Asp Thr
    290                 295                 300

Arg Glu Ala Asn Tyr Asp Asp Ser Phe Tyr Thr Glu Asn Thr Arg Ala
305                 310                 315                 320

Ala Tyr Pro Ile His Met Ile Asn Asn Ile Val Thr Pro Ser Met Ala
                325                 330                 335

Gly His Pro Ser Ala Ile Val Phe Leu Thr Ala Asp Ala Phe Gly Val
            340                 345                 350

Leu Pro Pro Ile Ser Lys Leu Thr Lys Glu Gln Val Met Tyr His Phe
        355                 360                 365

Leu Ser Gly Tyr Thr Ser Lys Leu Ala Gly Thr Glu Arg Gly Val Thr
    370                 375                 380

Ser Pro Glu Thr Thr Phe Ser Thr Cys Phe Gly Ser Pro Phe Leu Pro
385                 390                 395                 400

Leu Pro Ala His Val Tyr Ala Glu Met Leu Gly Lys Lys Ile Asp Glu
                405                 410                 415

His Gly Ala Asp Val Phe Leu Val Asn Thr Gly Trp Thr Gly Gly Gly
            420                 425                 430

Tyr Gly Thr Gly Glu Arg Met Lys Leu Ser Tyr Thr Arg Ala Met Val
        435                 440                 445

Lys Ala Ala Ile Glu Gly Lys Leu Glu Asp Ala Glu Met Ile Thr Asp
    450                 455                 460

Asp Ile Phe Gly Leu His Ile Pro Ala His Val Pro Gly Val Pro Asp
465                 470                 475                 480

His Ile Leu Gln Pro Glu Asn Thr Trp Thr Asn Lys Glu Glu Tyr Lys
                485                 490                 495

Glu Lys Ala Val Tyr Leu Ala Asn Glu Phe Lys Glu Asn Phe Lys Lys
            500                 505                 510

Phe Ala His Thr Asp Ala Ile Ala Gln Ala Gly Gly Pro Leu Val
        515                 520                 525


<210> SEQ ID NO 29
<211> LENGTH: 762
<212> TYPE: DNA
<213> ORGANISM: Bacillus subtilis

<400> SEQUENCE: 29

ttgttaacag ccttaaaaac agatacagga aaaatccgcc agcataatga agatgatgcg      60

gggatattca aggggaaaga tgaatttata ttagcggttg tcgctgatgg catgggcggc     120
```

```
catcttgctg gagatgttgc gagcaagatg gctgtgaaag ccatgggga gaaatggaat    180

gaagcagaga cgattccaac tgcgccctcg gaatgtgaaa aatggctcat tgaacagatt    240

ctatcggtaa acagcaaaat atacgatcac gctcaagccc acgaagaatg ccaaggcatg    300

gggacgacga ttgtatgtgc actttttacg ggaaaacgg tttctgttgc ccatatcgga    360

gacagcagat gctatttgct tcaggacgat gatttcgttc aagtgacaga agaccattcg    420

cttgtaaatg aactggttcg cactggagag atttccagag aagacgctga acatcatccg    480

cgaaaaaatg tgttgacgaa ggcgcttgga acagaccagt tagtcagtat tgacacccgt    540

tcctttgata tagaacccgg agacaaactg cttctatgtt ctgacggact gacaaataaa    600

gtggaaggca ctgagttaaa agacatcctg caaagcgatt cagctcctca ggaaaaagta    660

aacctgcttg tggacaaagc caatcagaat ggcggagaag acaacattac agcagttttg    720

cttgagcttg ctttacaagt tgaagagggt gaagatcagt gc                     762
```

<210> SEQ ID NO 30
<211> LENGTH: 254
<212> TYPE: PRT
<213> ORGANISM: Bacillus subtilis

<400> SEQUENCE: 30

```
Met Leu Thr Ala Leu Lys Thr Asp Thr Gly Lys Ile Arg Gln His Asn
 1               5                  10                  15

Glu Asp Asp Ala Gly Ile Phe Lys Gly Lys Asp Glu Phe Ile Leu Ala
            20                  25                  30

Val Val Ala Asp Gly Met Gly Gly His Leu Ala Gly Asp Val Ala Ser
        35                  40                  45

Lys Met Ala Val Lys Ala Met Gly Glu Lys Trp Asn Glu Ala Glu Thr
    50                  55                  60

Ile Pro Thr Ala Pro Ser Glu Cys Glu Lys Trp Leu Ile Glu Gln Ile
65                  70                  75                  80

Leu Ser Val Asn Ser Lys Ile Tyr Asp His Ala Gln Ala His Glu Glu
                85                  90                  95

Cys Gln Gly Met Gly Thr Thr Ile Val Cys Ala Leu Phe Thr Gly Lys
            100                 105                 110

Thr Val Ser Val Ala His Ile Gly Asp Ser Arg Cys Tyr Leu Leu Gln
        115                 120                 125

Asp Asp Asp Phe Val Gln Val Thr Glu Asp His Ser Leu Val Asn Glu
    130                 135                 140

Leu Val Arg Thr Gly Glu Ile Ser Arg Glu Asp Ala Glu His His Pro
145                 150                 155                 160

Arg Lys Asn Val Leu Thr Lys Ala Leu Gly Thr Asp Gln Leu Val Ser
                165                 170                 175

Ile Asp Thr Arg Ser Phe Asp Ile Glu Pro Gly Asp Lys Leu Leu Leu
            180                 185                 190

Cys Ser Asp Gly Leu Thr Asn Lys Val Glu Gly Thr Glu Leu Lys Asp
        195                 200                 205

Ile Leu Gln Ser Asp Ser Ala Pro Gln Glu Lys Val Asn Leu Leu Val
    210                 215                 220

Asp Lys Ala Asn Gln Asn Gly Gly Glu Asp Asn Ile Thr Ala Val Leu
225                 230                 235                 240

Leu Glu Leu Ala Leu Gln Val Glu Glu Gly Glu Asp Gln Cys
                245                 250
```

<210> SEQ ID NO 31
<211> LENGTH: 1545
<212> TYPE: DNA
<213> ORGANISM: Bacillus subtilis

<400> SEQUENCE: 31

```
atgacagtca catacgcgca cgaaccattt accgatttta cggaagcaaa gaataaaact      60

gcatttgggg agtcattggc ctttgtaaac actcagctcg gcaagcatta tccgcttgtc     120

ataaatggag aaaaaattga aacggaccgc aaaatcattt ctattaaccc ggcaaataaa     180

gaagagatca ttgggtacgc gtctacagcg gatcaagagc ttgctgaaaa agcgatgcaa     240

gccgcattgc aggcatttga ttcctggaaa aaacaaagac cggagcaccg cgcaaatatt     300

ctctttaagg cagcggctat tttgcgcaga agaaagcatg aattttcaag ctatcttgtg     360

aaggaagcag gaaaaccgtg gaaggaagca gatgcggaca cggctgaagc gatagacttt     420

ttagagttct acgcgcgcca aatgttaaag ctcaaggaag gggctccggt gaagagccgt     480

gctggcgagg tcaatcaata tcattacgaa gcgcttggcg tcggcatcgt catttctcca     540

tttaacttcc cgctcgcgat tatggcggga acagcggtgg cagcgattgt gacaggaaat     600

acgattctct taaaaccggc tgacgcagcc ccggtagtgg cagcaaaatt tgtcgaggtc     660

atggaggaag cgggtctgcc aaacggcgtt ctgaattaca ttccgggaga tggtgcggag     720

atcggtgatt tcttagttga gcatccgaag acacggtttg tctcatttac aggttcccgt     780

gcagtcggct gccggattta tgagcgagct gccaaagtgc agccgggcca aaaatggctc     840

aaacgggtaa ttgcagaaat gggcggaaaa gacacagtgc ttgtcgacaa ggacgctgat     900

cttgaccttg ctgcatcctc tatcgtgtat tcagcatttg gatattcagg acagaagtgt     960

tctgcgggct cccgcgcggt cattcatcag gatgtgtatg atgaagtggt ggaaaaagct    1020

gtggcgctga ccaaaacgct gactgtcggc aatccagaag atcctgatac gtatatgggt    1080

cccgtgattc atgaagcatc ctacaacaaa gtgatgaaat acattgaaat cggcaaatct    1140

gaaggcaagc tattggccgg cggagaaggc gatgattcaa aaggctactt tattcagccg    1200

acgatctttg cagatgttga tgaaaacgcc cgcttgatgc aggaagaaat tttcggcccg    1260

gttgttgcga tttgcaaagc gcgtgatttc gatcatatgc tggagattgc caataacacg    1320

gaatacggat taacaggtgc gcttctgacg aaaaaccgtg cgcacattga acgggcgcgc    1380

gaggatttcc atgtcggaaa cctatatttt aacagaggat gtaccggagc aattgtcggc    1440

tatcagccgt tcggcggttt taatatgtca ggaacagact caaaagcagg cggtcccgat    1500

tacttaattc ttcatatgca agccaaaaca acgtccgaag ctttt                    1545
```

<210> SEQ ID NO 32
<211> LENGTH: 515
<212> TYPE: PRT
<213> ORGANISM: Bacillus subtilis

<400> SEQUENCE: 32

```
Met Thr Val Thr Tyr Ala His Glu Pro Phe Thr Asp Phe Thr Glu Ala
1               5                   10                  15

Lys Asn Lys Thr Ala Phe Gly Glu Ser Leu Ala Phe Val Asn Thr Gln
            20                  25                  30

Leu Gly Lys His Tyr Pro Leu Val Ile Asn Gly Glu Lys Ile Glu Thr
        35                  40                  45

Asp Arg Lys Ile Ile Ser Ile Asn Pro Ala Asn Lys Glu Glu Ile Ile
    50                  55                  60
```

```
Gly Tyr Ala Ser Thr Ala Asp Gln Glu Leu Ala Glu Lys Ala Met Gln
65                  70                  75                  80

Ala Ala Leu Gln Ala Phe Asp Ser Trp Lys Lys Gln Arg Pro Glu His
                85                  90                  95

Arg Ala Asn Ile Leu Phe Lys Ala Ala Ala Ile Leu Arg Arg Arg Lys
            100                 105                 110

His Glu Phe Ser Ser Tyr Leu Val Lys Glu Ala Gly Lys Pro Trp Lys
        115                 120                 125

Glu Ala Asp Ala Asp Thr Ala Glu Ala Ile Asp Phe Leu Glu Phe Tyr
    130                 135                 140

Ala Arg Gln Met Leu Lys Leu Lys Glu Gly Ala Pro Val Lys Ser Arg
145                 150                 155                 160

Ala Gly Glu Val Asn Gln Tyr His Tyr Glu Ala Leu Gly Val Gly Ile
                165                 170                 175

Val Ile Ser Pro Phe Asn Phe Pro Leu Ala Ile Met Ala Gly Thr Ala
            180                 185                 190

Val Ala Ala Ile Val Thr Gly Asn Thr Ile Leu Leu Lys Pro Ala Asp
        195                 200                 205

Ala Ala Pro Val Val Ala Ala Lys Phe Val Glu Val Met Glu Glu Ala
    210                 215                 220

Gly Leu Pro Asn Gly Val Leu Asn Tyr Ile Pro Gly Asp Gly Ala Glu
225                 230                 235                 240

Ile Gly Asp Phe Leu Val Glu His Pro Lys Thr Arg Phe Val Ser Phe
                245                 250                 255

Thr Gly Ser Arg Ala Val Gly Cys Arg Ile Tyr Glu Arg Ala Ala Lys
            260                 265                 270

Val Gln Pro Gly Gln Lys Trp Leu Lys Arg Val Ile Ala Glu Met Gly
        275                 280                 285

Gly Lys Asp Thr Val Leu Val Asp Lys Asp Ala Asp Leu Asp Leu Ala
    290                 295                 300

Ala Ser Ser Ile Val Tyr Ser Ala Phe Gly Tyr Ser Gly Gln Lys Cys
305                 310                 315                 320

Ser Ala Gly Ser Arg Ala Val Ile His Gln Asp Val Tyr Asp Glu Val
                325                 330                 335

Val Glu Lys Ala Val Ala Leu Thr Lys Thr Leu Thr Val Gly Asn Pro
            340                 345                 350

Glu Asp Pro Asp Thr Tyr Met Gly Pro Val Ile His Glu Ala Ser Tyr
        355                 360                 365

Asn Lys Val Met Lys Tyr Ile Glu Ile Gly Lys Ser Glu Gly Lys Leu
    370                 375                 380

Leu Ala Gly Gly Glu Gly Asp Asp Ser Lys Gly Tyr Phe Ile Gln Pro
385                 390                 395                 400

Thr Ile Phe Ala Asp Val Asp Glu Asn Ala Arg Leu Met Gln Glu Glu
                405                 410                 415

Ile Phe Gly Pro Val Val Ala Ile Cys Lys Ala Arg Asp Phe Asp His
            420                 425                 430

Met Leu Glu Ile Ala Asn Asn Thr Glu Tyr Gly Leu Thr Gly Ala Leu
        435                 440                 445

Leu Thr Lys Asn Arg Ala His Ile Glu Arg Ala Arg Glu Asp Phe His
    450                 455                 460

Val Gly Asn Leu Tyr Phe Asn Arg Gly Cys Thr Gly Ala Ile Val Gly
465                 470                 475                 480
```

```
Tyr Gln Pro Phe Gly Gly Phe Asn Met Ser Gly Thr Asp Ser Lys Ala
                485                 490                 495

Gly Gly Pro Asp Tyr Leu Ile Leu His Met Gln Ala Lys Thr Thr Ser
            500                 505                 510

Glu Ala Phe
        515


<210> SEQ ID NO 33
<211> LENGTH: 1203
<212> TYPE: DNA
<213> ORGANISM: Bacillus subtilis

<400> SEQUENCE: 33

atgacagctt tatctaaatc caaagaaatt attgatcaga cgtctcatta cggagccaac      60

aattatcacc cgctcccgat tgttatttct gaagcgctgg gtgcttgggt aaaggacccg     120

gaaggcaatg aatatatgga tatgctgagt gcttactctg cggtaaacca ggggcacaga     180

cacccgaaaa tcattcaggc attaaaggat caggctgata aaatcaccct cacgtcacgc     240

gcgtttcata acgatcagct tgggccgttt tacgaaaaaa cagctaaact gacaggcaaa     300

gagatgattc tgccgatgaa tacaggagcc gaagcggttg aatccgcggt gaaagcggcg     360

agacgctggg cgtatgaagt gaagggcgta gctgacaatc aagcggaaat tatcgcatgt     420

gtcgggaact tccacggccg cacgatgctg gcggtatctc tttcttctga agaggaatat     480

aaacgaggat tcggcccgat gcttccagga atcaaactca ttccttacgg cgatgtggaa     540

gcgcttcgac aggccattac gccgaataca gcggcattct tgtttgaacc gattcaaggc     600

gaagcgggca ttgtgattcc gcctgaagga tttttacagg aagcggcggc gatttgtaag     660

gaagagaatg tcttgtttat tgcggatgaa attcagacgg gtctcggacg tacaggcaag     720

acgtttgcct gtgactggga cggcattgtt ccggatatgt atatcttggg caaagcgctt     780

ggcggcggtg tgttcccgat ctcttgcatt gcggcggacc gcgagatcct aggcgtgttt     840

aaccctggct cacacggctc aacatttggt ggaaacccgc ttgcatgtgc agtgtctatc     900

gcttcattag aagtgctgga ggatgaaaag ctggcggatc gttctcttga acttggtgaa     960

tactttaaaa gcgagcttga gagtattgac agccctgtca ttaaagaagt ccgcggcaga    1020

gggctgttta tcggtgtgga attgactgaa gcggcacgtc cgtattgtga gcgtttgaag    1080

gaagagggac ttttatgcaa ggaaacgcat gatacagtca ttcgttttgc accgccatta    1140

atcatttcca aagaggactt ggattgggcg atagagaaaa ttaagcacgt gctgcgaaac    1200

gca                                                                  1203


<210> SEQ ID NO 34
<211> LENGTH: 401
<212> TYPE: PRT
<213> ORGANISM: Bacillus subtilis

<400> SEQUENCE: 34

Met Thr Ala Leu Ser Lys Ser Lys Glu Ile Ile Asp Gln Thr Ser His
 1               5                  10                  15

Tyr Gly Ala Asn Asn Tyr His Pro Leu Pro Ile Val Ile Ser Glu Ala
            20                  25                  30

Leu Gly Ala Trp Val Lys Asp Pro Glu Gly Asn Glu Tyr Met Asp Met
        35                  40                  45

Leu Ser Ala Tyr Ser Ala Val Asn Gln Gly His Arg His Pro Lys Ile
    50                  55                  60
```

```
Ile Gln Ala Leu Lys Asp Gln Ala Asp Lys Ile Thr Leu Thr Ser Arg
65                  70                  75                  80

Ala Phe His Asn Asp Gln Leu Gly Pro Phe Tyr Glu Lys Thr Ala Lys
                85                  90                  95

Leu Thr Gly Lys Glu Met Ile Leu Pro Met Asn Thr Gly Ala Glu Ala
            100                 105                 110

Val Glu Ser Ala Val Lys Ala Ala Arg Arg Trp Ala Tyr Glu Val Lys
        115                 120                 125

Gly Val Ala Asp Asn Gln Ala Glu Ile Ile Ala Cys Val Gly Asn Phe
    130                 135                 140

His Gly Arg Thr Met Leu Ala Val Ser Leu Ser Ser Glu Glu Glu Tyr
145                 150                 155                 160

Lys Arg Gly Phe Gly Pro Met Leu Pro Gly Ile Lys Leu Ile Pro Tyr
                165                 170                 175

Gly Asp Val Glu Ala Leu Arg Gln Ala Ile Thr Pro Asn Thr Ala Ala
            180                 185                 190

Phe Leu Phe Glu Pro Ile Gln Gly Glu Ala Gly Ile Val Ile Pro Pro
        195                 200                 205

Glu Gly Phe Leu Gln Glu Ala Ala Ala Ile Cys Lys Glu Glu Asn Val
    210                 215                 220

Leu Phe Ile Ala Asp Glu Ile Gln Thr Gly Leu Gly Arg Thr Gly Lys
225                 230                 235                 240

Thr Phe Ala Cys Asp Trp Asp Gly Ile Val Pro Asp Met Tyr Ile Leu
                245                 250                 255

Gly Lys Ala Leu Gly Gly Gly Val Phe Pro Ile Ser Cys Ile Ala Ala
            260                 265                 270

Asp Arg Glu Ile Leu Gly Val Phe Asn Pro Gly Ser His Gly Ser Thr
        275                 280                 285

Phe Gly Gly Asn Pro Leu Ala Cys Ala Val Ser Ile Ala Ser Leu Glu
    290                 295                 300

Val Leu Glu Asp Glu Lys Leu Ala Asp Arg Ser Leu Glu Leu Gly Glu
305                 310                 315                 320

Tyr Phe Lys Ser Glu Leu Glu Ser Ile Asp Ser Pro Val Ile Lys Glu
                325                 330                 335

Val Arg Gly Arg Gly Leu Phe Ile Gly Val Glu Leu Thr Glu Ala Ala
            340                 345                 350

Arg Pro Tyr Cys Glu Arg Leu Lys Glu Glu Gly Leu Leu Cys Lys Glu
        355                 360                 365

Thr His Asp Thr Val Ile Arg Phe Ala Pro Pro Leu Ile Ile Ser Lys
    370                 375                 380

Glu Asp Leu Asp Trp Ala Ile Glu Lys Ile Lys His Val Leu Arg Asn
385                 390                 395                 400

Ala
```

<210> SEQ ID NO 35
<211> LENGTH: 888
<212> TYPE: DNA
<213> ORGANISM: Bacillus subtilis

<400> SEQUENCE: 35

```
atggataaaa cgatttcggt tattggaatg ccaatggatt taggacaagc acgacgcgga      60

gtggatatgg gcccgagtgc catccggtac gctcatctga tcgagaggct gtcagacatg     120

gggtatacgg ttgaagatct cggtgacatt ccgatcaatc gcgaaaaaat caaaaatgac     180
```

```
gaggaactga aaaacctgaa ttccgttttg gcgggaaatg aaaaactcgc gcaaaaggtc    240

aacaaagtca ttgaagagaa aaaattcccg cttgtcctgg gcggtgacca cagtattgcg    300

atcggcacgc ttgcaggcac agcgaagcat tacgataatc tcggcgtcat ctggtatgac    360

gcgcacggcg atttgaatac acttgaaact tcaccatcgg gcaatattca cggcatgccg    420

ctcgcggtca gcctaggcat tggccacgag tcactggtta accttgaagg ctacgcgcct    480

aaaatcaaac cggaaaacgt cgtcatcatt ggcgcccggt cacttgatga aggggagcgc    540

aagtacatta aggaaagcgg catgaaggtg tacacaatgc acgaaatcga tcgtcttggc    600

atgacaaagg tcattgaaga aaccccttgat tatttatcag catgtgatgg cgtccatctg    660

agccttgatc tggacggact tgatccgaac gacgcaccgg gtgtcggaac ccctgtcgtc    720

ggcggcatca gctaccggga gagccatttg gctatggaaa tgctgtatga cgcaggcatc    780

attacctcag ccgaattcgt tgaggttaac ccgatccttg atcacaaaaa caaaacgggc    840

aaaacagcag tagagctcgt agaatccctg ttagggaaga agctgctg                 888
```

<210> SEQ ID NO 36
<211> LENGTH: 296
<212> TYPE: PRT
<213> ORGANISM: Bacillus subtilis

<400> SEQUENCE: 36

```
Met Asp Lys Thr Ile Ser Val Ile Gly Met Pro Met Asp Leu Gly Gln
1               5                   10                  15

Ala Arg Arg Gly Val Asp Met Gly Pro Ser Ala Ile Arg Tyr Ala His
            20                  25                  30

Leu Ile Glu Arg Leu Ser Asp Met Gly Tyr Thr Val Glu Asp Leu Gly
        35                  40                  45

Asp Ile Pro Ile Asn Arg Glu Lys Ile Lys Asn Asp Glu Glu Leu Lys
    50                  55                  60

Asn Leu Asn Ser Val Leu Ala Gly Asn Glu Lys Leu Ala Gln Lys Val
65                  70                  75                  80

Asn Lys Val Ile Glu Glu Lys Lys Phe Pro Leu Val Leu Gly Gly Asp
                85                  90                  95

His Ser Ile Ala Ile Gly Thr Leu Ala Gly Thr Ala Lys His Tyr Asp
            100                 105                 110

Asn Leu Gly Val Ile Trp Tyr Asp Ala His Gly Asp Leu Asn Thr Leu
        115                 120                 125

Glu Thr Ser Pro Ser Gly Asn Ile His Gly Met Pro Leu Ala Val Ser
    130                 135                 140

Leu Gly Ile Gly His Glu Ser Leu Val Asn Leu Glu Gly Tyr Ala Pro
145                 150                 155                 160

Lys Ile Lys Pro Glu Asn Val Val Ile Ile Gly Ala Arg Ser Leu Asp
                165                 170                 175

Glu Gly Glu Arg Lys Tyr Ile Lys Glu Ser Gly Met Lys Val Tyr Thr
            180                 185                 190

Met His Glu Ile Asp Arg Leu Gly Met Thr Lys Val Ile Glu Glu Thr
        195                 200                 205

Leu Asp Tyr Leu Ser Ala Cys Asp Gly Val His Leu Ser Leu Asp Leu
    210                 215                 220

Asp Gly Leu Asp Pro Asn Asp Ala Pro Gly Val Gly Thr Pro Val Val
225                 230                 235                 240

Gly Gly Ile Ser Tyr Arg Glu Ser His Leu Ala Met Glu Met Leu Tyr
                245                 250                 255
```

```
Asp Ala Gly Ile Ile Thr Ser Ala Glu Phe Val Glu Val Asn Pro Ile
            260                 265                 270

Leu Asp His Lys Asn Lys Thr Gly Lys Thr Ala Val Glu Leu Val Glu
        275                 280                 285

Ser Leu Leu Gly Lys Lys Leu Leu
    290                 295


<210> SEQ ID NO 37
<211> LENGTH: 1041
<212> TYPE: DNA
<213> ORGANISM: Bacillus subtilis

<400> SEQUENCE: 37

atgcagagtg gaaagatgaa agctctaatg aaaaaggacg gggcgttcgg tgctgtgctg     60

actgaagttc ccattcctga gattgataaa catgaagtcc tcataaaagt gaaagccgct    120

tccatatgcg gcacggatgt ccacatttat aattgggatc aatgggcacg tcagagaatc    180

aaaacaccct atgttttcgg ccatgagttc agcggcatcg tagagggcgt gggagagaat    240

gtcagcagtg taaaagtggg agagtatgtg tctgcggaaa cacacattgt ctgtggtgaa    300

tgtgtccctt gcctaacagg aaaatctcat gtgtgtacca atactgctat aatcggagtg    360

gacacggcag gctgttttgc ggagtatgta aaagttccag ctgataacat ttggagaaat    420

cccgctgata tggacccgtc gattgcttcc attcaagagc ctttaggaaa tgcagttcat    480

accgtactcg agagccagcc tgcaggagga acgactgcag tcattggatg cggaccgatt    540

ggtcttatgg ctgttgcggt tgcaaaagca gcaggagctt ctcaggtgat agcgattgat    600

aagaatgaat acaggctgag gcttgcaaaa caaatgggag cgacttgtac tgtttctatt    660

gaaaaagaag acccgctcaa aattgtaagc gctttaacga gtggagaagg agcagatctt    720

gtttgtgaga tgtcgggcca tccctcagcg attgcccaag gtcttgcgat ggctgcgaat    780

ggcggaagat ttcatattct cagcttgccg gaacatccgg tgacaattga tttgacgaat    840

aaagtggtat ttaaagggct taccatccaa ggaatcacag gaagaaaaat gttttcaaca    900

tggcgccagg tgtctcagtt gatcagttca aacatgatcg atcttgcacc tgttattacc    960

catcagtttc cattagagga gtttgaaaaa ggtttcgaac tgatgagaag cgggcagtgc   1020

ggaaaagtaa ttttaattcc a                                             1041


<210> SEQ ID NO 38
<211> LENGTH: 347
<212> TYPE: PRT
<213> ORGANISM: Bacillus subtilis

<400> SEQUENCE: 38

Met Gln Ser Gly Lys Met Lys Ala Leu Met Lys Lys Asp Gly Ala Phe
 1               5                  10                  15

Gly Ala Val Leu Thr Glu Val Pro Ile Pro Glu Ile Asp Lys His Glu
            20                  25                  30

Val Leu Ile Lys Val Lys Ala Ala Ser Ile Cys Gly Thr Asp Val His
        35                  40                  45

Ile Tyr Asn Trp Asp Gln Trp Ala Arg Gln Arg Ile Lys Thr Pro Tyr
    50                  55                  60

Val Phe Gly His Glu Phe Ser Gly Ile Val Glu Gly Val Gly Glu Asn
65                  70                  75                  80

Val Ser Ser Val Lys Val Gly Glu Tyr Val Ser Ala Glu Thr His Ile
                85                  90                  95
```

```
Val Cys Gly Glu Cys Val Pro Cys Leu Thr Gly Lys Ser His Val Cys
            100                 105                 110

Thr Asn Thr Ala Ile Ile Gly Val Asp Thr Ala Gly Cys Phe Ala Glu
        115                 120                 125

Tyr Val Lys Val Pro Ala Asp Asn Ile Trp Arg Asn Pro Ala Asp Met
    130                 135                 140

Asp Pro Ser Ile Ala Ser Ile Gln Glu Pro Leu Gly Asn Ala Val His
145                 150                 155                 160

Thr Val Leu Glu Ser Gln Pro Ala Gly Gly Thr Thr Ala Val Ile Gly
                165                 170                 175

Cys Gly Pro Ile Gly Leu Met Ala Val Ala Val Ala Lys Ala Ala Gly
            180                 185                 190

Ala Ser Gln Val Ile Ala Ile Asp Lys Asn Glu Tyr Arg Leu Arg Leu
        195                 200                 205

Ala Lys Gln Met Gly Ala Thr Cys Thr Val Ser Ile Glu Lys Glu Asp
    210                 215                 220

Pro Leu Lys Ile Val Ser Ala Leu Thr Ser Gly Glu Gly Ala Asp Leu
225                 230                 235                 240

Val Cys Glu Met Ser Gly His Pro Ser Ala Ile Ala Gln Gly Leu Ala
                245                 250                 255

Met Ala Ala Asn Gly Gly Arg Phe His Ile Leu Ser Leu Pro Glu His
            260                 265                 270

Pro Val Thr Ile Asp Leu Thr Asn Lys Val Val Phe Lys Gly Leu Thr
        275                 280                 285

Ile Gln Gly Ile Thr Gly Arg Lys Met Phe Ser Thr Trp Arg Gln Val
    290                 295                 300

Ser Gln Leu Ile Ser Ser Asn Met Ile Asp Leu Ala Pro Val Ile Thr
305                 310                 315                 320

His Gln Phe Pro Leu Glu Glu Phe Glu Lys Gly Phe Glu Leu Met Arg
                325                 330                 335

Ser Gly Gln Cys Gly Lys Val Ile Leu Ile Pro
            340                 345
```

```
<210> SEQ ID NO 39
<211> LENGTH: 6127
<212> TYPE: DNA
<213> ORGANISM: Bacillus subtilis

<400> SEQUENCE: 39

taatacgata agaacagctt agaaatacac aagagtgtgt ataaagcaat tagaatgagt      60

tgagttagag aatagggtag cagagaatga gtttagttga gctgagacat tatgtttatt     120

ctacccaaaa gaagtctttc ttttgggttt atttgttata tagtatttta tcctctcatg     180

ccatcttctc attctccttg ccataaggag tgagagcaat gaatttccaa tcaaacattt     240

ccgcattttt agaggacagc ttgtcccacc acacgatacc gattgtggag accttcacag     300

tcgatacact gacacccatt caaatgatag agaagcttga cagggagatt acgtatcttc     360

ttgaaagcaa ggacgataca tccacttggt ccagatattc gtttatcggc ctgaatccat     420

ttctcacaat taaagaagag cagggccgtt tttcggccgc tgatcaggac agcaaatctc     480

tttacacagg aaatgaacta aaagaagtgc tgaactggat gaataccaca tacaaaatca     540

aaacacctga gcttggcatt ccttttgtcg gcggagctgt cgggtactta agctatgata     600

tgatcccgct gattgagcct tctgttcctt cgcataccaa agaaacagac atggaaaagt     660
```

```
gtatgctgtt tgtttgccgg acattaattg cgtatgatca tgaaaccaaa aacgtccact    720
ttatccaata tgcaaggctc actggagagg aaacaaaaaa cgaaaaaatg gatgtattcc    780
atcaaaatca tctggagctt caaaatctca ttgaaaaaat gatggaccaa aaaaacataa    840
aagagctgtt tctttctgct gattcataca agacacccag ctttgagaca gtatcttcta    900
attatgaaaa atcggctttt atggctgatg tagaaaaaat caaaagctat ataaaagcag    960
gcgatatctt ccagggtgtt ttatcacaaa aatttgaggt gccgataaaa gcagatgctt   1020
ttgagttata ccgagtgctt aggatcgtca atccttcgcc gtatatgtat tatatgaaac   1080
tgctagacag agaaatagtc ggcagctctc cggaacggtt aatacacgtt caagacgggc   1140
acttagaaat ccatccgatt gccggtacga gaaaacgcgg tgcagacaaa gctgaagatg   1200
agagactgaa ggttgagctc atgaaggatg aaaaagaaaa agcggagcat tacatgctcg   1260
ttgatcttgc ccgaaacgat atcggcagag tagcagagta tggttctgtt tctgtgccgg   1320
agttcacaaa aattgtttcc ttttcacatg tcatgcacat tatctcggtg gttacaggcc   1380
gattgaaaaa aggggttcat cctgtcgatg cactgatgtc tgctttcccg gcggggactt   1440
taacaggcgc acccaaaatc cgtgccatgc agcttttgca agaactcgag ccaacaccga   1500
gagagacata cggagggtgt attgcctaca ttgggtttga cgggaatatc gactcttgta   1560
ttacgattcg cacgatgagt gtaaagaacg gtgttgcatc gatacaggca ggtgctggca   1620
ttgttgctga ttctgttccg gaagccgaat acgaagaaag ctgtaataaa gccggtgcgc   1680
tgctgaaaac gattcatatt gcagaagaca tgtttcatag caaggaggat aaagctgatg   1740
aacagatttc tacaattgtg cgttgacgga aaaaccctta ctgccggtga ggctgaaacg   1800
ctgatgaata tgatgatggc agcggaaatg actccttctg aaatgggggg gatattgtca   1860
attcttgctc atcgggggga gacgccagaa gagcttgcgg gttttgtgaa ggcaatgcgg   1920
gcacacgctc ttacagtcga tggacttcct gatattgttg atacatgcgg aacaggggga   1980
gacggtattt ccacttttaa tatctcaacg gcctcggcaa ttgttgcctc ggcagctggt   2040
gcgaaaatcg ctaagcatgg caatcgctct gtctcttcta aaagcggaag cgctgatgtt   2100
ttagaggagc tagaggtttc tattcaaacc actcccgaaa aggtcaaaag cagcattgaa   2160
acaaacaaca tgggatttct ttttgcgccg ctttaccatt cgtctatgaa acatgtagca   2220
ggtactagaa aagagctagg tttcagaacg gtatttaatc tgcttgggcc gctcagcaat   2280
cctttacagg cgaagcgtca ggtgattggg gtctattctg ttgaaaaagc tggactgatg   2340
gcaagcgcac tggagacgtt tcagccgaag cacgttatgt ttgtatcaag ccgtgacggt   2400
ttagatgagc tttcaattac agcaccgacc gacgtgattg aattaaagga cggagagcgc   2460
cgggagtata ccgtttcacc cgaagatttc ggtttcacaa atggcagact tgaagattta   2520
caggtgcagt ctccgaaaga gagcgcttat ctcattcaga atatttttga aaataaaagc   2580
agcagttccg ctttatctat tacggctttt aatgcgggtg ctgcgattta cacggcggga   2640
attaccgcct cactgaagga aggaacggag ctggcgttag agacgattac aagcggaggc   2700
gctgccgcgc agcttgaacg actaaagcag aaagaggaag agatctatgc ttgaaaaaat   2760
catcaaacaa aagaaagaag aagtgaaaac actggttctg ccggtagagc agcctttcga   2820
gaaacgttca tttaaggagg cgccggcaag cccgaatcgg tttatcgggt tgattgccga   2880
agtgaagaaa gcatcgccgt caaaagggct tattaaagag gattttgtac ctgtgcagat   2940
tgcaaaagac tatgaggctg cgaaggcaga tgcgatttcc gttttaacag acaccccgtt   3000
ttttcaaggg gaaaacagct atttatcaga cgtaaagcgt gctgtttcga ttcctgtact   3060
```

```
tagaaaagat tttattattg attctcttca agtagaggaa tcaagaagaa tcggagcgga   3120
tgccatattg ttaatcggcg aggtgcttga tcccttacac cttcatgaat tatatcttga   3180
agcaggtgaa aaggggatgg acgtgttagt ggaggttcat gatgcatcaa cgctagaaca   3240
aatattgaaa gtgttcacac ccgacattct cggcgtaaat aatcgaaacc taaaaacgtt   3300
tgaaacatct gtaaagcaga cagaacaaat cgcatctctc gttccgaaag aatccttgct   3360
tgtcagcgaa agcggaatcg gttctttaga acatttaaca tttgtcaatg aacatggggc   3420
gcgagctgta cttatcggtg aatcattgat gagacaaact tctcagcgta aagcaatcca   3480
tgctttgttt agggagtgag gttgtgaaga aaccggcatt aaaatattgc ggtattcggt   3540
cactaaagga tttgcagctt gcggcggaat cacaggctga ttacctagga tttatttttg   3600
ctgaaagcaa acgaaaagta tctccggaag atgtgaaaaa atggctgaac caagttcgtg   3660
tcgaaaaaca ggttgcaggt gtttttgtta atgaatcaat agagacgatg tcacgtattg   3720
ccaagagctt gaagctcgac gtcattcagc ttcacggtga tgaaaaaccg gcggatgtcg   3780
ctgctcttcg caagctgaca ggctgtgaaa tatggaaggc gcttcaccat caagataaca   3840
caactcaaga aatagcccgc tttaaagata atgttgacgg ctttgtgatt gattcatctg   3900
taaaagggtc tagaggcgga actggtgttg cattttcttg ggactgtgtg ccggaatatc   3960
agcaggcggc tattggtaaa cgctgcttta tcgctggcgg cgtgaatccg gatagcatca   4020
cacgcctatt gaaatggcag ccagaaggaa ttgaccttgc cagcggaatt gaaaaaaacg   4080
gacaaaaaga tcagaatctg atgaggcttt tagaagaaag gatgaaccga tatgtatcca   4140
tatccgaatg aaataggcag atacggtgat tttggcggaa agtttgttcc ggaaacactc   4200
atgcagccgt tagatgaaat acaaacagca tttaaacaaa tcaaggatga tcccgctttt   4260
cgtgaagagt attataagct gttaaaggac tattccggac gcccgactgc attaacatac   4320
gctgatcgag tcactgaata cttaggcggc gcgaaaatct atttgaaacg agaagattta   4380
aaccatacag gttctcataa aatcaataat gcgctaggtc aagcgctgct tgctaaaaaa   4440
atgggcaaaa cgaaaatcat tgctgaaacc ggtgccggcc agcatggtgt tgccgctgca   4500
acagttgcag ccaaattcgg cttttcctgt actgtgttta tgggtgaaga ggatgttgcc   4560
cgccagtctc tgaacgtttt ccgcatgaag cttcttggag cggaggtagt gcctgtaaca   4620
agcggaaacg gaacattgaa ggatgccaca aatgaggcga tccggtactg ggttcagcat   4680
tgtgaggatc acttttatat gattggatca gttgtcggcc cgcatcctta tccgcaagtg   4740
gtccgtgaat ttcaaaaaat gatcggagag gaagcgaagg atcagttgaa acgtattgaa   4800
ggcactatgc ctgataaagt agtggcatgt gtaggcggag gaagcaatgc gatgggtatg   4860
tttcaggcat ttttaaatga agatgttgaa ctgatcggcg ctgaagcagc aggaaaagga   4920
attgatacac ctcttcatgc cgccactatt tcgaaaggaa ccgtaggggt tattcacggt   4980
tcattgactt atctcattca ggatgagttc gggcaaatta ttgagcccta ctctatttca   5040
gccggtctcg actatcctgg aatcggtccg gagcatgcat atttgcataa aagcggccgt   5100
gtcacttatg acagtataac cgatgaagaa gcggtggatg cattaaagct tttgtcagaa   5160
aaagagggga ttttgccggc aatcgaatct gcccatgcgt tagcgaaagc attcaaactc   5220
gccaaaggaa tggatcgcgg tcaactcatt ctcgtctgtt tatcaggccg gggagacaag   5280
gatgtcaaca cattaatgaa tgtattggaa gaagaggtga aagcccatgt ttaaattgga   5340
tcttcaacca tcagaaaaat tgtttatccc gtttattacg gcgggcgatc cagttcctga   5400
```

```
ggtttcgatt gaactggcga agtcactcca aaaagcaggc gccacagcat tggagcttgg   5460

tgttgcatac tctgacccgc ttgcagacgg tccggtgatc cagcgggctt caaagcgggc   5520

gcttgatcaa ggaatgaata tcgtaaaggc aatcgaatta ggcggagaaa tgaaaaaaaa   5580

cggagtgaat attccgatta tcctctttac gtattataat cctgtgttac aattgaacaa   5640

agaatacttt ttcgctttac tgcgggaaaa tcatattgac ggtctgcttg ttccggatct   5700

gccattagaa gaaagcaaca gccttcaaga ggaatgtaaa agccatgagg tgacgtatat   5760

ttctttagtt gcgccgacaa gcgaaagccg tttgaaaacc attattgaac aagccgaggg   5820

gttcgtctac tgtgtatctt ctctgggtgt gaccggtgtc cgcaatgagt tcaattcatc   5880

cgtgtacccg ttcattcgta ctgtgaagaa tctcagcact gttccggttg ctgtagggtt   5940

cggtatatca aaccgtgaac aggtcataaa gatgaatgaa attagtgacg gtgtcgtagt   6000

gggaagtgcg ctcgtcagaa aaatagaaga attaaaggac cggctcatca gcgctgaaac   6060

gagaaatcag gcgctgcagg agtttgagga ttatgcaatg gcgtttagcg gcttgtacag   6120

tttaaaa                                                             6127
```

<210> SEQ ID NO 40
<211> LENGTH: 801
<212> TYPE: DNA
<213> ORGANISM: Bacillus subtilis

<400> SEQUENCE: 40

```
atgtttaaat tggatcttca accatcagaa aaattgttta tcccgtttat tacggcgggc     60

gatccagttc ctgaggtttc gattgaactg gcgaagtcac tccaaaaagc aggcgccaca    120

gcattggagc ttggtgttgc atactctgac ccgcttgcag acggtccggt gatccagcgg    180

gcttcaaagc gggcgcttga tcaaggaatg aatatcgtaa aggcaatcga attaggcgga    240

gaaatgaaaa aaaacggagt gaatattccg attatcctct ttacgtatta taatcctgtg    300

ttacaattga acaaagaata ctttttcgct ttactgcggg aaaatcatat tgacggtctg    360

cttgttccgg atctgccatt agaagaaagc aacagccttc aagaggaatg taaaagccat    420

gaggtgacgt atatttcttt agttgcgccg acaagcgaaa gccgtttgaa aaccattatt    480

gaacaagccg aggggttcgt ctactgtgta tcttctctgg gtgtgaccgg tgtccgcaat    540

gagttcaatt catccgtgta cccgttcatt cgtactgtga agaatctcag cactgttccg    600

gttgctgtag ggttcggtat atcaaaccgt gaacaggtca taaagatgaa tgaaattagt    660

gacggtgtcg tagtgggaag tgcgctcgtc agaaaaatag aagaattaaa ggaccggctc    720

atcagcgctg aaacgagaaa tcaggcgctg caggagtttg aggattatgc aatggcgttt    780

agcggcttgt acagtttaaa a                                               801
```

<210> SEQ ID NO 41
<211> LENGTH: 267
<212> TYPE: PRT
<213> ORGANISM: Bacillus subtilis

<400> SEQUENCE: 41

```
Met Phe Lys Leu Asp Leu Gln Pro Ser Glu Lys Leu Phe Ile Pro Phe
 1               5                  10                  15

Ile Thr Ala Gly Asp Pro Val Pro Glu Val Ser Ile Glu Leu Ala Lys
            20                  25                  30

Ser Leu Gln Lys Ala Gly Ala Thr Ala Leu Glu Leu Gly Val Ala Tyr
        35                  40                  45
```

```
Ser Asp Pro Leu Ala Asp Gly Pro Val Ile Gln Arg Ala Ser Lys Arg
    50                  55                  60

Ala Leu Asp Gln Gly Met Asn Ile Val Lys Ala Ile Glu Leu Gly Gly
65                  70                  75                  80

Glu Met Lys Lys Asn Gly Val Asn Ile Pro Ile Ile Leu Phe Thr Tyr
                85                  90                  95

Tyr Asn Pro Val Leu Gln Leu Asn Lys Glu Tyr Phe Phe Ala Leu Leu
            100                 105                 110

Arg Glu Asn His Ile Asp Gly Leu Leu Val Pro Asp Leu Pro Leu Glu
        115                 120                 125

Glu Ser Asn Ser Leu Gln Glu Glu Cys Lys Ser His Glu Val Thr Tyr
    130                 135                 140

Ile Ser Leu Val Ala Pro Thr Ser Glu Ser Arg Leu Lys Thr Ile Ile
145                 150                 155                 160

Glu Gln Ala Glu Gly Phe Val Tyr Cys Val Ser Ser Leu Gly Val Thr
                165                 170                 175

Gly Val Arg Asn Glu Phe Asn Ser Ser Val Tyr Pro Phe Ile Arg Thr
            180                 185                 190

Val Lys Asn Leu Ser Thr Val Pro Val Ala Val Gly Phe Gly Ile Ser
        195                 200                 205

Asn Arg Glu Gln Val Ile Lys Met Asn Glu Ile Ser Asp Gly Val Val
    210                 215                 220

Val Gly Ser Ala Leu Val Arg Lys Ile Glu Glu Leu Lys Asp Arg Leu
225                 230                 235                 240

Ile Ser Ala Glu Thr Arg Asn Gln Ala Leu Gln Glu Phe Glu Asp Tyr
                245                 250                 255

Ala Met Ala Phe Ser Gly Leu Tyr Ser Leu Lys
            260                 265
```

<210> SEQ ID NO 42
<211> LENGTH: 1195
<212> TYPE: DNA
<213> ORGANISM: Bacillus subtilis

<400> SEQUENCE: 42

```
atgtatccat atccgaatga aataggcaga tacggtgatt ttggcggaaa gtttgttccg     60

gaaacactca tgcagccgtt agatgaaata caaacagcat ttaaacaaat caaggatgat    120

cccgcttttc gtgaagagta ttataagctg ttaaaggact attccggacg cccgactgca    180

ttaacatacg ctgatcgagt cactgaatac ttaggcggcg cgaaaatcta tttgaaacga    240

gaagatttaa accatacagg ttctcataaa atcaataatg cgctaggtca agcgctgctt    300

gctaaaaaaa tgggcaaaac gaaaatcatt gctgaaaccg gtgccggcca gcatggtgtt    360

gccgctgcaa cagttgcagc caaattcggc ttttcctgta ctgtgtttat gggtgaagag    420

gatgttgccc gccagtctct gaacgttttc cgcatgaagc ttcttggagc ggaggtagtg    480

cctgtaacaa gcggaaacgg aacattgaag gatgccacaa atgaggcgat ccggtactgg    540

gttcagcatt gtgaggatca cttttatatg attggatcag ttgtcggccc gcatccttat    600

ccgcaagtgg tccgtgaatt tcaaaaaatg atcggagagg aagcgaagga tcagttgaaa    660

cgtattgaag gcactatgcc tgataaagta gtggcatgtg taggcggagg aagcaatgcg    720

atgggtatgt ttcaggcatt tttaaatgaa gatgttgaac tgatcggcgc tgaagcagca    780

ggaaaaggaa ttgatacacc tcttcatgcc gccactattt cgaaaggaac cgtaggggtt    840

attcacggtt cattgactta tctcattcag gatgagttcg ggcaaattat tgagccctac    900
```

```
tctatttcag ccggtctcga ctatcctgga atcggtccgg agcatgcata tttgcataaa     960

agcggccgtg tcacttatga cagtataacc gatgaagaag cggtggatgc attaaagctt    1020

ttgtcagaaa aagaggggat tttgccggca atcgaatctg cccatgcgtt agcgaaagca    1080

ttcaaactcg ccaaaggaat ggatcgcggt caactcattc tcgtctgttt atcaggccgg    1140

ggagacaagg atgtcaacac attaatgaat gtattggaag aagaggtgaa agccc         1195


<210> SEQ ID NO 43
<211> LENGTH: 400
<212> TYPE: PRT
<213> ORGANISM: Bacillus subtilis

<400> SEQUENCE: 43

Met Tyr Pro Tyr Pro Asn Glu Ile Gly Arg Tyr Gly Asp Phe Gly Gly
1               5                   10                  15

Lys Phe Val Pro Glu Thr Leu Met Gln Pro Leu Asp Glu Ile Gln Thr
            20                  25                  30

Ala Phe Lys Gln Ile Lys Asp Asp Pro Ala Phe Arg Glu Glu Tyr Tyr
        35                  40                  45

Lys Leu Leu Lys Asp Tyr Ser Gly Arg Pro Thr Ala Leu Thr Tyr Ala
    50                  55                  60

Asp Arg Val Thr Glu Tyr Leu Gly Gly Ala Lys Ile Tyr Leu Lys Arg
65                  70                  75                  80

Glu Asp Leu Asn His Thr Gly Ser His Lys Ile Asn Asn Ala Leu Gly
                85                  90                  95

Gln Ala Leu Leu Ala Lys Lys Met Gly Lys Thr Lys Ile Ile Ala Glu
            100                 105                 110

Thr Gly Ala Gly Gln His Gly Val Ala Ala Ala Thr Val Ala Ala Lys
        115                 120                 125

Phe Gly Phe Ser Cys Thr Val Phe Met Gly Glu Glu Asp Val Ala Arg
    130                 135                 140

Gln Ser Leu Asn Val Phe Arg Met Lys Leu Leu Gly Ala Glu Val Val
145                 150                 155                 160

Pro Val Thr Ser Gly Asn Gly Thr Leu Lys Asp Ala Thr Asn Glu Ala
                165                 170                 175

Ile Arg Tyr Trp Val Gln His Cys Glu Asp His Phe Tyr Met Ile Gly
            180                 185                 190

Ser Val Val Gly Pro His Pro Tyr Pro Gln Val Val Arg Glu Phe Gln
        195                 200                 205

Lys Met Ile Gly Glu Glu Ala Lys Asp Gln Leu Lys Arg Ile Glu Gly
    210                 215                 220

Thr Met Pro Asp Lys Val Val Ala Cys Val Gly Gly Gly Ser Asn Ala
225                 230                 235                 240

Met Gly Met Phe Gln Ala Phe Leu Asn Glu Asp Val Glu Leu Ile Gly
                245                 250                 255

Ala Glu Ala Ala Gly Lys Gly Ile Asp Thr Pro Leu His Ala Ala Thr
            260                 265                 270

Ile Ser Lys Gly Thr Val Gly Val Ile His Gly Ser Leu Thr Tyr Leu
        275                 280                 285

Ile Gln Asp Glu Phe Gly Gln Ile Ile Glu Pro Tyr Ser Ile Ser Ala
    290                 295                 300

Gly Leu Asp Tyr Pro Gly Ile Gly Pro Glu His Ala Tyr Leu His Lys
305                 310                 315                 320
```

```
Ser Gly Arg Val Thr Tyr Asp Ser Ile Thr Asp Glu Glu Ala Val Asp
                325                 330                 335

Ala Leu Lys Leu Leu Ser Glu Lys Glu Gly Ile Leu Pro Ala Ile Glu
            340                 345                 350

Ser Ala His Ala Leu Ala Lys Ala Phe Lys Leu Ala Lys Gly Met Asp
        355                 360                 365

Arg Gly Gln Leu Ile Leu Val Cys Leu Ser Gly Arg Gly Asp Lys Asp
    370                 375                 380

Val Asn Thr Leu Met Asn Val Leu Glu Glu Glu Val Lys Ala His Val
385                 390                 395                 400


<210> SEQ ID NO 44
<211> LENGTH: 757
<212> TYPE: DNA
<213> ORGANISM: Bacillus subtilis

<400> SEQUENCE: 44

atgcttgaaa aaatcatcaa acaaaagaaa gaagaagtga aaacactggt tctgccggta      60

gagcagcctt tcgagaaacg ttcatttaag gaggcgccgg caagcccgaa tcggtttatc     120

gggttgattg ccgaagtgaa gaaagcatcg ccgtcaaaag ggcttattaa agaggatttt     180

gtacctgtgc agattgcaaa agactatgag gctgcgaagg cagatgcgat ttccgtttta     240

acagacaccc cgtttttca aggggaaaac agctatttat cagacgtaaa gcgtgctgtt     300

tcgattcctg tacttagaaa agattttatt attgattctc ttcaagtaga ggaatcaaga     360

agaatcggag cggatgccat attgttaatc ggcgaggtgc ttgatccctt acaccttcat     420

gaattatatc ttgaagcagg tgaaaagggg atggacgtgt tagtggaggt tcatgatgca     480

tcaacgctag aacaaatatt gaaagtgttc acacccgaca ttctcggcgt aaataatcga     540

aacctaaaaa cgtttgaaac atctgtaaag cagacagaac aaatcgcatc tctcgttccg     600

aaagaatcct tgcttgtcag cgaaagcgga atcggttctt tagaacattt aacatttgtc     660

aatgaacatg ggcgcgagc tgtacttatc ggtgaatcat tgatgagaca aacttctcag     720

cgtaaagcaa tccatgcttt gtttagggag tgaggtt                            757


<210> SEQ ID NO 45
<211> LENGTH: 250
<212> TYPE: PRT
<213> ORGANISM: Bacillus subtilis

<400> SEQUENCE: 45

Met Leu Glu Lys Ile Ile Lys Gln Lys Lys Glu Glu Val Lys Thr Leu
 1               5                  10                  15

Val Leu Pro Val Glu Gln Pro Phe Glu Lys Arg Ser Phe Lys Glu Ala
            20                  25                  30

Pro Ala Ser Pro Asn Arg Phe Ile Gly Leu Ile Ala Glu Val Lys Lys
        35                  40                  45

Ala Ser Pro Ser Lys Gly Leu Ile Lys Glu Asp Phe Val Pro Val Gln
    50                  55                  60

Ile Ala Lys Asp Tyr Glu Ala Ala Lys Ala Asp Ala Ile Ser Val Leu
65                  70                  75                  80

Thr Asp Thr Pro Phe Phe Gln Gly Glu Asn Ser Tyr Leu Ser Asp Val
                85                  90                  95

Lys Arg Ala Val Ser Ile Pro Val Leu Arg Lys Asp Phe Ile Ile Asp
            100                 105                 110

Ser Leu Gln Val Glu Glu Ser Arg Arg Ile Gly Ala Asp Ala Ile Leu
```

```
        115                 120                 125

Leu Ile Gly Glu Val Leu Asp Pro Leu His Leu His Glu Leu Tyr Leu
    130                 135                 140

Glu Ala Gly Glu Lys Gly Met Asp Val Leu Val Glu Val His Asp Ala
145                 150                 155                 160

Ser Thr Leu Glu Gln Ile Leu Lys Val Phe Thr Pro Asp Ile Leu Gly
                165                 170                 175

Val Asn Asn Arg Asn Leu Lys Thr Phe Glu Thr Ser Val Lys Gln Thr
            180                 185                 190

Glu Gln Ile Ala Ser Leu Val Pro Lys Glu Ser Leu Leu Val Ser Glu
        195                 200                 205

Ser Gly Ile Gly Ser Leu Glu His Leu Thr Phe Val Asn Glu His Gly
    210                 215                 220

Ala Arg Ala Val Leu Ile Gly Glu Ser Leu Met Arg Gln Thr Ser Gln
225                 230                 235                 240

Arg Lys Ala Ile His Ala Leu Phe Arg Glu
                245                 250


<210> SEQ ID NO 46
<211> LENGTH: 1009
<212> TYPE: DNA
<213> ORGANISM: Bacillus subtilis

<400> SEQUENCE: 46

atgaacagat ttctacaatt gtgcgttgac ggaaaaaccc ttactgccgg tgaggctgaa      60

acgctgatga atatgatgat ggcagcggaa atgactcctt ctgaaatggg ggggatattg     120

tcaattcttg ctcatcgggg ggagacgcca gaagagcttg cgggttttgt gaaggcaatg     180

cgggcacacg ctcttacagt cgatggactt cctgatattg ttgatacatg cggaacaggg     240

ggagacggta tttccacttt taatatctca acggcctcgg caattgttgc ctcggcagct     300

ggtgcgaaaa tcgctaagca tggcaatcgc tctgtctctt ctaaaagcgg aagcgctgat     360

gttttagagg agctagaggt ttctattcaa accactcccg aaaaggtcaa aagcagcatt     420

gaaacaaaca acatgggatt tctttttgcg ccgctttacc attcgtctat gaaacatgta     480

gcaggtacta gaaaagagct aggtttcaga acggtattta atctgcttgg gccgctcagc     540

aatcctttac aggcgaagcg tcaggtgatt ggggtctatt ctgttgaaaa agctggactg     600

atggcaagcg cactggagac gtttcagccg aagcacgtta tgtttgtatc aagccgtgac     660

ggtttagatg agctttcaat tacagcaccg accgacgtga ttgaattaaa ggacggagag     720

cgccgggagt ataccgtttc acccgaagat ttcggtttca caaatggcag acttgaagat     780

ttacaggtgc agtctccgaa agagagcgct tatctcattc agaatatttt tgaaaataaa     840

agcagcagtt ccgctttatc tattacggct tttaatgcgg gtgctgcgat ttacacggcg     900

ggaattaccg cctcactgaa ggaaggaacg gagctggcgt tagagacgat tacaagcgga     960

ggcgctgccg cgcagcttga acgactaaag cagaaagagg aagagatct                1009


<210> SEQ ID NO 47
<211> LENGTH: 338
<212> TYPE: PRT
<213> ORGANISM: Bacillus subtilis

<400> SEQUENCE: 47

Met Asn Arg Phe Leu Gln Leu Cys Val Asp Gly Lys Thr Leu Thr Ala
 1               5                  10                  15
```

```
Gly Glu Ala Glu Thr Leu Met Asn Met Met Met Ala Ala Glu Met Thr
            20                  25                  30

Pro Ser Glu Met Gly Gly Ile Leu Ser Ile Leu Ala His Arg Gly Glu
        35                  40                  45

Thr Pro Glu Glu Leu Ala Gly Phe Val Lys Ala Met Arg Ala His Ala
    50                  55                  60

Leu Thr Val Asp Gly Leu Pro Asp Ile Val Asp Thr Cys Gly Thr Gly
65                  70                  75                  80

Gly Asp Gly Ile Ser Thr Phe Asn Ile Ser Thr Ala Ser Ala Ile Val
                85                  90                  95

Ala Ser Ala Ala Gly Ala Lys Ile Ala Lys His Gly Asn Arg Ser Val
            100                 105                 110

Ser Ser Lys Ser Gly Ser Ala Asp Val Leu Glu Glu Leu Glu Val Ser
        115                 120                 125

Ile Gln Thr Thr Pro Glu Lys Val Lys Ser Ser Ile Glu Thr Asn Asn
    130                 135                 140

Met Gly Phe Leu Phe Ala Pro Leu Tyr His Ser Ser Met Lys His Val
145                 150                 155                 160

Ala Gly Thr Arg Lys Glu Leu Gly Phe Arg Thr Val Phe Asn Leu Leu
                165                 170                 175

Gly Pro Leu Ser Asn Pro Leu Gln Ala Lys Arg Gln Val Ile Gly Val
            180                 185                 190

Tyr Ser Val Glu Lys Ala Gly Leu Met Ala Ser Ala Leu Glu Thr Phe
        195                 200                 205

Gln Pro Lys His Val Met Phe Val Ser Ser Arg Asp Gly Leu Asp Glu
    210                 215                 220

Leu Ser Ile Thr Ala Pro Thr Asp Val Ile Glu Leu Lys Asp Gly Glu
225                 230                 235                 240

Arg Arg Glu Tyr Thr Val Ser Pro Glu Asp Phe Gly Phe Thr Asn Gly
                245                 250                 255

Arg Leu Glu Asp Leu Gln Val Gln Ser Pro Lys Glu Ser Ala Tyr Leu
            260                 265                 270

Ile Gln Asn Ile Phe Glu Asn Lys Ser Ser Ser Ser Ala Leu Ser Ile
        275                 280                 285

Thr Ala Phe Asn Ala Gly Ala Ala Ile Tyr Thr Ala Gly Ile Thr Ala
    290                 295                 300

Ser Leu Lys Glu Gly Thr Glu Leu Ala Leu Glu Thr Ile Thr Ser Gly
305                 310                 315                 320

Gly Ala Ala Ala Gln Leu Glu Arg Leu Lys Gln Lys Glu Glu Glu Ile
                325                 330                 335

Tyr Ala
```

<210> SEQ ID NO 48
<211> LENGTH: 1519
<212> TYPE: DNA
<213> ORGANISM: Bacillus subtilis

<400> SEQUENCE: 48

```
atgaatttcc aatcaaacat ttccgcattt ttagaggaca gcttgtccca ccacacgata      60

ccgattgtgg agaccttcac agtcgataca ctgacaccca ttcaaatgat agagaagctt     120

gacagggaga ttacgtatct tcttgaaagc aaggacgata catccacttg gtccagatat     180

tcgtttatcg gcctgaatcc atttctcaca attaaagaag agcagggccg tttttcggcc     240

gctgatcagg acagcaaatc tctttacaca ggaaatgaac taaaagaagt gctgaactgg     300
```

```
atgaatacca catacaaaat caaaacacct gagcttggca ttccttttgt cggcggagct    360

gtcgggtact taagctatga tatgatcccg ctgattgagc cttctgttcc ttcgcatacc    420

aaagaaacag acatggaaaa gtgtatgctg tttgtttgcc ggacattaat tgcgtatgat    480

catgaaacca aaaacgtcca ctttatccaa tatgcaaggc tcactggaga ggaaacaaaa    540

aacgaaaaaa tggatgtatt ccatcaaaat catctggagc ttcaaaatct cattgaaaaa    600

atgatggacc aaaaaaacat aaaagagctg tttctttctg ctgattcata caagacaccc    660

agctttgaga cagtatcttc taattatgaa aaatcggctt ttatggctga tgtagaaaaa    720

atcaaaagct atataaaagc aggcgatatc ttccagggtg ttttatcaca aaaatttgag    780

gtgccgataa aagcagatgc ttttgagtta taccgagtgc ttaggatcgt caatccttcg    840

ccgtatatgt attatatgaa actgctagac agagaaatag tcggcagctc tccggaacgg    900

ttaatacacg ttcaagacgg gcacttagaa atccatccga ttgccggtac gagaaaacgc    960

ggtgcagaca aagctgaaga tgagagactg aaggttgagc tcatgaagga tgaaaaagaa   1020

aaagcggagc attacatgct cgttgatctt gcccgaaacg atatcggcag agtagcagag   1080

tatggttctg tttctgtgcc ggagttcaca aaaattgttt ccttttcaca tgtcatgcac   1140

attatctcgg tggttacagg ccgattgaaa aaaggggttc atcctgtcga tgcactgatg   1200

tctgctttcc cggcggggac tttaacaggc gcacccaaaa tccgtgccat gcagcttttg   1260

caagaactcg agccaacacc gagagagaca tacggagggt gtattgccta cattgggttt   1320

gacgggaata tcgactcttg tattacgatt cgcacgatga gtgtaaagaa cggtgttgca   1380

tcgatacagg caggtgctgg cattgttgct gattctgttc cggaagccga atacgaagaa   1440

agctgtaata aagccggtgc gctgctgaaa acgattcata ttgcagaaga catgtttcat   1500

agcaaggagg ataaagctg                                                1519
```

```
<210> SEQ ID NO 49
<211> LENGTH: 515
<212> TYPE: PRT
<213> ORGANISM: Bacillus subtilis

<400> SEQUENCE: 49

Met Asn Phe Gln Ser Asn Ile Ser Ala Phe Leu Glu Asp Ser Leu Ser
 1               5                   10                  15

His His Thr Ile Pro Ile Val Glu Thr Phe Thr Val Asp Thr Leu Thr
            20                  25                  30

Pro Ile Gln Met Ile Glu Lys Leu Asp Arg Glu Ile Thr Tyr Leu Leu
        35                  40                  45

Glu Ser Lys Asp Asp Thr Ser Thr Trp Ser Arg Tyr Ser Phe Ile Gly
    50                  55                  60

Leu Asn Pro Phe Leu Thr Ile Lys Glu Glu Gln Gly Arg Phe Ser Ala
65                  70                  75                  80

Ala Asp Gln Asp Ser Lys Ser Leu Tyr Thr Gly Asn Glu Leu Lys Glu
                85                  90                  95

Val Leu Asn Trp Met Asn Thr Thr Tyr Lys Ile Lys Thr Pro Glu Leu
            100                 105                 110

Gly Ile Pro Phe Val Gly Gly Ala Val Gly Tyr Leu Ser Tyr Asp Met
        115                 120                 125

Ile Pro Leu Ile Glu Pro Ser Val Pro Ser His Thr Lys Glu Thr Asp
    130                 135                 140

Met Glu Lys Cys Met Leu Phe Val Cys Arg Thr Leu Ile Ala Tyr Asp
```

-continued

```
145                 150                 155                 160

His Glu Thr Lys Asn Val His Phe Ile Gln Tyr Ala Arg Leu Thr Gly
                165                 170                 175

Glu Glu Thr Lys Asn Glu Lys Met Asp Val Phe His Gln Asn His Leu
            180                 185                 190

Glu Leu Gln Asn Leu Ile Glu Lys Met Met Asp Gln Lys Asn Ile Lys
        195                 200                 205

Glu Leu Phe Leu Ser Ala Asp Ser Tyr Lys Thr Pro Ser Phe Glu Thr
    210                 215                 220

Val Ser Ser Asn Tyr Glu Lys Ser Ala Phe Met Ala Asp Val Glu Lys
225                 230                 235                 240

Ile Lys Ser Tyr Ile Lys Ala Gly Asp Ile Phe Gln Gly Val Leu Ser
                245                 250                 255

Gln Lys Phe Glu Val Pro Ile Lys Ala Asp Ala Phe Glu Leu Tyr Arg
            260                 265                 270

Val Leu Arg Ile Val Asn Pro Ser Pro Tyr Met Tyr Tyr Met Lys Leu
        275                 280                 285

Leu Asp Arg Glu Ile Val Gly Ser Ser Pro Glu Arg Leu Ile His Val
    290                 295                 300

Gln Asp Gly His Leu Glu Ile His Pro Ile Ala Gly Thr Arg Lys Arg
305                 310                 315                 320

Gly Ala Asp Lys Ala Glu Asp Glu Arg Leu Lys Val Glu Leu Met Lys
                325                 330                 335

Asp Glu Lys Glu Lys Ala Glu His Tyr Met Leu Val Asp Leu Ala Arg
            340                 345                 350

Asn Asp Ile Gly Arg Val Ala Glu Tyr Gly Ser Val Ser Val Pro Glu
        355                 360                 365

Phe Thr Lys Ile Val Ser Phe Ser His Val Met His Ile Ile Ser Val
    370                 375                 380

Val Thr Gly Arg Leu Lys Lys Gly Val His Pro Val Asp Ala Leu Met
385                 390                 395                 400

Ser Ala Phe Pro Ala Gly Thr Leu Thr Gly Ala Pro Lys Ile Arg Ala
                405                 410                 415

Met Gln Leu Leu Gln Glu Leu Glu Pro Thr Pro Arg Glu Thr Tyr Gly
            420                 425                 430

Gly Cys Ile Ala Tyr Ile Gly Phe Asp Gly Asn Ile Asp Ser Cys Ile
        435                 440                 445

Thr Ile Arg Thr Met Ser Val Lys Asn Gly Val Ala Ser Ile Gln Ala
    450                 455                 460

Gly Ala Gly Ile Val Ala Asp Ser Val Pro Glu Ala Glu Tyr Glu Glu
465                 470                 475                 480

Ser Cys Asn Lys Ala Gly Ala Leu Leu Lys Thr Ile His Ile Ala Glu
                485                 490                 495

Asp Met Phe His Ser Lys Glu Asp Lys Ala Asp Glu Gln Ile Ser Thr
            500                 505                 510

Ile Val Arg
        515


<210> SEQ ID NO 50
<211> LENGTH: 628
<212> TYPE: DNA
<213> ORGANISM: Bacillus subtilis

<400> SEQUENCE: 50
```

```
gtgaagaaac cggcattaaa atattgcggt attcggtcac taaaggattt gcagcttgcg      60

gcggaatcac aggctgatta cctaggattt atttttgctg aaagcaaacg aaaagtatct     120

ccggaagatg tgaaaaaatg gctgaaccaa gttcgtgtcg aaaaacaggt tgcaggtgtt     180

tttgttaatg aatcaataga gacgatgtca cgtattgcca agagcttgaa gctcgacgtc     240

attcagcttc acggtgatga aaaaccggcg gatgtcgctg ctcttcgcaa gctgacaggc     300

tgtgaaatat ggaaggcgct tcaccatcaa gataacacaa ctcaagaaat agcccgcttt     360

aaagataatg ttgacggctt tgtgattgat tcatctgtaa aagggtctag aggcggaact     420

ggtgttgcat ttcttggga ctgtgtgccg gaatatcagc aggcggctat tggtaaacgc     480

tgctttatcg ctggcggcgt gaatccggat agcatcacac gcctattgaa atggcagcca     540

gaaggaattg accttgccag cggaattgaa aaaaacggac aaaaagatca gaatctgatg     600

aggcttttag aagaaaggat gaaccgat                                        628
```

```
<210> SEQ ID NO 51
<211> LENGTH: 215
<212> TYPE: PRT
<213> ORGANISM: Bacillus subtilis

<400> SEQUENCE: 51

Met Lys Lys Pro Ala Leu Lys Tyr Cys Gly Ile Arg Ser Leu Lys Asp
 1               5                  10                  15

Leu Gln Leu Ala Ala Glu Ser Gln Ala Asp Tyr Leu Gly Phe Ile Phe
            20                  25                  30

Ala Glu Ser Lys Arg Lys Val Ser Pro Glu Asp Val Lys Lys Trp Leu
        35                  40                  45

Asn Gln Val Arg Val Glu Lys Gln Val Ala Gly Val Phe Val Asn Glu
    50                  55                  60

Ser Ile Glu Thr Met Ser Arg Ile Ala Lys Ser Leu Lys Leu Asp Val
65                  70                  75                  80

Ile Gln Leu His Gly Asp Glu Lys Pro Ala Asp Val Ala Ala Leu Arg
                85                  90                  95

Lys Leu Thr Gly Cys Glu Ile Trp Lys Ala Leu His His Gln Asp Asn
            100                 105                 110

Thr Thr Gln Glu Ile Ala Arg Phe Lys Asp Asn Val Asp Gly Phe Val
        115                 120                 125

Ile Asp Ser Ser Val Lys Gly Ser Arg Gly Gly Thr Gly Val Ala Phe
    130                 135                 140

Ser Trp Asp Cys Val Pro Glu Tyr Gln Gln Ala Ala Ile Gly Lys Arg
145                 150                 155                 160

Cys Phe Ile Ala Gly Gly Val Asn Pro Asp Ser Ile Thr Arg Leu Leu
                165                 170                 175

Lys Trp Gln Pro Glu Gly Ile Asp Leu Ala Ser Gly Ile Glu Lys Asn
            180                 185                 190

Gly Gln Lys Asp Gln Asn Leu Met Arg Leu Leu Glu Glu Arg Met Asn
        195                 200                 205

Arg Tyr Val Ser Ile Ser Glu
    210                 215


<210> SEQ ID NO 52
<211> LENGTH: 909
<212> TYPE: DNA
<213> ORGANISM: Bacillus subtilis

<400> SEQUENCE: 52
```

```
gtgatcacaa gagatttttt cttattttta tccaaaagcg gctttctcaa taaaatggcg     60

aggaactggg gaagtcgggt agcagcgggt aaaattatcg gcgggaatga ctttaacagt    120

tcaatcccga ccattcgaca gcttaacagc caaggcttgt cagttactgt cgatcattta    180

ggcgagtttg tgaacagcgc cgaggtcgca cgggagcgta cggaagagtg cattcaaacc    240

attgcgacca tcgcggatca ggagctgaac tcacacgttt ctttaaaaat gacgtcttta    300

ggtttggata tagatatgga tttggtgtat gaaaatatga caaaaatcct tcagacggcc    360

gagaaacata aaatcatggt caccattgac atggaggacg aagtcagatg ccagaaaacg    420

cttgatattt tcaaagattt cagaaagaaa tacgagcatg tgagcacagt gctgcaagcc    480

tatctgtacc ggacggaaaa agacattgac gatttggatt ctttaaaccc gttccttcgc    540

cttgtaaaag gagcttataa agaatcagaa aaagtagctt tcccggagaa aagcgatgtc    600

gatgaaaatt acaaaaaaat catccgaaag cagctcttaa acggtcacta tacagcgatt    660

gccacacatg acgacaaaat gatcgacttt acaaagcagc ttgccaagga acatggcatt    720

gccaatgaca agtttgaatt tcagatgctg tacggcatgc ggtcgcaaac ccagctcagc    780

ctcgtaaaag aaggttataa catgagagtc tacctgccat acggcgagga ttggtacggc    840

tactttatga gacgccttgc agaacgtccg tcaaacattg catttgcttt caaaggaatg    900

acaaagaag                                                            909
```

```
<210> SEQ ID NO 53
<211> LENGTH: 303
<212> TYPE: PRT
<213> ORGANISM: Bacillus subtilis

<400> SEQUENCE: 53

Met Ile Thr Arg Asp Phe Phe Leu Phe Leu Ser Lys Ser Gly Phe Leu
1               5                   10                  15

Asn Lys Met Ala Arg Asn Trp Gly Ser Arg Val Ala Ala Gly Lys Ile
            20                  25                  30

Ile Gly Gly Asn Asp Phe Asn Ser Ser Ile Pro Thr Ile Arg Gln Leu
        35                  40                  45

Asn Ser Gln Gly Leu Ser Val Thr Val Asp His Leu Gly Glu Phe Val
    50                  55                  60

Asn Ser Ala Glu Val Ala Arg Glu Arg Thr Glu Glu Cys Ile Gln Thr
65                  70                  75                  80

Ile Ala Thr Ile Ala Asp Gln Glu Leu Asn Ser His Val Ser Leu Lys
                85                  90                  95

Met Thr Ser Leu Gly Leu Asp Ile Asp Met Asp Leu Val Tyr Glu Asn
            100                 105                 110

Met Thr Lys Ile Leu Gln Thr Ala Glu Lys His Lys Ile Met Val Thr
        115                 120                 125

Ile Asp Met Glu Asp Glu Val Arg Cys Gln Lys Thr Leu Asp Ile Phe
    130                 135                 140

Lys Asp Phe Arg Lys Lys Tyr Glu His Val Ser Thr Val Leu Gln Ala
145                 150                 155                 160

Tyr Leu Tyr Arg Thr Glu Lys Asp Ile Asp Asp Leu Asp Ser Leu Asn
                165                 170                 175

Pro Phe Leu Arg Leu Val Lys Gly Ala Tyr Lys Glu Ser Glu Lys Val
            180                 185                 190

Ala Phe Pro Glu Lys Ser Asp Val Asp Glu Asn Tyr Lys Lys Ile Ile
        195                 200                 205
```

```
Arg Lys Gln Leu Leu Asn Gly His Tyr Thr Ala Ile Ala Thr His Asp
    210                 215                 220

Asp Lys Met Ile Asp Phe Thr Lys Gln Leu Ala Lys Glu His Gly Ile
225                 230                 235                 240

Ala Asn Asp Lys Phe Glu Phe Gln Met Leu Tyr Gly Met Arg Ser Gln
                245                 250                 255

Thr Gln Leu Ser Leu Val Lys Glu Gly Tyr Asn Met Arg Val Tyr Leu
            260                 265                 270

Pro Tyr Gly Glu Asp Trp Tyr Gly Tyr Phe Met Arg Arg Leu Ala Glu
        275                 280                 285

Arg Pro Ser Asn Ile Ala Phe Ala Phe Lys Gly Met Thr Lys Lys
    290                 295                 300


<210> SEQ ID NO 54
<211> LENGTH: 1545
<212> TYPE: DNA
<213> ORGANISM: Bacillus subtilis

<400> SEQUENCE: 54

atgacaacac cttacaaaca cgagccattc acaaatttcc aagatcaaaa ctacgtggaa     60

gcgtttaaaa aagcgcttgc gacagtaagc gaatatttag gaaaagacta tccgcttgtc    120

attaacggcg agagagtgga aacggaagcg aaaatcgttt caatcaaccc agctgataaa    180

gaagaagtcg tcggccgagt gtcaaaagcg tctcaagagc acgctgagca agcgattcaa    240

gcggctgcaa aagcatttga agagtggaga tacacgtctc ctgaagagag agcggctgtc    300

ctgttccgcg ctgctgccaa agtccgcaga agaaaacatg aattctcagc tttgcttgtg    360

aaagaagcag gaaagccttg gaacgaggcg gatgccgata cggctgaagc gattgacttc    420

atggagtatt atgcacgcca aatgatcgaa ctggcaaaag gcaaaccggt caacagccgt    480

gaaggcgaga aaaaccaata tgtatacacg ccgactggag tgacagtcgt tatcccgcct    540

tggaacttct tgtttgcgat catggcaggc acaacagtgg cgccgatcgt tactggaaac    600

acagtggttc tgaaacctgc gagtgctaca cctgttattg cagcaaaatt tgttgaggtg    660

cttgaagagt ccggattgcc aaaaggcgta gtcaactttg ttccgggaag cggatcggaa    720

gtaggcgact atcttgttga ccatccgaaa acaagcctta tcacatttac gggatcaaga    780

gaagttggta cgagaatttt cgaacgcgcg gcgaaggttc agccgggcca gcagcattta    840

aagcgtgtca tcgctgaaat gggcggtaaa gatacggttg ttgttgatga ggatgcggac    900

attgaattag cggctcaatc gatctttact tcagcattcg gctttgcggg acaaaaatgc    960

tctgcaggtt cacgtgcagt agttcatgaa aaagtgtatg atcaagtatt agagcgtgtc   1020

attgaaatta cggaatcaaa agtaacagct aaacctgaca gtgcagatgt ttatatggga   1080

cctgtcattg accaaggttc ttatgataaa attatgagct atattgagat cggaaaacag   1140

gaagggcgtt tagtaagcgg cggtactggt gatgattcga aaggatactt catcaaaccg   1200

acgatcttcg ctgaccttga tccgaaagca agactcatgc aggaagaaat tttcggacct   1260

gtcgttgcat tttgtaaagt gtcagacttt gatgaagctt tagaagtggc aaacaatact   1320

gaatatggtt tgacaggcgc ggttatcaca aacaaccgca agcacatcga gcgtgcgaaa   1380

caggaattcc atgtcggaaa cctatacttc aaccgcaact gtacaggtgc tatcgtcggc   1440

taccatccgt ttggcggctt caaaatgtcg ggaacggatt caaaagcagg cgggccggat   1500

tacttggctc tgcatatgca agcaaaaaca atcagtgaaa tgttc                    1545
```

<210> SEQ ID NO 55
<211> LENGTH: 515
<212> TYPE: PRT
<213> ORGANISM: Bacillus subtilis

<400> SEQUENCE: 55

```
Met Thr Thr Pro Tyr Lys His Glu Pro Phe Thr Asn Phe Gln Asp Gln
1               5                   10                  15

Asn Tyr Val Glu Ala Phe Lys Lys Ala Leu Ala Thr Val Ser Glu Tyr
            20                  25                  30

Leu Gly Lys Asp Tyr Pro Leu Val Ile Asn Gly Glu Arg Val Glu Thr
        35                  40                  45

Glu Ala Lys Ile Val Ser Ile Asn Pro Ala Asp Lys Glu Glu Val Val
    50                  55                  60

Gly Arg Val Ser Lys Ala Ser Gln Glu His Ala Glu Gln Ala Ile Gln
65                  70                  75                  80

Ala Ala Ala Lys Ala Phe Glu Glu Trp Arg Tyr Thr Ser Pro Glu Glu
                85                  90                  95

Arg Ala Ala Val Leu Phe Arg Ala Ala Ala Lys Val Arg Arg Arg Lys
            100                 105                 110

His Glu Phe Ser Ala Leu Leu Val Lys Glu Ala Gly Lys Pro Trp Asn
        115                 120                 125

Glu Ala Asp Ala Asp Thr Ala Glu Ala Ile Asp Phe Met Glu Tyr Tyr
    130                 135                 140

Ala Arg Gln Met Ile Glu Leu Ala Lys Gly Lys Pro Val Asn Ser Arg
145                 150                 155                 160

Glu Gly Glu Lys Asn Gln Tyr Val Tyr Thr Pro Thr Gly Val Thr Val
                165                 170                 175

Val Ile Pro Pro Trp Asn Phe Leu Phe Ala Ile Met Ala Gly Thr Thr
            180                 185                 190

Val Ala Pro Ile Val Thr Gly Asn Thr Val Val Leu Lys Pro Ala Ser
        195                 200                 205

Ala Thr Pro Val Ile Ala Ala Lys Phe Val Glu Val Leu Glu Glu Ser
    210                 215                 220

Gly Leu Pro Lys Gly Val Val Asn Phe Val Pro Gly Ser Gly Ser Glu
225                 230                 235                 240

Val Gly Asp Tyr Leu Val Asp His Pro Lys Thr Ser Leu Ile Thr Phe
                245                 250                 255

Thr Gly Ser Arg Glu Val Gly Thr Arg Ile Phe Glu Arg Ala Ala Lys
            260                 265                 270

Val Gln Pro Gly Gln Gln His Leu Lys Arg Val Ile Ala Glu Met Gly
        275                 280                 285

Gly Lys Asp Thr Val Val Val Asp Glu Asp Ala Asp Ile Glu Leu Ala
    290                 295                 300

Ala Gln Ser Ile Phe Thr Ser Ala Phe Gly Phe Ala Gly Gln Lys Cys
305                 310                 315                 320

Ser Ala Gly Ser Arg Ala Val Val His Glu Lys Val Tyr Asp Gln Val
                325                 330                 335

Leu Glu Arg Val Ile Glu Ile Thr Glu Ser Lys Val Thr Ala Lys Pro
            340                 345                 350

Asp Ser Ala Asp Val Tyr Met Gly Pro Val Ile Asp Gln Gly Ser Tyr
        355                 360                 365

Asp Lys Ile Met Ser Tyr Ile Glu Ile Gly Lys Gln Glu Gly Arg Leu
    370                 375                 380
```

```
Val Ser Gly Gly Thr Gly Asp Asp Ser Lys Gly Tyr Phe Ile Lys Pro
385                 390                 395                 400

Thr Ile Phe Ala Asp Leu Asp Pro Lys Ala Arg Leu Met Gln Glu Glu
                405                 410                 415

Ile Phe Gly Pro Val Val Ala Phe Cys Lys Val Ser Asp Phe Asp Glu
            420                 425                 430

Ala Leu Glu Val Ala Asn Asn Thr Glu Tyr Gly Leu Thr Gly Ala Val
        435                 440                 445

Ile Thr Asn Asn Arg Lys His Ile Glu Arg Ala Lys Gln Glu Phe His
    450                 455                 460

Val Gly Asn Leu Tyr Phe Asn Arg Asn Cys Thr Gly Ala Ile Val Gly
465                 470                 475                 480

Tyr His Pro Phe Gly Gly Phe Lys Met Ser Gly Thr Asp Ser Lys Ala
                485                 490                 495

Gly Gly Pro Asp Tyr Leu Ala Leu His Met Gln Ala Lys Thr Ile Ser
            500                 505                 510

Glu Met Phe
        515


<210> SEQ ID NO 56
<211> LENGTH: 762
<212> TYPE: DNA
<213> ORGANISM: Bacillus subtilis

<400> SEQUENCE: 56

atgcaatcct tgaattatga agatcaggtg ctttggacgc gctggaaaga gtggaaagat     60

cctaaagccg gtgacgactt aatgcgccgt tacatgccgc ttgtcacata tcatgtaggc    120

agaatttctg tcggactgcc gaaatcagtg cataaagacg atcttatgag ccttggtatg    180

cttggtttat atgatgccct tgaaaaattt gaccccagcc gggacttaaa atttgatacc    240

tacgcctcgt ttagaattcg cggcgcaatc atagacgggc ttcgtaaaga agattggctg    300

cccagaacct cgcgcgaaaa aacaaaaaag gttgaagcag caattgaaaa gcttgaacag    360

cggtatcttc ggaatgtatc gcccgcggaa attgcagagg aactcggaat gacggtacag    420

gatgtcgtgt caacaatgaa tgaaggtttt tttgcaaatc tgctgtcaat tgatgaaaag    480

ctccatgatc aagatgacgg ggaaaacatt caagtcatga tcagagatga caaaaatgtt    540

ccgcctgaag aaaagattat gaaggatgaa ctgattgcac agcttgcgga aaaaattcac    600

gaactctctg aaaaagaaca gctggttgtc agtttgttct acaaagagga gttgacactg    660

acagaaatcg gacaagtatt aaatctttct acgtcccgca tatctcagat ccattcaaag    720

gcattattta aattaaagaa tctgctggaa aaagtgatac aa                       762


<210> SEQ ID NO 57
<211> LENGTH: 254
<212> TYPE: PRT
<213> ORGANISM: Bacillus subtilis

<400> SEQUENCE: 57

Met Gln Ser Leu Asn Tyr Glu Asp Gln Val Leu Trp Thr Arg Trp Lys
 1               5                  10                  15

Glu Trp Lys Asp Pro Lys Ala Gly Asp Asp Leu Met Arg Arg Tyr Met
            20                  25                  30

Pro Leu Val Thr Tyr His Val Gly Arg Ile Ser Val Gly Leu Pro Lys
        35                  40                  45
```

```
Ser Val His Lys Asp Asp Leu Met Ser Leu Gly Met Leu Gly Leu Tyr
    50                  55                  60

Asp Ala Leu Glu Lys Phe Asp Pro Ser Arg Asp Leu Lys Phe Asp Thr
65                  70                  75                  80

Tyr Ala Ser Phe Arg Ile Arg Gly Ala Ile Ile Asp Gly Leu Arg Lys
                85                  90                  95

Glu Asp Trp Leu Pro Arg Thr Ser Arg Glu Lys Thr Lys Lys Val Glu
            100                 105                 110

Ala Ala Ile Glu Lys Leu Glu Gln Arg Tyr Leu Arg Asn Val Ser Pro
        115                 120                 125

Ala Glu Ile Ala Glu Glu Leu Gly Met Thr Val Gln Asp Val Val Ser
    130                 135                 140

Thr Met Asn Glu Gly Phe Phe Ala Asn Leu Leu Ser Ile Asp Glu Lys
145                 150                 155                 160

Leu His Asp Gln Asp Asp Gly Glu Asn Ile Gln Val Met Ile Arg Asp
                165                 170                 175

Asp Lys Asn Val Pro Pro Glu Glu Lys Ile Met Lys Asp Glu Leu Ile
            180                 185                 190

Ala Gln Leu Ala Glu Lys Ile His Glu Leu Ser Glu Lys Glu Gln Leu
        195                 200                 205

Val Val Ser Leu Phe Tyr Lys Glu Glu Leu Thr Leu Thr Glu Ile Gly
    210                 215                 220

Gln Val Leu Asn Leu Ser Thr Ser Arg Ile Ser Gln Ile His Ser Lys
225                 230                 235                 240

Ala Leu Phe Lys Leu Lys Asn Leu Leu Glu Lys Val Ile Gln
                245                 250


<210> SEQ ID NO 58
<211> LENGTH: 602
<212> TYPE: DNA
<213> ORGANISM: Bacillus subtilis

<400> SEQUENCE: 58

atgaatttc aaacaatcga gcttgacaca tggtatagaa aatcttattt tgaccattac      60

atgaaggaag cgaaatgttc tttcagcatc acggcaaacg tcaatgtgac aaatttgctc     120

gccgtgctca agaaaaagaa gctcaagctg tatccggctt ttatttatat cgtatcaagg     180

gtcattcatt cgcgccctga gtttagaaca acgtttgatg acaaaggaag ctgggttatt     240

gggaacaaat gcatccgtgc tatgcgattt ttcatcagga cgaccaaacg ttttccgccc     300

tctggacgga atactcagac gatttttcgc agttttatca tcaatatctt ctggacgccg     360

agcgctttgg agacaaaagg ggcctttggg ctaagccgga catcccgccc aatacgtttt     420

cagtttcttc tattccatgg gtgcgctttt caacattcaa tttaaacctt gataacagcg     480

aacacttgct gccgattatt acaaacggga aatacttttc agaaggcagg gaaacatttt     540

tgcccgtttc ctgcaagttc accatgcagt gtgtgacggc tatcatgccg gcgcttttat     600

aa                                                                    602


<210> SEQ ID NO 59
<211> LENGTH: 200
<212> TYPE: PRT
<213> ORGANISM: Bacillus subtilis

<400> SEQUENCE: 59

Met Asn Phe Gln Thr Ile Glu Leu Asp Thr Trp Tyr Arg Lys Ser Tyr
 1               5                  10                  15
```

```
Phe Asp His Tyr Met Lys Glu Ala Lys Cys Ser Phe Ser Ile Thr Ala
            20                  25                  30

Asn Val Asn Val Thr Asn Leu Leu Ala Val Leu Lys Lys Lys Lys Leu
        35                  40                  45

Lys Leu Tyr Pro Ala Phe Ile Tyr Ile Val Ser Arg Val Ile His Ser
    50                  55                  60

Arg Pro Glu Phe Arg Thr Thr Phe Asp Asp Lys Gly Gln Leu Gly Tyr
65                  70                  75                  80

Trp Glu Gln Met His Pro Cys Tyr Ala Ile Phe His Gln Asp Asp Gln
                85                  90                  95

Thr Phe Ser Ala Leu Trp Thr Glu Tyr Ser Asp Asp Phe Ser Gln Phe
            100                 105                 110

Tyr His Gln Tyr Leu Leu Asp Ala Glu Arg Phe Gly Asp Lys Arg Gly
        115                 120                 125

Leu Trp Ala Lys Pro Asp Ile Pro Pro Asn Thr Phe Ser Val Ser Ser
    130                 135                 140

Ile Pro Trp Val Arg Phe Ser Thr Phe Asn Leu Asn Leu Asp Asn Ser
145                 150                 155                 160

Glu His Leu Leu Pro Ile Ile Thr Asn Gly Lys Tyr Phe Ser Glu Gly
                165                 170                 175

Arg Glu Thr Phe Leu Pro Val Ser Cys Lys Phe Thr Met Gln Cys Val
            180                 185                 190

Thr Ala Ile Met Pro Ala Leu Leu
        195                 200
```

<210> SEQ ID NO 60
<211> LENGTH: 39
<212> TYPE: DNA
<213> ORGANISM: Artificial Sequence
<220> FEATURE:
<223> OTHER INFORMATION: primer

<400> SEQUENCE: 60
ctacattcta gacgatttgt ttgatcgata tgtggaagc 39

<210> SEQ ID NO 61
<211> LENGTH: 37
<212> TYPE: DNA
<213> ORGANISM: Artificial Sequence
<220> FEATURE:
<223> OTHER INFORMATION: primer

<400> SEQUENCE: 61
ggctgaggat ccattcctca gcccagaaga gaaccta 37

<210> SEQ ID NO 62
<211> LENGTH: 38
<212> TYPE: DNA
<213> ORGANISM: Artificial Sequence
<220> FEATURE:
<223> OTHER INFORMATION: primer

<400> SEQUENCE: 62
tccctcggat ccgaaatagg ttctgcttat tgtattcg 38

<210> SEQ ID NO 63
<211> LENGTH: 38
<212> TYPE: DNA
<213> ORGANISM: Artificial Sequence
<220> FEATURE:

<223> OTHER INFORMATION: primer

<400> SEQUENCE: 63
agcgttgagc tcgcgccatg ccattatatt ggctgctg 38

<210> SEQ ID NO 64
<211> LENGTH: 38
<212> TYPE: DNA
<213> ORGANISM: Artificial Sequence
<220> FEATURE:
<223> OTHER INFORMATION: primer

<400> SEQUENCE: 64
gtgacggaat tccacgtgcg tcttatattg ctgagctt 38

<210> SEQ ID NO 65
<211> LENGTH: 38
<212> TYPE: DNA
<213> ORGANISM: Artificial Sequence
<220> FEATURE:
<223> OTHER INFORMATION: primer

<400> SEQUENCE: 65
cgttttggat ccaaaaacac ccctttagat aatcttat 38

<210> SEQ ID NO 66
<211> LENGTH: 40
<212> TYPE: DNA
<213> ORGANISM: Artificial Sequence
<220> FEATURE:
<223> OTHER INFORMATION: primer

<400> SEQUENCE: 66
atcaaaggat ccgctatgct ccaaatgtac acctttccgt 40

<210> SEQ ID NO 67
<211> LENGTH: 39
<212> TYPE: DNA
<213> ORGANISM: Artificial Sequence
<220> FEATURE:
<223> OTHER INFORMATION: primer

<400> SEQUENCE: 67
atatttctgc aggctgatat aaataatact gtgtgttcc 39

<210> SEQ ID NO 68
<211> LENGTH: 37
<212> TYPE: DNA
<213> ORGANISM: Artificial Sequence
<220> FEATURE:
<223> OTHER INFORMATION: primer

<400> SEQUENCE: 68
catcttgaat tcaaagggta caagcacaga gacagag 37

<210> SEQ ID NO 69
<211> LENGTH: 37
<212> TYPE: DNA
<213> ORGANISM: Artificial Sequence
<220> FEATURE:
<223> OTHER INFORMATION: primer

<400> SEQUENCE: 69
tgacttggat ccggtaagtg ggcagtttgt gggcagt 37

<210> SEQ ID NO 70
<211> LENGTH: 37
<212> TYPE: DNA
<213> ORGANISM: Artificial Sequence
<220> FEATURE:
<223> OTHER INFORMATION: primer

<400> SEQUENCE: 70
tagataggat cctattgaaa actgtttaag aagagga 37

<210> SEQ ID NO 71
<211> LENGTH: 37
<212> TYPE: DNA
<213> ORGANISM: Artificial Sequence
<220> FEATURE:
<223> OTHER INFORMATION: primer

<400> SEQUENCE: 71
ctgattctgc aggagtgttt ttgaaggaag cttcatt 37

<210> SEQ ID NO 72
<211> LENGTH: 37
<212> TYPE: DNA
<213> ORGANISM: Artificial Sequence
<220> FEATURE:
<223> OTHER INFORMATION: primer

<400> SEQUENCE: 72
ctccgcggta ccgtcacgaa tgcgcctctt attctat 37

<210> SEQ ID NO 73
<211> LENGTH: 38
<212> TYPE: DNA
<213> ORGANISM: Artificial Sequence
<220> FEATURE:
<223> OTHER INFORMATION: primer

<400> SEQUENCE: 73
tcgctgggat ccttggcgcc gtggaatcga ttttgtcc 38

<210> SEQ ID NO 74
<211> LENGTH: 37
<212> TYPE: DNA
<213> ORGANISM: Artificial Sequence
<220> FEATURE:
<223> OTHER INFORMATION: primer

<400> SEQUENCE: 74
gcaatgggat cctatatcaa cggttatgaa ttcacaa 37

<210> SEQ ID NO 75
<211> LENGTH: 37
<212> TYPE: DNA
<213> ORGANISM: Artificial Sequence
<220> FEATURE:
<223> OTHER INFORMATION: primer

<400> SEQUENCE: 75
ccagaactgc aggagcgagg cgtctcgctg cctgaaa 37

<210> SEQ ID NO 76
<211> LENGTH: 41
<212> TYPE: DNA
<213> ORGANISM: Artificial Sequence
<220> FEATURE:
<223> OTHER INFORMATION: primer

<400> SEQUENCE: 76
gacaaggagc tcatgaaaaa aagcataaag ctttatgttg c 41

<210> SEQ ID NO 77
<211> LENGTH: 38
<212> TYPE: DNA
<213> ORGANISM: Artificial Sequence
<220> FEATURE:
<223> OTHER INFORMATION: primer

<400> SEQUENCE: 77
gacaagggat cccggcatgt ccgttattac ttaatttc 38

<210> SEQ ID NO 78
<211> LENGTH: 32
<212> TYPE: DNA
<213> ORGANISM: Artificial Sequence
<220> FEATURE:
<223> OTHER INFORMATION: primer

<400> SEQUENCE: 78
gacaagggat cctgccgctt accggaaacg ga 32

<210> SEQ ID NO 79
<211> LENGTH: 36
<212> TYPE: DNA
<213> ORGANISM: Artificial Sequence
<220> FEATURE:
<223> OTHER INFORMATION: primer

<400> SEQUENCE: 79
gacaagtcta gattatcgtt tgtgcagtat tacttg 36

<210> SEQ ID NO 80
<211> LENGTH: 36
<212> TYPE: DNA
<213> ORGANISM: Artificial Sequence
<220> FEATURE:
<223> OTHER INFORMATION: primer

<400> SEQUENCE: 80
actgatgagc tctgcctaaa cagcaaacag cagaac 36

<210> SEQ ID NO 81
<211> LENGTH: 39
<212> TYPE: DNA
<213> ORGANISM: Artificial Sequence
<220> FEATURE:
<223> OTHER INFORMATION: primer

<400> SEQUENCE: 81
acgaatggat ccatcataaa gccgcagcag attaaatat 39

<210> SEQ ID NO 82
<211> LENGTH: 36
<212> TYPE: DNA
<213> ORGANISM: Artificial Sequence
<220> FEATURE:
<223> OTHER INFORMATION: primer

<400> SEQUENCE: 82
actgatggat ccatcttcga taaatatgaa agtggc 36

<210> SEQ ID NO 83
<211> LENGTH: 38

<212> TYPE: DNA
<213> ORGANISM: Artificial Sequence
<220> FEATURE:
<223> OTHER INFORMATION: primer

<400> SEQUENCE: 83
actgattcta gagccttttt ctcttgatgc aattcttc 38

<210> SEQ ID NO 84
<211> LENGTH: 31
<212> TYPE: DNA
<213> ORGANISM: Artificial Sequence
<220> FEATURE:
<223> OTHER INFORMATION: primer

<400> SEQUENCE: 84
gagcctctag agcccattga atcatttgtt t 31

<210> SEQ ID NO 85
<211> LENGTH: 34
<212> TYPE: DNA
<213> ORGANISM: Artificial Sequence
<220> FEATURE:
<223> OTHER INFORMATION: primer

<400> SEQUENCE: 85
gagccggatc cttaaggatg tcgtttttgt gtct 34

<210> SEQ ID NO 86
<211> LENGTH: 32
<212> TYPE: DNA
<213> ORGANISM: Artificial Sequence
<220> FEATURE:
<223> OTHER INFORMATION: primer

<400> SEQUENCE: 86
gagccggatc catttcgggg ttctcaaaaa aa 32

<210> SEQ ID NO 87
<211> LENGTH: 31
<212> TYPE: DNA
<213> ORGANISM: Artificial Sequence
<220> FEATURE:
<223> OTHER INFORMATION: primer

<400> SEQUENCE: 87
gagccgagct catgcaaatg gaaaaattga t 31

<210> SEQ ID NO 88
<211> LENGTH: 35
<212> TYPE: DNA
<213> ORGANISM: Artificial Sequence
<220> FEATURE:
<223> OTHER INFORMATION: primer

<400> SEQUENCE: 88
gaagttctag agattgtaat tacaaaaggg gggtg 35

<210> SEQ ID NO 89
<211> LENGTH: 32
<212> TYPE: DNA
<213> ORGANISM: Artificial Sequence
<220> FEATURE:
<223> OTHER INFORMATION: primer

<400> SEQUENCE: 89
gaagtggatc ctttcaccga tcataaaagc cc 32

<210> SEQ ID NO 90
<211> LENGTH: 33
<212> TYPE: DNA
<213> ORGANISM: Artificial Sequence
<220> FEATURE:
<223> OTHER INFORMATION: primer

<400> SEQUENCE: 90
tgaaaggatc catttttcat tgattgttaa gtc 33

<210> SEQ ID NO 91
<211> LENGTH: 33
<212> TYPE: DNA
<213> ORGANISM: Artificial Sequence
<220> FEATURE:
<223> OTHER INFORMATION: primer

<400> SEQUENCE: 91
gaagttagag ctcggggggg cataaatttc ccg 33

<210> SEQ ID NO 92
<211> LENGTH: 32
<212> TYPE: DNA
<213> ORGANISM: Artificial Sequence
<220> FEATURE:
<223> OTHER INFORMATION: primer

<400> SEQUENCE: 92
gcttatggat ccgatacaag agaggtctct cg 32

<210> SEQ ID NO 93
<211> LENGTH: 31
<212> TYPE: DNA
<213> ORGANISM: Artificial Sequence
<220> FEATURE:
<223> OTHER INFORMATION: primer

<400> SEQUENCE: 93
gcttatggat ccctgtcatg gcgcattaac g 31

<210> SEQ ID NO 94
<211> LENGTH: 37
<212> TYPE: DNA
<213> ORGANISM: Artificial Sequence
<220> FEATURE:
<223> OTHER INFORMATION: primer

<400> SEQUENCE: 94
actgatggat ccatcgattt tcgttcgtga atacatg 37

<210> SEQ ID NO 95
<211> LENGTH: 36
<212> TYPE: DNA
<213> ORGANISM: Artificial Sequence
<220> FEATURE:
<223> OTHER INFORMATION: primer

<400> SEQUENCE: 95
actgatggat cccatatgca agggtttatt gttttc 36

<210> SEQ ID NO 96
<211> LENGTH: 37
<212> TYPE: DNA
<213> ORGANISM: Artificial Sequence
<220> FEATURE:
<223> OTHER INFORMATION: primer

<400> SEQUENCE: 96
gcacgttcta gaccaccgtc ccctgtgttg tatccac 37

<210> SEQ ID NO 97
<211> LENGTH: 37
<212> TYPE: DNA
<213> ORGANISM: Artificial Sequence
<220> FEATURE:
<223> OTHER INFORMATION: primer

<400> SEQUENCE: 97
aggaagggat ccagagcgag gaagatgtag gatgatc 37

<210> SEQ ID NO 98
<211> LENGTH: 36
<212> TYPE: DNA
<213> ORGANISM: Artificial Sequence
<220> FEATURE:
<223> OTHER INFORMATION: primer

<400> SEQUENCE: 98
tgacaaggat cctgtatcat accgcatagc agtgcc 36

<210> SEQ ID NO 99
<211> LENGTH: 37
<212> TYPE: DNA
<213> ORGANISM: Artificial Sequence
<220> FEATURE:
<223> OTHER INFORMATION: primer

<400> SEQUENCE: 99
ttccgcgagc tcggcgagag cttcagactc cgtcaga 37

<210> SEQ ID NO 100
<211> LENGTH: 31
<212> TYPE: DNA
<213> ORGANISM: Artificial Sequence
<220> FEATURE:
<223> OTHER INFORMATION: primer

<400> SEQUENCE: 100
gagcctctag atcagcgatt tgacgcggcg c 31

<210> SEQ ID NO 101
<211> LENGTH: 38
<212> TYPE: DNA
<213> ORGANISM: Artificial Sequence
<220> FEATURE:
<223> OTHER INFORMATION: primer

<400> SEQUENCE: 101
ttatctggat ccctgatgag caatgatggt aagataga 38

<210> SEQ ID NO 102
<211> LENGTH: 37
<212> TYPE: DNA
<213> ORGANISM: Artificial Sequence
<220> FEATURE:
<223> OTHER INFORMATION: primer

<400> SEQUENCE: 102
gggtaaggat cccccaaaag ggcatagtca ttctact 37

<210> SEQ ID NO 103
<211> LENGTH: 36
<212> TYPE: DNA
<213> ORGANISM: Artificial Sequence
<220> FEATURE:
<223> OTHER INFORMATION: primer

<400> SEQUENCE: 103
gagatcggta cccttttggg ccatatcgtg gatttc 36

<210> SEQ ID NO 104
<211> LENGTH: 36
<212> TYPE: DNA
<213> ORGANISM: Artificial Sequence
<220> FEATURE:
<223> OTHER INFORMATION: primer

<400> SEQUENCE: 104
gagccaagct tcattgacag caaccaggca gatctc 36

<210> SEQ ID NO 105
<211> LENGTH: 32
<212> TYPE: DNA
<213> ORGANISM: Artificial Sequence
<220> FEATURE:
<223> OTHER INFORMATION: primer

<400> SEQUENCE: 105
gcttataagc ttgatacaag agaggtctct cg 32

<210> SEQ ID NO 106
<211> LENGTH: 31
<212> TYPE: DNA
<213> ORGANISM: Artificial Sequence
<220> FEATURE:
<223> OTHER INFORMATION: primer

<400> SEQUENCE: 106
gcttataagc ttctgtcatg gcgcattaac g 31

<210> SEQ ID NO 107
<211> LENGTH: 36
<212> TYPE: DNA
<213> ORGANISM: Artificial Sequence
<220> FEATURE:
<223> OTHER INFORMATION: primer

<400> SEQUENCE: 107
gagccgagct ccatgccgat gaagtcatcg tcgagc 36

<210> SEQ ID NO 108
<211> LENGTH: 37
<212> TYPE: DNA
<213> ORGANISM: Artificial Sequence
<220> FEATURE:
<223> OTHER INFORMATION: primer

<400> SEQUENCE: 108
cgtgaaaagc tttcgcggga tgtatgaatt tgataag 37

<210> SEQ ID NO 109
<211> LENGTH: 37
<212> TYPE: DNA
<213> ORGANISM: Artificial Sequence
<220> FEATURE:
<223> OTHER INFORMATION: primer

<400> SEQUENCE: 109
tgtagggagc tcgatgcgcc acaatgtcgg tacaacg 37

<210> SEQ ID NO 110
<211> LENGTH: 36
<212> TYPE: DNA
<213> ORGANISM: Artificial Sequence
<220> FEATURE:
<223> OTHER INFORMATION: primer

<400> SEQUENCE: 110
cgagaatcta gaacaggatg aatcatctgt ggcggg 36

<210> SEQ ID NO 111
<211> LENGTH: 56
<212> TYPE: DNA
<213> ORGANISM: Artificial Sequence
<220> FEATURE:
<223> OTHER INFORMATION: primer

<400> SEQUENCE: 111
cgactgtcca gccgctcggc acatcggatc cgcttaccga aagccagact cagcaa 56

<210> SEQ ID NO 112
<211> LENGTH: 56
<212> TYPE: DNA
<213> ORGANISM: Artificial Sequence
<220> FEATURE:
<223> OTHER INFORMATION: primer

<400> SEQUENCE: 112
ttgctgagtc tggctttcgg taagcggatc cgatgtgccg agcggctgga cagtcg 56

<210> SEQ ID NO 113
<211> LENGTH: 56
<212> TYPE: DNA
<213> ORGANISM: Artificial Sequence
<220> FEATURE:
<223> OTHER INFORMATION: primer

<400> SEQUENCE: 113
cgttaatgcg ccatgacagc catgaggatc ccacaagccc gcacgccttg ccacac 56

<210> SEQ ID NO 114
<211> LENGTH: 56
<212> TYPE: DNA
<213> ORGANISM: Artificial Sequence
<220> FEATURE:
<223> OTHER INFORMATION: primer

<400> SEQUENCE: 114
gtgtggcaag gcgtgcgggc ttgtgggatc ctcatggctg tcatggcgca ttaacg 56

<210> SEQ ID NO 115
<211> LENGTH: 37
<212> TYPE: DNA
<213> ORGANISM: Artificial Sequence
<220> FEATURE:
<223> OTHER INFORMATION: primer

<400> SEQUENCE: 115
gacttcgtcg acgagtgcgg acggccagca tcaccac 37

<210> SEQ ID NO 116

<211> LENGTH: 34
<212> TYPE: DNA
<213> ORGANISM: Artificial Sequence
<220> FEATURE:
<223> OTHER INFORMATION: primer

<400> SEQUENCE: 116
ggcatatcta gagacatgaa gcgggaaaca gatg 34

<210> SEQ ID NO 117
<211> LENGTH: 34
<212> TYPE: DNA
<213> ORGANISM: Artificial Sequence
<220> FEATURE:
<223> OTHER INFORMATION: primer

<400> SEQUENCE: 117
ggtgcggagc tcgacagtat cacagccagc gctg 34

<210> SEQ ID NO 118
<211> LENGTH: 37
<212> TYPE: DNA
<213> ORGANISM: Artificial Sequence
<220> FEATURE:
<223> OTHER INFORMATION: primer

<400> SEQUENCE: 118
aagcgttcta gactgcggat gcagatcgat ctcggga 37

<210> SEQ ID NO 119
<211> LENGTH: 56
<212> TYPE: DNA
<213> ORGANISM: Artificial Sequence
<220> FEATURE:
<223> OTHER INFORMATION: primer

<400> SEQUENCE: 119
aaccttccgc tcacatgtga gcaggggatc cgcttaccga aagccagact cagcaa 56

<210> SEQ ID NO 120
<211> LENGTH: 56
<212> TYPE: DNA
<213> ORGANISM: Artificial Sequence
<220> FEATURE:
<223> OTHER INFORMATION: primer

<400> SEQUENCE: 120
ttgctgagtc tggctttcgg taagcggatc ccctgctcac atgtgagcgg aaggtt 56

<210> SEQ ID NO 121
<211> LENGTH: 56
<212> TYPE: DNA
<213> ORGANISM: Artificial Sequence
<220> FEATURE:
<223> OTHER INFORMATION: primer

<400> SEQUENCE: 121
cgttaatgcg ccatgacagc catgaggatc cgccttcagc cttcccgcgg ctggct 56

<210> SEQ ID NO 122
<211> LENGTH: 56
<212> TYPE: DNA
<213> ORGANISM: Artificial Sequence
<220> FEATURE:
<223> OTHER INFORMATION: primer

<400> SEQUENCE: 122
agccagccgc gggaaggctg aaggcggatc ctcatggctg tcatggcgca ttaacg 56

<210> SEQ ID NO 123
<211> LENGTH: 37
<212> TYPE: DNA
<213> ORGANISM: Artificial Sequence
<220> FEATURE:
<223> OTHER INFORMATION: primer

<400> SEQUENCE: 123
caagcactgc agcccacact tcaggcggct caggtcg 37

<210> SEQ ID NO 124
<211> LENGTH: 34
<212> TYPE: DNA
<213> ORGANISM: Artificial Sequence
<220> FEATURE:
<223> OTHER INFORMATION: primer

<400> SEQUENCE: 124
gagatatcta gaatggtatg aagcggaatt cccg 34

<210> SEQ ID NO 125
<211> LENGTH: 37
<212> TYPE: DNA
<213> ORGANISM: Artificial Sequence
<220> FEATURE:
<223> OTHER INFORMATION: primer

<400> SEQUENCE: 125
ataaacggta cccccctata gatgcgaacg ttagccc 37

<210> SEQ ID NO 126
<211> LENGTH: 37
<212> TYPE: DNA
<213> ORGANISM: Artificial Sequence
<220> FEATURE:
<223> OTHER INFORMATION: primer

<400> SEQUENCE: 126
aaggaggaat tccatcttga ggtatacaaa cagtcat 37

<210> SEQ ID NO 127
<211> LENGTH: 56
<212> TYPE: DNA
<213> ORGANISM: Artificial Sequence
<220> FEATURE:
<223> OTHER INFORMATION: primer

<400> SEQUENCE: 127
tctccgagaa agacaggcag gatcgggatc cgcttaccga aagccagact cagcaa 56

<210> SEQ ID NO 128
<211> LENGTH: 56
<212> TYPE: DNA
<213> ORGANISM: Artificial Sequence
<220> FEATURE:
<223> OTHER INFORMATION: primer

<400> SEQUENCE: 128
ttgctgagtc tggctttcgg taagcggatc ccgatcctgc ctgtctttct cggaga 56

<210> SEQ ID NO 129
<211> LENGTH: 37
<212> TYPE: DNA

<213> ORGANISM: Artificial Sequence
<220> FEATURE:
<223> OTHER INFORMATION: primer

<400> SEQUENCE: 129
aaggacggta ccggctcatt accctctttt caagggt 37

<210> SEQ ID NO 130
<211> LENGTH: 56
<212> TYPE: DNA
<213> ORGANISM: Artificial Sequence
<220> FEATURE:
<223> OTHER INFORMATION: primer

<400> SEQUENCE: 130
accaaagccg gactcccccg cgagaggatc cgcttaccga aagccagact cagcaa 56

<210> SEQ ID NO 131
<211> LENGTH: 56
<212> TYPE: DNA
<213> ORGANISM: Artificial Sequence
<220> FEATURE:
<223> OTHER INFORMATION: primer

<400> SEQUENCE: 131
ttgctgagtc tggctttcgg taagcggatc ctctcgcggg ggagtccggc tttggt 56

<210> SEQ ID NO 132
<211> LENGTH: 56
<212> TYPE: DNA
<213> ORGANISM: Artificial Sequence
<220> FEATURE:
<223> OTHER INFORMATION: primer

<400> SEQUENCE: 132
cgttaatgcg ccatgacagc catgaggatc ccatacgggg tacacaatgt accata 56

<210> SEQ ID NO 133
<211> LENGTH: 56
<212> TYPE: DNA
<213> ORGANISM: Artificial Sequence
<220> FEATURE:
<223> OTHER INFORMATION: primer

<400> SEQUENCE: 133
tatggtacat tgtgtacccc gtatgggatc ctcatggctg tcatggcgca ttaacg 56

<210> SEQ ID NO 134
<211> LENGTH: 37
<212> TYPE: DNA
<213> ORGANISM: Artificial Sequence
<220> FEATURE:
<223> OTHER INFORMATION: primer

<400> SEQUENCE: 134
gtcaacctgc agagcggccc aggtacaagt tggggaa 37

<210> SEQ ID NO 135
<211> LENGTH: 37
<212> TYPE: DNA
<213> ORGANISM: Artificial Sequence
<220> FEATURE:
<223> OTHER INFORMATION: primer

<400> SEQUENCE: 135
ggatcagagc tcgcttgtcc tcctgggaac agccgga 37

<210> SEQ ID NO 136
<211> LENGTH: 38
<212> TYPE: DNA
<213> ORGANISM: Artificial Sequence
<220> FEATURE:
<223> OTHER INFORMATION: primer

<400> SEQUENCE: 136
tatatgctgc agggctcaga cggtaccggt tgttccta 38

<210> SEQ ID NO 137
<211> LENGTH: 37
<212> TYPE: DNA
<213> ORGANISM: Artificial Sequence
<220> FEATURE:
<223> OTHER INFORMATION: primer

<400> SEQUENCE: 137
ctgaactcta gaccttcacc aggcacagag gaggtga 37

<210> SEQ ID NO 138
<211> LENGTH: 56
<212> TYPE: DNA
<213> ORGANISM: Artificial Sequence
<220> FEATURE:
<223> OTHER INFORMATION: primer

<400> SEQUENCE: 138
gccaataagt tctctttaga gaacaggatc cgcttaccga aagccagact cagcaa 56

<210> SEQ ID NO 139
<211> LENGTH: 57
<212> TYPE: DNA
<213> ORGANISM: Artificial Sequence
<220> FEATURE:
<223> OTHER INFORMATION: primer

<400> SEQUENCE: 139
ttgctgagtc tggctttcgg taagcggatc cttgttctct aaagagaact tattggc 57

<210> SEQ ID NO 140
<211> LENGTH: 56
<212> TYPE: DNA
<213> ORGANISM: Artificial Sequence
<220> FEATURE:
<223> OTHER INFORMATION: primer

<400> SEQUENCE: 140
cgttaatgcg ccatgacagc catgaggatc cgggctaacg ttcgcatcta tagggg 56

<210> SEQ ID NO 141
<211> LENGTH: 56
<212> TYPE: DNA
<213> ORGANISM: Artificial Sequence
<220> FEATURE:
<223> OTHER INFORMATION: primer

<400> SEQUENCE: 141
cccctataga tgcgaacgtt agcccggatc ctcatggctg tcatggcgca ttaacg 56

<210> SEQ ID NO 142
<211> LENGTH: 37
<212> TYPE: DNA
<213> ORGANISM: Artificial Sequence
<220> FEATURE:

<223> OTHER INFORMATION: primer

<400> SEQUENCE: 142
tgagacgagc tcgatgcata ggcgacggca gggcgcc 37

<210> SEQ ID NO 143
<211> LENGTH: 35
<212> TYPE: DNA
<213> ORGANISM: Artificial Sequence
<220> FEATURE:
<223> OTHER INFORMATION: primer

<400> SEQUENCE: 143
cgaaattcta gatcccgcga ttccgcccctt tgtgg 35

<210> SEQ ID NO 144
<211> LENGTH: 34
<212> TYPE: DNA
<213> ORGANISM: Artificial Sequence
<220> FEATURE:
<223> OTHER INFORMATION: primer

<400> SEQUENCE: 144
ttccaagagc tcgcggaata ccggaagcag cccc 34

<210> SEQ ID NO 145
<211> LENGTH: 37
<212> TYPE: DNA
<213> ORGANISM: Artificial Sequence
<220> FEATURE:
<223> OTHER INFORMATION: primer

<400> SEQUENCE: 145
caattctcta gagcggtcgg cgcaggtata ggagggg 37

<210> SEQ ID NO 146
<211> LENGTH: 56
<212> TYPE: DNA
<213> ORGANISM: Artificial Sequence
<220> FEATURE:
<223> OTHER INFORMATION: primer

<400> SEQUENCE: 146
gaaaagaaac caaaaagaat gggaaggatc cgcttaccga aagccagact cagcaa 56

<210> SEQ ID NO 147
<211> LENGTH: 56
<212> TYPE: DNA
<213> ORGANISM: Artificial Sequence
<220> FEATURE:
<223> OTHER INFORMATION: primer

<400> SEQUENCE: 147
ttgctgagtc tggctttcgg taagcggatc cttcccattc tttttggttt cttttc 56

<210> SEQ ID NO 148
<211> LENGTH: 56
<212> TYPE: DNA
<213> ORGANISM: Artificial Sequence
<220> FEATURE:
<223> OTHER INFORMATION: primer

<400> SEQUENCE: 148
cgttaatgcg ccatgacagc catgaggatc cgctatttaa catttgagaa taggga 56

<210> SEQ ID NO 149
<211> LENGTH: 56
<212> TYPE: DNA
<213> ORGANISM: Artificial Sequence
<220> FEATURE:
<223> OTHER INFORMATION: primer

<400> SEQUENCE: 149
tccctattct caaatgttaa atagcggatc ctcatggctg tcatggcgca ttaacg 56

<210> SEQ ID NO 150
<211> LENGTH: 37
<212> TYPE: DNA
<213> ORGANISM: Artificial Sequence
<220> FEATURE:
<223> OTHER INFORMATION: primer

<400> SEQUENCE: 150
caggcggagc tcccatttat gacgtgcttc cctaagc 37

<210> SEQ ID NO 151
<211> LENGTH: 37
<212> TYPE: DNA
<213> ORGANISM: Artificial Sequence
<220> FEATURE:
<223> OTHER INFORMATION: primer

<400> SEQUENCE: 151
tacgaatcta gagatcattg cggaagtaga agtggaa 37

<210> SEQ ID NO 152
<211> LENGTH: 56
<212> TYPE: DNA
<213> ORGANISM: Artificial Sequence
<220> FEATURE:
<223> OTHER INFORMATION: primer

<400> SEQUENCE: 152
tttagattga gttcatctgc agcggggatc cgcttaccga aagccagact cagcaa 56

<210> SEQ ID NO 153
<211> LENGTH: 56
<212> TYPE: DNA
<213> ORGANISM: Artificial Sequence
<220> FEATURE:
<223> OTHER INFORMATION: primer

<400> SEQUENCE: 153
ttgctgagtc tggctttcgg taagcggatc cccgctgcag atgaactcaa tctaaa 56

<210> SEQ ID NO 154
<211> LENGTH: 56
<212> TYPE: DNA
<213> ORGANISM: Artificial Sequence
<220> FEATURE:
<223> OTHER INFORMATION: primer

<400> SEQUENCE: 154
cgttaatgcg ccatgacagc catgaggatc cgccaatcag ccttagcccc tctcac 56

<210> SEQ ID NO 155
<211> LENGTH: 56
<212> TYPE: DNA
<213> ORGANISM: Artificial Sequence
<220> FEATURE:
<223> OTHER INFORMATION: primer

<400> SEQUENCE: 155
gtgagagggg ctaaggctga ttggcggatc ctcatggctg tcatggcgca ttaacg 56

<210> SEQ ID NO 156
<211> LENGTH: 37
<212> TYPE: DNA
<213> ORGANISM: Artificial Sequence
<220> FEATURE:
<223> OTHER INFORMATION: primer

<400> SEQUENCE: 156
atactcgtcg acatacgttg aattgccgag aagccgc 37

<210> SEQ ID NO 157
<211> LENGTH: 25
<212> TYPE: DNA
<213> ORGANISM: Artificial Sequence
<220> FEATURE:
<223> OTHER INFORMATION: primer

<400> SEQUENCE: 157
ctggagtacc tggatctgga tctcc 25

<210> SEQ ID NO 158
<211> LENGTH: 25
<212> TYPE: DNA
<213> ORGANISM: Artificial Sequence
<220> FEATURE:
<223> OTHER INFORMATION: primer

<400> SEQUENCE: 158
gctcggcttg tttcagctca tttcc 25

<210> SEQ ID NO 159
<211> LENGTH: 37
<212> TYPE: DNA
<213> ORGANISM: Artificial Sequence
<220> FEATURE:
<223> OTHER INFORMATION: primer

<400> SEQUENCE: 159
cggtttgagc tcgcgtcctg atctgcagaa gctcatt 37

<210> SEQ ID NO 160
<211> LENGTH: 56
<212> TYPE: DNA
<213> ORGANISM: Artificial Sequence
<220> FEATURE:
<223> OTHER INFORMATION: primer

<400> SEQUENCE: 160
ctaaagatga agtcgatcgg ctcatggatc cgcttaccga aagccagact cagcaa 56

<210> SEQ ID NO 161
<211> LENGTH: 56
<212> TYPE: DNA
<213> ORGANISM: Artificial Sequence
<220> FEATURE:
<223> OTHER INFORMATION: primer

<400> SEQUENCE: 161
ttgctgagtc tggctttcgg taagcggatc catgagccga tcgacttcat ctttag 56

<210> SEQ ID NO 162
<211> LENGTH: 56

<212> TYPE: DNA
<213> ORGANISM: Artificial Sequence
<220> FEATURE:
<223> OTHER INFORMATION: primer

<400> SEQUENCE: 162
cgttaatgcg ccatgacagc catgaggatc cgaagatccc tcgatggagt taatgt 56

<210> SEQ ID NO 163
<211> LENGTH: 56
<212> TYPE: DNA
<213> ORGANISM: Artificial Sequence
<220> FEATURE:
<223> OTHER INFORMATION: primer

<400> SEQUENCE: 163
acattaactc catcgaggga tcttcggatc ctcatggctg tcatggcgca ttaacg 56

<210> SEQ ID NO 164
<211> LENGTH: 38
<212> TYPE: DNA
<213> ORGANISM: Artificial Sequence
<220> FEATURE:
<223> OTHER INFORMATION: primer

<400> SEQUENCE: 164
gcttcggtcg actttgccgt ctggatatgc gtctctcg 38

<210> SEQ ID NO 165
<211> LENGTH: 37
<212> TYPE: DNA
<213> ORGANISM: Artificial Sequence
<220> FEATURE:
<223> OTHER INFORMATION: primer

<400> SEQUENCE: 165
gtcaaagagc tctatgacag cctcctcaaa ttgcagg 37

<210> SEQ ID NO 166
<211> LENGTH: 37
<212> TYPE: DNA
<213> ORGANISM: Artificial Sequence
<220> FEATURE:
<223> OTHER INFORMATION: primer

<400> SEQUENCE: 166
ttccatgtcg acgctgtgca aaaccgccgg cagcgcc 37

<210> SEQ ID NO 167
<211> LENGTH: 37
<212> TYPE: DNA
<213> ORGANISM: Artificial Sequence
<220> FEATURE:
<223> OTHER INFORMATION: primer

<400> SEQUENCE: 167
acattcgaat tcagcaggtc aatcagctcg ctgacgc 37

<210> SEQ ID NO 168
<211> LENGTH: 56
<212> TYPE: DNA
<213> ORGANISM: Artificial Sequence
<220> FEATURE:
<223> OTHER INFORMATION: primer

<400> SEQUENCE: 168
ccagcactgc gctccctcac ccgaaggatc cgcttaccga aagccagact cagcaa 56

<210> SEQ ID NO 169
<211> LENGTH: 56
<212> TYPE: DNA
<213> ORGANISM: Artificial Sequence
<220> FEATURE:
<223> OTHER INFORMATION: primer

<400> SEQUENCE: 169
ttgctgagtc tggctttcgg taagcggatc cttcgggtga gggagcgcag tgctgg 56

<210> SEQ ID NO 170
<211> LENGTH: 56
<212> TYPE: DNA
<213> ORGANISM: Artificial Sequence
<220> FEATURE:
<223> OTHER INFORMATION: primer

<400> SEQUENCE: 170
cgttaatgcg ccatgacagc catgaggatc ctcgagagat ccggatggtt ttcctg 56

<210> SEQ ID NO 171
<211> LENGTH: 56
<212> TYPE: DNA
<213> ORGANISM: Artificial Sequence
<220> FEATURE:
<223> OTHER INFORMATION: primer

<400> SEQUENCE: 171
caggaaaacc atccggatct ctcgaggatc ctcatggctg tcatggcgca ttaacg 56

<210> SEQ ID NO 172
<211> LENGTH: 37
<212> TYPE: DNA
<213> ORGANISM: Artificial Sequence
<220> FEATURE:
<223> OTHER INFORMATION: primer

<400> SEQUENCE: 172
agtcataagc tttctggcgt ttgatttcat caacggg 37

<210> SEQ ID NO 173
<211> LENGTH: 25
<212> TYPE: DNA
<213> ORGANISM: Artificial Sequence
<220> FEATURE:
<223> OTHER INFORMATION: primer

<400> SEQUENCE: 173
cagcgcgact tgttaaggga caata 25

<210> SEQ ID NO 174
<211> LENGTH: 25
<212> TYPE: DNA
<213> ORGANISM: Artificial Sequence
<220> FEATURE:
<223> OTHER INFORMATION: primer

<400> SEQUENCE: 174
ggctgctgtg atgaactttg tcgga 25

<210> SEQ ID NO 175
<211> LENGTH: 30
<212> TYPE: DNA
<213> ORGANISM: Artificial Sequence
<220> FEATURE:
<223> OTHER INFORMATION: primer

<400> SEQUENCE: 175
ctcagttcat ccatcaaatc accaagtccg 30

<210> SEQ ID NO 176
<211> LENGTH: 46
<212> TYPE: DNA
<213> ORGANISM: Artificial Sequence
<220> FEATURE:
<223> OTHER INFORMATION: primer

<400> SEQUENCE: 176
tacacgttag aagacggcta gatgcgtctg attgtgacag acggcg 46

<210> SEQ ID NO 177
<211> LENGTH: 26
<212> TYPE: DNA
<213> ORGANISM: Artificial Sequence
<220> FEATURE:
<223> OTHER INFORMATION: primer

<400> SEQUENCE: 177
aaccttccag tccggtttac tgtcgc 26

<210> SEQ ID NO 178
<211> LENGTH: 47
<212> TYPE: DNA
<213> ORGANISM: Artificial Sequence
<220> FEATURE:
<223> OTHER INFORMATION: primer

<400> SEQUENCE: 178
gtaccataag aagacggagc ttgccgtgtc cactccgatt atagcag 47

<210> SEQ ID NO 179
<211> LENGTH: 43
<212> TYPE: DNA
<213> ORGANISM: Artificial Sequence
<220> FEATURE:
<223> OTHER INFORMATION: primer

<400> SEQUENCE: 179
ccttgtcttg aagacggagc tggatccata acttcgtata atg 43

<210> SEQ ID NO 180
<211> LENGTH: 41
<212> TYPE: DNA
<213> ORGANISM: Artificial Sequence
<220> FEATURE:
<223> OTHER INFORMATION: primer

<400> SEQUENCE: 180
gtaccataag aagacggcta gaggatgcat atggcggccg c 41

<210> SEQ ID NO 181
<211> LENGTH: 25
<212> TYPE: DNA
<213> ORGANISM: Artificial Sequence
<220> FEATURE:
<223> OTHER INFORMATION: primer

<400> SEQUENCE: 181
catatgctcc ggctcttcaa gcaag 25

<210> SEQ ID NO 182
<211> LENGTH: 27
<212> TYPE: DNA
<213> ORGANISM: Artificial Sequence
<220> FEATURE:
<223> OTHER INFORMATION: primer

<400> SEQUENCE: 182
cctgagattg ataaacatga agtcctc 27

<210> SEQ ID NO 183
<211> LENGTH: 24
<212> TYPE: DNA
<213> ORGANISM: Artificial Sequence
<220> FEATURE:
<223> OTHER INFORMATION: primer

<400> SEQUENCE: 183
atattgaagt cggctggatt gtgg 24

<210> SEQ ID NO 184
<211> LENGTH: 29
<212> TYPE: DNA
<213> ORGANISM: Artificial Sequence
<220> FEATURE:
<223> OTHER INFORMATION: primer

<400> SEQUENCE: 184
gcggcagatc tcggcgcatt aagtcgtca 29

<210> SEQ ID NO 185
<211> LENGTH: 32
<212> TYPE: DNA
<213> ORGANISM: Artificial Sequence
<220> FEATURE:
<223> OTHER INFORMATION: primer

<400> SEQUENCE: 185
gcggcgaatt ctctgctgga aaaagtgata ca 32

<210> SEQ ID NO 186
<211> LENGTH: 19
<212> TYPE: DNA
<213> ORGANISM: Artificial Sequence
<220> FEATURE:
<223> OTHER INFORMATION: primer

<400> SEQUENCE: 186
ttcgctggga taacaacat 19

<210> SEQ ID NO 187
<211> LENGTH: 32
<212> TYPE: DNA
<213> ORGANISM: Artificial Sequence
<220> FEATURE:
<223> OTHER INFORMATION: primer

<400> SEQUENCE: 187
gcggcagatc ttaagctgga tccataactt cg 32

<210> SEQ ID NO 188
<211> LENGTH: 32
<212> TYPE: DNA
<213> ORGANISM: Artificial Sequence
<220> FEATURE:
<223> OTHER INFORMATION: primer

<400> SEQUENCE: 188
gcggcgaatt catatggcgg ccgcataact tc 32

<210> SEQ ID NO 189
<211> LENGTH: 19
<212> TYPE: DNA
<213> ORGANISM: Artificial Sequence
<220> FEATURE:
<223> OTHER INFORMATION: primer

<400> SEQUENCE: 189
caatttacgc ggggtggtg 19

<210> SEQ ID NO 190
<211> LENGTH: 21
<212> TYPE: DNA
<213> ORGANISM: Artificial Sequence
<220> FEATURE:
<223> OTHER INFORMATION: primer

<400> SEQUENCE: 190
gaataggtta cgcagttgtt g 21

<210> SEQ ID NO 191
<211> LENGTH: 21
<212> TYPE: DNA
<213> ORGANISM: Artificial Sequence
<220> FEATURE:
<223> OTHER INFORMATION: primer

<400> SEQUENCE: 191
ctcctgatcc aaacatgtaa g 21

<210> SEQ ID NO 192
<211> LENGTH: 19
<212> TYPE: DNA
<213> ORGANISM: Artificial Sequence
<220> FEATURE:
<223> OTHER INFORMATION: primer

<400> SEQUENCE: 192
aacccttgca tatgtctag 19

<210> SEQ ID NO 193
<211> LENGTH: 28
<212> TYPE: DNA
<213> ORGANISM: Artificial Sequence
<220> FEATURE:
<223> OTHER INFORMATION: primer

<400> SEQUENCE: 193
gcgcccttga tcctaagtca gatgaaac 28

<210> SEQ ID NO 194
<211> LENGTH: 28
<212> TYPE: DNA
<213> ORGANISM: Artificial Sequence
<220> FEATURE:
<223> OTHER INFORMATION: primer

<400> SEQUENCE: 194
cgggtccgat actgactgta agtttgac 28

<210> SEQ ID NO 195

<211> LENGTH: 42
<212> TYPE: DNA
<213> ORGANISM: Artificial Sequence
<220> FEATURE:
<223> OTHER INFORMATION: primer

<400> SEQUENCE: 195
gtaccataac catgccttgg ttaggatgca tatggcggcc gc 42

<210> SEQ ID NO 196
<211> LENGTH: 47
<212> TYPE: DNA
<213> ORGANISM: Artificial Sequence
<220> FEATURE:
<223> OTHER INFORMATION: primer

<400> SEQUENCE: 196
ccttgtcttc catcttgctg gagctggatc cataacttcg tataatg 47

<210> SEQ ID NO 197
<211> LENGTH: 25
<212> TYPE: DNA
<213> ORGANISM: Artificial Sequence
<220> FEATURE:
<223> OTHER INFORMATION: primer

<400> SEQUENCE: 197
gagagcaagg acatgacatt gacgc 25

<210> SEQ ID NO 198
<211> LENGTH: 27
<212> TYPE: DNA
<213> ORGANISM: Artificial Sequence
<220> FEATURE:
<223> OTHER INFORMATION: primer

<400> SEQUENCE: 198
gatcttcacc ctcttcaact tgtaaag 27

<210> SEQ ID NO 199
<211> LENGTH: 25
<212> TYPE: DNA
<213> ORGANISM: Artificial Sequence
<220> FEATURE:
<223> OTHER INFORMATION: primer

<400> SEQUENCE: 199
tttgcttcct cctgcacaag gcctc 25

<210> SEQ ID NO 200
<211> LENGTH: 26
<212> TYPE: DNA
<213> ORGANISM: Artificial Sequence
<220> FEATURE:
<223> OTHER INFORMATION: primer

<400> SEQUENCE: 200
cgttattgtg tgtgcatttc cattgt 26

<210> SEQ ID NO 201
<211> LENGTH: 39
<212> TYPE: DNA
<213> ORGANISM: Artificial Sequence
<220> FEATURE:
<223> OTHER INFORMATION: primer

<400> SEQUENCE: 201
caatggaaat gcacacacaa taacgtgact ggcaagaga 39

<210> SEQ ID NO 202
<211> LENGTH: 25
<212> TYPE: DNA
<213> ORGANISM: Artificial Sequence
<220> FEATURE:
<223> OTHER INFORMATION: primer

<400> SEQUENCE: 202
gtaatggccc tctcgtataa aaaac 25

<210> SEQ ID NO 203
<211> LENGTH: 46
<212> TYPE: DNA
<213> ORGANISM: Artificial Sequence
<220> FEATURE:
<223> OTHER INFORMATION: primer

<400> SEQUENCE: 203 gtttttata cgagagggcc attaccaatt agaatgaata tttccc 46

<210> SEQ ID NO 204
<211> LENGTH: 28
<212> TYPE: DNA
<213> ORGANISM: Artificial Sequence
<220> FEATURE:
<223> OTHER INFORMATION: primer

<400> SEQUENCE: 204
gaccaaaatg tttcgattca gcattcct 28

<210> SEQ ID NO 205
<211> LENGTH: 8142
<212> TYPE: DNA
<213> ORGANISM: Unknown
<220> FEATURE:
<223> OTHER INFORMATION: cre gene

<400> SEQUENCE: 205
ggggatctct gcagtgagat ctggtaatga ctctctagct tgaggcatca aataaaacga 60
aaggctcagt cgaaagactg ggcctttcgt tttatctgtt gtttgtcggt gaacgctctc 120
ctgagtagga caaatccgcc gctctagcta agcagaaggc catcctgacg gatggccttt 180
ttgcgtttct acaaactctt gttaactcta gagctgcctg ccgcgtttcg gtgatgaaga 240
tcttcccgat gattaattaa ttcagaacgc tcggttgccg ccgggcgttt tttatgcagc 300
aatggcaaga acgttgctct agaataattc tacacagccc agtccagact attcggcact 360
gaaattatgg gtgaagtggt caagacctca ctaggcacct taaaaatagc gcaccctgaa 420
gaagatttat ttgaggtagc ccttgcctac ctagcttcca agaaagatat cctaacagca 480
caagagcgga aagatgtttt gttctacatc cagaacaacc tctgctaaaa ttcctgaaaa 540
attttgcaaa aagttgttga ctttatctac aaggtgtggc ataatgtgtg gaattgtgag 600
cggataacaa ttaagcttag gagggagtgt taaatgtcca atttactgac cgtacaccaa 660
aatttgcctg cattaccggt cgatgcaacg agtgatgagg ttcgcaagaa cctgatggac 720
atgttcaggg atcgccaggc gttttctgag catacctgga aaatgcttct gtccgtttgc 780
cggtcgtggg cggcatggtg caagttgaat aaccggaaat ggtttcccgc agaacctgaa 840
gatgttcgcg attatcttct atatcttcag gcgcgcggtc tggcagtaaa aactatccag 900

```
caacatttgg gccagctaaa catgcttcat cgtcggtccg ggctgccacg accaagtgac    960
agcaatgctg tttcactggt tatgcggcgg atccgaaaag aaaacgttga tgccggtgaa   1020
cgtgcaaaac aggctctagc gttcgaacgc actgatttcg accaggttcg ttcactcatg   1080
gaaaatagcg atcgctgcca ggatatacgt aatctggcat ttctggggat tgcttataac   1140
accctgttac gtatagccga aattgccagg atcagggtta aagatatctc acgtactgac   1200
ggtgggagaa tgttaatcca tattggcaga acgaaaacgc tggttagcac cgcaggtgta   1260
gagaaggcac ttagcctggg ggtaactaaa ctggtcgagc gatggatttc cgtctctggt   1320
gtagctgatg atccgaataa ctacctgttt tgccgggtca gaaaaaatgg tgttgccgcg   1380
ccatctgcca ccagccagct atcaactcgc gccctggaag ggatttttga agcaactcat   1440
cgattgattt acggcgctaa ggatgactct ggtcagagat acctggcctg gtctggacac   1500
agtgcccgtg tcggagccgc gcgagatatg gcccgcgctg gagtttcaat accggagatc   1560
atgcaagctg gtggctggac caatgtaaat attgtcatga actatatccg taacctggat   1620
agtgaaacag gggcaatggt gcgcctgctg gaagatggcg attaggagct cgcatcacac   1680
gcaaaaagga aattggaata aatgcgaaat ttgagatgtt aattaaagac ctttttgagg   1740
tcttttttc ttagattttt ggggttattt aggggagaaa acataggggg gtactacgac   1800
ctcccccta ggtgtccatt gtccattgtc caaacaaata aataaatatt gggtttttaa   1860
tgttaaaagg ttgtttttta tgttaaagtg aaaaaaacag atgttgggag gtacagtgat   1920
agttgtagat agaaaagaag agaaaaaagt tgctgttact ttaagactta caacagaaga   1980
aaatgagata ttaaatagaa tcaaagaaaa atataatatt agcaaatcag atgcaaccgg   2040
tattctaata aaaaaatatg caaaggagga atacggtgca ttttaaacaa aaaaagatag   2100
acagcactgg catgctgcct atctatgact aaattttgtt aagtgtatta gcaccgttat   2160
tatatcatga gcgaaaatgt aataaaaagaa actgaaaaca agaaaaattc aagaggacgt   2220
aattggacat ttgttttata tccagaatca gcaaaagccg agtggttaga gtatttaaaa   2280
gagttacaca ttcaatttgt agtgtctcca ttacatgata gggatactga tacagaaggt   2340
aggatgaaaa aagagcatta tcatattcta gtgatgtatg agggtaataa atcttatgaa   2400
cagataaaaa taattaacag aagaattgaa tgcgactatt ccgcagattg caggaagtgt   2460
gaaaggtctt gtgagatata tgcttcacat ggacgatcct aataaattta aatatcaaaa   2520
agaagatatg atagtttatg gcggtgtaga tgttgatgaa ttattaaaga aaacaacaac   2580
agatagatat aaattaatta aagaaatgat tgagtttatt gatgaacaag gaatcgtaga   2640
atttaagagt ttaatggatt atgcaatgaa gtttaaattt gatgattggt tcccgctttt   2700
atgtgataac tcggcgtatg ttattcaaga atatataaaa tcaaatcggt ataaatctga   2760
ccgatagatt ttgaatttag gtgtcacaag acactctttt ttcgcaccag cgaaaactgg   2820
tttaagccga ctggagctcc tgcactggat ggtggcgctg gatggtaagc cgctggcaag   2880
cggtgaagtg cctctggatg tcgctccaca aggtaaacag ttgattgaac tgcctgaact   2940
accgcagccg gagagcgccg ggcaactctg gctcacagta cgcgtagtgc aaccgaacgc   3000
gaccgcatgg tcagaagccg ggcacatcag cgcctggcag cagtggcgtc tggcggaaaa   3060
cctcagtgtg acgctccccg ccgcgtccca cgccatcccg catctgacca ccagcgaaat   3120
ggatttttgc atcgagctgg gtaataagcg ttggcaattt aaccgccagt caggcttct    3180
ttcacagatg tggattggcg ataaaaaaca actgctgacg ccgctgcgcg atcagttcac   3240
ccgtgcaccg ctggataacg acattggcgt aagtgaagcg acccgcattg accctaacgc   3300
```

```
ctgggtcgaa cgctggaagg cggcgggcca ttaccaggcc gaagcagcgt tgttgcagtg   3360
cacggcagat acacttgctg atgcggtgct gattacgacc gctcacgcgt ggcagcatca   3420
ggggaaaacc ttatttatca gccggaaaac ctaccggatt gatggtagtg gtcaaatggc   3480
gattaccgtt gatgttgaag tggcgagcga tacaccgcat ccggcgcgga ttggcctgaa   3540
ctgccagctg gcgcaggtag cagagcgggt aaactggctc ggattagggc cgcaagaaaa   3600
ctatcccgac cgccttactg ccgcctgttt tgaccgctgg gatctgccat tgtcagacat   3660
gtataccccg tacgtcttcc cgagcgaaaa cggtctgcgc tgcgggacgc gcgaattgaa   3720
ttatggccca caccagtggc gcggcgactt ccagttcaac atcagccgct acagtcaaca   3780
gcaactgatg gaaaccagcc atcgccatct gctgcacgcg gaagaaggca catggctgaa   3840
tatcgacggt ttccatatgg ggattggtgg cgacgactcc tggagcccgt cagtatcggc   3900
ggaattccag ctgagcgccg gtcgctacca ttaccagttg gtctggtgtc aaaaataata   3960
ataaccgggc aggccatgtc tgcccgtatt tcgcgtaagg aaatccatta tgtactattt   4020
caagctaatt ccggtggaaa cgaggtcatc atttccttcc gaaaaaacgg ttgcatttaa   4080
atcttacata tgtaatactt tcaaagacta catttgtaag atttgatgtt tgagtcggct   4140
gaaagatcgt acgtaccaat tattgtttcg tgattgttca agccataaca ctgtagggat   4200
agtggaaaga gtgcttcatc tggttacgat caatcaaata ttcaaacgga gggagacgat   4260
tttgatgaaa ccagtaacgt tatacgatgt cgcagagtat gccggtgtct cttatcagac   4320
cgtttcccgc gtggtgaacc aggccagcca cgtttctgcg aaaacgcggg aaaaagtgga   4380
agcggcgatg gcggagctga attacattcc caaccgcgtg gcacaacaac tggcgggcaa   4440
acagtcgttg ctgattggcg ttgccacctc cagtctggcc ctgcacgcgc cgtcgcaaat   4500
tgtcgcggcg attaaatctc gcgccgatca actgggtgcc agcgtggtgg tgtcgatggt   4560
agaacgaagc ggcgtcgaag cctgtaaagc ggcggtgcac aatcttctcg cgcaacgcgt   4620
cagtgggctg atcattaact atccgctgga tgaccaggat gccattgctg tggaagctgc   4680
ctgcactaat gttccggcgt tatttcttga tgtctctgac cagacaccca tcaacagtat   4740
tattttctcc catgaagacg gtacgcgact gggcgtggag catctggtcg cattgggtca   4800
ccagcaaatc gcgctgttag cgggcccatt aagttctgtc tcggcgcgtc tgcgtctggc   4860
tggctggcat aaatatctca ctcgcaatca aattcagccg atagcggaac gggaaggcga   4920
ctggagtgcc atgtccggtt ttcaacaaac catgcaaatg ctgaatgagg gcatcgttcc   4980
cactgcgatg ctggttgcca acgatcagat ggcgctgggc gcaatgcgcg ccattaccga   5040
gtccgggctg cgcgttggtg cggatatctc ggtagtggga tacgacgata ccgaagacag   5100
ctcatgttat atcccgccgt caaccaccat caaacaggat tttcgcctgc tggggcaaac   5160
cagcgtggac cgcttgctgc aactctctca gggccaggcg gtgaagggca atcagctgtt   5220
gcccgtctca ctggtgaaaa gaaaaaccac cctggcgccc aatacgcaaa ccgcctctcc   5280
ccgcgcgttg gccgattcat taatgcagct ggcacgacag gtttcccgac tggaaagcgg   5340
gcagtgagcg caacgcaatt aatgtgagtt aggcatcgca tcctgcctcg cgcgtttcgg   5400
tgatgacggt gaaaacctct gacacatgca gctcccggag acggtcacag cttgtctgta   5460
agcggatgcc gggagcagac aagcccgtca gggcgcgtca gcgggtgttg gcgggtgtcg   5520
gggcgcagcc atgacccagt cacgtagcga tagcggagtg tatactggct taactatgcg   5580
gcatcagagc agattgtact gagagtgcac catatgcggt gtgaaatacc gcacagatgc   5640
```

```
gtaaggagaa aataccgcat caggcgctct tccgcttcct cgctcactga ctcgctgcgc   5700

tcggtcgttc ggctgcggcg agcggtatca gctcactcaa aggcggtaat acggttatcc   5760

acagaatcag gggataacgc aggaaagaac atgtgagcaa aaggccagca aaaggccagg   5820

aaccgtaaaa aggccgcgtt gctggcgttt ttccataggc tccgcccccc tgacgagcat   5880

cacaaaaatc gacgctcaag tcagaggtgg cgaaacccga caggactata aagataccag   5940

gcgtttcccc ctggaagctc cctcgtgcgc tctcctgttc cgaccctgcc gcttaccgga   6000

tacctgtccg cctttctccc ttcgggaagc gtggcgcttt ctcaatgctc acgctgtagg   6060

tatctcagtt cggtgtaggt cgttcgctcc aagctgggct gtgtgcacga accccccgtt   6120

cagcccgacc gctgcgcctt atccggtaac tatcgtcttg agtccaaccc ggtaagacac   6180

gacttatcgc cactggcagc agccactggt aacaggatta gcagagcgag gtatgtaggc   6240

ggtgctacag agttcttgaa gtggtggcct aactacggct acactagaag gacagtattt   6300

ggtatctgcg ctctgctgaa gccagttacc ttcggaaaaa gagttggtag ctcttgatcc   6360

ggcaaacaaa ccaccgctgg tagcggtggt ttttttgttt gcaagcagca gattacgcgc   6420

agaaaaaaag gatctcaaga agatcctttg atcttttcta cggggtctga cgctcagtgg   6480

aacgaaaact cacgttaagg gattttggtc atgagattat caaaaaggat cttcacctag   6540

atccttttaa attaaaaatg aagttttaaa tcaatctaaa gtatatatga gtaaacttgg   6600

tctgacagtt accaatgctt aatcagtgag gcacctatct cagcgatctg tctatttcgt   6660

tcatccatag ttgcctgact ccccgtcgtg tagataacta cgatacggga gggcttacca   6720

tctggcccca gtgctgcaat gataccgcga gacccacgct caccggctcc agatttatca   6780

gcaataaacc agccagccgg aagggccgag cgcagaagtg gtcctgcaac tttatccgcc   6840

tccatccagt ctattaattg ttgccgggaa gctagagtaa gtagttcgcc agttaatagt   6900

ttgcgcaacg ttgttgccat tgctacaggc atcgtggtgt cacgctcgtc gtttggtatg   6960

gcttcattca gctccggttc ccaacgatca aggcgagtta catgatcccc catgttgtgc   7020

aaaaaagcgg ttagctcctt cggtcctccg atcgttgtca gaagtaagtt ggccgcagtg   7080

ttatcactca tggttatggc agcactgcat aattctctta ctgtcatgcc atccgtaaga   7140

tgcttttctg tgactggtga gtactcaacc aagtcattct gagaatagtg tatgcggcga   7200

ccgagttgct cttgcccggc gtcaacacgg gataataccg cgccacatag cagaacttta   7260

aaagtgctca tcattggaaa acgttcttcg gggcgaaaac tctcaaggat cttaccgctg   7320

ttgagatcca gttcgatgta acccactcgt gcacccaact gatcttcagc atcttttact   7380

ttcaccagcg tttctgggtg agcaaaaaca ggaaggcaaa atgccgcaaa aaagggaata   7440

agggcgacac ggaaatgttg aatactcata ctcttccttt ttcaatatta ttgaagcatt   7500

tatcagggtt attgtctcat gagcggatac atatttgaat gtatttagaa aaataaacaa   7560

ataggggttc cgcgcacatt tccccgaaaa gtgccacctg acgtccaata gaccagttgc   7620

aatccaaacg agagtctaat agaatgaggt cgaaaagtaa atcgcgtaat aaggtaatag   7680

atttacatta gaaaatgaaa ggggatttta tgcgtgagaa tgttacagtc tatcccggca   7740

ttgccagtcg gggatattaa aaagagtata ggtttttatt gcgataaact aggtttcact   7800

ttggttcacc atgaagatgg attcgcagtt ctaatgtgta atgaggttcg gattcatcta   7860

tgggaggcaa gtgatgaagg ctggcgctct cgtagtaatg attcaccggt ttgtacaggt   7920

gcggagtcgt ttattgctgg tactgctagt tgccgcattg aagtagaggg aattgatgaa   7980

ttatatcaac atattaagcc tttgggcatt ttgcacccca atacatcatt aaaagatcag   8040
```

-continued

```
tggtgggatg aacgagactt tgcagtaatt gatcccgaca acaatttgat tacaaataaa   8100

aagctaaaat ctattattaa tctgttcctg caggagagac cg                      8142
```

ENHANCED PROTEIN EXPRESSION IN *BACILLUS*

CROSS-REFERENCE TO RELATED APPLICATIONS

The present application is a continuation of U.S. patent application Ser. No. 13/745,630, filed Jan. 18, 2013, now U.S. Pat. No. 9,175,294, which is a continuation of U.S. patent application Ser. No. 13/356,572, filed Jan. 23, 2012, now U.S. Pat. No. 8,383,366, which is a continuation of U.S. patent application Ser. No. 10/507,720, filed May 2, 2005, now U.S. Pat. No. 8,124,399, which is a U.S. National Stage Application of International Application No. PCT/US2003/009585, filed Mar. 28, 2003, which claims the benefit of U.S. Provisional Application Ser. No. 60/376,343, filed Apr. 29, 2002, 60/368,858, filed Mar. 29, 2002, and 60/368,949, filed Mar. 29, 2002, which are hereby incorporated by reference.

SEQUENCE LISTING

The sequence listing submitted via EFS, in compliance with 37 C.F.R. §1.52(e), is incorporated herein by reference. The sequence listing text file submitted via EFS contains the file NB30744-US-CNT-3 Sub-Sequence-Listing, created on Mar. 6, 2016, which is 152,667 bytes in size.

FIELD OF THE INVENTION

The present invention provides cells that have been genetically manipulated to have an altered capacity to produce expressed proteins. In particular, the present invention relates to Gram-positive microorganisms, such as *Bacillus* species having enhanced expression of a protein of interest, wherein one or more chromosomal genes have been inactivated, and preferably wherein one or more chromosomal genes have been deleted from the *Bacillus* chromosome. In some further embodiments, one or more indigenous chromosomal regions have been deleted from a corresponding wild-type *Bacillus* host chromosome.

BACKGROUND OF THE INVENTION

Genetic engineering has allowed the improvement of microorganisms used as industrial bioreactors, cell factories and in food fermentations. In particular, *Bacillus* species produce and secrete a large number of useful proteins and metabolites (Zukowski, "Production of commercially valuable products," In: Doi and McGloughlin (eds.) *Biology of Bacilli: Applications to Industry*, Butterworth-Heinemann, Stoneham. Mass pp 311-337 [1992]). The most common *Bacillus* species used in industry are *B. licheniformis, B. amyloliquefaciens* and *B. subtilis*. Because of their GRAS (generally recognized as safe) status, strains of these *Bacillus* species are natural candidates for the production of proteins utilized in the food and pharmaceutical industries. Important production enzymes include α-amylases, neutral proteases, and alkaline (or serine) proteases. However, in spite of advances in the understanding of production of proteins in *Bacillus* host cells, there remains a need for methods to increase expression of these proteins.

SUMMARY OF THE INVENTION

The present invention provides cells that have been genetically manipulated to have an altered capacity to produce expressed proteins. In particular, the present invention relates to Gram-positive microorganisms, such as *Bacillus* species having enhanced expression of a protein of interest, wherein one or more chromosomal genes have been inactivated, and preferably wherein one or more chromosomal genes have been deleted from the *Bacillus* chromosome. In some further embodiments, one or more indigenous chromosomal regions have been deleted from a corresponding wild-type *Bacillus* host chromosome. In some preferred embodiments, the present invention provides methods and compositions for the improved expression and/or secretion of a protein of interest in *Bacillus*.

In particularly preferred embodiments, the present invention provides means for improved expression and/or secretion of a protein of interest in *Bacillus*. More particularly, in these embodiments, the present invention involves inactivation of one or more chromosomal genes in a *Bacillus* host strain, wherein the inactivated genes are not necessary for strain viability. One result of inactivating one or more of the chromosomal genes is the production of an altered *Bacillus* strain that is able to express a higher level of a protein of interest over a corresponding non-altered *Bacillus* host strain.

Furthermore, in alternative embodiments, the present invention provides means for removing large regions of chromosomal DNA in a *Bacillus* host strain, wherein the deleted indigenous chromosomal region is not necessary for strain viability. One result of removing one or more indigenous chromosomal regions is the production of an altered *Bacillus* strain that is able to express a higher level of a protein of interest over a corresponding unaltered *Bacillus* strain. In some preferred embodiments, the *Bacillus* host strain is a recombinant host strain comprising a polynucleotide encoding a protein of interest. In some particularly preferred embodiments, the altered *Bacillus* strain is a *B. subtilis* strain. As explained in detail below, deleted indigenous chromosomal regions include, but are not limited to prophage regions, antimicrobial (e.g., antibiotic) regions, regulator regions, multi-contiguous single gene regions and operon regions.

In some embodiments, the present invention provides methods and compositions for enhancing expression of a protein of interest from a *Bacillus* cell. In some preferred embodiments, the methods comprise inactivating one or more chromosomal genes selected from the group consisting of sbo, slr, ybcO, csn, spoIISA, sigB, phrC, rapA, CssS trpA, trpB, trpC, trpD, trpE, trpF, tdh/kbl, alsD, sigD, prpC, gapB, pckA, fbp, rocA, ycgN, ycgM, rocF, and rocD in a *Bacillus* host strain to produce an altered *Bacillus* strain; growing the altered *Bacillus* strain under suitable growth conditions; and allowing a protein of interest to be expressed in the altered *Bacillus*, wherein the expression of the protein is enhanced, compared to the corresponding unaltered *Bacillus* host strain. In some embodiments, the protein of interest is a homologous protein, while in other embodiments, the protein of interest is a heterologous protein. In some embodiments, more than one protein of interest is produced. In some preferred embodiments, the *Bacillus* species is a *B. subtilis* strain. In yet further embodiments, inactivation of a chromosomal gene comprises the deletion of a gene to produce the altered *Bacillus* strain. In additional embodiments, inactivation of a chromosomal gene comprises insertional inactivation. In some preferred embodiments, the protein of interest is an enzyme. In some embodiments, the protein of interest is selected from proteases, cellulases, amylases, carbohydrases, lipases, isomerases, transferases, kinases and phosphatases, while in other embodiments, the protein of interest is selected from the group consisting of antibodies, hormones and growth factors.

In yet additional embodiments, the present invention provides altered *Bacillus* strains comprising the deletion of one or more chromosomal genes selected from the group of sbo, slr, ybcO, csn, spoIISA, sigB, phrC, rapA, CssS, trpA, trpB, trpC, trpD, trpE, trpF, tdh/kbl, alsD, sigD, prpC, gapB, pckA, fbp, rocA, ycgN, ycgM, rocF, and rocD. In some embodiments, the altered strain is a protease producing *Bacillus* strain. In an alternative embodiment, the altered *Bacillus* strain is a subtilisin producing strain. In yet other embodiments, the altered *Bacillus* strain further comprises a mutation in a gene selected from the group consisting of degU, degQ, degS, scoC4, spollE, and oppA.

In further embodiments, the present invention provides DNA constructs comprising an incoming sequence. In some embodiments, the incoming sequence includes a selective marker and a gene or gene fragment selected from the group consisting of sbo, slr, ybcO, csn, spoIISA, sigB, phrC, rapA, CssS, trpA, trpB, trpC, trpD, trpE, trpF, tdh/kbl, alsD, sigD, prpC, gapB, pckA, fbp, rocA, ycgN, ycgM, rocF, and rocD. In alternative embodiments, the selective marker is located in between two fragments of the gene. In other embodiments, the incoming sequence comprises a selective marker and a homology box, wherein the homology box flanks the 5' and/or 3' end of the marker. In additional embodiments, a host cell is transformed with the DNA construct. In further embodiments, the host cell is an *E. coli* or a *Bacillus* cell. In some preferred embodiments, the DNA construct is chromosomally integrated into the host cell.

The present invention also provides methods for obtaining an altered *Bacillus* strain expressing a protein of interest which comprises transforming a *Bacillus* host cell with the DNA construct of the present, wherein the DNA construct is integrated into the chromosome of the *Bacillus* host cell; producing an altered *Bacillus* strain, wherein one or more chromosomal genes have been inactivated; and growing the altered *Bacillus* strain under suitable growth conditions for the expression of a protein of interest. In some embodiments, the protein of interest is selected from proteases, cellulases, amylases, carbohydrases, lipases, isomerases, transferases, kinases and phosphatases, while in other embodiments, the protein of interest is selected from the group consisting of antibodies, hormones and growth factors. In yet additional embodiments, the *Bacillus* host strain is selected from the group consisting of *B. licheniformis, B. lentus, B. subtilis, B. amyloliquefaciens B. brevis, B. stearothermophilus, B. alkalophilus, B. coagulans, B. circulans, B. pumilus, B. thuringiensis, B. clausii, B. megaterium*, and preferably, *B. subtilis*. In some embodiments, the *Bacillus* host strain is a recombinant host. In yet additional embodiments, the protein of interest is recovered. In further embodiments, the selective marker is excised from the altered *Bacillus*.

The present invention further provides methods for obtaining an altered *Bacillus* strain expressing a protein of interest. In some embodiments, the method comprises transforming a *Bacillus* host cell with a DNA construct comprising an incoming sequence wherein the incoming sequence comprises a selective marker and a gene selected from the group consisting of sbo, slr, ybcO, csn, spoIISA, sigB, phrC, rapA, CssS, trpA, trpB, trpC, trpD, trpE, trpF, tdh/kbl, alsD, sigD, prpC, gapB, pckA, fbp, rocA, ycgN, ycgM, rocF, and rocD, wherein the DNA construct is integrated into the chromosome of the *Bacillus* host cell and results in the deletion of one or more gene(s); obtaining an altered *Bacillus* strain, and growing the altered *Bacillus* strain under suitable growth conditions for the expression of the protein of interest.

In some alternative embodiments, the present invention provides a DNA construct comprising an incoming sequence, wherein the incoming sequence includes a selective marker and a cssS gene, a cssS gene fragment or a homologous sequence thereto. In some embodiments, the selective marker is located between two fragments of the gene. In alternative embodiments, the incoming sequence comprises a selective marker and a homology box wherein the homology box flanks the 5' and/or 3' end of the marker. In yet other embodiments, a host cell is transformed with the DNA construct. In additional embodiments, the host cell is an *E. coli* or a *Bacillus* cell. In still further embodiments, the DNA construct is chromosomally integrated into the host cell.

The present invention also provides methods for obtaining *Bacillus subtilis* strains that demonstrate enhanced protease production. In some embodiments, the methods comprise the steps of transforming a *Bacillus subtilis* host cell with a DNA construct according to the invention; allowing homologous recombination of the DNA construct and a homologous region of the *Bacillus* chromosome wherein at least one of the following genes, sbo, slr, ybcO, csn, spoIISA, sigB, phrC, rapA, CssS, trpA, trpB, trpC, trpD, trpE, trpF, tdh/kbl, alsD, sigD, prpC, gapB, pckA, fbp, rocA, ycgN, ycgM, rocF, and rocD, is deleted from the *Bacillus* chromosome; obtaining an altered *Bacillus subtilis* strain; and growing the altered *Bacillus* strain under conditions suitable for the expression of a protease. In some embodiments, the protease producing *Bacillus* is a subtilisin producing strain. In alternative embodiments, the protease is a heterologous protease. In additional embodiments, the protease producing strain further includes a mutation in a gene selected from the group consisting of degU, degQ, degS, scoC4, spollE, and oppA. In some embodiments, the inactivation comprises the insertional inactivation of the gene.

The present invention further provides altered *Bacillus subtilis* strains comprising a deletion of one or more chromosomal genes selected from the group consisting of sbo, slr, ybcO, csn, spoIISA, sigB, phrC, rapA, CssS, trpA, trpB, trpC, trpD, trpE, trpF, tdh/kbl, alsD, sigD, prpC, gapB, pckA, fbp, rocA, ycgN, ycgM, rocF, and rocD, wherein the altered *Bacillus subtilis* strain is capable of expressing a protein of interest. In some embodiments, the protein of interest is an enzyme. In some additional embodiments, the protein of interest is a heterologous protein.

In some embodiments, the present invention provides altered *Bacillus* strains comprising a deletion of one or more indigenous chromosomal regions or fragments thereof, wherein the indigenous chromosomal region includes about 0.5 to 500 kilobases (kb) and wherein the altered *Bacillus* strains have an enhanced level of expression of a protein of interest compared to the corresponding unaltered *Bacillus* strains when grown under essentially the same growth conditions.

In yet additional embodiments, the present invention provides protease-producing *Bacillus* strains which comprise at least one deletion of an indigenous chromosomal region selected from the group consisting of a PBSX region, a skin region, a prophage 7 region, a SPβ region, a prophage 1 region, a prophage 2 region, a prophage 3 region, a prophage 4 region, a prophage 5 region, a prophage 6 region, a PPS region, a PKS region, a yvfF-yveK region, a DHB region and fragments thereof.

In further embodiments, the present invention provides methods for enhancing the expression of a protein of interest in *Bacillus* comprising: obtaining an altered *Bacillus* strain produced by introducing a DNA construct including a selective marker and an inactivating chromosomal segment into a *Bacillus* host strain, wherein the DNA construct is integrated into the *Bacillus* chromosome resulting in the deletion of an indigenous chromosomal region or fragment thereof from the *Bacillus* host cell; and growing the altered *Bacillus* strain under suitable growth conditions, wherein expression of a protein of interest is greater in the altered *Bacillus* strain compared to the expression of the protein of interest is the corresponding unaltered *Bacillus* host cell.

The present invention also provides methods for obtaining a protein of interest from a *Bacillus* strain comprising the steps of: transforming a *Bacillus* host cell with a DNA construct which comprises a selective marker and an inactivating chromosomal segment, wherein the DNA construct is integrated into the chromosome of the *Bacillus* strain and results in deletion of an indigenous chromosomal region or fragment thereof to form an altered *Bacillus* strain; culturing the altered *Bacillus* strain under suitable growth conditions to allow the expression of a protein of interest; and recovering the protein of interest.

The present invention also provides a means for the use of DNA microarray data to screen and/or identify beneficial mutations. In some particularly preferred embodiments, these mutations involve genes selected from the group consisting of trpA, trpB, trpC, trpD, trpE, trpF, tdh/kbl rocA, ycgN, ycgM, rocF, and rocD. In some preferred embodiments, these beneficial mutations are based on transcriptome evidence for the simultaneous expression of a given amino acid biosynthetic pathway and biodegradative pathway, and/or evidence that deletion of the degradative pathway results in a better performing strain and/or evidence that overexpression of the biosynthetic pathway results in a better performing strain. In additional embodiments, the present invention provides means for the use of DNA microarray data to provide beneficial mutations. In some particularly preferred embodiments, these mutations involve genes selected from the group consisting of trpA, trpB, trpC, trpD, trpE, trpF, tdh/kbl rocA, ycgN, ycgM, rocF, and rocD, when the expression of mRNA from genes comprising an amino acid biosynthetic pathway is not balanced and overexpression of the entire pathway provides a better performing strain than the parent (i.e., wild-type and/or originating) strain. Furthermore, the present invention provides means to improve production strains through the inactivation of gluconeogenic genes. In some of these preferred embodiments, the inactivated gluconeogenic genes are selected from the group consisting of pckA, gapB, and fbp.

The present invention provides methods for enhancing expression of a protein of interest from *Bacillus* comprising the steps of obtaining an altered *Bacillus* strain capable of producing a protein of interest, wherein the altered *Bacillus* strain has at least one inactivated chromosomal gene selected from the group consisting of sbo, slr, ybcO, csn, spoIISA, sigB, phrC, rapA, CssS, trpA, trpB, trpC, trpD, trpE, trpF, tdh/kbl, alsD, sigD, prpC, gapB, pckA, fbp, rocA, ycgN, ycgM, rocF, and rocD, and growing the altered *Bacillus* strain under conditions such that the protein of interest is expressed by the altered *Bacillus* strain, wherein the expression of the protein of interest is enhanced, compared to the expression of the protein of interest in an unaltered *Bacillus* host strain. In some embodiments, the protein of interest is selected from the group consisting of homologous proteins and heterologous proteins. In some embodiments, the protein of interest is selected from proteases, cellulases, amylases, carbohydrases, lipases, isomerases, transferases, kinases and phosphatases, while in other embodiments, the protein of interest is selected from the group consisting of antibodies, hormones and growth factors. In some particularly preferred embodiments, the protein of interest is a protease. In additional embodiments, the altered *Bacillus* strain is obtained by deleting one or more chromosomal genes selected from the group consisting of sbo, slr, ybcO, csn, spoIISA, sigB, phrC, rapA, CssS, trpA, trpB, trpC, trpD, trpE, trpF, tdh/kbl, alsD, sigD, prpC, gapB, pckA, fbp, rocA, ycgN, ycgM, rocF, and rocD.

The present invention also provides altered *Bacillus* strains obtained using the method described herein. In some preferred embodiments, the altered *Bacillus* strains comprise a chromosomal deletion of one or more genes selected from the group consisting of sbo, slr, ybcO, csn, spoIISA, sigB, phrC, rapA, CssS, trpA, trpB, trpC, trpD, trpE, trpF, tdh/kbl, alsD, sigD, prpC, gapB, pckA, fbp, rocA, ycgN, ycgM, rocF, and rocD. In some embodiments, more than one of these chromosomal genes have been deleted. In some particularly preferred embodiments, the altered strains are *B. subtilis* strains. In additional preferred embodiments, the altered *Bacillus* strains are protease producing strains. In some particularly preferred embodiments, the protease is a subtilisin. In yet additional embodiments, the subtilisin is selected from the group consisting of subtilisin 168, subtilisin BPN', subtilisin Carlsberg, subtilisin DY, subtilisin 147, subtilisin 309 and variants thereof. In yet further embodiments, altered *Bacillus* strains further comprise mutation(s) in at least one gene selected from the group consisting of degU, degQ, degS, scoC4, spoIIE, and oppA. In some particularly preferred embodiments, the altered *Bacillus* strains further comprise a heterologous protein of interest.

The present invention also provides DNA constructs comprising at least one gene selected from the group consisting of sbo, slr, ybcO, csn, spoIISA, sigB, phrC, rapA, CssS, trpA, trpB, trpC, trpD, trpE, trpF, tdh/kbl, alsD, sigD, prpC, gapB, pckA, fbp, rocA, ycgN, ss ycgM, rocF, and rocD, gene fragments thereof, and homologous sequences thereto. In some preferred embodiments, the DNA constructs comprise at least one nucleic acid sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO:17, SEQ ID NO:39, SEQ ID NO:40, SEQ ID NO:42, SEQ ID NO:44, SEQ ID NO:46, SEQ ID NO:48, SEQ ID NO:50, SEQ ID NO:37, SEQ ID NO:25, SEQ ID NO:21, SEQ ID NO:50, SEQ ID NO:29, SEQ ID NO:23, SEQ ID NO:27, SEQ ID NO:19, SEQ ID NO:31, SEQ ID NO:48, SEQ ID NO:46, SEQ ID NO:35, and SEQ ID NO:33. In some embodiments, the DNA constructs further comprise at least one polynucleotide sequence encoding at least one protein of interest.

The present invention also provides plasmids comprising the DNA constructs. In further embodiments, the present invention provides host cells comprising the plasmids comprising the DNA constructs. In some embodiments, the host cells are selected from the group consisting of *Bacillus* cells and *E. coli* cells. In some preferred embodiments, the host cell is *B. subtilis*. In some particularly preferred embodiments, the DNA construct is integrated into the chromosome of the host cell. In alternative embodiments, the DNA construct comprises at least one gene that encodes at least one amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO:18, SEQ ID NO:41, SEQ ID NO:43, SEQ ID NO:45, SEQ ID NO:47, SEQ ID NO:49, SEQ ID NO:51, SEQ ID NO:38, SEQ ID NO:26, SEQ ID NO:22, SEQ ID NO:57, SEQ ID NO:30, SEQ ID NO:24, SEQ ID NO:28, SEQ ID NO:20, SEQ ID NO:32, SEQ ID NO:55, SEQ ID NO:53, SEQ ID NO:36, and SEQ ID NO:34. In additional embodiments, the DNA constructs further comprise at least one selective marker, wherein the selective marker is flanked on each side by a fragment of the gene or homologous gene sequence thereto.

The present invention also provides DNA constructs comprising an incoming sequence, wherein the incoming sequence comprises a nucleic acid encoding a protein of interest, and a selective marker flanked on each side with a homology box, wherein the homology box includes nucleic acid sequences having 80 to 100% sequence identity to the sequence immediately flanking the coding regions of at least one gene selected from the group consisting of sbo, slr, ybcO, csn, spoIISA, sigB, phrC, rapA, CssS, trpA, trpB, trpC, trpD, trpE, trpF, tdh/kbl, alsD, sigD, prpC, gapB, pckA, fbp, rocA, ycgN, ycgM, rocF, and rocD. In some embodiments, the DNA constructs further comprise at least one nucleic acids which flanks the coding sequence of the gene. The present invention also provides plasmids comprising the DNA constructs. In further embodiments, the present invention provides host cells comprising the plasmids comprising the DNA constructs. In some embodiments, the host cells are selected from the group consisting of *Bacillus* cells and *E. coli* cells. In some preferred embodiments, the host cell is *B. subtilis*. In some particularly preferred embodiments, the DNA construct is integrated into the chromosome of the host cell. In additional preferred embodiments, the selective marker has been excised from the host cell chromosome.

The present invention further provides methods for obtaining an altered *Bacillus* strain with enhanced protease production comprising: transforming a *Bacillus* host cell with at least one DNA construct of the present invention, wherein the protein of interest in the DNA construct is a protease, and wherein the DNA construct is integrated into the chromosome of the *Bacillus* host cell under conditions such that at least one gene is inactivated to produce an altered *Bacillus* strain; and growing the altered *Bacillus* strain under conditions such that enhanced protease production is obtained. In some particularly preferred embodiments, the method further comprises recovering the protease. In alternative preferred embodiments, at least one inactivated gene is deleted from the chromosome of the altered *Bacillus* strain. The present invention also provides altered *Bacillus* strains produced using the methods described herein. In some embodiments, the *Bacillus* host strain is selected from the group consisting of *B. licheniformis, B. lentus, B. subtilis, B. amyloliquefaciens B. brevis, B. stearothermophilus, B. alkalophilus, B. coagulans, B. circulans, B. pumilus, B. lautus, B. clausii, B. megaterium*, and *B. thuringiensis*. In some preferred embodiments, the *Bacillus* host cell is *B. subtilis*.

The present invention also provides methods for enhancing expression of a protease in an altered *Bacillus* comprising: transforming a *Bacillus* host cell with a DNA construct of the present invention; allowing homologous recombination of the DNA construct and a region of the chromosome of the *Bacillus* host cell, wherein at least one gene of the chromosome of the *Bacillus* host cell is inactivated, to produce an altered *Bacillus* strain; and growing the altered *Bacillus* strain under conditions suitable for the expression of the protease, wherein the production of the protease is greater in the altered *Bacillus subtilis* strain compared to the *Bacillus subtilis* host prior to transformation. In some preferred embodiments, the protease is subtilisin. In additional embodiments, the protease is a recombinant protease. In yet further embodiments, inactivation is achieved by deletion of at least one gene. In still further embodiments, inactivation is by insertional inactivation of at least one gene. The present invention also provides altered *Bacillus* strains obtained using the methods described herein. In some embodiments, altered *Bacillus* strain comprises at least one inactivated gene selected from the group consisting of sbo, slr, ybcO, csn, spoIISA, sigB, phrC, rapA, CssS, trpA, trpB, trpC, trpD, trpE, trpF, tdh/kbl, alsD, sigD, prpC, gapB, pckA, fbp, rocA, ycgN, ycgM, rocF, and rocD. In some preferred embodiments, the inactivated gene has been inactivated by deletion. In additional embodiments, the altered *Bacillus* strains further comprise at least one mutation in a gene selected from the group consisting of degU, degS, degQ, scoC4, spollE, and oppA. In some preferred embodiments, the mutation is degU(Hy)32. In still further embodiments, the strain is a recombinant protease producing strain. In some preferred embodiments, the altered *Bacillus* strains are selected from the group consisting of *B. licheniformis, B. lentus, B. subtilis, B. amyloliquefaciens B. brevis, B. stearothermophilus, B. alkalophilus, B. coagulans, B. circulans, B. pumilus, B. lautus, B. clausii, B. megaterium*, and *B. thuringiensis.*

The present invention also provides altered *Bacillus* strains comprising a deletion of one or more indigenous chromosomal regions or fragments thereof, wherein the indigenous chromosomal region includes about 0.5 to 500 kb, and wherein the altered *Bacillus* strain has an enhanced level of expression of a protein of interest compared to a corresponding unaltered *Bacillus* strain when the altered and unaltered *Bacillus* strains are grown under essentially the same growth conditions. In preferred embodiments, the altered *Bacillus* strain is selected from the group consisting of *B. licheniformis, B. lentus, B. subtilis, B. amyloliquefaciens B. brevis, B. stearothermophilus, B. alkalophilus, B. coagulans, B. circulans, B. pumilus, B. lautus, B. clausii, B. megaterium*, and *B. thuringiensis*. In some preferred embodiments, the altered *Bacillus* strain is selected from the group consisting of *B. subtilis, B. licheniformis*, and *B. amyloliquefaciens*. In some particularly preferred embodiments, the altered *Bacillus* strain is a *B. subtilis* strain. In yet further embodiments, the indigenous chromosomal region is selected from the group consisting of a PBSX region, a skin region, a prophage 7 region, a SPβ region, a prophage 1 region, a prophage 2 region, a prophage 4 region, a prophage 3 region, a prophage 4 region, a prophage 5 region, a prophage 6, region, a PPS region, a PKS region, a YVFF-YVEK region, a DHB region and fragments thereof. In some preferred embodiments, two indigenous chromosomal regions or fragments thereof have been deleted. In some embodiments, the protein of interest is selected from proteases, cellulases, amylases, carbohydrases, lipases, isomerases, transferases, kinases and phosphatases, while in other embodiments, the protein of interest is selected from the group consisting of antibodies, hormones and growth factors. In yet additional embodiments, the protein of interest is a protease. In some preferred embodiments, the protease is a subtilisin. In some particularly preferred embodiments, the subtilisin is selected from the group consisting of subtilisin 168, subtilisin BPN', subtilisin Carlsberg, subtilisin DY, subtilisin 147 and subtilisin 309 and variants thereof. In further preferred embodiments, the *Bacillus* host is a recombinant strain. In some particularly preferred embodiments, the altered *Bacillus* strains further comprise at least one mutation in a gene selected from the group consisting of degU, degQ, degS, sco4, spollE and oppA. In some preferred embodiments, the mutation is degU(Hy)32.

The present invention further provides protease producing *Bacillus* strains comprising a deletion of an indigenous chromosomal region selected from the group consisting of a PBSX region, a skin region, a prophage 7 region, a SPβ region, a prophage 1 region, a prophage 2 region, a prophage 3 region, a prophage 4 region, a prophage 5 region, a prophage 6 region, a PPS region, a PKS region, a YVFF-YVEK region, a DHB region and fragments thereof. In some preferred embodiments, the protease is a subtilisin. In some embodiments, the protease is a heterologous protease. In some preferred embodiments, the altered *Bacillus* strain is selected from the group consisting of *B. licheniformis, B. lentus, B. subtilis, B. amyloliquefaciens B. brevis, B. stearothermophilus, B. alkalophilus, B. coagulans, B. circulans, B. pumilus, B. lautus, B. clausii, B. megaterium*, and *B. thuringiensis*. In additional embodiments, the *Bacillus* strain is a *B. subtilis* strain.

The present invention also provides methods for enhancing the expression of a protein of interest in *Bacillus* comprising: introducing a DNA construct including a selective marker and an inactivating chromosomal segment into a *Bacillus* host strain, wherein the DNA construct is integrated into the chromosome of the *Bacillus* host strain, resulting in the deletion of an indigenous chromosomal region or fragment thereof from the *Bacillus* host cell to produce an altered *Bacillus* strain; and growing the altered *Bacillus* strain under suitable conditions, wherein expression of a protein of interest is greater in the altered *Bacillus* strain compared to the expression of the protein of interest in a *Bacillus* host cell that has not been altered. In some preferred embodiments, the methods further comprise the step of recovering the protein of interest. In some embodiments, the methods further comprise the step of excising the selective marker from the altered *Bacillus* strain. In additional embodiments, the indigenous chromosomal region is selected from the group of regions consisting of PBSX, skin, prophage 7, SPβ, prophage 1, prophage 2, prophage 3, prophage 4, prophage 5, prophage 6, PPS, PKS, YVFF-YVEK, DHB and fragments thereof. In further embodiments, the altered *Bacillus* strain comprises deletion of at least two indigenous chromosomal regions. In some preferred embodiments, the protein of interest is an enzyme. In some embodiments, the protein of interest is selected from proteases, cellulases, amylases, carbohydrases, lipases, isomerases, transferases, kinases and phosphatases, while in other embodiments, the protein of interest is selected from the group consisting of antibodies, hormones and growth factors. In some embodiments, the *Bacillus* host strain is selected from the group consisting of *B. licheniformis, B. lentus, B. subtilis, B. amyloliquefaciens B. brevis, B. stearothermophilus, B. clausii, B. alkalophilus, B. coagulans, B. circulans, B. pumilus* and *B. thuringiensis*. The present invention also provides altered *Bacillus* strains produced using the methods described herein.

The present invention also provides methods for obtaining a protein of interest from a *Bacillus* strain comprising: transforming a *Bacillus* host cell with a DNA construct comprising a selective marker and an inactivating chromosomal segment, wherein the DNA construct is integrated into the chromosome of the *Bacillus* strain resulting in deletion of an indigenous chromosomal region or fragment thereof, to produce an altered *Bacillus* strain, culturing the altered *Bacillus* strain under suitable growth conditions to allow the expression of a protein of interest, and recovering the protein of interest. In some preferred embodiments, the protein of interest is an enzyme. In some particularly preferred embodiments, the *Bacillus* host comprises a heterologous gene encoding a protein of interest. In additional embodiments, the *Bacillus* host cell is selected from the group consisting of *B. licheniformis, B. lentus, B. subtilis, B. amyloliquefaciens B. brevis, B. stearothermophilus, B. clausii, B. alkalophilus, B. coagulans, B. circulans, B. pumilus* and *B. thuringiensis*. In some preferred embodiments, the indigenous chromosomal region is selected from the group of regions consisting of PBSX, skin, prophage 7, SPβ, prophage 1, prophage 2, prophage 3, prophage 4, prophage 5, prophage 6, PPS, PKS, YVFF-YVEK, DHB and fragments thereof. In some particularly preferred embodiments the altered *Bacillus* strains further comprise at least one mutation in a gene selected from the group consisting of degU, degQ, degS, sco4, spollE and oppA. In some embodiments, the protein of interest is an enzyme selected from the group consisting of proteases, cellulases, amylases, carbohydrases, lipases, isomerases, transferases, kinases, and phosphatases. In some particularly preferred embodiments, the enzyme is a protease. In some preferred embodiments, the protein of interest is an enzyme. In other embodiments, the protein of interest is selected from the group consisting of antibodies, hormones and growth factors.

The present invention further provides methods for enhancing the expression of a protein of interest in *Bacillus* comprising: obtaining nucleic acid from at least one *Bacillus* cell; performing transcriptome DNA array analysis on the nucleic acid from said *Bacillus* cell to identify at least one gene of interest; modifying at least one gene of interest to produce a DNA construct; introducing the DNA construct into a *Bacillus* host cell to produce an altered *Bacillus* strain, wherein the altered *Bacillus* strain is capable of producing a protein of interest, under conditions such that expression of the protein of interest is enhanced as compared to the expression of the protein of interest in a *Bacillus* that has not been altered. In some embodiments, the protein of interest is associated with at least one biochemical pathway selected from the group consisting of amino acid biosynthetic pathways and biodegradative pathways. In some embodiments, the methods involve disabling at least one biodegradative pathway. In some embodiments, the biodegradative pathway is disabled due to the transcription of the gene of interest. However, it is not intended that the present invention be limited to these pathways, as it is contemplated that the methods will find use in the modification of other biochemical pathways within cells such that enhanced expression of a protein of interest results. In some particularly preferred embodiments, the *Bacillus* host comprises a heterologous gene encoding a protein of interest. In additional embodiments, the *Bacillus* host cell is selected from the group consisting of *B. licheniformis, B. lentus, B. subtilis, B. amyloliquefaciens B. brevis, B. stearothermophilus, B. clausii, B. alkalophilus, B. coagulans, B. circulans, B. pumilus* and *B. thuringiensis*. In some embodiments, the protein of interest is an enzyme. In some preferred embodiments, the protein of interest is selected from proteases, cellulases, amylases, carbohydrases, lipases, isomerases, transferases, kinases and phosphatases, while in other embodiments, the protein of interest is selected from the group consisting of antibodies, hormones and growth factors.

The present invention further provides methods for enhancing the expression of a protein of interest in *Bacillus*, comprising: obtaining nucleic acid containing at least one gene of interest from at least one *Bacillus* cell; fragmenting said nucleic acid; amplifying said fragments to produce a pool of amplified fragments comprising said at least one gene of interest; ligating said amplified fragments to produce a DNA construct; directly transforming said DNA construct into a *Bacillus* host cell to produce an altered *Bacillus* strain; culturing said altered *Bacillus* strain under conditions such that expression of said protein of interest is enhanced as compared to the expression of said protein of interest in a *Bacillus* that has not been altered. In some preferred embodiments, said amplifying comprises using the polymerase chain reaction. In some embodiments, the altered *Bacillus* strain comprises modified gene selected from the group consisting of prpC, sigD and tdh/kbl. In some particularly preferred embodiments, the *Bacillus* host comprises a heterologous gene encoding a protein of interest. In additional embodiments, the *Bacillus* host cell is selected from the group consisting of *B. licheniformis, B. lentus, B. subtilis, B. amyloliquefaciens B. brevis, B. stearothermophilus, B. clausii, B. alkalophilus, B. coagulans, B. circulans, B. pumilus* and *B. thuringiensis*. In some embodiments, the protein of interest is an enzyme. In some preferred embodiments, the protein of interest is selected from proteases, cellulases, amylases, carbohydrases, lipases, isomerases, transferases, kinases and phosphatases, while in other embodiments, the protein of interest is selected from the group consisting of antibodies, hormones and growth factors.

The present invention further provides isolated nucleic acids comprising the sequences set forth in nucleic acid sequences selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO:39, SEQ ID NO:40, SEQ ID NO:42, SEQ ID NO:44, SEQ ID NO:46, SEQ ID NO:48, SEQ ID NO:50, SEQ ID NO:37, SEQ ID NO:25, SEQ ID NO:21, SEQ ID NO:50, SEQ ID NO:23, SEQ ID NO:27, SEQ ID NO:19, SEQ ID NO:31, SEQ ID NO:48, SEQ ID NO:46, SEQ ID NO:35, and SEQ ID NO:33.

The present invention also provides isolated nucleic acid sequences encoding amino acids, wherein the amino acids are selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO:41, SEQ ID NO:43, SEQ ID NO:45, SEQ ID NO:47, SEQ ID NO:49, SEQ ID NO:51, SEQ ID NO:38, SEQ ID NO:26, SEQ ID NO:22, SEQ ID NO:57, SEQ ID NO:24, SEQ ID NO:28, SEQ ID NO:20, SEQ ID NO:32, SEQ ID NO:55, SEQ ID NO:53, SEQ ID NO:36, and SEQ ID NO:34.

The present invention further provides isolated amino acid sequences, wherein the amino acid sequences are selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO:41, SEQ ID NO:43, SEQ ID NO:45, SEQ ID NO:47, SEQ ID NO:49, SEQ ID NO:51, SEQ ID NO:38, SEQ ID NO:26, SEQ ID NO:22, SEQ ID NO:57, SEQ ID NO:24, SEQ ID NO:28, SEQ ID NO:20, SEQ ID NO:32, SEQ ID NO:55, SEQ ID NO:53, SEQ ID NO:36, and SEQ ID NO:34.

DESCRIPTION OF THE INVENTION

Figure 1A:
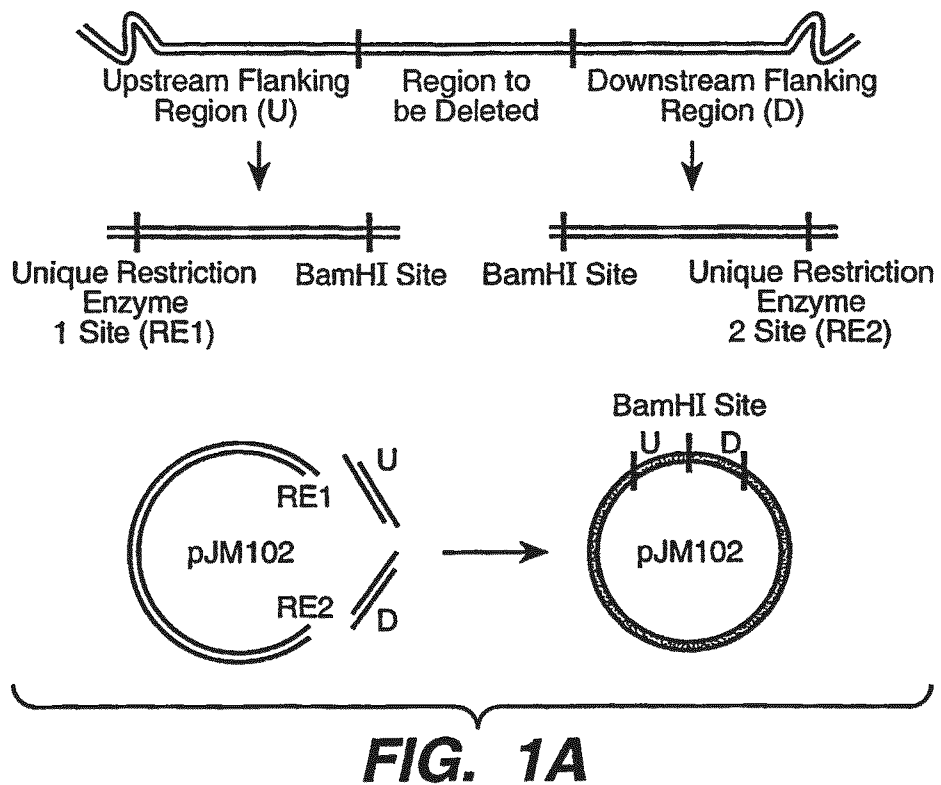
FIG. 1A and FIG. 1B illustrate a general schematic diagram of one method ("Method 1" See, Example 1) provided by the present invention. In this method, flanking regions of a gene and/or an indigenous chromosomal region are amplified out of a wild-type *Bacillus* chromosome, cut with restriction enzymes (including at least BamHI) and ligated into pJM102. The construct is cloned through *E. coli* and the plasmid is isolated, linearized with BamHI and ligated to an antimicrobial marker with complementary ends. After cloning again in *E. coli*, a liquid culture is grown and used to isolate plasmid DNA for use in transforming a *Bacillus* host strain (preferably, a competent *Bacillus* host strain).

The present invention provides cells that have been genetically manipulated to have an altered capacity to produce expressed proteins. In particular, the present invention relates to Gram-positive microorganisms, such as *Bacillus* species having enhanced expression of a protein of interest, wherein one or more chromosomal genes have been inactivated or otherwise modified. In some preferred embodiments, one or more chromosomal genes have been deleted from the *Bacillus* chromosome. In some further embodiments, one or more indigenous chromosomal regions have been deleted from a corresponding wild-type *Bacillus* host chromosome.

Definitions

All patents and publications, including all sequences disclosed within such patents and publications, referred to herein are expressly incorporated by reference. Unless defined otherwise herein, all technical and scientific terms used herein have the same meaning as commonly understood by one of ordinary skill in the art to which this invention belongs (See e.g., Singleton et al., Dictionary of Microbiology and Molecular Biology, 2d Ed., John Wiley and Sons, New York [1994]; and Hale and Marham, The Harper Collins Dictionary of Biology, Harper Perennial, NY [1991], both of which provide one of skill with a general dictionary of many of the terms used herein). Although any methods and materials similar or equivalent to those described herein can be used in the practice or testing of the present invention, the preferred methods and materials are described. Numeric ranges are inclusive of the numbers defining the range. As used herein and in the appended claims, the singular "a", "an" and "the" includes the plural reference unless the context clearly dictates otherwise. Thus, for example, reference to a "host cell" includes a plurality of such host cells.

Unless otherwise indicated, nucleic acids are written left to right in 5' to 3' orientation; amino acid sequences are written left to right in amino to carboxy orientation, respectively. The headings provided herein are not limitations of the various aspects or embodiments of the invention that can be had by reference to the specification as a whole. Accordingly, the terms defined immediately below are more fully defined by reference to the Specification as a whole.

As used herein, "host cell" refers to a cell that has the capacity to act as a host or expression vehicle for a newly introduced DNA sequence. In preferred embodiments of the present invention, the host cells are *Bacillus* sp. or *E. coli* cells.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

As used herein, "nucleic acid" refers to a nucleotide or polynucleotide sequence, and fragments or portions thereof, as well as to DNA, cDNA, and RNA of genomic or synthetic origin which may be double-stranded or single-stranded, whether representing the sense or antisense strand. It will be understood that as a result of the degeneracy of the genetic code, a multitude of nucleotide sequences may encode a given protein.

As used herein the term "gene" means a chromosomal segment of DNA involved in producing a polypeptide chain that may or may not include regions preceding and following the coding regions (e.g. 5' untranslated (5' UTR) or leader sequences and 3' untranslated (3' UTR) or trailer sequences, as well as intervening sequence (introns) between individual coding segments (exons)).

In some embodiments, the gene encodes therapeutically significant proteins or peptides, such as growth factors, cytokines, ligands, receptors and inhibitors, as well as vaccines and antibodies. The gene may encode commercially important industrial proteins or peptides, such as enzymes (e.g., proteases, carbohydrases such as amylases and glucoamylases, cellulases, oxidases and lipases). However, it is not intended that the present invention be limited to any particular enzyme or protein. In some embodiments, the gene of interest is a naturally-occurring gene, while in other embodiments, it is a mutated gene or a synthetic gene.

As used herein, the term "vector" refers to any nucleic acid that can be replicated in cells and can carry new genes or DNA segments into cells. Thus, the term refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

As used herein, the terms "DNA construct," "expression cassette," and "expression vector," refer to a nucleic acid construct generated recombinantly or synthetically, with a series of specified nucleic acid elements that permit transcription of a particular nucleic acid in a target cell (i.e., these are vectors or vector elements, as described above). The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In some embodiments, DNA constructs also include a series of specified nucleic acid elements that permit transcription of a particular nucleic acid in a target cell. In one embodiment, a DNA construct of the invention comprises a selective marker and an inactivating chromosomal segment as defined herein.

As used herein, "transforming DNA," "transforming sequence," and "DNA construct" refer to DNA that is used to introduce sequences into a host cell or organism. Transforming DNA is DNA used to introduce sequences into a host cell or organism. The DNA may be generated in vitro by PCR or any other suitable techniques. In some preferred embodiments, the transforming DNA comprises an incoming sequence, while in other preferred embodiments it further comprise an incoming sequence flanked by homology boxes. In yet a further embodiment, the transforming DNA comprises other non-homologous sequences, added to the ends (i.e., stuffer sequences or flanks). The ends can be closed such that the transforming DNA forms a closed circle, such as, for example, insertion into a vector.

As used herein, the term "plasmid" refers to a circular double-stranded (ds) DNA construct used as a cloning vector, and which forms an extrachromosomal self-replicating genetic element in many bacteria and some eukaryotes. In some embodiments, plasmids become incorporated into the genome of the host cell.

As used herein, the terms "isolated" and "purified" refer to a nucleic acid or amino acid (or other component) that is removed from at least one component with which it is naturally associated.

As used herein, the term "enhanced expression" is broadly construed to include enhanced production of a protein of interest. Enhanced expression is that expression above the normal level of expression in the corresponding host strain that has not been altered according to the teachings herein but has been grown under essentially the same growth conditions.

In some preferred embodiments, "enhancement" is achieved by any modification that results in an increase in a desired property. For example, in some particularly preferred embodiments, the present invention provides means for enhancing protein production, such that the enhanced strains produced a greater quantity and/or quality of a protein of interest than the parental strain (e.g., the wild-type and/or originating strain).

As used herein the term "expression" refers to a process by which a polypeptide is produced based on the nucleic acid sequence of a gene. The process includes both transcription and translation.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction (See e.g., Ferrari et al., "*Genetics*," in Hardwood et al, (eds.), *Bacillus*, Plenum Publishing Corp., pages 57-72, [1989]).

As used herein, the terms "transformed" and "stably transformed" refers to a cell that has a non-native (heterologous) polynucleotide sequence integrated into its genome or as an episomal plasmid that is maintained for at least two generations.

As used herein "an incoming sequence" refers to a DNA sequence that is introduced into the *Bacillus* chromosome. In some preferred embodiments, the incoming sequence is part of a DNA construct. In preferred embodiments, the incoming sequence encodes one or more proteins of interest. In some embodiments, the incoming sequence comprises a sequence that may or may not already be present in the genome of the cell to be transformed (i.e., it may be either a homologous or heterologous sequence). In some embodiments, the incoming sequence encodes one or more proteins of interest, a gene, and/or a mutated or modified gene. In alternative embodiments, the incoming sequence encodes a functional wild-type gene or operon, a functional mutant gene or operon, or a non-functional gene or operon. In some embodiments, the non-functional sequence may be inserted into a gene to disrupt function of the gene. In some embodiments, the incoming sequence encodes one or more functional wild-type genes, while in other embodiments, the incoming sequence encodes one or more functional mutant genes, and in yet additional embodiments, the incoming sequence encodes one or more non-functional genes. In another embodiment, the incoming sequence encodes a sequence that is already present in the chromosome of the host cell to be transformed. In a preferred embodiment, the incoming sequence comprises a gene selected from the group consisting of sbo, slr, ybcO, csn, spoIISA, phrC, sigB, rapA, CssS, trpA, trpB, trpC, trpD, trpE, trpF, tdh/kbl, alsD, sigD, prpC, gapB, pckA, fbp, rocA, ycgN, ycgM, rocF, and rocD, and fragments thereof. In yet another embodiment, the incoming sequence includes a selective marker. In a further embodiment the incoming sequence includes two homology boxes.

In some embodiments, the incoming sequence encodes at least one heterologous protein including, but not limited to hormones, enzymes, and growth factors. In another embodiment, the enzyme includes, but is not limited to hydrolases, such as protease, esterase, lipase, phenol oxidase, permease, amylase, pullulanase, cellulase, glucose isomerase, laccase and protein disulfide isomerase.

As used herein, "homology box" refers to a nucleic acid sequence, which is homologous to a sequence in the *Bacillus* chromosome. More specifically, a homology box is an upstream or downstream region having between about 80 and 100% sequence identity, between about 90 and 100% sequence identity, or between about 95 and 100% sequence identity with the immediate flanking coding region of a gene or part of a gene to be inactivated according to the invention. These sequences direct where in the *Bacillus* chromosome a DNA construct is integrated and directs what part of the *Bacillus* chromosome is replaced by the incoming sequence. While not meant to limit the invention, a homology box may include about between 1 base pair (bp) to 200 kilobases (kb). Preferably, a homology box includes about between 1 bp and 10.0 kb; between 1 bp and 5.0 kb; between 1 bp and 2.5 kb; between 1 bp and 1.0 kb, and between 0.25 kb and 2.5 kb. A homology box may also include about 10.0 kb, 5.0 kb, 2.5 kb, 2.0 kb, 1.5 kb, 1.0 kb, 0.5 kb, 0.25 kb and 0.1 kb. In some embodiments, the 5' and 3' ends of a selective marker are flanked by a homology box wherein the homology box comprises nucleic acid sequences immediately flanking the coding region of the gene.

As used herein, the term "selectable marker-encoding nucleotide sequence" refers to a nucleotide sequence which is capable of expression in the host cells and where expression of the selectable marker confers to cells containing the expressed gene the ability to grow in the presence of a corresponding selective agent or lack of an essential nutrient.

As used herein, the terms "selectable marker" and "selective marker" refer to a nucleic acid (e.g., a gene) capable of expression in host cell which allows for ease of selection of those hosts containing the vector. Examples of such selectable markers include but are not limited to antimicrobials. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation. A "residing selectable marker" is one that is located on the chromosome of the microorganism to be transformed. A residing selectable marker encodes a gene that is different from the selectable marker on the transforming DNA construct. Selective markers are well known to those of skill in the art. As indicated above, preferably the marker is an antimicrobial resistant marker (e.g., $amp^R$; $phleo^R$; $spec^R$; $kan^R$; $ery^R$; $tet^R$; $cmp^R$; and $neo^R$; See e.g., Guerot-Fleury, Gene, 167: 335-337 [1995]; Palmeros et al., Gene 247:255-264 [2000]; and Trieu-Cuot et al., *Gene,* 23:331-341 [1983]). In some particularly preferred embodiments, the present invention provides a chloramphenicol resistance gene (e.g., the gene present on pC194, as well as the resistance gene present in the *Bacillus licheniformis* genome). This resistance gene is particularly useful in the present invention, as well as in embodiments involving chromosomal amplification of chromosomally integrated cassettes and integrative plasmids (See e.g., Albertini and Galizzi, Bacteriol., 162:1203-1211 [1985]; and Stahl and Ferrari, J. Bacteriol., 158:411-418 [1984]). The DNA sequence of this naturally-occurring chloramphenicol resistance gene is shown below:

```
                                            (SEQ ID NO: 58)
ATGAATTTTCAAACAATCGAGCTTGACACATGGTATAGAAAATCTTATTT

TGACCATTACATGAAGGAAGCGAAATGTTCTTTCAGCATCACGGCAAACG

TCAATGTGACAAATTTGCTCGCCGTGCTCAAGAAAAAGAAGCTCAAGCTG

TATCCGGCTTTTATTTATATCGTATCAAGGGTCATTCATTCGCGCCCTGA

GTTTAGAACAACGTTTGATGACAAAGGAAGCTGGGTTATTGGGAACAAAT

GCATCCGTGCTATGCGATTTTTCATCAGGACGACCAAACGTTTTCCGCCC

TCTGGACGGAATACTCAGACGATTTTTCGCAGTTTTATCATCAATATCTT

CTGGACGCCGAGCGCTTTGGAGACAAAAGGGGCCTTTGGGCTAAGCCGGA

CATCCCGCCCAATACGTTTTCAGTTTCTTCTATTCCATGGGTGCGCTTTT

CAACATTCAATTTAAACCTTGATAACAGCGAACACTTGCTGCCGATTATT

ACAAACGGGAAATACTTTTCAGAAGGCAGGGAAACATTTTTGCCCGTTTC

CTGCAAGTTCACCATGCAGTGTGTGACGGCTATCATGCCGGCGCTTTTAT

AA.
```

The deduced amino acid sequence of this chloramphenicol resistance protein is:

```
                                            (SEQ ID NO: 59)
MNFQTIELDTVVYRKSYFDHYMKEAKCSFSITANVNVTNLLAVLKKKKLK

LYPAFIYIVSRVIHSRPEFRTTFDDKGQLGYWEQMHPCYAIFHQDDQTFS

ALWTEYSDDFSQFYHQYLLDAERFGDKRGLWAKPDIPPNTFSVSSIPWVR

FSTFNLNLDNSEHLLPIITNGKYFSEGRETFLPVSCKFTMQCVTAIMPAL

L.
```

Other markers useful in accordance with the invention include, but are not limited to auxotrophic markers, such as tryptophan; and detection markers, such as β-galactosidase.

As used herein, the term "promoter" refers to a nucleic acid sequence that functions to direct transcription of a downstream gene. In preferred embodiments, the promoter is appropriate to the host cell in which the target gene is being expressed. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "inactivation" includes any method that prevents the functional expression of one or more of the sbo, slr, ybcO, csn, spoIISA, sigB, phrC, rapA, CssS, trpA, trpB, trpC, trpD, trpE, trpF, tdh/kbl, aisD, sigD, prpC, gapB, pckA, fbp, rocA, ycgN, ycgM, rocF, and rocD chromosomal genes, wherein the gene or gene product is unable to exert its known function. Inactivation or enhancement occurs via any suitable means, including deletions, substitutions (e.g., mutations), interruptions, and/or insertions in the nucleic acid gene sequence. In one embodiment, the expression product of an inactivated gene is a truncated protein with a corresponding change in the biological activity of the protein. In some embodiments, the change in biological activity is an increase in activity, while in preferred embodiments, the change is results in the loss of biological activity. In some embodiments, an altered *Bacillus* strain comprises inactivation of one or more genes that results preferably in stable and non-reverting inactivation.

In some preferred embodiments, inactivation is achieved by deletion. In some preferred embodiments, the gene is deleted by homologous recombination. For example, in some embodiments when sbo is the gene to be deleted, a DNA construct comprising an incoming sequence having a selective marker flanked on each side by a homology box is used. The homology box comprises nucleotide sequences homologous to nucleic acids flanking regions of the chromosomal sbo gene. The DNA construct aligns with the homologous sequences of the *Bacillus* host chromosome and in a double crossover event the sbo gene is excised out of the host chromosome.

As used herein, "deletion" of a gene refers to deletion of the entire coding sequence, deletion of part of the coding sequence, or deletion of the coding sequence including flanking regions. The deletion may be partial as long as the sequences left in the chromosome provides the desired biological activity of the gene. The flanking regions of the coding sequence may include from about 1 bp to about 500 bp at the 5' and 3' ends. The flanking region may be larger than 500 bp but will preferably not include other genes in the region which may be inactivated or deleted according to the invention. The end result is that the deleted gene is effectively non-functional. In simple terms, a "deletion" is defined as a change in either nucleotide or amino acid sequence in which one or more nucleotides or amino acid residues, respectively, have been removed (i.e., are absent). Thus, a "deletion mutant" has fewer nucleotides or amino acids than the respective wild-type organism.

In still another embodiment of the present invention, deletion of a gene active at an inappropriate time as determined by DNA array analysis (e.g., transcriptome analysis, as described herein) provides enhanced expression of a product protein. In some preferred embodiments, deletion of one or more of genes selected from the group consisting of pckA, gapB, fbp, and/or alsD, provides an improved strain for the improved efficiency of feed utilization. As used herein, "transcriptome analysis" refers to the analysis of gene transcription.

In another embodiment of the present invention, a gene is considered to be "optimized" by the deletion of a regulatory sequence in which this deletion results in increased expression of a desired product. In some preferred embodiments of the present invention, the tryptophan operon (i.e., comprising genes trpA trpB, trpC, trpD, trpE, trpF) is optimized by the deletion of the DNA sequence coding for the TRAP binding RNA sequence (See, Yang, et. al., J Mol. Biol., 270:696-710 [1997]). This deletion is contemplated to increase expression of the desired product from the host strain.

In another preferred embodiment, inactivation is by insertion. For example, in some embodiments, when sbo is the gene to be inactivated, a DNA construct comprises an incoming sequence having the sbo gene interrupted by a selective marker. The selective marker will be flanked on each side by sections of the sbo coding sequence. The DNA construct aligns with essentially identical sequences of the sbo gene in the host chromosome and in a double crossover event the sbo gene is inactivated by the insertion of the selective marker. In simple terms, an "insertion" or "addition" is a change in a nucleotide or amino acid sequence which has resulted in the addition of one or more nucleotides or amino acid residues, respectively, as compared to the naturally occurring sequence.

In another embodiment, activation is by insertion in a single crossover event with a plasmid as the vector. For example, a sbo chromosomal gene is aligned with a plasmid comprising the gene or part of the gene coding sequence and a selective marker. In some embodiments, the selective marker is located within the gene coding sequence or on a part of the plasmid separate from the gene. The vector is integrated into the *Bacillus* chromosome, and the gene is inactivated by the insertion of the vector in the coding sequence.

In alternative embodiments, inactivation results due to mutation of the gene. Methods of mutating genes are well known in the art and include but are not limited to site-directed mutation, generation of random mutations, and gapped-duplex approaches (See e.g., U.S. Pat. No. 4,760,025; Moring et al., Biotech. 2:646 [1984]; and Kramer et al., Nucleic Acids Res., 12:9441 [1984]).

As used herein, a "substitution" results from the replacement of one or more nucleotides or amino acids by different nucleotides or amino acids, respectively.

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "ortholog" and "orthologous genes" refer to genes in different species that have evolved from a common ancestral gene (i.e., a homologous gene) by speciation. Typically, orthologs retain the same function in during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "homology" refers to sequence similarity or identity, with identity being preferred. This homology is determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

As used herein, an "analogous sequence" is one wherein the function of the gene is essentially the same as the gene designated from *Bacillus subtilis* strain 168. Additionally, analogous genes include at least 60%, 65%, 70%, 75%, 80%, 85%, 90%, 95%, 97%, 98%, 99% or 100% sequence identity with the sequence of the *Bacillus subtilis* strain 168 gene. Alternately, analogous sequences have an alignment of between 70 to 100% of the genes found in the *B. subtilis* 168 region and/or have at least between 5-10 genes found in the region aligned with the genes in the *B. subtilis* 168 chromosome. In additional embodiments more than one of the above properties applies to the sequence. Analogous sequences are determined by known methods of sequence alignment. A commonly used alignment method is BLAST, although as indicated above and below, there are other methods that also find use in aligning sequences.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps.

Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). A particularly useful BLAST program is the WU-BLAST-2 program (See, Altschul et al., Meth. Enzymol., 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical with the nucleotide residues of the sequence shown in the nucleic acid figures. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer nucleosides than those of the nucleic acid figures, it is understood that the percentage of homology will be determined based on the number of homologous nucleosides in relation to the total number of nucleosides. Thus, for example, homology of sequences shorter than those of the sequences identified herein and as discussed below, will be determined using the number of nucleosides in the shorter sequence.

As used herein, the term "hybridization" refers to the process by which a strand of nucleic acid joins with a complementary strand through base pairing, as known in the art.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while an intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5×SSC, 5×Denhardt's solution, 0.5% SDS and 100 μg/ml denatured carrier DNA followed by washing two times in 2×SSC and 0.5% SDS at room temperature and two additional times in 0.1×SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denaturated sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination, "recombining," or generating a "recombined" nucleic acid is generally the assembly of two or more nucleic acid fragments wherein the assembly gives rise to a chimeric gene.

In a preferred embodiment, mutant DNA sequences are generated with site saturation mutagenesis in at least one codon. In another preferred embodiment, site saturation mutagenesis is performed for two or more codons. In a further embodiment, mutant DNA sequences have more than 40%, more than 45%, more than 50%, more than 55%, more than 60%, more than 65%, more than 70%, more than 75%, more than 80%, more than 85%, more than 90%, more than 95%, or more than 98% homology with the wild-type sequence. In alternative embodiments, mutant DNA is generated in vivo using any known mutagenic procedure such as, for example, radiation, nitrosoguanidine and the like. The desired DNA sequence is then isolated and used in the methods provided herein.

In an alternative embodiment, the transforming DNA sequence comprises homology boxes without the presence of an incoming sequence. In this embodiment, it is desired to delete the endogenous DNA sequence between the two homology boxes. Furthermore, in some embodiments, the transforming sequences are wild-type, while in other embodiments, they are mutant or modified sequences. In addition, in some embodiments, the transforming sequences are homologous, while in other embodiments, they are heterologous.

As used herein, the term "target sequence" refers to a DNA sequence in the host cell that encodes the sequence where it is desired for the incoming sequence to be inserted into the host cell genome. In some embodiments, the target sequence encodes a functional wild-type gene or operon, while in other embodiments the target sequence encodes a functional mutant gene or operon, or a non-functional gene or operon.

As used herein, a "flanking sequence" refers to any sequence that is either upstream or downstream of the sequence being discussed (e.g., for genes A-B-C, gene B is flanked by the A and C gene sequences). In a preferred embodiment, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in preferred embodiments, it is on each side of the sequence being flanked. The sequence of each homology box is homologous to a sequence in the *Bacillus* chromosome. These sequences direct where in the *Bacillus* chromosome the new construct gets integrated and what part of the *Bacillus* chromosome will be replaced by the incoming sequence. In a preferred embodiment, the 5' and 3' ends of a selective marker are flanked by a polynucleotide sequence comprising a section of the inactivating chromosomal segment. In some embodiments, a flanking sequence is present on only a single side (either 3' or 5'), while in preferred embodiments, it is present on each side of the sequence being flanked.

As used herein, the term "stuffer sequence" refers to any extra DNA that flanks homology boxes (typically vector sequences). However, the term encompasses any non-homologous DNA sequence. Not to be limited by any theory, a stuffer sequence provides a noncritical target for a cell to initiate DNA uptake.

As used herein, the term "library of mutants" refers to a population of cells which are identical in most of their genome but include different homologues of one or more genes. Such libraries find use for example, in methods to identify genes or operons with improved traits.

As used herein, the terms "hypercompetent" and "super competent" mean that greater than 1% of a cell population is transformable with chromosomal DNA (e.g., *Bacillus* DNA). Alternatively, the terms are used in reference to cell populations in which greater than 10% of a cell population is transformable with a self-replicating plasmid (e.g., a *Bacillus* plasmid). Preferably, the super competent cells are transformed at a rate greater than observed for the wild-type or parental cell population. Super competent and hypercompetent are used interchangeably herein.

As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "co-amplification" refers to the introduction into a single cell of an amplifiable marker in conjunction with other gene sequences (i.e., comprising one or more non-selectable genes such as those contained within an expression vector) and the application of appropriate selective pressure such that the cell amplifies both the amplifiable marker and the other, non-selectable gene sequences. The amplifiable marker may be physically linked to the other gene sequences or alternatively two separate pieces of DNA, one containing the amplifiable marker and the other containing the non-selectable marker, may be introduced into the same cell.

As used herein, the terms "amplifiable marker," "amplifiable gene," and "amplification vector" refer to a gene or a vector encoding a gene which permits the amplification of that gene under appropriate growth conditions.

"Template specificity" is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (See e.g., Kacian et al., Proc. Natl. Acad. Sci. USA 69:3038 [1972]). Other nucleic acids are not replicated by this amplification enzyme. Similarly, in the case of T7 RNA polymerase, this amplification enzyme has a stringent specificity for its own promoters (See, Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (See, Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "amplifiable nucleic acid" refers to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, the terms "restriction endonucleases" and "restriction enzymes" refer to bacterial enzymes, each of which cut double-stranded DNA at or near a specific nucleotide sequence.

A "restriction site" refers to a nucleotide sequence recognized and cleaved by a given restriction endonuclease and is frequently the site for insertion of DNA fragments. In certain embodiments of the invention restriction sites are engineered into the selective marker and into 5' and 3' ends of the DNA construct.

As used herein "an inactivating chromosomal segment" comprises two sections. Each section comprises polynucleotides that are homologous with the upstream or downstream genomic chromosomal DNA that immediately flanks an indigenous chromosome region as defined herein. "Immediately flanks" means the nucleotides comprising the inactivating chromosomal segment do not include the nucleotides defining the indigenous chromosomal region. The inactivating chromosomal segment directs where in the *Bacillus* chromosome the DNA construct gets integrated and what part of the *Bacillus* chromosome will be replaced.

As used herein, "indigenous chromosomal region" and "a fragment of an indigenous chromosomal region" refer to a segment of the *Bacillus* chromosome which is deleted from a *Bacillus* host cell in some embodiments of the present invention. In general, the terms "segment," "region," "section," and "element" are used interchangeably herein. In some embodiments, deleted segments include one or more genes with known functions, while in other embodiments, deleted segments include one or more genes with unknown functions, and in other embodiments, the deleted segments include a combination of genes with known and unknown functions. In some embodiments, indigenous chromosomal regions or fragments thereof include as many as 200 genes or more.

In some embodiments, an indigenous chromosomal region or fragment thereof has a necessary function under certain conditions, but the region is not necessary for *Bacillus* strain viability under laboratory conditions. Preferred laboratory conditions include but are not limited to conditions such as growth in a fermenter, in a shake flask on plated media, etc., at standard temperatures and atmospheric conditions (e.g., aerobic).

An indigenous chromosomal region or fragment thereof may encompass a range of about 0.5 kb to 500 kb; about 1.0 kb to 500 kb; about 5 kb to 500 kb; about 10 kb to 500 kb; about 10 kb to 200 kb; about 10 kb to 100 kb; about 10 kb to 50 kb; about 100 kb to 500 kb; and about 200 kb to 500 kb of the *Bacillus* chromosome. In another aspect, when an indigenous chromosomal region or fragment thereof has been deleted, the chromosome of the altered *Bacillus* strain may include 99%, 98%, 97%, 96%, 95%, 94%, 93%, 92%, 91%, 90%, 85%, 80%, 75% or 70% of the corresponding unaltered *Bacillus* host chromosome. Preferably, the chromosome of an altered *Bacillus* strain according to the invention will include about 99 to 90%; 99 to 92%; and 98 to 94% of the corresponding unaltered *Bacillus* host strain chromosome genome.

As used herein, "strain viability" refers to reproductive viability. The deletion of an indigenous chromosomal region or fragment thereof, does not deleteriously affect division and survival of the altered *Bacillus* strain under laboratory conditions.

As used herein, "altered *Bacillus* strain" refers to a genetically engineered *Bacillus* sp. wherein a protein of interest has an enhanced level of expression and/or production as compared to the expression and/or production of the same protein of interest in a corresponding unaltered *Bacillus* host strain grown under essentially the same growth conditions. In some embodiments, the enhanced level of expression results from the inactivation of one or more chromosomal genes. In one embodiment, the enhanced level of expression results from the deletion of one or more chromosomal genes. In some embodiments, the altered *Bacillus* strains are genetically engineered *Bacillus* sp. having one or more deleted indigenous chromosomal regions or fragments thereof, wherein a protein of interest has an enhanced level of expression or production, as compared to a corresponding unaltered *Bacillus* host strain grown under essentially the same growth conditions. In an alternative embodiment, the enhanced level of expression results from the insertional inactivation of one or more chromosomal genes. In some alternate embodiments, enhanced level of expression results due to increased activation or an otherwise optimized gene. In some preferred embodiments, the inactivated genes are selected from the group consisting of sbo, slr, ybcO, csn, spoIISA, phrC, sigB, rapA, CssS, trpA, trpB, trpC, trpD, trpE, trpF, tdh/kbl, alsD, sigD, prpC, gapB, pckA, fbp, rocA, ycgN, ycgM, rocF, and rocD.

In certain embodiments, the altered *Bacillus* strain comprise two inactivated genes, while in other embodiments, there are three inactivated genes, four inactivated genes, five inactivated genes, six inactivated genes, or more. Thus, it is not intended that the number of inactivated genes be limited to an particular number of genes. In some embodiments, the inactivated genes are contiguous to each another, while in other embodiments, they are located in separate regions of the *Bacillus* chromosome. In some embodiments, an inactivated chromosomal gene has a necessary function under certain conditions, but the gene is not necessary for *Bacillus* strain viability under laboratory conditions. Preferred laboratory conditions include but are not limited to conditions such as growth in a fermenter, in a shake flask, plated media, etc., suitable for the growth of the microorganism.

As used herein, a "corresponding unaltered *Bacillus* strain" is the host strain (e.g., the originating and/or wild-type strain) from which the indigenous chromosomal region or fragment thereof is deleted or modified and from which the altered strain is derived.

As used herein, the term "chromosomal integration" refers to the process whereby the incoming sequence is introduced into the chromosome of a host cell (e.g., *Bacillus*). The homologous regions of the transforming DNA align with homologous regions of the chromosome. Subsequently, the sequence between the homology boxes is replaced by the incoming sequence in a double crossover (i.e., homologous recombination). In some embodiments of the present invention, homologous sections of an inactivating chromosomal segment of a DNA construct align with the flanking homologous regions of the indigenous chromosomal region of the *Bacillus* chromosome. Subsequently, the indigenous chromosomal region is deleted by the DNA construct in a double crossover (i.e., homologous recombination).

"Homologous recombination" means the exchange of DNA fragments between two DNA molecules or paired chromosomes at the site of identical or nearly identical nucleotide sequences. In a preferred embodiment, chromosomal integration is homologous recombination.

"Homologous sequences" as used herein means a nucleic acid or polypeptide sequence having 100%, 99%, 98%, 97%, 96%, 95%, 94%, 93%, 92%, 91%, 90%, 88%, 85%, 80%, 75%, or 70% sequence identity to another nucleic acid or polypeptide sequence when optimally aligned for comparison. In some embodiments, homologous sequences have between 85% and 100% sequence identity, while in other embodiments there is between 90% and 100% sequence identity, and in more preferred embodiments, there is 95% and 100% sequence identity.

As used herein "amino acid" refers to peptide or protein sequences or portions thereof. The terms "protein", "peptide" and "polypeptide" are used interchangeably.

As used herein, "protein of interest" and "polypeptide of interest" refer to a protein/polypeptide that is desired and/or being assessed. In some embodiments, the protein of interest is intracellular, while in other embodiments, it is a secreted polypeptide. Particularly preferred polypeptides include enzymes, including, but not limited to those selected from amylolytic enzymes, proteolytic enzymes, cellulytic enzymes, oxidoreductase enzymes and plant cell-wall degrading enzymes. More particularly, these enzyme include, but are not limited to amylases, proteases, xylanases, lipases, laccases, phenol oxidases, oxidases, cutinases, cellulases, hemicellulases, esterases, perioxidases, catalases, glucose oxidases, phytases, pectinases, glucosidases, isomerases, transferases, galactosidases and chitinases. In some particularly preferred embodiments of the present invention, the polypeptide of interest is a protease. In some embodiments, the protein of interest is a secreted polypeptide which is fused to a signal peptide (i.e., an amino-terminal extension on a protein to be secreted). Nearly all secreted proteins use an amino-terminal protein extension which plays a crucial role in the targeting to and translocation of precursor proteins across the membrane. This extension is proteolytically removed by a signal peptidase during or immediately following membrane transfer.

In some embodiments of the present invention, the polypeptide of interest is selected from hormones, antibodies, growth factors, receptors, etc. Hormones encompassed by the present invention include but are not limited to, follicle-stimulating hormone, luteinizing hormone, corticotropin-releasing factor, somatostatin, gonadotropin hormone, vasopressin, oxytocin, erythropoietin, insulin and the like. Growth factors include, but are not limited to platelet-derived growth factor, insulin-like growth factors, epidermal growth factor, nerve growth factor, fibroblast growth factor, transforming growth factors, cytokines, such as interleukins (e.g., IL-1 through IL-13), interferons, colony stimulating factors, and the like. Antibodies include but are not limited to immunoglobulins obtained directly from any species from which it is desirable to produce antibodies. In addition, the present invention encompasses modified antibodies. Polyclonal and monoclonal antibodies are also encompassed by the present invention. In particularly preferred embodiments, the antibodies are human antibodies.

As used herein, the term "heterologous protein" refers to a protein or polypeptide that does not naturally occur in the host cell. Examples of heterologous proteins include enzymes such as hydrolases including proteases, cellulases, amylases, carbohydrases, and lipases; isomerases such as racemases, epimerases, tautomerases, or mutases; transferases, kinases and phophatases. In some embodiments, the proteins are therapeutically significant proteins or peptides, including but not limited to growth factors, cytokines, ligands, receptors and inhibitors, as well as vaccines and antibodies. In additional embodiments, the proteins are commercially important industrial proteins/peptides (e.g., proteases, carbohydrases such as amylases and glucoamylases, cellulases, oxidases and lipases). In some embodiments, the gene encoding the proteins are naturally occurring genes, while in other embodiments, mutated and/or synthetic genes are used.

As used herein, "homologous protein" refers to a protein or polypeptide native or naturally occurring in a cell. In preferred embodiments, the cell is a Gram-positive cell, while in particularly preferred embodiments, the cell is a *Bacillus* host cell. In alternative embodiments, the homologous protein is a native protein produced by other organisms, including but not limited to *E. coli*. The invention encompasses host cells producing the homologous protein via recombinant DNA technology.

As used herein, an "operon region" comprises a group of contiguous genes that are transcribed as a single transcription unit from a common promoter, and are thereby subject to co-regulation. In some embodiments, the operon includes a regulator gene. In most preferred embodiments, operons that are highly expressed as measured by RNA levels, but have an unknown or unnecessary function are used.

As used herein, a "multi-contiguous single gene region" is a region wherein at least the coding regions of two genes occur in tandem and in some embodiments, include intervening sequences preceding and following the coding regions. In some embodiments, an antimicrobial region is included.

As used herein, an "antimicrobial region" is a region containing at least one gene that encodes an antimicrobial protein.

DETAILED DESCRIPTION OF THE INVENTION

The present invention provides cells that have been genetically manipulated to have an altered capacity to produce expressed proteins. In particular, the present invention relates to Gram-positive microorganisms, such as *Bacillus* species having enhanced expression of a protein of interest, wherein one or more chromosomal genes have been inactivated, and preferably wherein one or more chromosomal genes have been deleted from the *Bacillus* chromosome. In some further embodiments, one or more indigenous chromosomal regions have been deleted from a corresponding wild-type *Bacillus* host chromosome. Indeed, the present invention provides means for deletion of single or multiple genes, as well as large chromosomal deletions. In preferred embodiments, such deletions provide advantages such as improved production of a protein of interest.

A. Gene Deletions

As indicated above, the present invention includes embodiments that involve singe or multiple gene deletions and/or mutations, as well as large chromosomal deletions.

In some preferred embodiments, the present invention includes a DNA construct comprising an incoming sequence. The DNA construct is assembled in vitro, followed by direct cloning of the construct into a competent *Bacillus* host, such that the DNA construct becomes integrated into the *Bacillus* chromosome. For example, PCR fusion and/or ligation can be employed to assemble a DNA construct in vitro. In some embodiments, the DNA construct is a non-plasmid construct, while in other embodiments it is incorporated into a vector (e.g., a plasmid). In some embodiments, circular plasmids are used. In preferred embodiments, circular plasmids are designed to use an appropriate restriction enzyme (i.e., one that does not disrupt the DNA construct). Thus, linear plasmids find use in the present invention (See, FIG. 1A and FIG. 1B). However, other methods are suitable for use in the present invention, as known to those in the art (See e.g., Perego, "Integrational Vectors for Genetic Manipulation in *Bacillus subtilis*," in (Sonenshein et al. (eds.), *Bacillus subtilis and Other Gram-Positive Bacteria*, American Society for Microbiology, Washington, D.C. [1993]).

In some embodiments, the incoming sequence includes a selective marker. In some preferred embodiments, the incoming sequence includes a chromosomal gene selected from the group consisting of sbo, slr, ybcO, csn, spoIISA, phrC, sigB, rapA, CssS, trpA, trpB, trpC, trpD, trpE, trpF, tdh/kbl, alsD, sigD, prpC, gapB, pckA, fbp, rocA, ycgN, ycgM, rocF, and rocD or fragments of any of these genes (alone or in combination). In additional embodiments, the incoming sequence includes a homologous sbo, slr, ybcO, csn, spoIISA, phrC, sigB, rapA, CssS trpA, trpB, trpC, trpD, trpE, trpF, tdh/kbl, alsD, sigD, prpC, gapB, pckA, fbp, rocA, ycgN, ycgM, rocF, and/or rocD gene sequence. A homologous sequence is a nucleic acid sequence having at least 99%, 98%, 97%, 96%, 95%, 94% 93%, 92%, 91%, 90%, 88%, 85% or 80% sequence identity to a sbo, slr, ybcO, csn, spoIISA, phrC, sigB, rapA, CssS trpA, trpB, trpC, trpD, trpE, trpF, tdh/kbl, alsD, sigD, prpC, gapB, pckA, fbp, rocA, ycgN, ycgM, rocF, and rocD gene or gene fragment thereof, which may be included in the incoming sequence. In preferred embodiments, the incoming sequence comprising a homologous sequence comprises at least 95% sequence identity to a sbo, slr, ybcO, csn, spoIISA, phrC, sigB, rapA, CssS trpA, trpB, trpC, trpD, trpE, trpF, tdh/kbl, alsD, sigD, prpC, gapB, pckA, fbp, rocA, ycgN, ycgM, rocF, or rocD gene or gene fragment of any of these genes. In yet other embodiments, the incoming sequence comprises a selective marker flanked on the 5' and 3' ends with a fragment of the gene sequence. In some embodiments, when the DNA construct comprising the selective marker and gene, gene fragment or homologous sequence thereto is transformed into a host cell, the location of the selective marker renders the gene non-functional for its intended purpose. In some embodiments, the incoming sequence comprises the selective marker located in the promoter region of the gene. In other embodiments, the incoming sequence comprises the selective marker located after the promoter region of gene. In yet other embodiments, the incoming sequence comprises the selective marker located in the coding region of the gene. In further embodiments, the incoming sequence comprises a selective marker flanked by a homology box on both ends. In still further embodiments, the incoming sequence includes a sequence that interrupts the transcription and/or translation of the coding sequence. In yet additional embodiments, the DNA construct includes restriction sites engineered at the upstream and downstream ends of the construct.

Whether the DNA construct is incorporated into a vector or used without the presence of plasmid DNA, it is used to transform microorganisms. It is contemplated that any suitable method for transformation will find use with the present invention. In preferred embodiments, at least one copy of the DNA construct is integrated into the host *Bacillus* chromosome. In some embodiments, one or more DNA constructs of the invention are used to transform host cells. For example, one DNA construct may be used to inactivate a slr gene and another construct may be used to inactivate a phrC gene. Of course, additional combinations are contemplated and provided by the present invention.

In some preferred embodiments, the DNA construct also includes a polynucleotide encoding a protein of interest. In some of these preferred embodiments, the DNA construct also includes a constitutive or inducible promoter that is operably linked to the sequence encoding the protein of interest. In some preferred embodiments in which the protein of interest is a protease, the promoter is selected from the group consisting of a tac promoter, a β-lactamase promoter, or an aprE promoter (DeBoer et al., Proc. Natl. Acad. Sci. USA 80:21-25 [1983]). However, it is not intended that the present invention be limited to any particular promoter, as any suitable promoter known to those in the art finds use with the present invention. Nonetheless, in particularly preferred embodiments, the promoter is the *B. subtilis* aprE promoter.

Various methods are known for the transformation of *Bacillus* species. Indeed, methods for altering the chromosome of *Bacillus* involving plasmid constructs and transformation of the plasmids into *E. coli* are well known. In most methods, plasmids are subsequently isolated from *E. coli* and transformed into *Bacillus*. However, it is not essential to use such intervening microorganisms such as *E. coli*, and in some preferred embodiments, the DNA construct is directly transformed into a competent *Bacillus* host.

In some embodiments, the well-known *Bacillus subtilis* strain 168 finds use in the present invention. Indeed, the genome of this strain has been well-characterized (See, Kunst et al., Nature 390:249-256 [1997]; and Henner et al., Microbiol. Rev., 44:57-82 [1980]). The genome is comprised of one 4215 kb chromosome. While the coordinates used herein refer to the 168 strain, the invention encompasses analogous sequences from *Bacillus* strains.

In some embodiments, the incoming chromosomal sequence includes one or more genes selected from the group consisting of sbo, slr, ybcO, csn, spoIISA, sigB, phrC, rapA, CssS, trpA, trpB, trpC, trpD, trpE, trpF, tdh/kbl, alsD, sigD, prpC, gapB, pckA, fbp, rocA, ycgN, ycgM, rocF, and rocD gene fragments thereof and homologous sequences thereto. The DNA coding sequences of these genes from *B. subtilis* 168 are provided in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO:17, SEQ ID NO:39, SEQ ID NO:40, SEQ ID NO:42, SEQ ID NO:44, SEQ ID NO:46, SEQ ID NO:48, SEQ ID NO:50, SEQ ID NO:37, SEQ ID NO:25, SEQ ID NO:21, SEQ ID NO:50, SEQ ID NO:29, SEQ ID NO:23, SEQ ID NO:27, SEQ ID NO:19, SEQ ID NO:31, SEQ ID NO:48, SEQ ID NO:46, SEQ ID NO:35, and SEQ ID NO:33.

As mentioned above, in some embodiments, the incoming sequence which comprises a sbo, slr, ybcO, csn, spoIISA, sigB, phrC, rapA, CssS, trpA, trpB, trpC, trpD, trpE, trpF, tdh, kbl, alsD, sigD, prpC, gapB, pckA, fbp, rocA, ycgN, ycgM, rocF, and rocD gene, a gene fragment thereof, or a homologous sequence thereto includes the coding region and may further include immediate chromosomal coding region flanking sequences. In some embodiments the coding region flanking sequences include a range of about 1 bp to 2500 bp; about 1 bp to 1500 bp, about 1 bp to 1000 bp, about 1 bp to 500 bp, and 1 bp to 250 bp. The number of nucleic acid sequences comprising the coding region flanking sequence may be different on each end of the gene coding sequence. For example, in some embodiments, the 5' end of the coding sequence includes less than 25 bp and the 3' end of the coding sequence includes more than 100 bp. Sequences of these genes and gene products are provided below. The numbering used herein is that used in subtilist (See e.g., Moszer et al., Microbiol., 141:261-268 [1995]).

The sbo coding sequence of *B. subtilis* 168 is shown below:

```
                                        (SEQ ID NO: 1)
ATGAAAAAAGCTGTCATTGTAGAAAACAAAGGTTGTGCAACATGCTCGAT

CGGAGCCGCTTGTCTAGTGGACGGTCCTATCCCTGATTTTGAAATTGCCG

GTGCAACAGGTCTATTCGGTCTATGGGGG.
```

The deduced amino acid sequence for Sbo is:

```
                                        (SEQ ID NO: 2)
   MKKAVIVENKGCATCSIGAACLVDGPIPDFEIAGATGLFGLWG.
```

In one embodiment, the gene region found at about 3834868 to 3835219 bp of the *B. subtilis* 168 chromosome was deleted using the present invention. The sbo coding region found at about 3835081 to 3835209 produces subtilisin A, an antimicrobial that has activity against some Gram-positive bacteria. (See, Zheng et al., J. Bacteriol., 181:7346-7355 [1994]).

The slr coding sequence of *B. subtilis* 168 is shown below:

```
                                        (SEQ ID NO: 3)
ATGATTGGAAGAATTATCCGTTTGTACCGTAAAAGAAAAGGCTATTCTAT

TAATCAGCTGGCTGTTGAGTCAGGCGTATCCAAATCCTATTTAAGCAAGA

TTGAAAGAGGCGTTCACACGAATCCGTCCGTTCAATTTTTAAAAAAAGTT

TCTGCCACACTGGAAGTTGAATTAACAGAATTATTTGACGCAGAAACAAT

GATGTATGAAAAAATCAGCGGCGGTGAAGAAGAATGGCGCGTACATTTAG

TGCAAGCCGTACAAGCCGGGATGGAAAAGGAAGAATTGTTCACTTTTACG

AACAGACTCAAGAAAGAACAGCCTGAAACTGCCTCTTACCGCAACCGCAA

ACTGACGGAATCCAATATAGAAGAATGGAAAGCGCTGATGGCGGAGGCAA

GAGAAATCGGCTTGTCTGTCCATGAAGTCAAATCCTTTTTAAAAACAAAG

GGAAGA.
```

The deduced amino acid sequence for Slr is:

```
                                        (SEQ ID NO: 4)
MIGRIIRLYRKRKGYSINQLAVESGVSKSYLSKIERGVHTNPSVQFLKKV

SATLEVELTELFDAETMMYEKISGGEEEWRVHLVQAVQAGMEKEELFTFT

NRLKKEQPETASYRNRKLTESNIEEWKALMAEAREIGLSVHEVKSFLKTK

GR.
```

In one embodiment, the sequence found at about 3529014-3529603 bp of the *B. subtilis* 168 chromosome was deleted using the present invention. The slr coding sequence is found at about 3529131 to 3529586 of the chromosome.

The phrC coding sequence of *B. subtilis* 168 is provided below:

(SEQ ID NO: 13)
ATGAAATTGAAATCTAAGTTGTTTGTTATTTGTTTGGCCGCAGCCGCGAT
TTTTACAGCGGCTGGCGTTTCTGCTAATGCGGAAGCACTCGACTTTCATG
TGACAGAAAGAGGAATGACG.

The deduced amino acid sequence for PhrC is:

(SEQ ID NO: 14)
MKLKSKLFVICLAAAAIFTAAGVSANAEALDFHVTERGMT

Additionally, the coding region found at about 429531 to 429650 bp of the *B. subtilis* 168 chromosome was inactivated by an insertion of a selective marker at 429591 of the coding sequence.

The sigB coding sequence of *B. subtilis* 168 is shown below:

(SEQ ID NO: 9)
TTGATCATGACACAACCATCAAAAACTACGAAACTAACTAAAGATGAAGT
CGATCGGCTCATAAGCGATTACCAAACAAAGCAAGATGAACAAGCGCAGG
AAACGCTTGTGCGGGTGTATACAAATCTGGTTGACATGCTTGCGAAAAAA
TACTCAAAAGGCAAAAGCTTCCACGAGGATCTCCGCCAGGTCGGCATGAT
CGGGCTGCTAGGCGCGATTAAGCGATACGATCCTGTTGTCGGCAAATCGT
TTGAAGCTTTTGCAATCCCGACAATCATCGGTGAAATTAAACGTTTCCTC
AGAGATAAAACATGGAGCGTTCATGTGCCGAGACGAATTAAAGAACTCGG
TCCAAGAATCAAAATGGCGGTTGATCAGCTGACCACTGAAACACAAAGAT
CGCCGAAAGTCGAAGAGATTGCCGAATTCCTCGATGTTTCTGAAGAAGAG
GTTCTTGAAACGATGGAAATGGGCAAAAGCTATCAAGCCTTATCCGTTGA
CCACAGCATTGAAGCGGATTCGGACGGAAGCACTGTCACGATTCTTGATA
TCGTCGGATCACAGGAGGACGGATATGAGCGGGTCAACCAGCAATTGATG
CTGCAAAGCGTGCTTCATGTCCTTTCAGACCGTGAGAAACAAATCATAGA
CCTTACGTATATTCAAAACAAAAGCCAAAAAGAAACTGGGGACATTCTCG
GTATATCTCAAATGCACGTCTCGCGCTTGCAACGCAAAGCTGTGAAGAAG
CTCAGAGAGGCCTTGATTGAAGATCCCTCGATGGAGTTAATG.

The deduced amino acid sequence for SigB is:

(SEQ ID NO: 10)
MIMTQPSKTTKLTKDEVDRLISDYQTKQDEQAQETLVRVYTNLVDMLAKK
YSKGKSFHEDLRQVGMIGLLGAIKRYDPVVGKSFEAFAIPTIIGEIKRFL
RDKTWSVHVPRRIKELGPRIKMAVDQLTTETQRSPKVEEIAEFLDVSEEE
VLETMEMGKSYQALSVDHSIEADSDGSTVTILDIVGSQEDGYERVNQQLM
LQSVLHVLSDREKQIIDLTYIQNKSQKETGDILGISQMHVSRLQRKAVKK
LREALIEDPSMELM.

Additionally, the coding sequence is found at about 522417 to 5232085 bp of the *B. subtilis* 168 chromosome.

The spoIISA coding sequence of *B. subtilis* 168 is shown below:

(SEQ ID NO: 11)
ATGGTTTTATTCTTTCAGATCATGGTCTGGTGCATCGTGGCCGGACTGGG
GTTATACGTGTATGCCACGTGGCGTTTCGAAGCGAAGGTCAAAGAAAAAA
TGTCCGCCATTCGGAAAACTTGGTATTTGCTGTTTGTTCTGGGCGCTATG
GTATACTGGACATATGAGCCCACTTCCCTATTTACCCACTGGGAACGGTA
TCTCATTGTCGCAGTCAGTTTTGCTTTGATTGATGCTTTTATCTTCTTAA
GTGCATATGTCAAAAAACTGGCCGGCAGCGAGCTTGAAACAGACACAAGA
GAAATTCTTGAAGAAAACAACGAAATGCTCCACATGTATCTCAATCGGCT
GAAAACATACCAATACCTATTGAAAAACGAACCGATCCATGTTTATTATG
GAAGTATAGATGCTTATGCTGAAGGTATTGATAAGCTGCTGAAAACCTAT
GCTGATAAAATGAACTTAACGGCTTCTCTTTGCCACTATTCGACACAGGC
TGATAAAGACCGGTTAACCGAGCATATGGATGATCCGGCAGATGTACAAA
CACGGCTCGATCGAAAGGATGTTTATTACGACCAATACGGAAAAGTGGTT
CTCATCCCTTTTACCATCGAGACACAGAACTATGTCATCAAGCTGACGTC
TGACAGCATTGTCACGGAATTTGATTATTTGCTATTTACGTCATTAACGA
GCATATATGATTTGGTGCTGCCAATTGAGGAGGAAGGTGAAGGA.

The deduced amino acid sequence for SpoIISA is:

(SEQ ID NO: 12)
MVLFFQIMVWCIVAGLGLYVYATANRFEAKVKEKMSAIRKTWYLLFVLGA
MVYWTYEPTSLFTHWERYLIVAVSFALIDAFIFLSAYVKKLAGSELETDT
REILEENNEMLHMYLNRLKTYQYLLKNEPIHVYYGSIDAYAEGIDKLLKT
YADKMNLTASLCHYSTQADKDRLTEHMDDPADVQTRLDRKDVYYDQYGKV
VLIPFTIETQNYVIKLTSDSIVTEFDYLLFTSLTSIYDLVLPIEEEGEG.

Additionally, the coding region is found at about 1347587 to 1348714 bp of the *B. subtilis* 168 chromosome.

The can coding sequence of *B. subtilis* 168 is shown below:

(SEQ ID NO: 7)
ATGAAAAATCAGTATGCAAAAAGCAGATTTTTGGAAAAAAGCAGCGATCTC
ATTACTTGTTTTCACCATGTTTTTTACCCTGATGATGAGCGAAACGGTTT
TTGCGGCGGGACTGAATAAAGATCAAAAGCGCCGGGCGGAACAGCTGACA
AGTATCTTTGAAAACGGCACAACGGAGATCCAATATGGATATGTAGAGCG
ATTGGATGACGGGCGAGGCTATACATGCGGACGGGCAGGCTTTACAACGG
CTACCGGGGATGCATTGGAAGTAGTGGAAGTATACACAAAGGCAGTTCCG
AATAACAAACTGAAAAAGTATCTGCCTGAATTGCGCCGTCTGGCCAAGGA
AGAAAGCGATGATACAAGCAATCTCAAGGGATTCGCTTCTGCCTGGAAGT
CGCTTGCAAATGATAAGGAATTTCGCGCCGCTCAAGACAAAGTAAATGAC
CATTTGTATTATCAGCCTGCCATGAAACGATCGGATAATGCCGGACTAAA
AACAGCATTGGCAAGAGCTGTGATGTACGATACGGTTATTCAGCATGGCG
ATGGTGATGACCCTGACTCTTTTTATGCCTTGATTAAACGTACGAACAAA
AAAGCGGGCGGATCACCTAAAGACGGAATAGACGAGAAGAAGTGGTTGAA
TAAATTCTTGGACGTACGCTATGACGATCTGATGAATCCGGCCAATCATG

-continued

ACACCCGTGACGAATGGAGAGAATCAGTTGCCCGTGTGGACGTGCTTCGC

TCTATCGCCAAGGAGAACAACTATAATCTAAACGGACCGATTCATGTTCG

TTCAAACGAGTACGGTAATTTTGTAATCAAA.

The deduced amino acid sequence for Csn is:

(SEQ ID NO: 8)

MKISMQKADFWKKAAISLLVFTMFFTLMMSETVFAAGLNKDQKRRAEQLT

SIFENGTTEIQYGYVERLDDGRGYTCGRAGFTTATGDALEVVEVYTKAVP

NNKLKKYLPELRRLAKEESDDTSNLKGFASAWKSLANDKEFRAAQDKVND

HLYYQPAMKRSDNAGLKTALARAVMYDTVIQHGDGDDPDSFYALIKRTNK

KAGGSPKDGIDEKKWLNKFLDVRYDDLMNPANHDTRDEWRESVARVDVLR

SIAKENNYNLNGPIHVRSNEYGNFVIK.

Additionally, the coding region is found at about 2747213 to 2748043 bp of the *B. subtilis* 168 chromosome.

The ybcO coding sequence of *B. subtilis* 168 is shown below:

(SEQ ID NO: 5)

ATGAAAAGAAACCAAAAAGAATGGGAATCTGTGAGTAAAAAAGGACTTAT

GAAGCCGGGAGGTACTTCGATTGTGAAAGCTGCTGGCTGCATGGGCTGTT

GGGCCTCGAAGAGTATTGCTATGACACGTGTTTGTGCACTTCCGCATCCT

GCTATGAGAGCTATT.

The deduced amino acid sequence for YbcO is:

(SEQ ID NO: 6)

MKRNQKEWESVSKKGLMKPGGTSIVKAAGCMGCWASKSIAMTRVCALPHP

AMRAI.

Additionally, the coding region is found at about 213926 to 214090 bp of the *B. subtilis* 168 chromosome.

The rapA coding sequence of *B. subtilis* 168 is shown below:

(SEQ ID NO: 15)

TTGAGGATGAAGCAGACGATTCCGTCCTCTTATGTCGGGCTTAAAATTAA

TGAATGGTATACTCATATCCGGCAGTTCCACGTCGCTGAAGCCGAACGGG

TCAAGCTCGAAGTAGAAAGAGAAATTGAGGATATGGAAGAAGACCAAGAT

TTGCTGCTGTATTATTCTTTAATGGAGTTCAGGCACCGTGTCATGCTGGA

TTACATTAAGCCTTTTGGAGAGGACACGTCGCAGCTAGAGTTTTCAGAAT

TGTTAGAAGACATCGAAGGGAATCAGTACAAGCTGACAGGGCTTCTCGAA

TATTACTTTAATTTTTTTCGAGGAATGTATGAATTTAAGCAGAAGATGTT

TGTCAGTGCCATGATGTATTATAAACGGGCAGAAAAGAATCTTGCCCTCG

TCTCGGATGATATTGAGAAAGCAGAGTTTGCTTTTAAAATGGCTGAGATT

TTTTACAATTTAAAACAAACCTATGTTTCGATGAGCTACGCCGTTCAGGC

ATTAGAAACATACCAAATGTATGAAACGTACACCGTCCGCAGAATCCAAT

GTGAATTCGTTATTGCAGGTAATTATGATGATATGCAGTATCCAGAAAGA

-continued

GCATTGCCCCACTTAGAACTGGCTTTAGATCTTGCAAAGAAAGAAGGCAA

TCCCCGCCTGATCAGTTCTGCCCTATATAATCTCGGAAACTGCTATGAGA

AAATGGGTGAACTGCAAAAGGCAGCCGAATACTTTGGGAAATCTGTTTCT

ATTTGCAAGTCGGAAAAGTTCGATAATCTTCCGCATTCTATCTACTCTTT

AACACAAGTTCTGTATAAACAAAAAAATGACGCCGAAGCGCAAAAAAAGT

ATCGTGAAGGATTGGAAATCGCCCGTCAATACAGTGATGAATTATTTGTG

GAGCTTTTTCAATTTTTACATGCGTTATACGGAAAAAACATTGACACAGA

ATCAGTCTCACACACCTTTCAATTTCTTGAAGAACATATGCTGTATCCTT

ATATTGAAGAGCTGGCGCATGATGCTGCCCAATTCTATATAGAAAACGGA

CAGCCCGAAAAAGCACTTTCATTTTATGAGAAAATGGTGCACGCACAAAA

ACAAATCCAGAGAGGAGATTGTTTATATGAAATC.

The deduced amino acid sequence for RapA is:

(SEQ ID NO: 16)

MRMKQTIPSSYVGLKINEWYTHIRQFHVAEAERVKLEVEREIEDMEEDQD

LLLYYSLMEFRHRVMLDYIKPFGEDTSQLEFSELLEDIEGNQYKLTGLLE

YYFNFFRGMYEFKQKMFVSAMMYYKRAEKNLALVSDDIEKAEFAFKMAEI

FYNLKQTYVSMSYAVQALETYQMYETYTVRRIQCEFVIAGNYDDMQYPER

ALPHLELALDLAKKEGNPRLISSALYNLGNCYEKMGELQKAAEYFGKSVS

ICKSEKFDNLPHSIYSLTQVLYKQKNDAEAQKKYREGLEIARQYSDELFV

ELFQFLHALYGKNIDTESVSHTFQFLEEHMLYPYIEELAHDAAQFYIENG

QPEKALSFYEKMVHAQKQIQRGDCLYEI

Additionally, the coding region is found at about 1315179 to 1316312 bp of the *B. subtilis* 168 chromosome.

The Css coding sequence of *B. subtilis* 168 is shown below:

(SEQ ID NO: 17)

ATGAAAAAACAAGCCGCTCGCGTTTCAGATATGGGTTGTCATATCCGGCAT

CCTGTTAGCGATATCGATTTTACTGCTTGTGTTATTTTCAAACACGCTGC

GAGATTTTTTCACTAATGAAACGTATACGACGATTGAAAATGAGCAGCAT

GTTCTGACAGAGTACCGCCTGCCAGGTTCGATTGAAAGGCGCTATTACAG

CGAGGAAGCGACGGCGCCGACAACTGTCCGCTCCGTACAGCACGTGCTCC

TTCCTGAAAATGAAGAGGCTTCTTCAGACAAGGATTTAAGCATTCTGTCA

TCTTCATTTATCCACAAGGTGTACAAGCTGGCTGATAAGCAGGAAGCTAA

AAAGAAACGTTACAGCGCCGACGTCAATGGAGAGAAAGTGTTTTTTGTCA

TTAAAAAGGGACTTTCCGTCAATGGACAATCAGCGATGATGCTCTCTTAC

GCGCTTGATTCTTATCGGGACGATTTGGCCTATACCTTGTTCAAACAGCT

TCTGTTTATTATAGCTGTCGTCATTTTTATTAAGCTGGATTCCGGCTATTT

GGCTTGCAAAGTATTTATCAAGGCCTCTTGTATCATTTGAAAAACACGTC

AAACGGATTTCTGAACAGGATTGGGATGACCCAGTAAAAGTGGACCGGAA

AGATGAAATCGGCAAATTGGGCCATACCATCGAAGAGATGCGCCAAAAGC

TTGTGCAAAAGGATGAAACAGAAAGAACTCTATTGCAAAATATCTCTCAT

-continued

GATTTAAAAACGCCGGTCATGGTCATCAGAGGCTATACACAATCAATTAA

AGACGGGATTTTTCCTAAAGGAGACCTTGAAAACACTGTAGATGTTATTG

AATGCGAAGCTCTTAAGCTGGAGAAAAAAATAAAGGATTTATTATATTTA

ACGAAGCTGGATTATTTAGCGAAGCAAAAAGTGCAGCACGACATGTTCAG

TATTGTGGAAGTGACAGAAGAAGTCATCGAACGATTGAAGTGGGCGCGGA

AAGAACTATCGTGGGAAATTGATGTAGAAGAGGATATTTTGATGCCGGGC

GATCCGGAGCAATGGAACAAACTCCTCGAAAACATTTTGGAAAATCAAAT

CCGCTATGCTGAGACAAAAATAGAAATCAGCATGAAACAAGATGATCGAA

ATATCGTGATCACCATTAAAAATGACGGTCCGCATATTGAAGATGAGATG

CTCTCCAGCCTCTATGAGCCTTTTAATAAAGGGAAGAAAGGCGAATTCGG

CATTGGTCTAAGCATCGTAAAACGAATTTTAACTCTTCATAAGGCATCTA

TCTCAATTGAAAATGACAAAACGGGTGTATCATACCGCATAGCAGTGCCA

AAA.

The deduced amino acid sequence for Css (GenBank Accession No. O32193) is:

(SEQ ID NO: 18)

MKNKPLAFQIWVVISGILLAISILLLVLFSNTLRDFFTNETYTTIENEQH

VLTEYRLPGSIERRYYSEEATAPTTVRSVQHVLLPENEEASSDKDLSILS

SSFIHKVYKLADKQEAKKKRYSADVNGEKVFFVIKKGLSVNGQSAMMLSY

ALDSYRDDLAYTLFKQLLFIIAVVILLSWIPAIWLAKYLSRPLVSFEKHV

KRISEQDWDDPVKVDRKDEIGKLGHTIEEMRQKLVQKDETERTLLQNISH

DLKTPVMVIRGYTQSIKDGIFPKGDLENTVDVIECEALKLEKKIKDLLYL

TKLDYLAKQKVQHDMFSIVEVTEEVIERLKWARKELSWEIVEEDILMPGD

PEQWNKLLENILENQIRYAETKIEISMKQDDRNIVITIKNDGPHIEDEML

SSLYEPFNKGKKGEFGIGLSIVKRILTLHKASISIENDKTGVSYRIAVP

K.

Additionally, the gene region is found at about 3384612 to 3386774 bp of the *B. subtilis* 168 chromosome.

The fbp coding sequence of the Fbp protein (fructose-1, 6-biophosphatase) of *B. subtilis* 168 is shown below:

(SEQ ID NO: 19)

ATGTTTAAAAATAATGTCATACTTTTAAATTCACCTTATCATGCACATGC

TCATAAAGAGGGGTTTATTCTAAAAAGGGGATGGACGGTTTTGGAAAGCA

AGTACCTAGATCTACTCGCACAAAAATACGATTGTGAAGAAAAAGTGGTA

ACAGAAATCATCAATTTGAAAGCGATATTGAACCTGCCAAAAGGCACCGA

GCATTTTGTCAGTGATCTGCACGGAGAGTATCAGGCATTCCAGCACGTGT

TGCGCAATGGTTCAGGACGAGTCAAAGAGAAGATACGCGACATCTTCAGC

GGTGTCATTTACGATAGAGAAATTGATGAATTAGCAGCATTGGTCTATTA

TCCGGAAGACAAACTGAAATTAATCAAACATGACTTTGATGCGAAAGAAG

CGTTAAACGAGTGGTATAAAGAAACGATTCATCGAATGATTAAGCTCGTT

TCATATTGCTCCTCTAAGTATACCCGCTCCAAATTACGCAAAGCACTGCC

TGCCCAATTTGCTTATATTACGGAGGAGCTGTTATACAAAACAGAACAAG

-continued

CTGGCAACAAGGAGCAATATTACTCCGAAATCATTGATCAGATCATTGAA

CTTGGCCAAGCCGATAAGCTGATCACCGGCCTTGCTTACAGCGTTCAGCG

ATTGGTGGTCGACCATCTGCATGTGGTCGGCGATATTTATGACCGCGGCC

CGCAGCCGGATAGAATTATGGAAGAACTGATCAACTATCATTCTGTCGAT

ATTCAGTGGGGAAATCACGATGTCCTTTGGATCGGCGCCTATTCCGGTTC

CAAAGTGTGCCTGGCCAATATTATCCGCATCTGTGCCCGCTACGACAACC

TGGATATTATTGAGGACGTGTACGGCATCAACCTGAGACCGCTGCTGAAC

CTGGCCGAAAAATATTATGATGATAATCCAGCGTTCCGTCCAAAAGCAGA

CGAAAACAGGCCAGAGGATGAGATTAAGCAAATCACAAAAATCCATCAAG

CGATTGCCATGATCCAATTCAAGCTTGAGAGCCCGATTATCAAGAGACGG

CCGAACTTTAATATGGAAGAGCGGCTGTTATTAGAGAAAATAGACTATGA

CAAAAATGAAATCACGCTGAACGGAAAAACATATCAACTGGAAAACACCT

GCTTTGCGACGATTAATCCGGAGCAGCCAGATCAGCTATTAGAAGAAGAA

GCAGAAAGTCATAGACAAGCTGCTATTCTCTGTCCAGCATTCCGAAAAGCT

GGGCCGCCATATGAATTTTATGATGAAAAAAGGCAGCCTTTATTTAAAAT

ATAACGGCAACCTGTTGATTCACGGCTGTATTCCAGTTGATGAAAACGGC

AATATGGAAACGATGATGATTGAGGATAAACCGTATGCGGGCCGTGAGCT

GCTCGATGTATTTGAACGATTCTTGCGGGAAGCCTTTGCCCACCCGGAAG

AAACCGATGACCTGGCGACAGATATGGCTTGGTATTTATGGACAGGCGAA

TACTCCTCCCTCTTCGGAAAACGCGCCATGACGACATTTGAGCGCTATTT

CATCAAAGAGAAGGAAACGCATAAAGAGAAGAAAAACCCGTATTATTATT

TACGAGAAGACGAGGCAACCTGCCGAAACATCCTGGCAGAATTCGGCCTC

AATCCAGATCACGGCCATATCATCAACGGCCATACACCTGTAAAAGAAAT

CGAAGGAGAAGACCCAATCAAAGCAAACGGAAAAATGATCGTCATCGACG

GCGGCTTCTCCAAAGCCTACCAATCCACAACAGGCATCGCCGGCTACACG

CTGCTATACAACTCCTACGGCATGCAGCTCGTCGCCCATAAACACTTCAA

TTCCAAGGCAGAAGTCCTAAGCACCGGAACCGACGTCTTAACGGTCAAAC

GATTAGTGGACAAAGAGCTTGAGCGGAAGAAAGTGAAGGAAACGAATGTG

GGTGAGGAATTGTTGCAGGAAGTTGCGATTTTAGAGAGTTTGCGGGAGTA

TCGGTATATGAAG.

The deduced amino acid sequence of the Fbp protein is:

(SEQ ID NO: 20)

MFKNNVILLNSPYHAHAHKEGFILKRGWTVLESKYLDLLAQKYDCEEKVV

TEIINLKAILNLPKGTEHFVSDLHGEYQAFQHVLRNGSGRVKEKIRDIFS

GVIYDREIDELAALVYYPEDKLKLIKHDFDAKEALNEWYKETIHRMIKLV

SYCSSKYTRSKLRKALPAQFAYITEELLYKTEQAGNKEQYYSEIIDQIIE

LGQADKLITGLAYSVQRLVVDHLHVVGDIYDRGPQPDRIMEELINYHSVD

IQWGNHDVLWIGAYSGSKVCLANIIRICARYDNLDIIEDVYGINLRPLLN

LAEKYYDDNPAFRPKADENRPEDEIKQITKIHQAIAMIQFKLESPIIKRR

PNFNMEERLLLEKIDYDKNEITLNGKTYQLENTCFATINPEQPDQLLEEE

-continued

AEVIDKLLFSVQHSEKLGRHMNFMMKKGSLYLKYNGNLLIHGCIPVDENG

NMETMMIEDKPYAGRELLDVFERFLREAFAHPEETDDLATDMAWYLWTGE

YSSLFGKRAMTTFERYFIKEKETHKEKKNPYYYLREDEATCRNILAEFGL

NPDHGHIINGHTPVKEIEGEDPIKANGKMIVIDGGFSKAYQSTTGIAGYT

LLYNSYGMQLVAHKHFNSKAEVLSTGTDVLTVKRLVDKELERKKVKETNV

GEELLQEVAILESLREYRYMK.

Additionally, the coding region is found at about 4127053 to 4129065 bp of the *B. subtilis* 168 chromosome.

The alsD coding sequence of the alsD protein (alpha-acetolactate decarboxylase) of *B. subtilis* 168 is shown below:

(SEQ ID NO: 21)

ATGAAACGAGAAAGCAACATTCAAGTGCTCAGCCGTGGTCAAAAAGATCA

GCCTGTGAGCCAGATTTATCAAGTATCAACAATGACTTCTCTATTAGACG

GAGTATATGACGGAGATTTTGAACTGTCAGAGATTCCGAAATATGGAGAC

TTCGGTATCGGAACCTTTAACAAGCTTGACGGAGAGCTGATTGGGTTTGA

CGGCGAATTTTACCGTCTTCGCTCAGACGGAACCGCGACACCGGTCCAAA

ATGGAGACCGTTCACCGTTCTGTTCATTTACGTTCTTTACACCGGACATG

ACGCACAAAATTGATGCGAAAATGACACGCGAAGACTTTGAAAAAGAGAT

CAACAGCATGCTGCCAAGCAGAAACTTATTTTATGCAATTCGCATTGACG

GATTGTTTAAAAAGGTGCAGACAAGAACAGTAGAACTTCAAGAAAAACCT

TACGTGCCAATGGTTGAAGCGGTCAAAACACAGCCGATTTTCAACTTCGA

CAACGTGAGAGGAACGATTGTAGGTTTCTTGACACCAGCTTATGCAAACG

GAATCGCCGTTTCTGGCTATCACCTGCACTTCATTGACGAAGGACGCAAT

TCAGGCGGACACGTTTTTGACTATGTGCTTGAGGATTGCACGGTTACGAT

TTCTCAAAAAATGAACATGAATCTCAGACTTCCGAACACAGCGGATTTCT

TTAATGCGAATCTGGATAACCCTGATTTTGCGAAAGATATCGAAACAACT

GAAGGAAGCCCTGAA.

The deduced amino acid sequence AlsD protein sequence is:

(SEQ ID NO: 22)

MKRESNIQVLSRGQKDQPVSQIYQVSTMTSLLDGVYDGDFELSEIPKYGD

FGIGTFNKLDGELIGFDGEFYRLRSDGTATPVQNGDRSPFCSFTFFTPDM

THKIDAKMTREDFEKEINSMLPSRNLFYAIRIDGLFKKVQTRTVELQEKP

YVPMVEAVKTQPIFNFDNVRGTIVGFLTPAYANGIAVSGYHLHFIDEGRN

SGGHVFDYVLEDCTVTISQKMNMNLRLPNTADFFNANLDNPDFAKDIETT

EGSPE.

Additionally, the coding region is found at about 3707829-3708593 bp of the *B. subtilis* 168 chromosome.

The gapB coding sequence of the gapB protein (glyceraldehyde-3-phosphate dehydrogenase) of *B. subtilis* 168 is shown below:

(SEQ ID NO: 23)

ATGAAGGTAAAAGTAGCGATCAACGGGTTTGGAAGAATCGGAAGAATGGT

TTTTAGAAAAGCGATGTTAGACGATCAAATTCAAGTAGTGGCCATTAACG

CCAGCTATTCCGCAGAAACGCTGGCTCATTTAATAAAGTATGACACAATT

CACGGCAGATACGACAAAGAGGTTGTGGCTGGTGAAGATAGCCTGATCGT

AAATGGAAAGAAAGTGCTTTTGTTAAACAGCCGTGATCCAAAACAGCTGC

CTTGGCGGGAATATGATATTGACATAGTCGTCGAAGCAACAGGGAAGTTT

AATGCTAAAGATAAAGCGATGGGCCATATAGAAGCAGGTGCAAAAAAAGT

GATTTTGACCGCTCCGGGAAAAAATGAAGACGTTACCATTGTGATGGGCG

TAAATGAGGACCAATTCGACGCTGAGCGCCATGTCATTATTTCAAATGCG

TCATGCACGACAAATTGCCTTGCGCCTGTTGTAAAAGTGCTGGATGAAGA

GTTTGGCATTGAGAGCGGTCTGATGACTACAGTTCATGCGTATACGAATG

ACCAAAAAAATATTGATAACCCGCACAAAGATTTGCGCCGGGCGCGGGCT

TGCGGTGAATCCATCATTCCAACAACAACAGGAGCGGCAAAGGCGCTTTC

GCTTGTGCTGCCGCATCTGAAAGGAAAACTTCACGGCCTCGCCTTGCGTG

TCCCTGTTCCGAACGTCTCATTGGTTGATCTCGTTGTTGATCTGAAAACG

GATGTTACGGCTGAAGAAGTAAACGAGGCATTTAAACGCGCTGCCAAAAC

GTCGATGTACGGTGTACTTGATTACTCAGATGAACCGCTCGTTTCGACTG

ATTATAATACGAATCCGCATTCAGCGGTCATTGACGGGCTTACAACAATG

GTAATGGAAGACAGGAAAGTAAAGGTGCTGGCGTGGTATGACAACGAATG

GGGCTACTCCTGCAGAGTTGTTGATCTAATCCGCCATGTAGCGGCACGAA

TGAAACATCCGTCTGCTGTA.

The deduced amino acid sequence of the GapB protein is:

(SEQ ID NO: 24)

MKVKVAINGFGRIGRMVFRKAMLDDQIQVVAINASYSAETLAHLIKYDTI

HGRYDKEVVAGEDSLIVNGKKVLLLNSRDPKQLPWREYDIDIVVEATGKF

NAKDKAMGHIEAGAKKVILTAPGKNEDVTIVMGVNEDQFDAERHVIISNA

SCTTNCLAPVVKVLDEEFGIESGLMTTVHAYTNDQKNIDNPHKDLRRARA

CGESIIPTTTGAAKALSLVLPHLKGKLHGLALRVPVPNVSLVDLVVDLKT

DVTAEEVNEAFKRAAKTSMYGVLDYSDEPLVSTDYNTNPHSAVIDGLTTM

VMEDRKVKVLAWYDNEWGYSCRVVDLIRHVAARMKHPSAV.

Additionally, the coding region is found at about 2966075-2967094 bp of the *B. subtilis* 168 chromosome.

The Kbl coding sequence of the Kbl protein (2-amino-3-ketobutyrate CoA ligase) is shown below:

(SEQ ID NO: 25)

ATGACGAAGGAATTTGAGTTTTTAAAAGCAGAGCTTAATAGTATGAAAGA

AAACCATACATGGCAAGACATAAAACAGCTTGAATCTATGCAGGGCCCAT

CTGTCACAGTGAATCACCAAAAAGTCATTCAGCTATCTTCTAATAATTAC

-continued

CTCGGATTCACTTCACATCCTAGACTCATCAACGCCGCACAGGAGGCCGT

TCAGCAGTATGGAGCCGGCACCGGATCAGTGAGAACGATTGCGGGTACAT

TTACAATGCATCAAGAGCTTGAGAAAAAGCTGGCAGCCTTTAAAAAAACG

GAGGCGGCACTTGTATTCCAATCAGGCTTCACAACAAACCAAGGCGTACT

TTCAAGTATTCTATCAAAAGAGGACATTGTCATCTCAGATGAATTGAACC

ATGCCTCTATTATTGACGGAATTCGACTGACAAAGGCGGATAAAAAGGTG

TATCAGCACGTCAATATGAGTGATTTAGAGCGGGTGCTGAGAAAGTCAAT

GAATTATCGGATGCGTCTGATTGTGACAGACGGCGTATTTTCCATGGATG

GCAACATAGCTCCTCTGCCTGATATTGTAGAGCTCGCTGAGAAATATGAC

GCATTTGTGATGGTGGATGACGCCCATGCATCCGGAGTACTTGGCGAAAA

CGGCAGGGGAACGGTGAATCACTTCGGTCTTGACGGCAGAGTGCATATTC

AGGTCGGAACATTAAGCAAGGCAATCGGAGTGCTCGGCGGCTACGCTGCA

GGTTCAAAGGTGCTGATCGATTATTTGCGCCATAAAGGCCGTCCATTTTT

ATTCAGCACATCTCATCCGCCGGCAGTCACTGCAGCTTGTATGGAAGCGA

TTGATGTCTTGCTTGAAGAGCCGGAGCATATGGAGCGCTTGTGGGAGAAT

ACTGCCTATTTTAAAGCAATGCTTGTGAAAATGGGTCTGACTCTCACGAA

GAGTGAAACGCCGATTCTTCCTATTTTAATAGGTGATGAAGGTGTGGCAA

AGCAATTTTCAGATCAGCTCCTTTCTCGCGGTGTTTTTGCCCAAAGTATC

GTTTTCCCGACTGTAGCAAAGGGAAAAGCCAGAATTCGCACGATTATAAC

AGCAGAGCACACCAAAGATGAACTGGATCAGGCGCTTGATGTCATCGAAA

AGACGGCAAAGGAGCTCCAGCTATTG.

The deduced amino acid sequence of the Kbl protein is:

(SEQ ID NO: 26)

MTKEFEFLKAELNSMKENHTWQDIKQLESMQGPSVTVNHQKVIQLSSNNY

LGFTSHPRLINAAQEAVQQYGAGTGSVRTIAGTFTMHQELEKKLAAFKKT

EAALVFQSGFTTNQGVLSSILSKEDIVISDELNHASIIDGIRLTKADKKV

YQHVNMSDLERVLRKSMNYRMRLIVTDGVFSMDGNIAPLPDIVELAEKYD

AFVMVDDAHASGVLGENGRGTVNHFGLDGRVHIQVGTLSKAIGVLGGYAA

GSKVLIDYLRHKGRPFLFSTSHPPAVTAACMEAIDVLLEEPEHMERLWEN

TAYFKAMLVKMGLTLTKSETPILPILIGDEGVAKQFSDQLLSRGVFAQSI

VFPTVAKGKARIRTIITAEHTKDELDQALDVIEKTAKELQLL.

Additionally, the coding region is found at about 1770787-1771962 bp of the *B. subtilis* 168 chromosome.

The PckA coding sequence of the PckA (phosphoenolpyruvate carboxykinase) of *B. subtilis* 168 is shown below:

(SEQ ID NO: 27)

ATGAACTCAGTTGATTTGACCGCTGATTTACAAGCCTTATTAACATGTCC

AAATGTGCGTCATAATTTATCAGCAGCACAGCTAACAGAAAAAGTCCTCT

CCCGAAACGAAGGCATTTTAACATCCACAGGTGCTGTTCGCGCGACAACA

GGCGCTTACACAGGACGCTCACCTAAAGATAAATTCATCGTGGAGGAAGA

AAGCACGAAAAATAAGATCGATTGGGGCCCGGTGAATCAGCCGATTTCAG

-continued

AAGAAGCGTTTGAGCGGCTGTACACGAAAGTTGTCAGCTATTTAAAGGAG

CGAGATGAACTGTTTGTTTTCGAAGGATTTGCCGGAGCAGACGAGAAATA

CAGGCTGCCGATCACTGTCGTAAATGAGTTCGCATGGCACAATTTATTTG

CGCGGCAGCTGTTTATCCGTCCGGAAGGAAATGATAAGAAAACAGTTGAG

CAGCCGTTCACCATTCTTTCTGCTCCGCATTTCAAAGCGGATCCAAAAAC

AGACGGCACTCATTCCGAAACGTTTATTATTGTCTCTTTCGAAAAGCGGA

CAATTTTAATCGGCGGAACTGAGTATGCCGGTGAAATGAAGAAGTCCATT

TTCTCCATTATGAATTTCCTGCTGCCTGAAAGAGATATTTTATCTATGCA

CTGCTCCGCCAATGTCGGTGAAAAAGGCGATGTCGCCCTTTTCTTCGGAC

TGTCAGGAACAGGAAAGACCACCCTGTCGGCAGATGCTGACCGCAAGCTG

ATCGGTGACGATGAACATGGCTGGTCTGATACAGGCGTCTTTAATATTGA

AGGCGGATGCTACGCTAAGTGTATTCATTTAAGCGAGGAAAAGGAGCCGC

AAATCTTTAACGCGATCCGCTTCGGGTCTGTTCTCGAAAATGTCGTTGTG

GATGAAGATACACGCGAAGCCAATTATGATGATTCCTTCTATACTGAAAA

CACGCGGGCAGCTTACCCGATTCATATGATTAATAACATCGTGACTCCAA

GCATGGCCGGCCATCCGTCAGCCATTGTATTTTTGACGGCTGATGCCTTC

GGAGTCCTGCCGCCGATCAGCAAACTAACGAAGGAGCAGGTGATGTACCA

TTTTTTGAGCGGTTACACGAGTAAGCTTGCCGGAACCGAACGTGGTGTCA

CGTCTCCTGAAACGACGTTTTCTACATGCTTCGGCTCACCGTTCCTGCCG

CTTCCTGCTCACGTCTATGCTGAAATGCTCGGCAAAAAGATCGATGAACA

CGGCGCAGACGTTTTCTTAGTCAATACCGGATGGACCGGGGGCGGCTACG

GCACAGGCGAACGAATGAAGCTTTCTTACACTAGAGCAATGGTCAAAGCA

GCGATTGAAGGCAAATTAGAGGATGCTGAAATGATAACTGACGATATTTT

CGGCCTGCACATTCCGGCCCATGTTCCTGGCGTTCCTGATCATATCCTTC

AGCCTGAAAACACGTGGACCAACAAGGAAGAATACAAAGAAAAAGCAGTC

TACCTTGCAAATGAATTCAAAGAGAACTTTAAAAAGTTCGCACATACCGA

TGCCATCGCCCAGGCAGGCGGCCCTCTCGTA.

The deduced amino acid sequence of the PckA protein is:

(SEQ ID NO: 28)

MNSVDLTADLQALLTCPNVRHNLSAAQLTEKVLSRNEGILTSTGAVRATT

GAYTGRSPKDKFIVEEESTKNKIDWGPVNQPISEEAFERLYTKVVSYLKE

RDELFVFEGFAGADEKYRLPITVVNEFAWHNLFARQLFIRPEGNDKKTVE

QPFTILSAPHFKADPKTDGTHSETFIIVSFEKRTILIGGTEYAGEMKKSI

FSIMNFLLPERDILSMHCSANVGEKGDVALFFGLSGTGKTTLSADADRKL

IGDDEHGWSDTGVFNIEGGCYAKCIHLSEEKEPQIFNAIRFGSVLENVVV

DEDTREANYDDSFYTENTRAAYPIHMINNIVTPSMAGHPSAIVFLTADAF

GVLPPISKLTKEQVMYHFLSGYTSKLAGTERGVTSPETTFSTCFGSPFLP

LPAHVYAEMLGKKIDEHGADVFLVNTGWTGGGYGTGERMKLSYTRAMVKA

AIEGKLEDAEMITDDIFGLHIPAHVPGVPDHILQPENTWTNKEEYKEKAV

YLANEFKENFKKFAHTDAIAQAGGPLV.

Additionally, the coding region is found at about 3128579-3130159 bp of the *B. subtilis* 168 chromosome.

The prpC coding sequence of the prpC protein (protein phosphatase) of *B. subtilis* 168 is shown below:

```
                                          (SEQ ID NO: 29)
TTGTTAACAGCCTTAAAAACAGATACAGGAAAAATCCGCCAGCATAATGA

AGATGATGCGGGGATATTCAAGGGGAAAGATGAATTTATATTAGCGGTTG

TCGCTGATGGCATGGGCGGCCATCTTGCTGGAGATGTTGCGAGCAAGATG

GCTGTGAAAGCCATGGGGGAGAAATGGAATGAAGCAGAGACGATTCCAAC

TGCGCCCTCGGAATGTGAAAAATGGCTCATTGAACAGATTCTATCGGTAA

ACAGCAAAATATACGATCACGCTCAAGCCCACGAAGAATGCCAAGGCATG

GGGACGACGATTGTATGTGCACTTTTTACGGGGAAAACGGTTTCTGTTGC

CCATATCGGAGACAGCAGATGCTATTTGCTTCAGGACGATGATTTCGTTC

AAGTGACAGAAGACCATTCGCTTGTAAATGAACTGGTTCGCACTGGAGAG

ATTTCCAGAGAAGACGCTGAACATCATCCGCGAAAAAATGTGTTGACGAA

GGCGCTTGGAACAGACCAGTTAGTCAGTATTGACACCCGTTCCTTTGATA

TAGAACCCGGAGACAAACTGCTTCTATGTTCTGACGGACTGACAAATAAA

GTGGAAGGCACTGAGTTAAAAGACATCCTGCAAAGCGATTCAGCTCCTCA

GGAAAAAGTAAACCTGCTTGTGGACAAAGCCAATCAGAATGGCGGAGAAG

ACAACATTACAGCAGTTTTGCTTGAGCTTGCTTTACAAGTTGAAGAGGGT

GAAGATCAGTGC.
```

The deduced amino acid sequence of the prpC protein is:

```
                                          (SEQ ID NO: 30)
MLTALKTDTGKIRQHNEDDAGIFKGKDEFILAVVADGMGGHLAGDVASKM

AVKAMGEKWNEAETIPTAPSECEKWLIEQILSVNSKIYDHAQAHEECQGM

GTTIVCALFTGKTVSVAHIGDSRCYLLQDDDFVQVTEDHSLVNELVRTGE

ISREDAEHHPRKNVLTKALGTDQLVSIDTRSFDIEPGDKLLLCSDGLTNK

VEGTELKDILQSDSAPQEKVNLLVDKANQNGGEDNITAVLLELALQVEEG

EDQC.
```

Additionally, the coding region is found at about 1649684-1650445 bp of the *B. subtilis* 168 chromosome.

The rocA coding sequence of the rocA protein (pyrroline-5 carboxylate dehydrogenase) of *B. subtilis* 168 is shown below:

```
                                          (SEQ ID NO: 31)
ATGACAGTCACATACGCGCACGAACCATTTACCGATTTTACGGAAGCAAA

GAATAAAACTGCATTTGGGGAGTCATTGGCCTTTGTAAACACTCAGCTCG

GCAAGCATTATCCGCTTGTCATAAATGGAGAAAAAATTGAAACGGACCGC

AAAATCATTTCTATTAACCCGGCAAATAAAGAAGAGATCATTGGGTACGC

GTCTACAGCGGATCAAGAGCTTGCTGAAAAAGCGATGCAAGCCGCATTGC

AGGCATTTGATTCCTGGAAAAAACAAAGACCGGAGCACCGCGCAAATATT

CTCTTTAAGGCAGCGGCTATTTTGCGCAGAAGAAAGCATGAATTTTCAAG

CTATCTTGTGAAGGAAGCAGGAAAACCGTGGAAGGAAGCAGATGCGGACA
```

-continued

```
CGGCTGAAGCGATAGACTTTTTAGAGTTCTACGCGCGCCAAATGTTAAAG

CTCAAGGAAGGGGCTCCGGTGAAGAGCCGTGCTGGCGAGGTCAATCAATA

TCATTACGAAGCGCTTGGCGTCGGCATCGTCATTTCTCCATTTAACTTCC

CGCTCGCGATTATGGCGGGAACAGCGGTGGCAGCGATTGTGACAGGAAAT

ACGATTCTCTTAAAACCGGCTGACGCAGCCCCGGTAGTGGCAGCAAAATT

TGTCGAGGTCATGGAGGAAGCGGGTCTGCCAAACGGCGTTCTGAATTACA

TTCCGGGAGATGGTGCGGAGATCGGTGATTTCTTAGTTGAGCATCCGAAG

ACACGGTTTGTCTCATTTACAGGTTCCCGTGCAGTCGGCTGCCGGATTTA

TGAGCGAGCTGCCAAAGTGCAGCCGGGCCAAAAATGGCTCAAACGGGTAA

TTGCAGAAATGGGCGGAAAAGACACAGTGCTTGTCGACAAGGACGCTGAT

CTTGACCTTGCTGCATCCTCTATCGTGTATTCAGCATTTGGATATTCAGG

ACAGAAGTGTTCTGCGGGCTCCCGCGCGGTCATTCATCAGGATGTGTATG

ATGAAGTGGTGGAAAAAGCTGTGGCGCTGACCAAAACGCTGACTGTCGGC

AATCCAGAAGATCCTGATACGTATATGGGTCCCGTGATTCATGAAGCATC

CTACAACAAAGTGATGAAATACATTGAAATCGGCAAATCTGAAGGCAAGC

TATTGGCCGGCGGAGAAGGCGATGATTCAAAAGGCTACTTTATTCAGCCG

ACGATCTTTGCAGATGTTGATGAAAACGCCCGCTTGATGCAGGAAGAAAT

TTTCGGCCCGGTTGTTGCGATTTGCAAAGCGCGTGATTTCGATCATATGC

TGGAGATTGCCAATAACACGGAATACGGATTAACAGGTGCGCTTCTGACG

AAAAACCGTGCGCACATTGAACGGGCGCGCGAGGATTTCCATGTCGGAAA

CCTATATTTTAACAGAGGATGTACCGGAGCAATTGTCGGCTATCAGCCGT

TCGGCGGTTTTAATATGTCAGGAACAGACTCAAAAGCAGGCGGTCCCGAT

TACTTAATTCTTCATATGCAAGCCAAAACAACGTCCGAAGCTTTT.
```

The deduced amino acid sequence of the RocA protein is:

```
                                          (SEQ ID NO: 32)
MTVTYAHEPFTDFTEAKNKTAFGESLAFVNTQLGKHYPLVINGEKIETDR

KIISINPANKEEIIGYASTADQELAEKAMQAALQAFDSWKKQRPEHRANI

LFKAAAILRRRKHEFSSYLVKEAGKPWKEADADTAEAIDFLEFYARQMLK

LKEGAPVKSRAGEVNQYHYEALGVGIVISPFNFPLAIMAGTAVAAIVTGN

TILLKPADAAPVVAAKFVEVMEEAGLPNGVLNYIPGDGAEIGDFLVEHPK

TRFVSFTGSRAVGCRIYERAAKVQPGQKWLKRVIAEMGGKDTVLVDKDAD

LDLAASSIVYSAFGYSGQKCSAGSRAVIHQDVYDEVVEKAVALTKTLTVG

NPEDPDTYMGPVIHEASYNKVMKYIEIGKSEGKLLAGGEGDDSKGYFIQP

TIFADVDENARLMQEEIFGPVVAICKARDFDHMLEIANNTEYGLTGALLT

KNRAHIERAREDFHVGNLYFNRGCTGAIVGYQPFGGFNMSGTDSKAGGPD

YLILHMQAKTTSEAF.
```

Additionally, the coding region is found at about 3877991-3879535 bp of the *B. subtilis* 168 chromosome.

The rocD coding sequence of the rocD protein (ornithine aminotransferase) of *B. subtilis* 168 is shown below:

(SEQ ID NO: 33)

ATGACAGCTTTATCTAAATCCAAAGAAATTATTGATCAGACGTCTCATTA

CGGAGCCAACAATTATCACCCGCTCCCGATTGTTATTTCTGAAGCGCTGG

GTGCTTGGGTAAAGGACCCGGAAGGCAATGAATATATGGATATGCTGAGT

GCTTACTCTGCGGTAAACCAGGGGCACAGACACCCGAAAATCATTCAGGC

ATTAAAGGATCAGGCTGATAAAATCACCCTCACGTCACGCGCGTTTCATA

ACGATCAGCTTGGGCCGTTTTACGAAAAAACAGCTAAACTGACAGGCAAA

GAGATGATTCTGCCGATGAATACAGGAGCCGAAGCGGTTGAATCCGCGGT

GAAAGCGGCGAGACGCTGGGCGTATGAAGTGAAGGGCGTAGCTGACAATC

AAGCGGAAATTATCGCATGTGTCGGGAACTTCCACGGCCGCACGATGCTG

GCGGTATCTCTTTCTTCTGAAGAGGAATATAAACGAGGATTCGGCCCGAT

GCTTCCAGGAATCAAACTCATTCCTTACGGCGATGTGGAAGCGCTTCGAC

AGGCCATTACGCCGAATACAGCGGCATTCTTGTTTGAACCGATTCAAGGC

GAAGCGGGCATTGTGATTCCGCCTGAAGGATTTTTACAGGAAGCGGCGGC

GATTTGTAAGGAAGAGAATGTCTTGTTTATTGCGGATGAAATTCAGACGG

GTCTCGGACGTACAGGCAAGACGTTTGCCTGTGACTGGGACGGCATTGTT

CCGGATATGTATATCTTGGGCAAAGCGCTTGGCGGCGGTGTGTTCCCGAT

CTCTTGCATTGCGGCGGACCGCGAGATCCTAGGCGTGTTTAACCCTGGCT

CACACGGCTCAACATTTGGTGGAAACCCGCTTGCATGTGCAGTGTCTATC

GCTTCATTAGAAGTGCTGGAGGATGAAAAGCTGGCGGATCGTTCTCTTGA

ACTTGGTGAATACTTTAAAAGCGAGCTTGAGAGTATTGACAGCCCTGTCA

TTAAAGAAGTCCGCGGCAGAGGGCTGTTTATCGGTGTGGAATTGACTGAA

GCGGCACGTCCGTATTGTGAGCGTTTGAAGGAAGAGGGACTTTTATGCAA

GGAAACGCATGATACAGTCATTCGTTTTGCACCGCCATTAATCATTTCCA

AAGAGGACTTGGATTGGGCGATAGAGAAAATTAAGCACGTGCTGCGAAAC

GCA.

The deduced amino acid sequence of the RocD protein is:

(SEQ ID NO: 34)

MTALSKSKEIIDQTSHYGANNYHPLPIVISEALGAWVKDPEGNEYMDMLS

AYSAVNQGHRHPKIIQALKDQADKITLTSRAFHNDQLGPFYEKTAKLTGK

EMILPMNTGAEAVESAVKAARRWAYEVKGVADNQAEIIACVGNFHGRTML

AVSLSSEEEYKRGFGPMLPGIKLIPYGDVEALRQAITPNTAAFLFEPIQG

EAGIVIPPEGFLQEAAAICKEENVLFIADEIQTGLGRTGKTFACDWDGIV

PDMYILGKALGGGVFPISCIAADREILGVFNPGSHGSTFGGNPLACAVSI

ASLEVLEDEKLADRSLELGEYFKSELESIDSPVIKEVRGRGLFIGVELTE

AARPYCERLKEEGLLCKETHDTVIRFAPPLIISKEDLDWAIEKIKHVLRN

A.

Additionally, the coding region is found at about 4143328-4144530 bp of the *B. subtilis* 168 chromosome.

The rocF coding sequence of the rocF protein (arginase) of *B. subtilis* 168 is shown below:

(SEQ ID NO: 35)

ATGGATAAAACGATTTCGGTTATTGGAATGCCAATGGATTTAGGACAAGC

ACGACGCGGAGTGGATATGGGCCCGAGTGCCATCCGGTACGCTCATCTGA

TCGAGAGGCTGTCAGACATGGGGTATACGGTTGAAGATCTCGGTGACATT

CCGATCAATCGCGAAAAAATCAAAAATGACGAGGAACTGAAAAACCTGAA

TTCCGTTTTGGCGGGAAATGAAAAACTCGCGCAAAAGGTCAACAAAGTCA

TTGAAGAGAAAAAATTCCCGCTTGTCCTGGGCGGTGACCACAGTATTGCG

ATCGGCACGCTTGCAGGCACAGCGAAGCATTACGATAATCTCGGCGTCAT

CTGGTATGACGCGCACGGCGATTTGAATACACTTGAAACTTCACCATCGG

GCAATATTCACGGCATGCCGCTCGCGGTCAGCCTAGGCATTGGCCACGAG

TCACTGGTTAACCTTGAAGGCTACGCGCCTAAAATCAAACCGGAAAACGT

CGTCATCATTGGCGCCCGGTCACTTGATGAAGGGGAGCGCAAGTACATTA

AGGAAAGCGGCATGAAGGTGTACACAATGCACGAAATCGATCGTCTTGGC

ATGACAAAGGTCATTGAAGAAACCCTTGATTATTTATCAGCATGTGATGG

CGTCCATCTGAGCCTTGATCTGGACGGACTTGATCCGAACGACGCACCGG

GTGTCGGAACCCCTGTCGTCGGCGGCATCAGCTACCGGGAGAGCCATTTG

GCTATGGAAATGCTGTATGACGCAGGCATCATTACCTCAGCCGAATTCGT

TGAGGTTAACCCGATCCTTGATCACAAAAACAAAACGGGCAAAACAGCAG

TAGAGCTCGTAGAATCCCTGTTAGGGAAGAAGCTGCTG.

The deduced amino acid sequence of the RocF protein:

(SEQ ID NO: 36)

MDKTISVIGMPMDLGQARRGVDMGPSAIRYAHLIERLSDMGYTVEDLGDI

PINREKIKNDEELKNLNSVLAGNEKLAQKVNKVIEEKKFPLVLGGDHSIA

IGTLAGTAKHYDNLGVIWYDAHGDLNTLETSPSGNIHGMPLAVSLGIGHE

SLVNLEGYAPKIKPENVVIIGARSLDEGERKYIKESGMKVYTMHEIDRLG

MTKVIEETLDYLSACDGVHLSLDLDGLDPNDAPGVGTPVVGGISYRESHL

AMEMLYDAGIITSAEFVEVNPILDHKNKTGKTAVELVESLLGKKLL.

Additionally, the coding region is found at about 4140738-4141625 bp of the *B. subtilis* 168 chromosome.

The Tdh coding sequence of the Tdh protein (threonine 3-dehydrogenase) of *B. subtilis* 168 is shown below:

(SEQ ID NO: 37)

ATGCAGAGTGGAAAGATGAAAGCTCTAATGAAAAAGGACGGGGCGTTCGG

TGCTGTGCTGACTGAAGTTCCCATTCCTGAGATTGATAAACATGAAGTCC

TCATAAAAGTGAAAGCCGCTTCCATATGCGGCACGGATGTCCACATTTAT

AATTGGGATCAATGGGCACGTCAGAGAATCAAAACACCCTATGTTTTCGG

CCATGAGTTCAGCGGCATCGTAGAGGGCGTGGGAGAGAATGTCAGCAGTG

TAAAAGTGGGAGAGTATGTGTCTGCGGAAACACACATTGTCTGTGGTGAA

TGTGTCCCTTGCCTAACAGGAAAATCTCATGTGTGTACCAATACTGCTAT

AATCGGAGTGGACACGGCAGGCTGTTTTGCGGAGTATGTAAAAGTTCCAG

-continued

```
CTGATAACATTTGGAGAAATCCCGCTGATATGGACCCGTCGATTGCTTCC
ATTCAAGAGCCTTTAGGAAATGCAGTTCATACCGTACTCGAGAGCCAGCC
TGCAGGAGGAACGACTGCAGTCATTGGATGCGGACCGATTGGTCTTATGG
CTGTTGCGGTTGCAAAAGCAGCAGGAGCTTCTCAGGTGATAGCGATTGAT
AAGAATGAATACAGGCTGAGGCTTGCAAAACAAATGGGAGCGACTTGTAC
TGTTTCTATTGAAAAAGAAGACCCGCTCAAAATTGTAAGCGCTTTAACGA
GTGGAGAAGGAGCAGATCTTGTTTGTGAGATGTCGGGCCATCCCTCAGCG
ATTGCCCAAGGTCTTGCGATGGCTGCGAATGGCGGAAGATTTCATATTCT
CAGCTTGCCGGAACATCCGGTGACAATTGATTTGACGAATAAAGTGGTAT
TTAAAGGGCTTACCATCCAAGGAATCACAGGAAGAAAAATGTTTTCAACA
TGGCGCCAGGTGTCTCAGTTGATCAGTTCAAACATGATCGATCTTGCACC
TGTTATTACCCATCAGTTTCCATTAGAGGAGTTTGAAAAAGGTTTCGAAC
TGATGAGAAGCGGGCAGTGCGGAAAAGTAATTTTAATTCCA.
```

The deduced amino acid sequence of the Tdh protein is:

(SEQ ID NO: 38)

```
MQSGKMKALMKKDGAFGAVLTEVPIPEIDKHEVLIKVKAASICGTDVHIY
NWDQWARQRIKTPYVFGHEFSGIVEGVGENVSSVKVGEYVSAETHIVCGE
CVPCLTGKSHVCTNTAIIGVDTAGCFAEYVKVPADNIWRNPADMDPSIAS
IQEPLGNAVHTVLESQPAGGTTAVIGCGPIGLMAVAVAKAAGASQVIAID
KNEYRLRLAKQMGATCTVSIEKEDPLKIVSALTSGEGADLVCEMSGHPSA
IAQGLAMAANGGRFHILSLPEHPVTIDLTNKVVFKGLTIQGITGRKMFST
WRQVSQLISSNMIDLAPVITHQFPLEEFEKGFELMRSGQCGKVILIP.
```

Additionally, the coding region is found at about 1769731-1770771 bp of the *B. subtilis* 168 chromosome.

The coding sequences for the tryptophan operon regulatory region and genes trpE (SEQ ID NO:48), trpD (SEQ ID NO:46), trpC (SEQ ID NO:44), trpF (SEQ ID NO:50), trpB (SEQ ID NO:42), and trpA (SEQ ID NO:40) are shown below. The operon regulatory region is underlined. The trpE start (ATG) is shown in bold, followed as well by the trpD, trpC trpF, trpB, and trpA starts (also indicated in bold, in the order shown).

(SEQ ID NO: 39)

TAATACGATAAGAACAGCTTAGAAATACACAAGAGTGTGTATAAAGCAAT
TAGAATGAGTTGAGTTAGAGAATAGGGTAGCAGAGAATGAGTTTAGTTGA
GCTGAGACATTATGTTTATTCTACCCAAAAGAAGTCTTTCTTTTGGGTTT
ATTTGTTATATAGTATTTTATCCTCTCATGCCATCTTCTCATTCTCCTTG
CCATAAGGAGTGAGAGCAATGAATTTCCAATCAAACATTTCCGCATTTTT

```
AGAGGACAGCTTGTCCCACCACACGATACCGATTGTGGAGACCTTCACAG
TCGATACACTGACACCCATTCAAATGATAGAGAAGCTTGACAGGGAGATT
ACGTATCTTCTTGAAAGCAAGGACGATACATCCACTTGGTCCAGATATTC
GTTTATCGGCCTGAATCCATTTCTCACAATTAAAGAAGAGCAGGGCCGTT
TTTCGGCCGCTGATCAGGACAGCAAATCTCTTTACACAGGAAATGAACTA
AAAGAAGTGCTGAACTGGATGAATACCACATACAAAATCAAAACACCTGA
```

-continued

```
GCTTGGCATTCCTTTTGTCGGCGGAGCTGTCGGGTACTTAAGCTATGATA
TGATCCCGCTGATTGAGCCTTCTGTTCCTTCGCATACCAAAGAAACAGAC
ATGGAAAAGTGTATGCTGTTTGTTTGCCGGACATTAATTGCGTATGATCA
TGAAACCAAAAACGTCCACTTTATCCAATATGCAAGGCTCACTGGAGAGG
AAACAAAAAACGAAAAAATGGATGTATTCCATCAAAATCATCTGGAGCTT
CAAAATCTCATTGAAAAAATGATGGACCAAAAAAACATAAAAGAGCTGTT
TCTTTCTGCTGATTCATACAAGACACCCAGCTTTGAGACAGTATCTTCTA
ATTATGAAAAATCGGCTTTTATGGCTGATGTAGAAAAAATCAAAAGCTAT
ATAAAAGCAGGCGATATCTTCCAGGGTGTTTTATCACAAAAATTTGAGGT
GCCGATAAAAGCAGATGCTTTTGAGTTATACCGAGTGCTTAGGATCGTCA
ATCCTTCGCCGTATATGTATTATATGAAACTGCTAGACAGAGAAATAGTC
GGCAGCTCTCCGGAACGGTTAATACACGTTCAAGACGGGCACTTAGAAAT
CCATCCGATTGCCGGTACGAGAAAACGCGGTGCAGACAAAGCTGAAGATG
AGAGACTGAAGGTTGAGCTCATGAAGGATGAAAAAGAAAAAGCGGAGCAT
TACATGCTCGTTGATCTTGCCCGAAACGATATCGGCAGAGTAGCAGAGTA
TGGTTCTGTTTCTGTGCCGGAGTTCACAAAAATTGTTTCCTTTTCACATG
TCATGCACATTATCTCGGTGGTTACAGGCCGATTGAAAAAAGGGGTTCAT
CCTGTCGATGCACTGATGTCTGCTTTCCCGGCGGGGACTTTAACAGGCGC
ACCCAAAATCCGTGCCATGCAGCTTTTGCAAGAACTCGAGCCAACACCGA
GAGAGACATACGGAGGGTGTATTGCCTACATTGGGTTTGACGGGAATATC
GACTCTTGTATTACGATTCGCACGATGAGTGTAAAGAACGGTGTTGCATC
GATACAGGCAGGTGCTGGCATTGTTGCTGATTCTGTTCCGGAAGCCGAAT
ACGAAGAAAGCTGTAATAAAGCCGGTGCGCTGCTGAAAACGATTCATATT
GCAGAAGACATGTTTCATAGCAAGGAGGATAAAGCTGATGAACAGATTTC
TACAATTGTGCGTTGACGGAAAAACCCTTACTGCCGGTGAGGCTGAAACG
CTGATGAATATGATGATGGCAGCGGAAATGACTCCTTCTGAAATGGGGGG
GATATTGTCAATTCTTGCTCATCGGGGGGAGACGCCAGAAGAGCTTGCGG
GTTTTGTGAAGGCAATGCGGGCACACGCTCTTACAGTCGATGGACTTCCT
GATATTGTTGATACATGCGGAACAGGGGGAGACGGTATTTCCACTTTTAA
TATCTCAACGGCCTCGGCAATTGTTGCCTCGGCAGCTGGTGCGAAAATCG
CTAAGCATGGCAATCGCTCTGTCTCTTCTAAAAGCGGAAGCGCTGATGTT
TTAGAGGAGCTAGAGGTTTCTATTCAAACCACTCCCGAAAAGGTCAAAAG
CAGCATTGAAACAAACAACATGGGATTTCTTTTTGCGCCGCTTTACCATT
CGTCTATGAAACATGTAGCAGGTACTAGAAAAGAGCTAGGTTTCAGAACG
GTATTTAATCTGCTTGGGCCGCTCAGCAATCCTTTACAGGCGAAGCGTCA
GGTGATTGGGGTCTATTCTGTTGAAAAAGCTGGACTGATGGCAAGCGCAC
TGGAGACGTTTCAGCCGAAGCACGTTATGTTTGTATCAAGCCGTGACGGT
TTAGATGAGCTTTCAATTACAGCACCGACCGACGTGATTGAATTAAAGGA
CGGAGAGCGCCGGGAGTATACCGTTTCACCCGAAGATTTCGGTTTCACAA
ATGGCAGACTTGAAGATTTACAGGTGCAGTCTCCGAAAGAGAGCGCTTAT
```

-continued

CTCATTCAGAATATTTTTGAAAATAAAAGCAGCAGTTCCGCTTTATCTAT

TACGGCTTTTAATGCGGGTGCTGCGATTTACACGGCGGGAATTACCGCCT

CACTGAAGGAAGGAACGGAGCTGGCGTTAGAGACGATTACAAGCGGAGGC

GCTGCCGCGCAGCTTGAACGACTAAAGCAGAAAGAGGAAGAGATCTATGC

TTGAAAAAATCATCAAACAAAAGAAAGAAGAAGTGAAAACACTGGTTCTG

CCGGTAGAGCAGCCTTTCGAGAAACGTTCATTTAAGGAGGCGCCGGCAAG

CCCGAATCGGTTTATCGGGTTGATTGCCGAAGTGAAGAAAGCATCGCCGT

CAAAAGGGCTTATTAAAGAGGATTTTGTACCTGTGCAGATTGCAAAAGAC

TATGAGGCTGCGAAGGCAGATGCGATTTCCGTTTTAACAGACACCCCGTT

TTTTCAAGGGGAAAACAGCTATTTATCAGACGTAAAGCGTGCTGTTTCGA

TTCCTGTACTTAGAAAAGATTTTATTATTGATTCTCTTCAAGTAGAGGAA

TCAAGAAGAATCGGAGCGGATGCCATATTGTTAATCGGCGAGGTGCTTGA

TCCCTTACACCTTCATGAATTATATCTTGAAGCAGGTGAAAAGGGGATGG

ACGTGTTAGTGGAGGTTCATGATGCATCAACGCTAGAACAAATATTGAAA

GTGTTCACACCCGACATTCTCGGCGTAAATAATCGAAACCTAAAAACGTT

TGAAACATCTGTAAAGCAGACAGAACAAATCGCATCTCTCGTTCCGAAAG

AATCCTTGCTTGTCAGCGAAAGCGGAATCGGTTCTTTAGAACATTTAACA

TTTGTCAATGAACATGGGGCGCGAGCTGTACTTATCGGTGAATCATTGAT

GAGACAAACTTCTCAGCGTAAAGCAATCCATGCTTTGTTTAGGGAGTGAG

GTTGTGAAGAAACCGGCATTAAAATATTGCGGTATTCGGTCACTAAAGGA

TTTGCAGCTTGCGGCGGAATCACAGGCTGATTACCTAGGATTTATTTTTG

CTGAAAGCAAACGAAAAGTATCTCCGGAAGATGTGAAAAAAATGGCTGAAC

CAAGTTCGTGTCGAAAAACAGGTTGCAGGTGTTTTTGTTAATGAATCAAT

AGAGACGATGTCACGTATTGCCAAGAGCTTGAAGCTCGACGTCATTCAGC

TTCACGGTGATGAAAAACCGGCGGATGTCGCTGCTCTTCGCAAGCTGACA

GGCTGTGAAATATGGAAGGCGCTTCACCATCAAGATAACACAACTCAAGA

AATAGCCCGCTTTAAAGATAATGTTGACGGCTTTGTGATTGATTCATCTG

TAAAAGGGTCTAGAGGCGGAACTGGTGTTGCATTTTCTTGGGACTGTGTG

CCGGAATATCAGCAGGCGGCTATTGGTAAACGCTGCTTTATCGCTGGCGG

CGTGAATCCGGATAGCATCACACGCCTATTGAAATGGCAGCCAGAAGGAA

TTGACCTTGCCAGCGGAATTGAAAAAAACGGACAAAAAGATCAGAATCTG

ATGAGGCTTTTAGAAGAAAGGATGAACCGATATGTATCCATATCCGAATG

AAATAGGCAGATACGGTGATTTTGGCGGAAAGTTTGTTCCGGAAACACTC

ATGCAGCCGTTAGATGAAATACAAACAGCATTTAAACAAATCAAGGATGA

TCCCGCTTTTCGTGAAGAGTATTATAAGCTGTTAAAGGACTATTCCGGAC

GCCCGACTGCATTAACATACGCTGATCGAGTCACTGAATACTTAGGCGGC

GCGAAAATCTATTTGAAACGAGAAGATTTAAACCATACAGGTTCTCATAA

AATCAATAATGCGCTAGGTCAAGCGCTGCTTGCTAAAAAAATGGGCAAAA

CGAAAATCATTGCTGAAACCGGTGCCGGCCAGCATGGTGTTGCCGCTGCA

ACAGTTGCAGCCAAATTCGGCTTTTCCTGTACTGTGTTTATGGGTGAAGA

GGATGTTGCCCGCCAGTCTCTGAACGTTTTCCGCATGAAGCTTCTTGGAG

-continued

CGGAGGTAGTGCCTGTAACAAGCGGAAACGGAACATTGAAGGATGCCACA

AATGAGGCGATCCGGTACTGGGTTCAGCATTGTGAGGATCACTTTTATAT

GATTGGATCAGTTGTCGGCCCGCATCCTTATCCGCAAGTGGTCCGTGAAT

TTCAAAAAATGATCGGAGAGGAAGCGAAGGATCAGTTGAAACGTATTGAA

GGCACTATGCCTGATAAAGTAGTGGCATGTGTAGGCGGAGGAAGCAATGC

GATGGGTATGTTTCAGGCATTTTTAAATGAAGATGTTGAACTGATCGGCG

CTGAAGCAGCAGGAAAAGGAATTGATACACCTCTTCATGCCGCCACTATT

TCGAAAGGAACCGTAGGGGTTATTCACGGTTCATTGACTTATCTCATTCA

GGATGAGTTCGGGCAAATTATTGAGCCCTACTCTATTTCAGCCGGTCTCG

ACTATCCTGGAATCGGTCCGGAGCATGCATATTTGCATAAAAGCGGCCGT

GTCACTTATGACAGTATAACCGATGAAGAAGCGGTGGATGCATTAAAGCT

TTTGTCAGAAAAAGAGGGGATTTTGCCGGCAATCGAATCTGCCCATGCGT

TAGCGAAAGCATTCAAACTCGCCAAAGGAATGGATCGCGGTCAACTCATT

CTCGTCTGTTTATCAGGCCGGGGAGACAAGGATGTCAACACATTAATGAA

TGTATTGGAAGAAGAGGTGAAAGCCCATGTTTAAATTGGATCTTCAACCA

TCAGAAAAATTGTTTATCCCGTTTATTACGGCGGGCGATCCAGTTCCTGA

GGTTTCGATTGAACTGGCGAAGTCACTCCAAAAAGCAGGCGCCACAGCAT

TGGAGCTTGGTGTTGCATACTCTGACCCGCTTGCAGACGGTCCGGTGATC

CAGCGGGCTTCAAAGCGGGCGCTTGATCAAGGAATGAATATCGTAAAGGC

AATCGAATTAGGCGGAGAAATGAAAAAAAACGGAGTGAATATTCCGATTA

TCCTCTTTACGTATTATAATCCTGTGTTACAATTGAACAAAGAATACTTT

TTCGCTTTACTGCGGGAAAATCATATTGACGGTCTGCTTGTTCCGGATCT

GCCATTAGAAGAAAGCAACAGCCTTCAAGAGGAATGTAAAAGCCATGAGG

TGACGTATATTTCTTTAGTTGCGCCGACAAGCGAAAGCCGTTTGAAAACC

ATTATTGAACAAGCCGAGGGGTTCGTCTACTGTGTATCTTCTCTGGGTGT

GACCGGTGTCCGCAATGAGTTCAATTCATCCGTGTACCCGTTCATTCGTA

CTGTGAAGAATCTCAGCACTGTTCCGGTTGCTGTAGGGTTCGGTATATCA

AACCGTGAACAGGTCATAAAGATGAATGAAATTAGTGACGGTGTCGTAGT

GGGAAGTGCGCTCGTCAGAAAAATAGAAGAATTAAAGGACCGGCTCATCA

GCGCTGAAACGAGAAATCAGGCGCTGCAGGAGTTTGAGGATTATGCAATG

GCGTTTAGCGGCTTGTACAGTTTAAAA.

The deduced TrpA protein (tryptophan synthase (alpha subunit)) sequence is:

(SEQ ID NO: 41)

MFKLDLQPSEKLFIPFITAGDPVPEVSIELAKSLQKAGATALELGVAYSD

PLADGPVIQRASKRALDQGMNIVKAIELGGEMKKNGVNIPIILFTYYNPV

LQLNKEYFFALLRENHIDGLLVPDLPLEESNSLQEECKSHEVTYISLVAP

TSESRLKTIIEQAEGFVYCVSSLGVTGVRNEFNSSVYPFIRTVKNLSTVP

VAVGFGISNREQVIKMNEISDGVVVGSALVRKIEELKDRLISAETRNQAL

QEFEDYAMAFSGLYSLK.

The deduced TrpB protein (tryptophan synthase (beta subunit)) sequence is:

(SEQ ID NO: 43)

```
MYPYPNEIGRYGDFGGKFVPETLMQPLDEIQTAFKQIKDDPAFREEYYKL
LKDYSGRPTALTYADRVTEYLGGAKIYLKREDLNHTGSHKINNALGQALL
AKKMGKTKIIAETGAGQHGVAAATVAAKFGFSCTVFMGEEDVARQSLNVF
RMKLLGAEVVPVTSGNGTLKDATNEAIRYWVQHCEDHFYMIGSVVGPHPY
PQVVREFQKMIGEEAKDQLKRIEGTMPDKVVACVGGGSNAMGMFQAFLNE
DVELIGAEAAGKGIDTPLHAATISKGTVGVIHGSLTYLIQDEFGQIIEPY
SISAGLDYPGIGPEHAYLHKSGRVTYDSITDEEAVDALKLLSEKEGILPA
IESAHALAKAFKLAKGMDRGQLILVCLSGRGDKDVNTLMNVLEEEVKA
HV.
```

The deduced TrpC protein indol-3-glycerol phosphate synthase) sequence is:

(SEQ ID NO: 45)

```
MLEKIIKQKKEEVKTLVLPVEQPFEKRSFKEAPASPNRFIGLIAEVKKAS
PSKGLIKEDFVPVQIAKDYEAAKADAISVLTDTPFFQGENSYLSDVKRAV
SIPVLRKDFIIDSLQVEESRRIGADAILLIGEVLDPLHLHELYLEAGEKG
MDVLVEVHDASTLEQILKVFTPDILGVNNRNLKTFETSVKQTEQIASLVP
KESLLVSESGIGSLEHLTFVNEHGARAVLIGESLMRQTSQRKAIHALF
RE.
```

The deduced TrpD protein (anthranilate phosphoribosyl-transferase) sequence is:

(SEQ ID NO: 47)

```
MNRFLQLCVDGKTLTAGEAETLMNMMMAAEMTPSEMGGILSILAHRGETP
EELAGFVKAMRAHALTVDGLPDIVDTCGTGGDGISTFNISTASAIVASAA
GAKIAKHGNRSVSSKSGSADVLEELEVSIQTTPEKVKSSIETNNMGFLFA
PLYHSSMKHVAGTRKELGFRTVFNLLGPLSNPLQAKRQVIGVYSVEKAGL
MASALETFQPKHVMFVSSRDGLDELSITAPTDVIELKDGERREYTVSPED
FGFTNGRLEDLQVQSPKESAYLIQNIFENKSSSSALSITAFNAGAAIYTA
GITASLKEGTELALETITSGGAAAQLERLKQKEEEIYA.
```

The deduced TrpE protein (anthranilate synthase) sequence is:

(SEQ ID NO: 49)

```
MNFQSNISAFLEDSLSHHTIPIVETFTVDTLTPIQMIEKLDREITYLLES
KDDTSTWSRYSFIGLNPFLTIKEEQGRFSAADQDSKSLYTGNELKEVLNW
MNTTYKIKTPELGIPFVGGAVGYLSYDMIPLIEPSVPSHTKETDMEKCML
FVCRTLIAYDHETKNVHFIQYARLTGEETKNEKMDVFHQNHLELQNLIEK
MMDQKNIKELFLSADSYKTPSFETVSSNYEKSAFMADVEKIKSYIKAGDI
FQGVLSQKFEVPIKADAFELYRVLRIVNPSPYMYYMKLLDREIVGSSPER
LIHVQDGHLEIHPIAGTRKRGADKAEDERLKVELMKDEKEKAEHYMLVDL
ARNDIGRVAEYGSVSVPEFTKIVSFSHVMHIISVVTGRLKKGVHPVDALM
```

-continued

```
SAFPAGTLTGAPKIRAMQLLQELEPTPRETYGGCIAYIGFDGNIDSCITI
RTMSVKNGVASIQAGAGIVADSVPEAEYEESCNKAGALLKTIHIAEDMFH
SKEDKADEQISTIVR.
```

The deduced TrpF protein (phosphoribosyl anthranilate isomerase) sequence is:

(SEQ ID NO: 51)

```
MKKPALKYCGIRSLKDLQLAAESQADYLGFIFAESKRKVSPEDVKKWLNQ
VRVEKQVAGVFVNESIETMSRIAKSLKLDVIQLHGDEKPADVAALRKLTG
CEIWKALHHQDNTTQEIARFKDNVDGFVIDSSVKGSRGGTGVAFSWDCVP
EYQQAAIGKRCFIAGGVNPDSITRLLKWQPEGIDLASGIEKNGQKDQNLM
RLLEERMNRYVSISE.
```

Additionally, the coding region is found at about 2370707 bp to 2376834 bp (first bp=2376834; last bp=2370707) by of the *B. subtilis* 168 chromosome.

The ycgM coding sequence of the ycgM protein (similar to proline oxidase) of *B. subtilis* 168 is shown below:

(SEQ ID NO: 52)

```
GTGATCACAAGAGATTTTTTCTTATTTTTATCCAAAAGCGGCTTTCTCAA
TAAAATGGCGAGGAACTGGGGAAGTCGGGTAGCAGCGGGTAAAATTATCG
GCGGGAATGACTTTAACAGTTCAATCCCGACCATTCGACAGCTTAACAGC
CAAGGCTTGTCAGTTACTGTCGATCATTTAGGCGAGTTTGTGAACAGCGC
CGAGGTCGCACGGGAGCGTACGGAAGAGTGCATTCAAACCATTGCGACCA
TCGCGGATCAGGAGCTGAACTCACACGTTTCTTTAAAAATGACGTCTTTA
GGTTTGGATATAGATATGGATTTGGTGTATGAAAATATGACAAAAATCCT
TCAGACGGCCGAGAAACATAAAATCATGGTCACCATTGACATGGAGGACG
AAGTCAGATGCCAGAAAACGCTTGATATTTTCAAAGATTTCAGAAAGAAA
TACGAGCATGTGAGCACAGTGCTGCAAGCCTATCTGTACCGGACGGAAAA
AGACATTGACGATTTGGATTCTTTAAACCCGTTCCTTCGCCTTGTAAAAG
GAGCTTATAAAGAATCAGAAAAAGTAGCTTTCCCGGAGAAAAGCGATGTC
GATGAAAATTACAAAAAAATCATCCGAAAGCAGCTCTTAAACGGTCACTA
TACAGCGATTGCCACACATGACGACAAAATGATCGACTTTACAAAGCAGC
TTGCCAAGGAACATGGCATTGCCAATGACAAGTTTGAATTTCAGATGCTG
TACGGCATGCGGTCGCAAACCCAGCTCAGCCTCGTAAAAGAAGGTTATAA
CATGAGAGTCTACCTGCCATACGGCGAGGATTGGTACGGCTACTTTATGA
GACGCCTTGCAGAACGTCCGTCAAACATTGCATTTGCTTTCAAAGGAATG
ACAAAGAAG.
```

The deduced amino acid sequence of the YcgM protein is:

(SEQ ID NO: 53)

```
MITRDFFLFLSKSGFLNKMARNWGSRVAAGKIIGGNDFNSSIPTIRQLNS
QGLSVTVDHLGEFVNSAEVARERTEECIQTIATIADQELNSHVSLKMTSL
GLDIDMDLVYENMTKILQTAEKHKIMVTIDMEDEVRCQKTLDIFKDFRKK
```

-continued

YEHVSTVLQAYLYRTEKDIDDLDSLNPFLRLVKGAYKESEKVAFPEKSDV

DENYKKIIRKQLLNGHYTAIATHDDKMIDFTKQLAKEHGIANDKFEFQML

YGMRSQTQLSLVKEGYNMRVYLPYGEDWYGYFMRRLAERPSNIAFAFKGM

TKK.

Additionally, the coding region is found at about 344111-345019 bp of the *B. subtilis* 168 chromosome.

The ycgN coding sequence of the ycgN protein (similar to 1-pyrroline-5-carboxylate dehydrogenase) of *B. subtilis* 168 is shown below:

(SEQ ID NO: 54)

ATGACAACACCTTACAAACACGAGCCATTCACAAATTTCCAAGATCAAAA

CTACGTGGAAGCGTTTAAAAAAGCGCTTGCGACAGTAAGCGAATATTTAG

GAAAAGACTATCCGCTTGTCATTAACGGCGAGAGAGTGGAAACGGAAGCG

AAAATCGTTTCAATCAACCCAGCTGATAAAGAAGAAGTCGTCGGCCGAGT

GTCAAAAGCGTCTCAAGAGCACGCTGAGCAAGCGATTCAAGCGGCTGCAA

AAGCATTTGAAGAGTGGAGATACACGTCTCCTGAAGAGAGAGCGGCTGTC

CTGTTCCGCGCTGCTGCCAAAGTCCGCAGAAGAAAACATGAATTCTCAGC

TTTGCTTGTGAAAGAAGCAGGAAAGCCTTGGAACGAGGCGGATGCCGATA

CGGCTGAAGCGATTGACTTCATGGAGTATTATGCACGCCAAATGATCGAA

CTGGCAAAAGGCAAACCGGTCAACAGCCGTGAAGGCGAGAAAAACCAATA

TGTATACACGCCGACTGGAGTGACAGTCGTTATCCCGCCTTGGAACTTCT

TGTTTGCGATCATGGCAGGCACAACAGTGGCGCCGATCGTTACTGGAAAC

ACAGTGGTTCTGAAACCTGCGAGTGCTACACCTGTTATTGCAGCAAAATT

TGTTGAGGTGCTTGAAGAGTCCGGATTGCCAAAAGGCGTAGTCAACTTTG

TTCCGGGAAGCGGATCGGAAGTAGGCGACTATCTTGTTGACCATCCGAAA

ACAAGCCTTATCACATTTACGGGATCAAGAGAAGTTGGTACGAGAATTTT

CGAACGCGCGGCGAAGGTTCAGCCGGGCCAGCAGCATTTAAAGCGTGTCA

TCGCTGAAATGGGCGGTAAAGATACGGTTGTTGTTGATGAGGATGCGGAC

ATTGAATTAGCGGCTCAATCGATCTTTACTTCAGCATTCGGCTTTGCGGG

ACAAAAATGCTCTGCAGGTTCACGTGCAGTAGTTCATGAAAAAGTGTATG

ATCAAGTATTAGAGCGTGTCATTGAAATTACGGAATCAAAAGTAACAGCT

AAACCTGACAGTGCAGATGTTTATATGGGACCTGTCATTGACCAAGGTTC

TTATGATAAAATTATGAGCTATATTGAGATCGGAAAACAGGAAGGGCGTT

TAGTAAGCGGCGGTACTGGTGATGATTCGAAAGGATACTTCATCAAACCG

ACGATCTTCGCTGACCTTGATCCGAAAGCAAGACTCATGCAGGAAGAAAT

TTTCGGACCTGTCGTTGCATTTTGTAAAGTGTCAGACTTTGATGAAGCTT

TAGAAGTGGCAAACAATACTGAATATGGTTTGACAGGCGCGGTTATCACA

AACAACCGCAAGCACATCGAGCGTGCGAAACAGGAATTCCATGTCGGAAA

CCTATACTTCAACCGCAACTGTACAGGTGCTATCGTCGGCTACCATCCGT

TTGGCGGCTTCAAAATGTCGGGAACGGATTCAAAAGCAGGCGGGCCGGAT

TACTTGGCTCTGCATATGCAAGCAAAAACAATCAGTGAAATGTTC.

The deduced amino acid sequence of YcgN protein is:

(SEQ ID NO: 55)

MTTPYKHEPFTNFQDQNYVEAFKKALATVSEYLGKDYPLVINGERVETEA

KIVSINPADKEEVVGRVSKASQEHAEQAIQAAAKAFEEWRYTSPEERAAV

LFRAAAKVRRRKHEFSALLVKEAGKPWNEADADTAEAIDFMEYYARQMIE

LAKGKPVNSREGEKNQYVYTPTGVTVVIPPWNFLFAIMAGTTVAPIVTGN

TVVLKPASATPVIAAKFVEVLEESGLPKGVVNFVPGSGSEVGDYLVDHPK

TSLITFTGSREVGTRIFERAAKVQPGQQHLKRVIAEMGGKDTVVVDEDAD

IELAAQSIFTSAFGFAGQKCSAGSRAVVHEKVYDQVLERVIEITESKVTA

KPDSADVYMGPVIDQGSYDKIMSYIEIGKQEGRLVSGGTGDDSKGYFIKP

TIFADLDPKARLMQEEIFGPVVAFCKVSDFDEALEVANNTEYGLTGAVIT

NNRKHIERAKQEFHVGNLYFNRNCTGAIVGYHPFGGFKMSGTDSKAGGPD

YLALHMQAKTISEMF.

Additionally, the coding region is found at about 345039-346583 bp of the *B. subtilis* 168 chromosome.

The sigD coding sequence of the sigD protein (RNA polymerase flagella, motility, chemotaxis and autolysis sigma factor) of *B. subtilis* 168 is shown below:

(SEQ ID NO: 56)

ATGCAATCCTTGAATTATGAAGATCAGGTGCTTTGGACGCGCTGGAAAGA

GTGGAAAGATCCTAAAGCCGGTGACGACTTAATGCGCCGTTACATGCCGC

TTGTCACATATCATGTAGGCAGAATTTCTGTCGGACTGCCGAAATCAGTG

CATAAAGACGATCTTATGAGCCTTGGTATGCTTGGTTTATATGATGCCCT

TGAAAAATTTGACCCCAGCCGGGACTTAAAATTTGATACCTACGCCTCGT

TTAGAATTCGCGGCGCAATCATAGACGGGCTTCGTAAAGAAGATTGGCTG

CCCAGAACCTCGCGCGAAAAAACAAAAAAGGTTGAAGCAGCAATTGAAAA

GCTTGAACAGCGGTATCTTCGGAATGTATCGCCCGCGGAAATTGCAGAGG

AACTCGGAATGACGGTACAGGATGTCGTGTCAACAATGAATGAAGGTTTT

TTTGCAAATCTGCTGTCAATTGATGAAAAGCTCCATGATCAAGATGACGG

GGAAAACATTCAAGTCATGATCAGAGATGACAAAAATGTTCCGCCTGAAG

AAAAGATTATGAAGGATGAACTGATTGCACAGCTTGCGGAAAAAATTCAC

GAACTCTCTGAAAAAGAACAGCTGGTTGTCAGTTTGTTCTACAAAGAGGA

GTTGACACTGACAGAAATCGGACAAGTATTAAATCTTTCTACGTCCCGCA

TATCTCAGATCCATTCAAAGGCATTATTTAAATTAAAGAATCTGCTGGAA

AAAGTGATACAA.

The deduced amino acid sequence of the SigD is:

(SEQ ID NO: 57)

MQSLNYEDQVLWTRWKEWKDPKAGDDLMRRYMPLVTYHVGRISVGLPKSV

HKDDLMSLGMLGLYDALEKFDPSRDLKFDTYASFRIRGAIIDGLRKEDWL

PRTSREKTKKVEAAIEKLEQRYLRNVSPAEIAEELGMTVQDVVSTMNEGF

FANLLSIDEKLHDQDDGENIQVMIRDDKNVPPEEKIMKDELIAQLAEKIH

ELSEKEQLVVSLFYKEELTLTEIGQVLNLSTSRISQIHSKALFKLKNLLE

KVIQ.

Additionally, the coding region is found at about 1715786-1716547 bp of the *B. subtilis* 168 chromosome.

As indicated above, it is contemplated that inactivated analogous genes found in other *Bacillus* hosts will find use in the present invention.

In some preferred embodiments, the host cell is a member of the genus *Bacillus*, while in some embodiments, the *Bacillus* strain of interest is alkalophilic. Numerous alkalophilic *Bacillus* strains are known (See e.g., U.S. Pat. No. 5,217,878; and Aunstrup et al., Proc IV IFS: Ferment. Technol. Today, 299-305 [1972]). In some preferred embodiments, the *Bacillus* strain of interest is an industrial *Bacillus* strain. Examples of industrial *Bacillus* strains include, but are not limited to *B. licheniformis, B. lentus, B. subtilis*, and *B. amyloliquefaciens*. In additional embodiments, the *Bacillus* host strain is selected from the group consisting of *B. lentus, B. brevis, B. stearothermophilus, B. alkalophilus, B. coagulans, B. circulans, B. pumilus, B. thuringiensis, B. clausii*, and *B. megaterium*, as well as other organisms within the genus *Bacillus*, as discussed above. In some particularly preferred embodiments, *B. subtilis* is used. For example, U.S. Pat. Nos. 5,264,366 and 4,760,025 (RE 34,606) describe various *Bacillus* host strains that find use in the present invention, although other suitable strains are contemplated for use in the present invention.

An industrial strain may be a non-recombinant strain of a *Bacillus* sp., a mutant of a naturally occurring strain or a recombinant strain. Preferably, the host strain is a recombinant host strain wherein a polynucleotide encoding a polypeptide of interest has been introduced into the host. A further preferred host strain is a *Bacillus subtilis* host strain and particularly a recombinant *Bacillus subtilis* host strain. Numerous *B. subtilis* strains are known, including but not limited to 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain (See e.g., Hoch et al., Genetics, 73:215-228 [1973]; U.S. Pat. Nos. 4,450,235; 4,302,544; and EP 0134048). The use of *B. subtilis* as an expression host is further described by Palva et al. and others (See, Palva et al., Gene 19:81-87 [1982]; also see Fahnestock and Fischer, J. Bacteriol., 165: 796-804 [1986]; and Wang et al., Gene 69:39-47 [1988]).

Industrial protease producing *Bacillus* strains provide particularly preferred expression hosts. In some preferred embodiments, use of these strains in the present invention provides further enhancements in efficiency and protease production. Two general types of proteases are typically secreted by *Bacillus* sp., namely neutral (or "metalloproteases") and alkaline (or "serine") proteases. Serine proteases are enzymes which catalyze the hydrolysis of peptide bonds in which there is an essential serine residue at the active site. Serine proteases have molecular weights in the 25,000 to 30,000 range (See, Priest, Bacteriol. Rev., 41:711-753 [1977]). Subtilisin is a preferred serine protease for use in the present invention. A wide variety of *Bacillus* subtilisins have been identified and sequenced, for example, subtilisin 168, subtilisin BPN', subtilisin Carlsberg, subtilisin DY, subtilisin 147 and subtilisin 309 (See e.g., EP 414279 B; WO 89/06279; and Stahl et al., J. Bacteriol., 159:811-818 [1984]). In some embodiments of the present invention, the *Bacillus* host strains produce mutant (e.g., variant) proteases. Numerous references provide examples of variant proteases and reference (See e.g., WO 99/20770; WO 99/20726; WO 99/20769; WO 89/06279; RE 34,606; U.S. Pat. Nos. 4,914,031; 4,980,288; 5,208,158; 5,310,675; 5,336,611; 5,399,283; 5,441,882; 5,482,849; 5,631,217; 5,665,587; 5,700,676; 5,741,694; 5,858,757; 5,880,080; 6,197,567; and 6,218,165).

In yet another embodiment, a preferred *Bacillus* host is a *Bacillus* sp. that includes a mutation or deletion in at least one of the following genes, degU, degS, degR and degQ. Preferably the mutation is in a degU gene, and more preferably the mutation is degU(Hy)32. (See, Msadek et al., J. Bacteriol., 172:824-834 [1990]; and Olmos et al., Mol. Gen. Genet., 253:562-567 [1997]). A most preferred host strain is a *Bacillus subtilis* carrying a degU32(Hy) mutation. In a further embodiment, the *Bacillus* host comprises a mutation or deletion in scoC4, (See, Caldwell et al., J. Bacteriol., 183:7329-7340 [2001]); spollE (See, Arigoni et al., Mol. Microbiol., 31:1407-1415 [1999]); oppA or other genes of the opp operon (See, Perego et al., Mol. Microbiol., 5:173-185 [1991]). Indeed, it is contemplated that any mutation in the opp operon that causes the same phenotype as a mutation in the oppA gene will find use in some embodiments of the altered *Bacillus* strain of the present invention. In some embodiments, these mutations occur alone, while in other embodiments, combinations of mutations are present. In some embodiments, an altered *Bacillus* of the invention is obtained from a *Bacillus* host strain that already includes a mutation to one or more of the above-mentioned genes. In alternate embodiments, an altered *Bacillus* of the invention is further engineered to include mutation of one or more of the above-mentioned genes.

In yet another embodiment, the incoming sequence comprises a selective marker located between two loxP sites (See, Kuhn and Torres, Meth. Mol. Biol., 180:175-204 [2002]), and the antimicrobial is then deleted by the action of Cre protein. In some embodiments, this results in the insertion of a single loxP site, as well as a deletion of native DNA, as determined by the primers used to construct homologous flanking DNA and antimicrobial-containing incoming DNA.

Those of skill in the art are well aware of suitable methods for introducing polynucleotide sequences into *Bacillus* cells (See e.g., Ferrari et al., "Genetics," in Harwood et al. (ed.), *Bacillus*, Plenum Publishing Corp. [1989], pages 57-72; See also, Saunders et al., J. Bacteriol., 157:718-726 [1984]; Hoch et al., J. Bacteriol., 93:1925-1937 [1967]; Mann et al., Current Microbiol., 13:131-135 [1986]; and Holubova, Folia Microbiol., 30:97 [1985]; for *B. subtilis*, Chang et al., Mol. Gen. Genet., 168:11-115 [1979]; for *B. megaterium*, Vorobjeva et al., FEMS Microbiol. Lett., 7:261-263 [1980]; for *B. amyloliquefaciens*, Smith et al, Appl. Env. Microbiol., 51:634 (1986); for *B. thuringiensis*, Fisher et al., Arch. Microbiol., 139:213-217 [1981]; and for *B. sphaericus*, McDonald, J. Gen. Microbiol., 130:203 [1984]). Indeed, such methods as transformation including protoplast transformation and congression, transduction, and protoplast fusion are known and suited for use in the present invention. Methods of transformation are particularly preferred to introduce a DNA construct provided by the present invention into a host cell.

In addition to commonly used methods, in some embodiments, host cells are directly transformed (i.e., an intermediate cell is not used to amplify, or otherwise process, the DNA construct prior to introduction into the host cell). Introduction of the DNA construct into the host cell includes those physical and chemical methods known in the art to introduce DNA into a host cell without insertion into a plasmid or vector. Such methods include, but are not limited to calcium chloride precipitation, electroporation, naked DNA, liposomes and the like. In additional embodiments, DNA constructs are co-transformed with a plasmid, without being inserted into the plasmid. In further embodiments, a selective marker is deleted from the altered *Bacillus* strain by methods known in the art (See, Stahl et al., J. Bacteriol., 158:411-418 [1984]; and Palmeros et al., Gene 247:255-264 [2000]).

In some embodiments, host cells are transformed with one or more DNA constructs according to the present invention to produce an altered *Bacillus* strain wherein two or more genes have been inactivated in the host cell. In some embodiments, two or more genes are deleted from the host cell chromosome. In alternative embodiments, two or more genes are inactivated by insertion of a DNA construct. In some embodiments, the inactivated genes are contiguous (whether inactivated by deletion and/or insertion), while in other embodiments, they are not contiguous genes.

There are various assays known to those of ordinary skill in the art for detecting and measuring activity of intracellularly and extracellularly expressed polypeptides. In particular, for proteases, there are assays based on the release of acid-soluble peptides from casein or hemoglobin measured as absorbance at 280 nm or colorimetrically using the Folin method (See e.g., Bergmeyer et al, "Methods of Enzymatic Analysis" vol. 5, *Peptidases, Proteinases and their Inhibitors*, Verlag Chemie, Weinheim [1984]). Other assays involve the solubilization of chromogenic substrates (See e.g., Ward, "Proteinases," in Fogarty (ed.)., *Microbial Enzymes and Biotechnology*, Applied Science, London, [1983], pp 251-317). Other exemplary assays include succinyl-Ala-Ala-Pro-Phe-para nitroanilide assay (SAAPFpNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem., 223:119-129 [1994]; and Hsia et al., Anal Biochem., 242:221-227 [1999]).

Means for determining the levels of secretion of a protein of interest in a host cell and detecting expressed proteins include the use of immunoassays with either polyclonal or monoclonal antibodies specific for the protein. Examples include enzyme-linked immunosorbent assay (ELISA), radioimmunoassay (RIA), fluorescence immunoassay (FIA), and fluorescent activated cell sorting (FACS). However, other methods are known to those in the art and find use in assessing the protein of interest (See e.g., Hampton et al., *Serological Methods, A Laboratory Manual*, APS Press, St. Paul, Minn. [1990]; and Maddox et al., J. Exp. Med., 158:1211 [1983]). In some preferred embodiments, secretion of a protein of interest is higher in the altered strain obtained using the present invention than in a corresponding unaltered host. As known in the art, the altered *Bacillus* cells produced using the present invention are maintained and grown under conditions suitable for the expression and recovery of a polypeptide of interest from cell culture (See e.g., Hardwood and Cutting (eds.) *Molecular Biological Methods for Bacillus*, John Wiley & Sons [1990]).

B. Large Chromosomal Deletions

As indicated above, in addition to single and multiple gene deletions, the present invention provides large chromosomal deletions. In some preferred embodiments of the present invention, an indigenous chromosomal region or fragment thereof is deleted from a *Bacillus* host cell to produce an altered *Bacillus* strain. In some embodiments, the indigenous chromosomal region includes prophage regions, antimicrobial regions, (e.g., antibiotic regions), regulator regions, multi-contiguous single gene regions and/or operon regions. The coordinates delineating indigenous chromosomal regions referred to herein are specified according to the *Bacillus subtilis* strain 168 chromosome map. Numbers generally relate to the beginning of the ribosomal binding site, if present, or the end of the coding region, and generally do not include a terminator that might be present. The *Bacillus subtilis* genome of strain 168 is well known (See, Kunst et al., Nature 390:249-256 [1997]; and Henner et al., Microbiol. Rev., 44:57-82 [1980]), and is comprised of one 4215 kb chromosome. However, the present invention also includes analogous sequences from any *Bacillus* strain. Particularly preferred are other *B. subtilis* strains, *B. licheniformis* strains and *B. amyloliquefaciens* strains.

In some embodiments, the indigenous chromosomal region includes prophage segments and fragments thereof. A "prophage segment" is viral DNA that has been inserted into the bacterial chromosome wherein the viral DNA is effectively indistinguishable from normal bacterial genes. The *B. subtilis* genome is comprised of numerous prophage segments; these segments are not infective. (Seaman et al., Biochem., 3:607-613 [1964]; and Stickler et al., Virol., 26:142-145 [1965]). Although any one of the *Bacillus subtilis* prophage regions may be deleted, reference is made to the following non-limiting examples.

One prophage region that is deleted in some embodiments of the present invention is a sigma K intervening "skin" element. This region is found at about 2652600 bp (spoIVCA) to 2700579 bp (yqaB) of the *B. subtilis* 168 chromosome. Using the present invention, about a 46 kb segment was deleted, corresponding to 2653562 bp to 2699604 bp of the chromosome. This element is believed to be a remnant of an ancestral temperate phage which is position within the SIGK ORF, between the genes spoIVCB and spoIIIC. However, it is not intended that the present invention be limited to any particular mechanism or mode of action involving the deleted region. The element has been shown to contain 57 open reading frames with putative ribosome binding sites (See, Takemaru et al., Microbiol., 141:323-327 [1995]). During spore formation in the mother cell, the skin element is excised leading to the reconstruction of the sigK gene.

Another region suitable for deletion is a prophage 7 region. This region is found at about 2701208 bp (yrkS) to 2749572 bp (yraK) of the *B. subtilis* 168 chromosome. Using the present invention, about a 48.5 kb segment was deleted, corresponding to 2701087 bp to 2749642 bp of the chromosome.

A further region is a skin+prophage 7 region. This region is found at about 2652151 bp to 2749642 bp of the *B. subtilis* 168 chromosome. Using the present invention, a segment of about 97.5 kb was deleted. This region also includes the intervening spoIIIC gene. The skin/prophage 7 region includes but is not limited to the following genes: spoIVCA-DNA recombinase, bit (multidrug resistance), cypA (cytochrome P450-like enzyme), czcD (cation-efflux system membrane protein), and rapE (response regulator aspartate phosphatase).

Yet another region is the PBSX region. This region is found at about 1319884 bp (xkdA) to 1347491 bp (xlyA) of the *B. subtilis* 168 chromosome. Using the present invention, a segment of about 29 kb was deleted, corresponding to 1319663 to 1348691 bp of the chromosome. Under normal non-induced conditions this prophage element is non-infective and is not bactericidal (except for a few sensitive strains such as W23 and S31). It is inducible with mitomycin C and activated by the SOS response and results in cell lysis with the release of phage-like particles. The phage particles contain bacterial chromosomal DNA and kill sensitive bacteria without injecting DNA. (Canosi et al., J. Gen. Virol. 39: 81-90 [1978]). This region includes the following non-limiting list of genes: xtmA-B; xkdA-K and M-X, xre, xtrA, xpf, xep, xhlA-B and xlyA.

A further region is the SPβ region. This region is found at about 2150824 bp (yodU) to 2286246 bp (ypqP) of the *B. subtilis* 168 chromosome. Using the present invention, a segment of about 133.5 kb was deleted, corresponding to 2151827 to 2285246 bp of the chromosome. This element is a temperate prophage whose function has not yet been characterized. However, genes in this region include putative spore coat proteins (yodU, sspC, yokH), putative stress response proteins (yorD, yppQ, ypnP and other genes that have homology to genes in the spore coat protein and stress response genes such as members of the yom operon. Other genes is this region include: yot; yos, yoq, yop, yon, yom, yoz, yol, yok, ypo, and ypm.

An additional region is the prophage 1 region. This region is found at about 202098 bp (ybbU) to 220015 bp (ybdE) of the *B. subtilis* 168 chromosome. Using the present invention, a segment of about 18.0 kb was deleted, corresponding to 202112 to 220141 bp of the chromosome. Genes in this region include the AdaA/B operon which provides an adaptive response to DNA alkylation and ndhF which codes for NADH dehydrogenase, subunit 5.

A further region is the prophage 2 region. This region is found at about 529069 bp (ydcL) to 569493 bp (ydeJ) of the *B. subtilis* 168 chromosome. Using the present invention, a segment of about 40.5 kb was deleted, corresponding to 529067 to 569578 bp of the chromosome. Genes in this region include rapI/phrI (response regulator asparate phosphatase), sacV (transcriptional regulator of the levansucrase) and cspC.

Another region is the prophage 3 region. Using the present invention, a segment of about 50.7 kb segment was deleted, corresponding to about 652000 to 664300 bp of the *B. subtilis* 168 chromosome.

Yet another region is the prophage 4 region. This region is found at about 1263017 bp (yjcM) to 1313627 bp (yjoA) of the *B. subtilis* 168 chromosome. Using the present invention, a segment of about 2.3 kb was deleted, corresponding to 1262987 to 1313692 bp of the chromosome.

An additional region is the prophage 5 region. Using the present invention a segment of about 20.8 kb segment was deleted, corresponding to about 1879200 to 1900000 bp of the *B. subtilis* 168 chromosome.

Another region is the prophage 6 region. Using the present invention a segment of about a 31.9 kb segment was deleted, corresponding to about 2046050 to 2078000 bp in the *B. subtilis* 168 chromosome.

In further embodiments, the indigenous chromosomal region includes one or more operon regions, multi-contiguous single gene regions, and/or anti-microbial regions. In some embodiments, these regions include the following:

1) The PPS operon region:

This region is found at about 1959410 bp (ppsE) to 1997178 bp (ppsA) of the *Bacillus subtilis* 168 chromosome. Using the present invention, a segment of about 38.6 kb was deleted, corresponding to about 1960409 to 1998026 bp of the chromosome. This operon region is involved in antimicrobial synthesis and encodes plipastatin synthetase;

2) The PKS operon region:

This region is found at about 1781110 bp (pksA) to 1857712 bp (pksR) of the *B. subtilis* 168 chromosome. Using the present invention, a segment of about 76.2 kb was deleted, corresponding to about 1781795 to 1857985 bp of the chromosome. This region encodes polyketide synthase and is involved in anti-microbial synthesis. (Scotti et al., Gene, 130:65-71 [1993]);

3) The yvfF-yveK operon region:

This region is found at about 3513149 bp (yvfF) to 3528184 bp (yveK) of the *B. subtilis* 168 chromosome. Using the present invention, a segment of about 15.8 kb was deleted, corresponding to about 3513137 to 3528896 bp of the chromosome. This region codes for a putative polysaccharide (See, Dartois et al., Seventh International Conference on *Bacillus* (1993) Institute Pasteur [1993], page 56). This region includes the following genes; yvfA-F, yveK-T and slr. The slr gene region which is found at about 3529014-3529603 bp of the *B. subtilis* 168 chromosome encompasses about a 589 bp segment. This region is the regulator region of the yvfF-yveK operon;

4) The DHB operon region:

This region is found at about 3279750 bp (yukL) to 3293206 bp (yuiH) of the *B. subtilis* 168 chromosome. Using the present invention, a segment of about 13.0 kb was deleted, corresponding to 3279418-3292920 bp of the chromosome. This region encodes the biosynthetic template for the catecholic siderophone 2,3-dihydroxy benzoate-glycine-threonine trimeric ester bacilibactin. (See, May et al., J. Biol. Chem., 276:7209-7217 [2001]). This region includes the following genes: yukL, yukM, dhbA-C, E and F, and yuil-H.

While the regions, as described above, are examples of preferred indigenous chromosomal regions to be deleted, in some embodiments of the present invention, a fragment of the region is also deleted. In some embodiments, such fragments include a range of about 1% to 99% of the indigenous chromosomal region. In other embodiments, fragments include a range of about 5% to 95% of the indigenous chromosomal region. In yet additional embodiments, fragments comprise at least 99%, 98%, 97%, 96%, 95%, 94%, 93%, 92%, 90%, 88%, 85%, 80%, 75%, 70%, 65%, 50%, 40%, 30%, 25%, 20% and 10% of the indigenous chromosomal region.

Further non-limiting examples of fragments of indigenous chromosomal regions to be deleted with reference to the chromosomal location in the *B. subtilis* 168 chromosome include the following:

a) for the skin region:

i) a coordinate location of about 2666663 to 2693807, which includes yqcC to yqaM, and ii) a coordinate location of about 2658440 to 2659688, which includes rapE to phrE;

b) for the PBSX prophage region:

i) a coordinate location of about 1320043 to 1345263, which includes xkdA to xkdX, and ii) a coordinate location of about 1326662 to 1345102, which includes xkdE to xkdW;

c) for the SPβ region:

i) a coordinate location of about 2149354 to 2237029, which includes yodV to yonA;

d) for the DHB region:

i) a coordinate location of about 3282879 to 3291353, which includes dhbF to dhbA;

e) for the yvfF-yveK region:

i) a coordinate location of about 3516549 to 3522333, which includes yvfB to yveQ, ii) a coordinate location of about 3513181 to 3528915, which includes yvfF to yveK, and iii) a coordinate location of about 3521233 to 3528205, which includes yveQ to yveL;

f) for the prophage 1 region:

i) a coordinate location of about 213926 to 220015, which includes ybcO to ybdE, and ii) a coordinate location of about 214146 to 220015, which includes ybcP to ybdE;

g) for the prophage 2 region:

i) a coordinate location of about 546867 to 559005, which includes rapt to cspC; and h) for the prophage 4 region:

i) a coordinate location of about 1263017 to 675421, which includes yjcM to ydjJ.

The number of fragments of indigenous chromosomal regions which are suitable for deletion are numerous, because a fragment may be comprised of only a few bps less than the identified indigenous chromosomal region. Furthermore, many of the identified indigenous chromosomal regions encompass a large number of genes. Those of skill in the art are capable of easily determining which fragments of the indigenous chromosomal regions are suitable for deletion for use in a particular application.

The definition of an indigenous chromosomal region is not so strict as to exclude a number of adjacent nucleotides to the defined segment. For example, while the SPβ region is defined herein as located at coordinates 2150824 to 2286246 of the *B. subtilis* 168 chromosome, an indigenous chromosomal region may include a further 10 to 5000 bp, a further 100 to 4000 bp, or a further 100 to 1000 bp on either side of the region. The number of by on either side of the region is limited by the presence of another gene not included in the indigenous chromosomal region targeted for deletion.

As stated above, the location of specified regions herein disclosed are in reference to the *B. subtilis* 168 chromosome. Other analogous regions from *Bacillus* strains are included in the definition of an indigenous chromosomal region. While the analogous region may be found in any *Bacillus* strain, particularly preferred analogous regions are regions found in other *Bacillus subtilis* strains, *Bacillus licheniformis* strains and *Bacillus amyloliquefaciens* strains.

In certain embodiments, more than one indigenous chromosomal region or fragment thereof is deleted from a *Bacillus* strain. However, the deletion of one or more indigenous chromosomal regions or fragments thereof does not deleteriously affect reproductive viability of the strain which includes the deletion. In some embodiments, two indigenous chromosomal regions or fragments thereof are deleted. In additional embodiments, three indigenous chromosomal regions or fragments thereof are deleted. In yet another embodiment, four indigenous chromosomal regions or fragments thereof are deleted. In a further embodiment, five indigenous chromosomal regions or fragments thereof are deleted. In another embodiment, as many as 14 indigenous chromosomal regions or fragments thereof are deleted. In some embodiments, the indigenous chromosomal regions or fragments thereof are contiguous, while in other embodiments, they are located on separate regions of the *Bacillus* chromosome.

A strain of any member of the genus *Bacillus* comprising a deleted indigenous chromosomal region or fragment thereof finds use in the present invention. In some preferred embodiments, the *Bacillus* strain is selected from the group consisting of *B. subtilis* strains, *B. amyloliquefaciens* strains, *B. lentus* strains, and *B. licheniformis* strains. In some preferred embodiments, the strain is an industrial *Bacillus* strain, and most preferably an industrial *B. subtilis* strain. In a further preferred embodiment, the altered *Bacillus* strain is a protease-producing strain. In some particularly preferred embodiments, it is a *B. subtilis* strain that has been previously engineered to include a polynucleotide encoding a protease enzyme.

As indicated above, a *Bacillus* strain in which an indigenous chromosomal region or fragment thereof has been deleted is referred to herein as "an altered *Bacillus* strain." In preferred embodiments of the present invention, the altered *Bacillus* strain has an enhanced level of expression of a protein of interest (i.e., the expression of the protein of interest is enhanced, compared to a corresponding unaltered *Bacillus* strain grown under the same growth conditions).

One measure of enhancement is the secretion of the protein of interest. In some embodiments, production of the protein of interest is enhanced by at least 0.5%, 1.0%, 1.5%, 2.0%, 2.5%, 3.0%, 4.0%, 5.0%, 8.0%, 10%, 15%, 20% and 25% or more, compared to the corresponding unaltered *Bacillus* strain. In other embodiments, production of the protein of interest is enhanced by between about 0.25% to 20%; 0.5% to 15% and 1.0% to 10%, compared to the corresponding unaltered *Bacillus* strain as measured in grams of protein produced per liter.

The altered *Bacillus* strains provided by the present invention comprising a deletion of an indigenous chromosomal region or fragment thereof are produced using any suitable methods, including but not limited to the following means. In one general embodiment, a DNA construct is introduced into a *Bacillus* host. The DNA construct comprises an inactivating chromosomal segment, and in some embodiments, further comprises a selective marker. Preferably, the selective marker is flanked on both the 5' and 3' ends by one section of the inactivating chromosomal segment.

In some embodiments, the inactivating chromosomal segment, while preferably having 100% sequence identity to the immediate upstream and downstream nucleotides of an indigenous chromosomal region to be deleted (or a fragment of said region), has between about 70 to 100%, about 80 to 100%, about 90 to 100%, and about 95 to 100% sequence identity to the upstream and downstream nucleotides of the indigenous chromosomal region. Each section of the inactivating chromosomal segment must include sufficient 5' and 3' flanking sequences of the indigenous chromosomal region to provide for homologous recombination with the indigenous chromosomal region in the unaltered host.

In some embodiments, each section of the inactivating chromosomal segment comprises about 50 to 10,000 base pairs (bp). However, lower or higher by sections find use in the present invention. Preferably, each section is about 50 to 5000 bp, about 100 to 5000 bp, about 100 to 3000 bp; 100 to 2000 bp; about 100 to 1000 bp; about 200 to 4000 bp, about 400 to 3000 bp, about 500 to 2000 bp, and also about 800 to 1500 bp.

In some embodiments, a DNA construct comprising a selective marker and an inactivating chromosomal segment is assembled in vitro, followed by direct cloning of said construct into a competent *Bacillus* host, such that the DNA construct becomes integrated into the *Bacillus* chromosome. For example, PCR fusion and/or ligation are suitable for assembling a DNA construct in vitro. In some embodiments, the DNA construct is a non-plasmid construct, while in other embodiments, it is incorporated into a vector (i.e., a plasmid). In some embodiments, a circular plasmid is used, and the circular plasmid is cut using an appropriate restriction enzyme (i.e., one that does not disrupt the DNA construct). Thus, linear plasmids find use in the present invention (See e.g., FIG. 1A and FIG. 1B; and Perego, "Integrational Vectors for Genetic Manipulation in *Bacillus subtilis*," in

*Bacillus subtilis and other Gram-Positive Bacteria*, Sonenshein. et al., Eds., Am. Soc. Microbiol., Washington, D.C. [1993]).

In some embodiments, a DNA construct or vector, preferably a plasmid including an inactivating chromosomal segment includes a sufficient amount of the 5' and 3' flanking sequences (seq) of the indigenous chromosomal segment or fragment thereof to provide for homologous recombination with the indigenous chromosomal region or fragment thereof in the unaltered host. In another embodiment, the DNA construct includes restriction sites engineered at upstream and downstream ends of the construct. Non-limiting examples of DNA constructs useful according to the invention and identified according to the coordinate location include:

1. A DNA construct for deleting a PBSX region: [5' flanking seq 1318874-1319860 bp which includes the end of yjqB and the entire yjpC including the ribosome binding site (RBS)]-marker gene-[3' flanking seq 1348691-1349656 bp which includes a terminator and upstream section of the pit].

2. A DNA construct for deleting a prophage 1 region: [5' flanking seq 201248-202112 bp which contains the entire glmS including the RBS and terminator and the ybbU RBS]-marker gene-[3' flanking seq 220141-221195 bp which includes the entire ybgd including the RBS].

3. A DNA construct for deleting a prophage 2 region: [5' flanking seq 527925-529067 bp which contains the end of ydcK, the entire tRNAs as follows: trnS-Asn, trnS-Ser, trnS-Glu, trnS-Gln, trnS-Lys, trnS-Leu1 and trnS-leu2]-marker gene-[3' flanking seq 569578-571062 bp which contains the entire ydeK and upstream part of ydeL].

4. A DNA construct for deleting a prophage 4 region: [5' flanking seq 1263127-1264270 bp which includes part of yjcM]-marker gene-[3' flanking seq 1313660-1314583 bp which contains part of yjoB including the RBS].

5. A DNA construct for deleting a yvfF-yveK region: [5' flanking seq 3512061-3513161 bp which includes part of sigL, the entire yvfG and the start of yvfF]-marker gene-[3' flanking seq 3528896-3529810 bp which includes the entire slr and the start of pnbA.

6. A DNA construct for deleting a DHB operon region: [5' flanking seq 3278457-3280255 which includes the end of aid including the terminator, the entire yuxI including the RBS, the entire yukJ including the RBS and terminator and the end of yukL]-marker gene-[3' flanking seq 3292919-3294076 which includes the end of yuiH including the RBS, the entire yuiG including the RBS and terminator and the upstream end of yuiF including the terminator.

Whether the DNA construct is incorporated into a vector or used without the presence of plasmid DNA, it is introduced into a microorganism, preferably an *E. coli* cell or a competent *Bacillus* cell.

Methods for introducing DNA into *Bacillus* cells involving plasmid constructs and transformation of plasmids into *E. coli* are well known. The plasmids are subsequently isolated from *E. coli* and transformed into *Bacillus*. However, it is not essential to use intervening microorganisms such as *E. coli*, and in some embodiments, a DNA construct or vector is directly introduced into a *Bacillus* host.

In a preferred embodiment, the host cell is a *Bacillus* sp. (See e.g., U.S. Pat. Nos. 5,264,366, 4,760,025, and RE 34,6060). In some embodiments, the *Bacillus* strain of interest is an alkalophilic *Bacillus*. Numerous alkalophilic *Bacillus* strains are known (See e.g., U.S. Pat. No. 5,217,878; and Aunstrup et al., Proc IV IFS: Ferment. Tech. Today, 299-305 [1972]). Another type of *Bacillus* strain of particular interest is a cell of an industrial *Bacillus* strain. Examples of industrial *Bacillus* strains include, but are not limited to *B. licheniformis, B. lentus, B. subtilis*, and *B. amyloliquefaciens*. In additional embodiments, the *Bacillus* host strain is selected from the group consisting of *B. licheniformis, B subtilis, B. lentus, B. brevis, B. stearothermophilus, B. alkalophilus, B. amyloliquefaciens, B. coagulans, B. circulans, B. pumilus, B. thuringiensis, B. clausii*, and *B. megaterium*. In particularly preferred embodiments, *B. subtilis* cells are used.

In some embodiments, the industrial host strains are selected from the group consisting of non-recombinant strains of *Bacillus* sp., mutants of a naturally-occurring *Bacillus* strain, and recombinant *Bacillus* host strains. Preferably, the host strain is a recombinant host strain, wherein a polynucleotide encoding a polypeptide of interest has been previously introduced into the host. A further preferred host strain is a *Bacillus subtilis* host strain, and particularly a recombinant *Bacillus subtilis* host strain. Numerous *B. subtilis* strains are known and suitable for use in the present invention (See e.g., 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain; Hoch et al., Genetics, 73:215-228 [1973]; U.S. Pat. Nos. 4,450,235; 4,302,544; EP 0134048; Palva et al., Gene, 19:81-87 [1982]; Fahnestock and Fischer, J. Bacteriol., (1986) 165:796-804 [1986]; and Wang et al., Gene 69:39-47 [1988]). Of particular interest as expression hosts are industrial protease-producing *Bacillus* strains. By using these strains, the high efficiency seen for production of the protease is further enhanced by the altered *Bacillus* strain of the present invention.

Industrial protease producing *Bacillus* strains provide particularly preferred expression hosts. In some preferred embodiments, use of these strains in the present invention provides further enhancements in efficiency and protease production. As indicated above, there are two general types of proteases are typically secreted by *Bacillus* sp., namely neutral (or "metalloproteases") and alkaline (or "serine") proteases. Also as indicated above, subtilisin is a preferred serine protease for use in the present invention. A wide variety of *Bacillus* subtilisins have been identified and sequenced, for example, subtilisin 168, subtilisin BPN', subtilisin Carlsberg, subtilisin DY, subtilisin 147 and subtilisin 309 (See e.g., EP 414279 B; WO 89/06279; and Stahl et al., J. Bacteriol., 159:811-818 [1984]). In some embodiments of the present invention, the *Bacillus* host strains produce mutant (e.g., variant) proteases. Numerous references provide examples of variant proteases and reference (See e.g., WO 99/20770; WO 99/20726; WO 99/20769; WO 89/06279; RE 34,606; U.S. Pat. Nos. 4,914,031; 4,980,288; 5,208,158; 5,310,675; 5,336,611; 5,399,283; 5,441,882; 5,482,849; 5,631,217; 5,665,587; 5,700,676; 5,741,694; 5,858,757; 5,880,080; 6,197,567; and 6,218,165.

In yet another embodiment, a preferred *Bacillus* host is a *Bacillus* sp. that includes a mutation or deletion in at least one of the following genes, degU, degS, degR and degQ. Preferably the mutation is in a degU gene, and more preferably the mutation is degU(Hy)32. (See, Msadek et al., J. Bacteriol., 172:824-834 [1990]; and Olmos et al., Mol. Gen. Genet., 253:562-567 [1997]). A most preferred host strain is a *Bacillus subtilis* carrying a degU32(Hy) mutation. In a further embodiment, the *Bacillus* host comprises a mutation or deletion in scoC4, (See, Caldwell et al., J. Bacteriol., 183:7329-7340 [2001]); spollE (See, Arigoni et al., Mol. Microbiol., 31:1407-1415 [1999]); oppA or other genes of the opp operon (See, Perego et al., Mol. Microbiol., 5:173-185 [1991]). Indeed, it is contemplated that any mutation in the opp operon that causes the same phenotype as a mutation in the oppA gene will find use in some embodiments of the altered *Bacillus* strain of the present invention. In some embodiments, these mutations occur alone, while in other embodiments, combinations of mutations are present. In some embodiments, an altered *Bacillus* of the invention is obtained from a *Bacillus* host strain that already includes a mutation in one or more of the above-mentioned genes. In alternate embodiments, an altered *Bacillus* of the invention is further engineered to include mutation in one or more of the above-mentioned genes.

In some embodiments, two or more DNA constructs are introduced into a *Bacillus* host cell, resulting in the deletion of two or more indigenous chromosomal regions in an altered *Bacillus*. In some embodiments, these regions are contiguous, (e.g., the skin plus prophage 7 region), while in other embodiments, the regions are separated (e.g., the PBSX region and the PKS region; the skin region and the DHB region; or the PKS region, the SPβ region and the yvfF-yveK region).

Those of skill in the art are well aware of suitable methods for introducing polynucleotide sequences into bacterial (e.g., *E. coli* and *Bacillus*) cells (See e.g., Ferrari et al., "Genetics," in Harwood et al. (ed.), *Bacillus*, Plenum Publishing Corp. [1989], pages 57-72; See also, Saunders et al., J. Bacteriol., 157:718-726 [1984]; Hoch et al., J. Bacteriol., 93:1925-1937 [1967]; Mann et al., Current Microbiol., 13:131-135 [1986]; and Holubova, Folia Microbiol., 30:97 [1985]; for *B. subtilis*, Chang et al., Mol. Gen. Genet., 168:11-115 [1979]; for *B. megaterium*, Vorobjeva et al., FEMS Microbiol. Lett., 7:261-263 [1980]; for *B amyloliquefaciens*, Smith et al., Appl. Env. Microbiol., 51:634 (1986); for *B. thuringiensis*, Fisher et al., Arch. Microbiol., 139:213-217 [1981]; and for *B. sphaericus, McDonald, J. Gen. Microbiol.,* 130:203 [1984]). Indeed, such methods as transformation including protoplast transformation and congression, transduction, and protoplast fusion are known and suited for use in the present invention. Methods of transformation are particularly preferred to introduce a DNA construct provided by the present invention into a host cell.

In addition to commonly used methods, in some embodiments, host cells are directly transformed (i.e., an intermediate cell is not used to amplify, or otherwise process, the DNA construct prior to introduction into the host cell). Introduction of the DNA construct into the host cell includes those physical and chemical methods known in the art to introduce DNA into a host cell, without insertion into a plasmid or vector. Such methods include but are not limited to calcium chloride precipitation, electroporation, naked DNA, liposomes and the like. In additional embodiments, DNA constructs are co-transformed with a plasmid without being inserted into the plasmid. In a further embodiments, a selective marker is deleted or substantially excised from the altered *Bacillus* strain by methods known in the art (See, Stahl et al., J. Bacteriol., 158:411-418 [1984]; and the conservative site-specific recombination [CSSR] method of Palmeros et al., described in Palmeros et al., Gene 247:255-264 [2000]). In some preferred embodiments, resolution of the vector from a host chromosome leaves the flanking regions in the chromosome while removing the indigenous chromosomal region.

In some embodiments, host cells are transformed with one or more DNA constructs according to the present invention to produce an altered *Bacillus* strain wherein two or more genes have been inactivated in the host cell. In some embodiments, two or more genes are deleted from the host cell chromosome. In alternative embodiments, two or more genes are inactivated by insertion of a DNA construct. In some embodiments, the inactivated genes are contiguous (whether inactivated by deletion and/or insertion), while in other embodiments, they are not contiguous genes.

As indicated above, there are various assays known to those of ordinary skill in the art for detecting and measuring activity of intracellularly and extracellularly expressed polypeptides. In particular, for proteases, there are assays based on the release of acid-soluble peptides from casein or hemoglobin measured as absorbance at 280 nm or colorimetrically using the Folin method (See e.g., Bergmeyer et al., "Methods of Enzymatic Analysis" vol. 5, *Peptidases, Proteinases and their Inhibitors*, Verlag Chemie, Weinheim [1984]). Other assays involve the solubilization of chromogenic substrates (See e.g., Ward, "Proteinases," in Fogarty (ed.)., *Microbial Enzymes and Biotechnology*, Applied Science, London, [1983], pp 251-317). Other exemplary assays include succinyl-Ala-Ala-Pro-Phe-para nitroanilide assay (SAAPFpNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem., 223:119-129 [1994]; and Hsia et al., Anal Biochem., 242:221-227 [1999]).

Also as indicated above, means for determining the levels of secretion of a protein of interest in a host cell and detecting expressed proteins include the use of immunoassays with either polyclonal or monoclonal antibodies specific for the protein. Examples include enzyme-linked immunosorbent assay (ELISA), radioimmunoassay (RIA), fluorescence immunoassay (FIA), and fluorescent activated cell sorting (FACS). However, other methods are known to those in the art and find use in assessing the protein of interest (See e.g., Hampton et al., *Serological Methods, A Laboratory Manual*, APS Press, St. Paul, Minn. [1990]; and Maddox et al., J. Exp. Med., 158:1211 [1983]). In some preferred embodiments, secretion of a protein of interest is higher in the altered strain obtained using the present invention than in a corresponding unaltered host. As known in the art, the altered *Bacillus* cells produced using the present invention are maintained and grown under conditions suitable for the expression and recovery of a polypeptide of interest from cell culture (See e.g., Hardwood and Cutting (eds.) *Molecular Biological Methods for Bacillus*, John Wiley & Sons [1990]).

The manner and method of carrying out the present invention may be more fully understood by those of skill in the art by reference to the following examples, which examples are not intended in any manner to limit the scope of the present invention or of the claims directed thereto.

EXPERIMENTAL

The following Examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); $H_2O$ (water); $dH_2O$ (deionized water); (HCl (hydrochloric acid); aa (amino acid); bp (base pair); kb (kilobase pair); kD (kilodaltons); gm (grams); μg (micrograms); mg (milligrams); ng (nanograms); μl (microliters); ml (milliliters); mm (millimeters); nm (nanometers); μm (micrometer); M (molar); mM (millimolar); μM (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{600}$ (optical density at 600 nm); PAGE (polyacrylamide gel electrophoresis); PBS (phosphate buffered saline [150 mM NaCl, 10 mM sodium phosphate buffer, pH 7.2]); PEG (polyethylene glycol); PCR (polymerase chain reaction); RT-PCR (reverse transcription PCR); SDS (sodium dodecyl sulfate); Tris (tris(hydroxymethyl)aminomethane); w/v (weight to volume); v/v (volume to volume); LA medium (per liter: Difco Tryptone Peptone 20 g, Difco Yeast Extract 10 g, EM Science NaCl 1 g, EM Science Agar 17.5 g, dH20 to 1 L); ATCC (American Type Culture Collection, Rockville, Md.); Clontech (CLONTECH Laboratories, Palo Alto, Calif.); Difco (Difco Laboratories, Detroit, Mich.); GIBCO BRL or Gibco BRL (Life Technologies, Inc., Gaithersburg, Md.); Invitrogen (Invitrogen Corp., San Diego, Calif.); NEB (New England Biolabs, Beverly, Mass.); Sigma (Sigma Chemical Co., St. Louis, Mo.); Takara (Takara Bio Inc. Otsu, Japan); Roche Diagnostics and Roche (Roche Diagnostics, a division of F. Hoffmann La Roche, Ltd., Basel, Switzerland); EM Science (EM Science, Gibbstown, N.J.); Qiagen (Qiagen, Inc., Valencia, Calif.); Stratagene (Stratagene Cloning Systems, La Jolla, Calif.); Affymetrix (Affymetrix, Santa Clara, Calif.).

Example 1

Creation of Deletion Strains

Figure 1B:
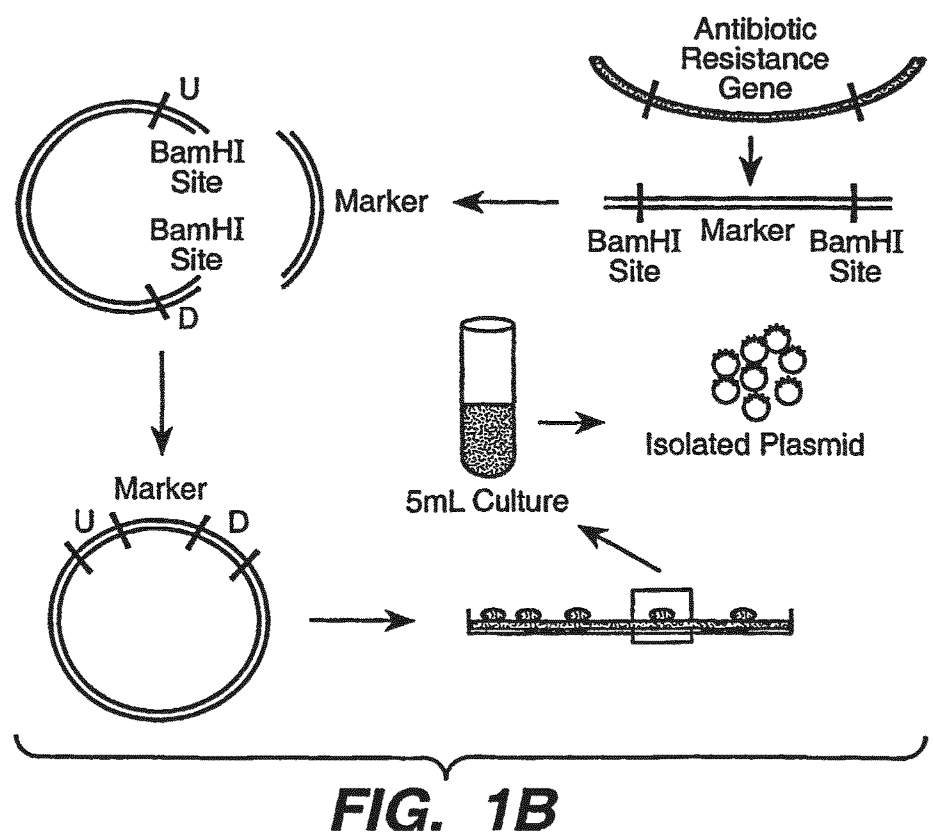
Figure 2:
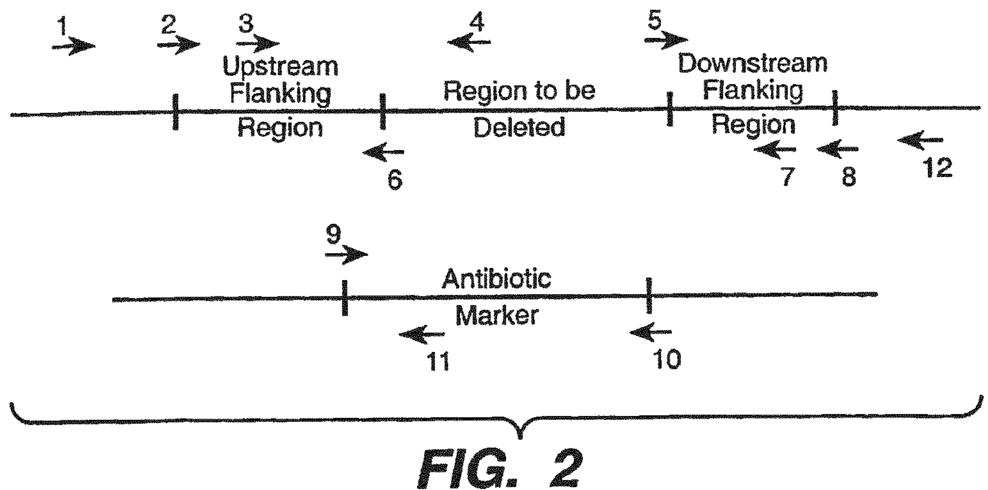
FIG. 2 illustrates the location of primers used in the construction of a DNA cassette according to some embodiments of the present invention. The diagram provides an explanation of the primer naming system used herein. Primers 1 and 4 are used for checking the presence of the deletion. These primers are referred to as "DeletionX-UF-chk" and "DeletionX-UR-chk-del." DeletionX-UF-chk is also used in a PCR reaction with a reverse primer inside the antimicrobial marker (Primer 11: called for example PBSX-UR-chk-Del) for a positive check of the cassette's presence in the chromosome. Primers 2 and 6 are used to amplify the upstream flanking region. These primers are referred to as "DeletionX-UF" and "DeletionX-UR," and contain engineered restriction sites at the black vertical bars. Primers 5 and 8 are used to amplify the downstream flanking region. These primers are referred to as "DeletionX-DF" and "DeletionX-DR." These primers may either contain engineered BamHI sites for ligation and cloning, or 25 base pair tails homologous to an appropriate part of the *Bacillus subtilis* chromosome for use in PCR fusion. In some embodiments, primers 3 and 7 are used to fuse the cassette together in the case of those cassettes created by PCR fusion, while in other embodiments, they are used to check for the presence of the insert. These primers are referred to as "DeletionX-UF-nested" and "DeletionX-DR-nested." In some embodiments, the sequence corresponding to an "antibiotic marker" is a Spc resistance marker and the region to be deleted is the CssS gene.

This Example describes "Method 1," which is also depicted in FIGS. 1A and 1B. In this method, *E. coli* was used to produce a pJM102 plasmid vector carrying the DNA construct to be transformed into *Bacillus* strains. (See, Perego, supra). Regions immediately flanking the 5' and 3' ends of the deletion site were PCR amplified. PCR primers were designed to be approximately 37 base pairs in length, including 31 base pairs homologous to the *Bacillus subtilis* chromosome and a 6 base pair restriction enzyme site located 6 base pairs from the 5' end of the primer. Primers were designed to engineer unique restriction sites at the upstream and downstream ends of the construct and a BamHI site between the two fragments for use in cloning. Primers for the antimicrobial markers contained BamHI sites at both ends of the fragment. Where possible, PCR primers were designed to remove promoters of deleted indigenous chromosomal regions, but to leave all terminators in the immediate area. The primary source of chromosome sequence, gene localization, and promoter and terminator information was obtained from Kunst et al., (1997) supra and also obtainable from the SubtiList World Wide Web Server known to those in the art (See e.g., Moszer et al., supra). Numerous deletions have been made using the present invention. A list of primer sequences from deletions created by this method is provided in Table 1. Reference is also made to FIG. 2 for an explanation of the primer naming system.

TABLE 1

| Primers | | | |
|---|---|---|---|
| Primer Name | Restriction Enzyme Engineered Into Primer | Primer Sequence | SEQ ID NO |
| PBSX-UF | XbaI | CTACATTCTAGACGATTTGTTTGATCGATATGTGGAAGC | 60 |
| PBSX-UR | BamHI | GGCTGAGGATCCATTCCTCAGCCCAGAAGAGAACCTA | 61 |
| PBSX-DF | BamHI | TCCCTCGGATCCGAAATAGGTTCTGCTTATTGTATTCG | 62 |
| PBSX-DR | SacI | AGCGTTGAGCTCGCGCCATGCCATTATATTGGCTGCTG | 63 |
| Pphage 1- | EcoRI | GTGACGGAATTCCACGTGCGTCTTATATTGCTGAGCTT | 64 |
| Pphage 1- | BamHI | CGTTTTGGATCCAAAAACACCCCTTTAGATAATCTTAT | 65 |
| Pphage 1- | BamHI | ATCAAAGGATCCGCTATGCTCCAAATGTACACCTTTCCGT | 66 |
| Pphage 1- | PstI | ATATTTCTGCAGGCTGATATAAATAATACTGTGTGTTCC | 67 |
| Pphage 2- | SacI | CATCTTGAATTCAAAGGGTACAAGCACAGAGACAGAG | 68 |
| Pphage 2- | BamHI | TGACTTGGATCCGGTAAGTGGGCAGTTTGTGGGCAGT | 69 |
| Pphage 2- | BamHI | TAGATAGGATCCTATTGAAAACTGTTTAAGAAGAGGA | 70 |
| Pphage 2- | PstI | CTGATTCTGCAGGAGTGTTTTTGAAGGAAGCTTCATT | 71 |
| Pphage 4- | KpnI | CTCCGCGGTACCGTCACGAATGCGCCTCTTATTCTAT | 72 |
| Pphage 4- | BamHI | TCGCTGGGATCCTTGGCGCCGTGGAATCGATTTTGTCC | 73 |
| Pphage 4- | BamHI | GCAATGGGATCCTATATCAACGGTTATGAATTCACAA | 74 |
| Pphage 4- | PstI | CCAGAACTGCAGGAGCGAGGCGTCTCGCTGCCTGAAA | 75 |
| PPS-UF | SacI | GACAAGGAGCTCATGAAAAAAAGCATAAAGCTTTATGTTGC | 76 |
| PPS-UR | BamHI | GACAAGGGATCCCGGCATGTCCGTTATTACTTAATTTC | 77 |

TABLE 1-continued

| Primers | | | |
|---|---|---|---|
| Primer Name | Restriction Enzyme Engineered Into Primer | Primer Sequence | SEQ ID NO |
| PPS-DF | BamHI | GACAAGGGATCCTGCCGCTTACCGGAAACGGA | 78 |
| PPS-DR | XbaI | GACAAGTCTAGATTATCGTTTGTGCAGTATTACTTG | 79 |
| SPβ-UF | SacI | ACTGATGAGCTCTGCCTAAACAGCAAACAGCAGAAC | 80 |
| SPβ-UR | BamHI | ACGAATGGATCCATCATAAAGCCGCAGCAGATTAAATAT | 81 |
| SPβ-DF | BamHI | ACTGATGGATCCATCTTCGATAAATATGAAAGTGGC | 82 |
| SPβ-DR | XbaI | ACTGATTCTAGAGCCTTTTTCTCTTGATGCAATTCTTC | 83 |
| PKS-UF | XbaI | GAGCCTCTAGAGCCCATTGAATCATTTGTTT | 84 |
| PKS-UR | BamHI | GAGCCGGATCCTTAAGGATGTCGTTTTTGTGTCT | 85 |
| PKS-DF | BamHI | GAGCCGGATCCATTTCGGGGTTCTCAAAAAAA | 86 |
| PKS-DR | SacI | GAGCCGAGCTCATGCAAATGGAAAAATTGAT | 87 |
| Skin-UF | XbaI | GAAGTTCTAGAGATTGTAATTACAAAAGGGGGGTG | 88 |
| Skin-UR | BamHI | GAAGTGGATCCTTTCACCGATCATAAAAGCCC | 89 |
| Skin-DF | BamHI | TGAAAGGATCCATTTTTCATTGATTGTTAAGTC | 90 |
| Skin-DR | SacI | GAAGTTAGAGCTCGGGGGGGCATAAATTTCCCG | 91 |
| Phleo-UF | BamHI | GCTTATGGATCCGATACAAGAGAGGTCTCTCG | 92 |
| Phleo-DR | BamHI | GCTTATGGATCCCTGTCATGGCGCATTAACG | 93 |
| Spec-UF | BamHI | ACTGATGGATCCATCGATTTTCGTTCGTGAATACATG | 94 |
| Spec-DR | BamHI | ACTGATGGATCCCATATGCAAGGGTTTATTGTTTTC | 95 |
| CssS-UF | XbaI | GCACGTTCTAGACCACCGTCCCCTGTGTTGTATCCAC | 96 |
| CssS-UR | BamHI | AGGAAGGGATCCAGAGCGAGGAAGATGTAGGATGATC | 97 |
| CssS-DF | BamHI | TGACAAGGATCCTGTATCATACCGCATAGCAGTGCC | 98 |
| CssS-DR | SacI | TTCCGCGAGCTCGGCGAGAGCTTCAGACTCCGTCAGA | 99 |
| SBO- | XbaI | GAGCCTCTAGATCAGCGATTTGACGCGGCGC | 100 |
| SBO- | BamHI | TTATCTGGATCCCTGATGAGCAATGATGGTAAGATAGA | 101 |
| SBO- | BamHI | GGGTAAGGATCCCCCAAAAGGGCATAGTCATTCTACT | 102 |
| SBO- | Asp718 | GAGATCGGTACC CTTTTGGGCCATATCGTGGATTTC | 103 |
| PhrC-UF | HindIII | GAGCC AAGCTT CATTGACAGCAACCAGGCAGATCTC | 104 |
| PhrC-DF | PstI | GCTTATAAGCTTGATACAAGAGAGGTCTCTCG | 105 |
| PhrC-UR | PstI | GCTTATAAGCTTCTGTCATGGCGCATTAACG | 106 |
| PhrC-DR | SacI | GAGCCGAGCTC CATGCCGATGAAGTCATCGTCGAGC | 107 |
| PhrC-UF- | HindIII | CGTGAA AAGCTT TCGCGGGATGTATGAATTTGATAAG | 108 |
| PhrC-DR- | SacI | TGTAGGGAGCTC GATGCGCCACAATGTCGGTACAACG | 109 |

The restriction sites are designated as follows: XbaI is TCTAGA; BamHI is GGATCC; SacI is GAGCTC; Asp718 is GGTACC; PstI is CTGCAG and HindIII is AAGCTT. Also prophage is designated as "Pphage."

In this method, 100 μL PCR reactions carried out in 150μL Eppendorf tubes containing 84 μL water, 10 μL PCR buffer, 1 μL of each primer (i.e., PKS-UF and PKS-UR), 2 μL of dNTPs, 1 μL of wild type *Bacillus* chromosomal DNA template, and 1 μL of polymerase. DNA polymerases used included Taq Plus Precision polymerase and Herculase (Stratagene). Reactions were carried out in a Hybaid PCR-Express thermocycler using the following program. The samples were first heated at 94° C. for 5 minutes, then cooled to a 50° hold. Polymerase was added at this point. Twenty-five cycles of amplification consisted of 1 minute at 95° C., 1 minute at 50° C. and 1 minute at 72° C. A final 10 minutes at 72° C. ensured complete elongation. Samples were held at 4° C. for analysis.

Figure 5:
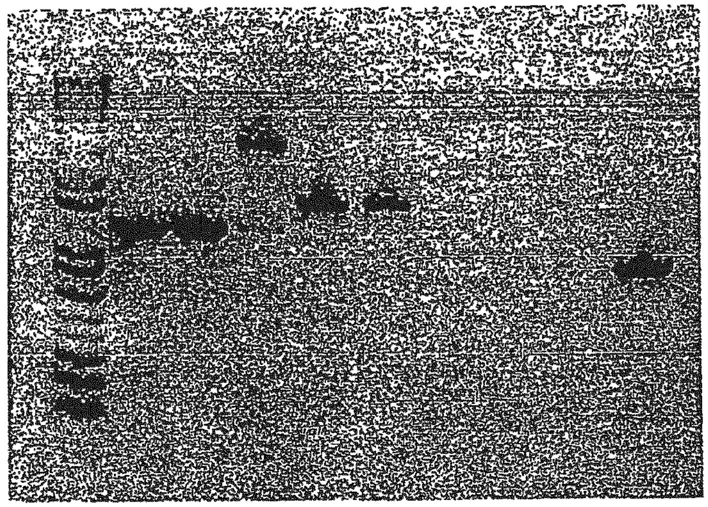
FIG. 5 illustrates gel electrophoresis of two clones of a production strain of *Bacillus subtilis* (wild-type) wherein slr is replaced with a phleomycin (phleo) marker which results in a deletion of the slr gene. Lanes 1 and 2 represent the clones amplified with primers at locations 1 and 11. Lane 3 is the wild-type chromosomal DNA amplified with the same primers. A 1.2 kb band is observed for the insert. Lanes 4 and 5 represent the clones amplified with primers at locations 9 and 12. Lane 6 is the wild-type chromosomal DNA amplified with the same primers. Correct transformants include a 2 kb band. Lanes 7 and 8 represent the clones amplified with primers at locations 2 and 4. Lane 9 is the wild-type chromosomal DNA amplified with the same primers. No band is observed for the deletion strains, but a band around 1 kb is observed in the wild-type. Reference is made to FIG. 2 for an explanation of primer locations.
Figure 6:
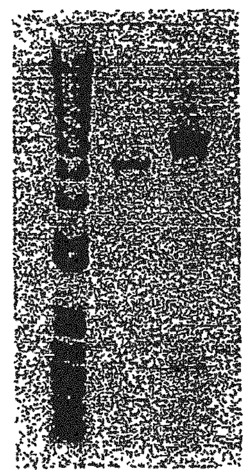
FIG. 6 provides an electrophoresis gel of a clone of a production strain of *Bacillus subtilis* (wild-type) wherein cssS is inactivated by the integration of a spc marker into the chromosome. Lane 1 is a control without the integration and is approximately 1.5 kb smaller.

After completion of the PCR, 10 μL of each reaction were run on an Invitrogen 1.2% agarose E-gel at 60 volts for 30 minutes to check for the presence of a band at the correct size. All the gel electrophoresis methods described herein used these conditions. If a band was present, the remainder of the reaction tube was purified using the Qiagen Qiaquick® PCR purification kit according to the manufacturer's instructions, then cut with the appropriate restriction enzyme pair. Digests were performed at 37° C. for 1 hour as a 20 μL reaction consisting of 9 μL of water, 2 μL of 10×BSA, 2 μL of an appropriate NEB restriction buffer (according to the 2000-01 NEB Catalog and Technical Reference), 5 μL of template, and 1 μL of each restriction enzyme. For example, the PBSX upstream fragment and CssS upstream fragments were cut with XbaI and BamHI in NEB (New England BioLabs) restriction buffer B. The digested fragments were purified by gel electrophoresis and extraction using the Qiagen Qiaquick gel extraction kit following the manufacturer's instructions. FIGS. 5 and 6 provide gels showing the results for various deletions.

Ligation of the fragments into a plasmid vector was done in two steps, using either the Takara ligation kit following the manufacturer's instructions or T4 DNA ligase (Reaction contents: 5 μL each insert fragment, 1 μL cut pJM102 plasmid, 3 μL T4 DNA ligase buffer, and 1 μL T4 DNA ligase). First, the cut upstream and downstream fragments were ligated overnight at 15° C. into unique restriction sites in the pJM102 plasmid polylinker, connecting at the common BamHI site to re-form a circular plasmid. The pJM102 plasmid was cut with the unique restriction enzyme sites appropriate for each deletion (See, Table 2; for cssS, XbaI and SacI were used) and purified as described above prior to ligation. This re-circularized plasmid was transformed into Invitrogen's "Top Ten" *E. coli* cells, using the manufacturers One Shot transformation protocol.

Transformants were selected on Luria-Bertani broth solidified with 1.5% agar (LA) plus 50 ppm carbanicillin containing X-gal for blue-white screening. Clones were picked and grown overnight at 37° C. in 5 mL of Luria Bertani broth (LB) plus 50 ppm carbanicillin and plasmids were isolated using Qiagen's Qiaquick Mini-Prep kit. Restriction analysis confirmed the presence of the insert by cutting with the restriction sites at each end of the insert to drop an approximately 2 kb band out of the plasmid. Confirmed plasmids with the insert were cut with BamHI to linearize them in digestion reactions as described above (with an additional 1 μL of water in place of a second restriction enzyme), treated with 1 μL calf intestinal and shrimp phosphatases for 1 hour at 37° C. to prevent re-circularization, and ligated to the antimicrobial resistance marker as listed in Table 2. Antimicrobial markers were cut with BamHI and cleaned using the Qiagen Gel Extraction Kit following manufacturer's instructions prior to ligation. This plasmid was cloned into *E. coli* as before, using 5 ppm phleomycin (phl) or 100 ppm spectinomycin (spc) as appropriate for selection. Confirmation of marker insertion in isolated plasmids was done as described above by restriction analysis with BamHI. Prior to transformation into *B. subtilis*, the plasmid was linearized with ScaI to ensure a double crossover event.

TABLE 2

Unique Restriction Enzyme Pairs Used in Deletion Constructs

| Deletion Name | Unique Restriction Enzyme Pair | Antimicrobial Marker |
|---|---|---|
| Sbo | XbaI-Asp718 | spc |
| Slr | XbaI-SacI | phleo |
| YbcO | XbaI-SacI | spc |
| Csn | XbaI-SalI | phleo |
| PBSX | XbaI-SacI | phl |
| PKS | XbaI-SacI | phl |
| SPβ | XbaI-SacI | spec |
| PPS | XbaI-SacI | spec |
| Skin | XbaI-SacI | phl |

Example 2

Creation of DNA Constructs Using PCR Fusion to Bypass *E. coli*

Figure 3:
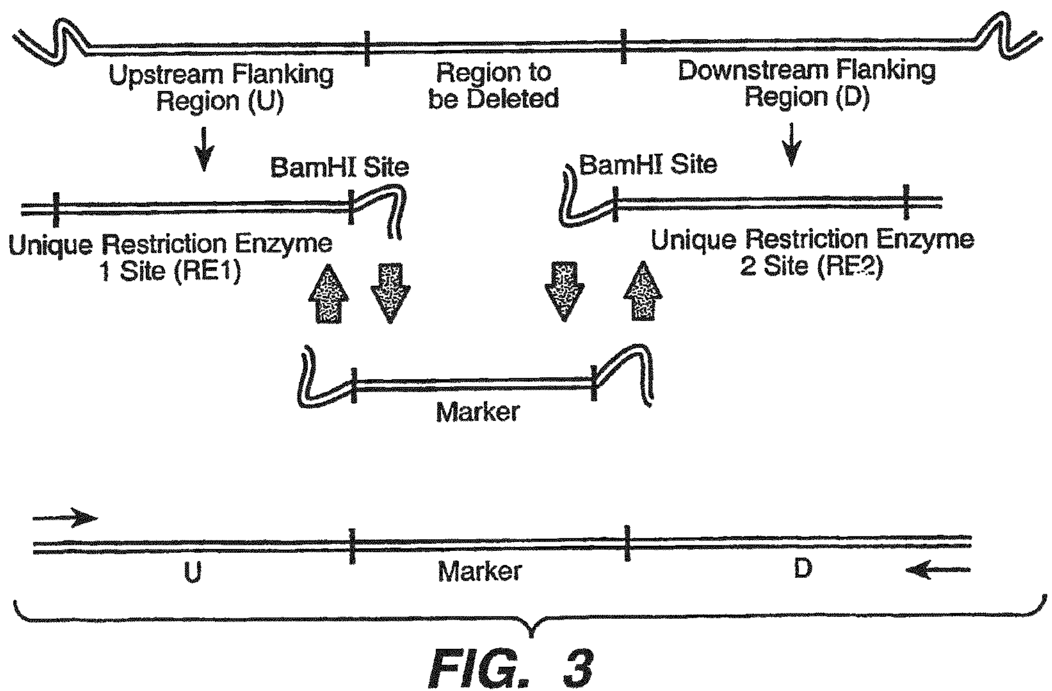
FIG. 3 is a general schematic diagram of one method ("Method 2"; See Example 2) of the present invention. Flanking regions are engineered to include 25 bp of sequence complementary to a selective marker sequence. The selective marker sequence also includes 25 bp tails that complement DNA of one flanking region. Primers near the ends of the flanking regions are used to amplify all three templates in a single reaction tube, thereby creating a fusion fragment. This fusion fragment or DNA construct is directly transformed into a competent *Bacillus* host strain.

This Example describes "Method 2," which is also depicted in FIG. 3. Upstream and downstream fragments were amplified as in Method 1, except the primers were designed with 25 bp "tails" complementary to the antimicrobial marker's primer sequences. A "tail" is defined herein as base pairs on the 5' end of a primer that are not homologous to the sequence being directly amplified, but are complementary to another sequence of DNA. Similarly, the primers for amplifying the antimicrobial contain "tails" that are complementary to the fragments' primers. For any given deletion, the DeletionX-UFfus and DeletionX-URfus are direct complements of one another. This is also true for the DF-fus and DR-fus primer sets. In addition, in some embodiments, these primers contain restriction enzyme sites similar to those used in Method 1 for use in creating a plasmid vector (See, Table 3 and U.S. Pat. No. 5,023,171). Table 3 provides a list of primers useful for creation of deletion constructs by PCR fusion. Table 4 provides an additional list of primers useful for creation of deletion constructs by PCR fusion. However, in this Table, all deletion constructs would include the phleo$^R$ marker.

TABLE 3

Primers

| Primer name | Restriction enzyme engineered into primer | Sequence | SEQ ID. NO. |
|---|---|---|---|
| DHB-UF | XbaI | CGAGAATCTAGAACAGGATGAATCATCTGTGGCGGG | 110 |
| DHB-UFfus-phleo | BamHI | CGACTGTCCAGCCGCTCGGCACATCGGATCCGCTTA CCGAAAGCCAGACTCAGCAA | 111 |

TABLE 3-continued

| Primers | | | |
|---|---|---|---|
| Primer name | Restriction enzyme engineered into primer | Sequence | SEQ ID. NO. |
| DHB-URfus-phleo | BamHI | TTGCTGAGTCTGGCTTTCGGTAAGCGGATCCGATGTG CCGAGCGGCTGGACAGTCG | 112 |
| DHB-DFfus-phleo | BamHI | CGTTAATGCGCCATGACAGCCATGAGGATCCCACAA GCCCGCACGCCTTGCCACAC | 113 |
| DHB-DRfus-phleo | BamHI | GTGTGGCAAGGCGTGCGGGCTTGTGGGATCCTCATG GCTGTCATGGCGCATTAACG | 114 |
| DHB-DR | SacI | GACTTCGTCGACGAGTGCGGACGGCCAGCATCACCA | 115 |
| DHB-UF-nested | XbaI | GGCATATCTAGAGACATGAAGCGGGAAACAGATG | 116 |
| DHB-DR-nested | SacI | GGTGCGGAGCTCGACAGTATCACAGCCAGCGCTG | 117 |
| YvfF-yveK-UF | XbaI | AAGCGTTCTAGACTGCGGATGCAGATCGATCTCGGG | 118 |
| YvfF-yveK-UF-phleo | BamHI | AACCTTCCGCTCACATGTGAGCAGGGGATCC GCTTACCGAAAGCCAGACTCAGCAA | 119 |
| YvfF-yveK-UR-phleo | BamHI | TTGCTGAGTCTGGCTTTCGGTAAGCGGATCC CCTGCTCACATGTGAGCGGAAGGTT | 120 |
| YvfF-yveK-DF-phleo | BamHI | CGTTAATGCGCCATGACAGCCATGAGGATCC GCCTTCAGCCTTCCCGCGGCTGGCT | 121 |
| YvfF-yveK-DR-phleo | BamHI | AGCCAGCCGCGGGAAGGCTGAAGGCGGATCC TCATGGCTGTCATGGCGCATTAACG | 122 |
| YvfF-yveK-DR | PstI | CAAGCACTGCAGCCCACACTTCAGGCGGCTCAGGTC | 123 |
| YvfF-yveK-UF- | XbaI | GAGATATCTAGAATGGTATGAAGCGGAATTCCCG | 124 |
| YvfF-yveK-DR- | KpnI | ATAAACGGTACCCCCCTATAGATGCGAACGTTAGCCC | 125 |
| Prophage7-UF | EcoRI | AAGGAGGAATTCCATCTTGAGGTATACAAACAGTCAT | 126 |
| Prophage 7-UF- | BamHI | TCTCCGAGAAAGACAGGCAGGATCGGGATCC | 127 |
| Prophage 7-UR- | BamHI | TTGCTGAGTCTGGCTTTCGGTAAGCGGATCC | 128 |
| Skin + prophage7- | Asp718 | AAGGACGGTACCGGCTCATTACCCTCTTTTCAAGGGT | 129 |
| Skin + pro7-UF-phleo | BamHI | ACCAAAGCCGGACTCCCCCGCGAGAGGATCC GCTTACCGAAAGCCAGACTCAGCAA | 130 |
| Skin + pro7-UR-phleo | BamHI | TTGCTGAGTCTGGCTTTCGGTAAGCGGATCC TCTCGCGGGGGAGTCCGGCTTTGGT | 131 |
| Skin + pro7-DF-phleo | BamHI | CGTTAATGCGCCATGACAGCCATGA GGATCCCATACGGGGTACACAATGTACCATA | 132 |
| Skin + pro7-DR-phleo | BamHI | TATGGTACATTGTGTACCCCGTATGGGATCC TCATGGCTGTCATGGCGCATTAACG | 133 |
| Skin + pro7-DR | PstI | GTCAACCTGCAGAGCGGCCCAGGTACAAGTTGGGGA | 134 |
| Skin + pro7-UF- | SacI | GGATCAGAGCTCGCTTGTCCTCCTGGGAACAGCCGG | 135 |
| Skin + pro7-DR- | PstI | TATATGCTGCAGGGCTCAGACGGTACCGGTTGTTCCT | 136 |

The restriction sites are designated as follows: XbaI is TCTAGA; BamHI is GGATCC; SacI is GAGCTC; Asp718 is GGTACC; PstI is CTGCAG and HindIII is AAGCTT.

TABLE 4

Additional Primers Used to Create Deletion Constructs by PCR Fusion*.

| Primer Name | Restriction Enzyme Engineered Into Primer | Sequence | SEQ ID NO: |
|---|---|---|---|
| Slr-UF | XbaI | CTGAACTCTAGACCTTCACCAGGCACAGAGGAGGTGA | 137 |
| Slr-Uffus | BamHI | GCCAATAAGTTCTCTTTAGAGAACAGGATCC GCTTACCGAAAGCCAGACTCAGCAA | 138 |
| Slr-Urfus | BamHI | TTGCTGAGTCTGGCTTTCGGTAAGCGGATCCTTGTTCTCT AAAGAGAACTTATTGGC | 139 |
| Slr-Dffus | BamHI | CGTTAATGCGCCATGACAGCCATGAGGATCC GGGCTAACGTTCGCATCTATAGGGG | 140 |
| Slr-Drfus | BamHI | CCCCTATAGATGCGAACGTTAGCCC GGATCC TCATGGCTGTCATGGCGCATTAACG | 141 |
| Slr-DR | SacI | TGAGACGAGCTCGATGCATAGGCGACGGCAGGGCGCC | 142 |
| Slr-UF-nested | XbaI | CGAAATTCTAGATCCCGCGATTCCGCCCCTTTGTGG | 143 |
| Slr-DR-nested | SacI | TTCCAAGAGCTCGCGGAATACCGGAAGCAGCCCC | 144 |
| YbcO-UF | XbaI | CAATTCTCTAGAGCGGTCGGCGCAGGTATAGGAGGGG | 145 |
| YbcO-UF | BamHI | GAAAAGAAACCAAAAAGAATGGGAAGGATCC GCTTACCGAAAGCCAGACTCAGCAA | 146 |
| YbcO-UR | BamHI | TTGCTGAGTCTGGCTTTCGGTAAGCGGATCC TTCCCATTCTTTTTGGTTTCTTTTC | 147 |
| YbcO-DF | BamHI | CGTTAATGCGCCATGACAGCCATGAGGATCC GCTATTTAACATTTGAGAATAGGGA | 148 |
| YbcO-DR | BamHI | TCCCTATTCTCAAATGTTAAATAGCGGATCC TCATGGCTGTCATGGCGCATTAACG | 149 |
| YbcO-DR | SacI | CAGGCGGAGCTCCCATTTATGACGTGCTTCCCTAAGC | 150 |
| Csn-UF | XbaI | TACGAATCTAGAGATCATTGCGGAAGTAGAAGTGGAA | 151 |
| Csn-UF | BamHI | TTTAGATTGAGTTCATCTGCAGCGGGGATCC GCTTACCGAAAGCCAGACTCAGCAA | 152 |
| Csn-UR | BamHI | TTGCTGAGTCTGGCTTTCGGTAAGCGGATCC CCGCTGCAGATGAACTCAATCTAAA | 153 |
| Csn-DF | BamHI | CGTTAATGCGCCATGACAGCCATGAGGATCC GCCAATCAGCCTTAGCCCCTCTCAC | 154 |
| Csn-DR | BamHI | GTGAGAGGGGCTAAGGCTGATTGGCGGATCC TCATGGCTGTCATGGCGCATTAACG | 155 |
| Csn-DR | SalI | ATACTCGTCGACATACGTTGAATTGCCGAGAAGCCGC | 156 |
| Csn-UF- | NA | CTGGAGTACCTGGATCTGGATCTCC | 157 |
| Csn-DR- | NA | GCTCGGCTTGTTTCAGCTCATTTCC | 158 |
| SigB-UF | SacI | CGGTTTGAGCTCGCGTCCTGATCTGCAGAAGCTCATT | 159 |
| SigB-UF | BamHI | CTAAAGATGAAGTCGATCGGCTCATGGATCC GCTTACCGAAAGCCAGACTCAGCAA | 160 |
| SigB-UR | BamHI | TTGCTGAGTCTGGCTTTCGGTAAGCGGATCC ATGAGCCGATCGACTTCATCTTTAG | 161 |
| SigB-DF | BamHI | CGTTAATGCGCCATGACAGCCATGAGGATCC GAAGATCCCTCGATGGAGTTAATGT | 162 |

TABLE 4-continued

Additional Primers Used to Create Deletion Constructs by PCR Fusion*.

| Primer Name | Restriction Enzyme Engineered Into Primer | Sequence | SEQ ID NO: |
|---|---|---|---|
| SigB-DR | BamHI | ACATTAACTCCATCGAGGGATCTTCGGATCC TCATGGCTGTCATGGCGCATTAACG | 163 |
| SigB-DR | SalI | GCTTCGGTCGACTTTGCCGTCTGGATATGCGTCTCTCG | 164 |
| Sig B-UF- | SacI | GTCAAAGAGCTCTATGACAGCCTCCTCAAATTGCAGG | 165 |
| SigB-DR- | SalI | TTCCATGTCGACGCTGTGCAAAACCGCCGGCAGCGCC | 166 |
| SpoIISA-UF | EcoRI | ACATTCGAATTCAGCAGGTCAATCAGCTCGCTGACGC | 167 |
| SpoIISA-UF | BamHI | CCAGCACTGCGCTCCCTCACCCGAAGGATCC GCTTACCGAAAGCCAGACTCAGCAA | 168 |
| SpoIISA-UR | BamHI | TTGCTGAGTCTGGCTTTCGGTAAGCGGATCC TTCGGGTGAGGGAGCGCAGTGCTGG | 169 |
| SpoIISA-DF | BamHI | CGTTAATGCGCCATGACAGCCATGAGGATCC TCGAGAGATCCGGATGGTTTTCCTG | 170 |
| SpoIISA-DR | BamHI | CAGGAAAACCATCCGGATCTCTCGAGGATCC TCATGGCTGTCATGGCGCATTAACG | 171 |
| SpoIISA-DR | HindIII | AGTCAT AAGCTTTCTGGCGTTTGATTTCATCAACGGG | 172 |
| SpoIISA-UF- | NA | CAGCGCGACTTGTTAAGGGACAATA | 173 |
| SpoIISA-DR- | NA | GGCTGCTGTGATGAACTTTGTCGGA | 174 |

*All deletion constructs include the phleo$^R$ marker

The fragments listed in Tables 3 and 4 were size-verified by gel electrophoresis as described above. If correct, 1 μL each of the upstream, downstream, and antimicrobial resistance marker fragments were placed in a single reaction tube with the DeletionX-UF and DeletionX-DR primers or nested primers where listed. Nested primers are 25 base pairs of DNA homologous to an internal portion of the upstream or downstream fragment, usually about 100 base pairs from the outside end of the fragment (See, FIG. 2). The use of nested primers frequently enhances the success of fusion. The PCR reaction components were similar to those described above, except 82 μL of water was used to compensate for additional template volume. The PCR reaction conditions were similar to those described above, except the 72° C. extension was lengthened to 3 minutes. During extension, the antimicrobial resistance gene was fused in between the upstream and downstream pieces. This fusion fragment can be directly transformed into *Bacillus* without any purification steps or with a simple Qiagen Qiaquick PRC purification done according to manufacturer's instructions.

Example 3

Creation of DNA Constructs Using Ligation of PCR Fragments and Direct Transformation of *Bacillus subtilis* to Bypass the *E. coli* Cloning Step In this Example, a method ("Method 3") for creating DNA constructs using ligation of PCR fragments and direct transformation of *Bacillus* are described. By way of example, modification of prpC, sigD and tdh/kbl are provided to demonstrate the method of ligation. Indeed, sigD and tdh/kbl were constructed by one method and prpC by an alternate method.

A. Tdh/Kbl and SigD

The upstream and downstream fragments adjacent to the tdh/kbl region of the *Bacillus subtilis* chromosome were amplified by PCR similar to as described in Method 1, except that the inside primer of the flanking DNA was designed to contain type II s restriction sites. Primers for the loxP-spectinomycin-loxP cassette were designed with the same type II s restriction site as the flanks and complementary overhangs. Unique overhangs for the left flank and the right flank allowed directional ligation of the antimicrobial cassette between the upstream and downstream flanking DNA. All DNA fragments were digested with the appropriate restriction enzymes, and the fragments were purified with a Qiagen Qiaquick PCR purification kit using the manufacturer's instructions. This purification was followed by desalting in a 1 mL spin column containing BioRad P-6 gel and equilibrated with 2 mM Tris-HCl, pH 7.5. Fragments were concentrated to 124 to 250 ng/μL using a Savant Speed Vac SC110 system. Three piece ligations of 0.8 to 1 μg of each fragment were performed with 12U T4 ligase (Roche) in a 15 to 25 μL reaction volume at 14 to 16° C. for 16 hours. The total yield of the desired ligation product was >100 ng per reaction, as estimated by comparison to a standard DNA ladder on an agarose gel. The ligation mixture was used without purification for transformation reactions. Primers for this construction are shown in Table 5, below

TABLE 5

Primers for tdh/kbl Deletion

| Primer Name | Restriction Enzyme Engineered Into Primer | Primer Sequence | SEQ ID NO: |
|---|---|---|---|
| p70 DR | none | CTCAGTTCATCCATCAAATCACCAAGTCCG | 175 |
| P82 DF | BbsI | TACACGTTAGAAGACGGCTAGATGCGTCTGATTGTGACAGAC GGCG | 176 |
| p71 UF | none | AACCTTCCAGTCCGGTTTACTGTCGC | 177 |
| P83 UR | BbsI | GTACCATAAGAAGACGGAGCTTGCCGTGTCCACTCCGATTAT AGCAG | 178 |
| p98spc F | BbsI | CCTTGTCTTGAAGACGGAGCTGGATCCATAACTTCGTATAATG | 179 |
| p106 spc R | BbsI | GTACCATAAGAAGACGGCTAGAGGATGCATATGGCGGCCGC | 180 |
| p112 UF* | none | CATATGCTCCGGCTCTTCAAGCAAG (analytical primer) | 181 |
| p113 DR* | none | CCTGAGATTGATAAACATGAAGTCCTC (analytical primer) | 182 |

*primers for analytical PCR

The construct for the sigD deletion closely followed construction of tdh/kbl. The primers used for the sigD construction are provided in Table 6.

TABLE 6

Primers for sigD Construction

| Primer Name | Restriction Enzyme Engineered Into Primer | Primer Sequence | SEQ ID NO: |
|---|---|---|---|
| SigD UF | none | ATATTGAAGTCGGCTGGATTGTGG | 183 |
| SigD UR | BglII | GCGGCAGATCTCGGCGCATTAAGTCGTCA | 184 |
| SigD DF | EcoRI | GCGGCGAATTCTCTGCTGGAAAAAGTGATACA | 185 |
| SigD DR | none | TTCGCTGGGATAACAACAT | 186 |
| Loxspc UF | BglII | GCGGCAGATCTTAAGCTGGATCCATAACTTCG | 187 |
| Loxspc DR | EcoRI | GCGGCGAATTCATATGGCGGCCGCATAACTTC | 188 |
| SigD UO | none | CAATTTACGCGGGGTGGTG | 189 |
| SigD DO | none | GAATAGGTTACGCAGTTGTTG | 190 |
| Spc UR | none | CTCCTGATCCAAACATGTAAG | 191 |
| Spc DF | none | AACCCTTGCATATGTCTAG | 192 |

B. PrpC

An additional example of creating a DNA molecule by ligation of PCR amplified DNA fragments for direct transformation of *Bacillus* involved a partial in-frame deletion of the gene prpC. A 3953 bp fragment of *Bacillus subtilis* chromosomal DNA containing the prpC gene was amplified by PCR using primers p95 and p96. The fragment was cleaved at unique restriction sites PflMI and BstXI. This yielded three fragments, an upstream, a downstream, and a central fragment. The latter is the fragment deleted and consists of 170 bp located internal to the prpC gene. The digestion mixture was purified with a Qiagen Qiaquick PCR purification kit, followed by desalting in a 1 mL spin column containing BioRad P-6 gel and equilibrated with 2 mM Tris-HCl, pH 7.5. In a second PCR reaction, the antimicrobial cassette, loxP-spectinomycin-loxP, was amplified with the primer containing a BstXI site and the downstream primer containing a PflMI site both with cleavage sites complementary to the sites in the genomic DNA fragment. The fragment was digested with PflMI and BstXI and purified as described for the chromosomal fragment above. A three piece ligation of the upstream, antimicrobial cassette, and the downstream fragments was carried out as for tdh/kbl, described above. The yield of desired ligation product was similar and the ligation product was used without further treatment for the transformation of xylR-comK competent *Bacillus subtilis*, as described in greater detail below.

TABLE 7

| Primers for prpC Deletion | | | |
|---|---|---|---|
| Primer Name | Restriction Enzyme Engineered Into Primer | Primer Sequence | SEQ ID NO: |
| p95 DF | none | GCGCCCTTGATCCTAAGTCAGATGAAAC | 193 |
| p96 UR | none | CGGGTCCGATACTGACTGTAAGTTTGAC | 194 |
| p100 spc R | PflMI | GTACCATAACCATGCCTTGGTTAGGATGCATATGGCGGCCGC | 195 |
| p101 spc F | BstXI | CCTTGTCTTCCATCTTGCTGGAGCTGGATCCATAACTTCGTATAATG | 196 |
| p114 anal. | none | GAGAGCAAGGACATGACATTGACGC | 197 |
| p115 anal.,* | none | GATCTTCACCCTCTTCAACTTGTAAAG | 198 |

*anal., analytical PCR primer

C. PckA Deletion

In addition to the above deletions, pckA was also modified. The PCR primers pckA UF, pckA-2Urfus, spc ffus, spc rfus, pckA Dffus and pckA DR, were used for PCR and PCR fusion reactions using the chromosomal DNA of a *Bacillus subtilis* I168 derivative and pDG1726 (See, Guerout-Fleury et al., Gene 167(1-2):335-6 [1995]) as template. The primers are shown in Table 8. The method used in constructing these deletion mutants was the same as Method 1, described above.

TABLE 8

| Primers Used for PckA Deletion | | | |
|---|---|---|---|
| Primer Name | Restriction Enzyme Engineered Into Primer | Primer Sequence | Seq ID NO: |
| pckA UF | none | TTTGCTTCCTCCTGCACAAGGCCTC | 199 |
| pckA-2URfus | none | CGTTATTGTGTGTGCATTTCCATTGT | 200 |
| spc ffus | none | CAATGGAAATGCACACACAATAACGTGACTGGCAA GAGA | 201 |
| pckA DFfus | none | GTAATGGCCCTCTCGTATAAAAAAC | 202 |
| spc rfus | none | GTTTTTTATACGAGAGGGCCATTACCAATTAGAAT GAATATTTCCC | 203 |
| pckA DR | none | GACCAAAATGTTTCGATTCAGCATTCCT | 204 |

D. Xylose-Induced Competence Host Cell Transformation with Ligated DNA.

Cells of a host strain *Bacillus subtilis* with partial genotype xylRcomK, were rendered competent by growth for 2 hours in Luria-Bertani medium containing 1% xylose, as described in U.S. patent application Ser. No. 09/927,161, filed Aug. 10, 2001, herein incorporated by reference, to an $OD_{550}$ of 1. This culture was seeded from a 6 hour culture. All cultures were grown at 37° C., with shaking at 300 rpm. Aliquots of 0.3 mL of were frozen as 1:1 mixtures of culture and 30% glycerol in round bottom 2 mL tubes and stored in liquid nitrogen for future use.

For transformation, frozen competent cells were thawed at 37° C. and immediately after thawing was completed, DNA from ligation reaction mixtures was added at a level of 5 to 15 μL per tube. Tubes were then shaken at 1400 rpm (Tekmar VXR S-10) for 60 min at 37° C. The transformation mixture was plated without dilution in 100 μL aliquots on 8 cm LA plates containing 100 ppm of spectinomycin. After growth over night, transformants were picked into Luria-Bertani (100 ppm spectinomycin) and grown at 37° C. for genomic DNA isolation performed as known in the art (See e.g., Harwood and Cuttings, *Molecular Biological Methods for Bacillus*, John Wiley and Son, New York, N.Y. [1990], at p. 23). Typically 400 to 1400 transformants were obtained from 100 uL transformation mix, when 5 uL of ligation reaction mix was used in the transformation.

When the antimicrobial marker was located between two loxP sites in the incoming DNA, the marker could be removed by transforming the strain with a plasmid containing the cre gene capable of expression the Cre protein. Cells were transformed with pCRM-TS-pleo (See below) cultured at 37° C. to 42° C., plated onto LA and after colonies formed patched onto LA containing 100 ppm spectinomycin. Patches which did not grow after overnight incubation were deemed to have lost the antimicrobial maker. Loss of maker was verified by PCR assay with primers appropriate for the given gene.

pCRM-TS-pleo has the following sequence (SEQ ID NO: 205):

```
GGGGATCTCTGCAGTGAGATCTGGTAATGACTCTCTAGCTTGAGGCATCA
AATAAAACGAAAGGCTCAGTCGAAAGACTGGGCCTTTCGTTTTATCTGTT
GTTTGTCGGTGAACGCTCTCCTGAGTAGGACAAATCCGCCGCTCTAGCTA
AGCAGAAGGCCATCCTGACGGATGGCCTTTTTGCGTTTCTACAAACTCTT
GTTAACTCTAGAGCTGCCTGCCGCGTTTCGGTGATGAAGATCTTCCCGAT
GATTAATTAATTCAGAACGCTCGGTTGCCGCCGGGCGTTTTTTATGCAGC
AATGGCAAGAACGTTGCTCTAGAATAATTCTACACAGCCCAGTCCAGACT
ATTCGGCACTGAAATTATGGGTGAAGTGGTCAAGACCTCACTAGGCACCT
TAAAAATAGCGCACCCTGAAGAAGATTTATTTGAGGTAGCCCTTGCCTAC
CTAGCTTCCAAGAAAGATATCCTAACAGCACAAGAGCGGAAAGATGTTTT
GTTCTACATCCAGAACAACCTCTGCTAAAATTCCTGAAAAATTTTGCAAA
AAGTTGTTGACTTTATCTACAAGGTGTGGCATAATGTGTGGAATTGTGAG
CGGATAACAATTAAGCTTAGGAGGGAGTGTTAAATGTCCAATTTACTGAC
CGTACACCAAAATTTGCCTGCATTACCGGTCGATGCAACGAGTGATGAGG
TTCGCAAGAACCTGATGGACATGTTCAGGGATCGCCAGGCGTTTTCTGAG
CATACCTGGAAAATGCTTCTGTCCGTTTGCCGGTCGTGGGCGGCATGGTG
CAAGTTGAATAACCGGAAATGGTTTCCCGCAGAACCTGAAGATGTTCGCG
ATTATCTTCTATATCTTCAGGCGCGCGGTCTGGCAGTAAAAACTATCCAG
CAACATTTGGGCCAGCTAAACATGCTTCATCGTCGGTCCGGGCTGCCACG
ACCAAGTGACAGCAATGCTGTTTCACTGGTTATGCGGCGGATCCGAAAAG
AAAACGTTGATGCCGGTGAACGTGCAAAACAGGCTCTAGCGTTCGAACGC
ACTGATTTCGACCAGGTTCGTTCACTCATGGAAAATAGCGATCGCTGCCA
GGATATACGTAATCTGGCATTTCTGGGGATTGCTTATAACACCCTGTTAC
GTATAGCCGAAATTGCCAGGATCAGGGTTAAAGATATCTCACGTACTGAC
GGTGGGAGAATGTTAATCCATATTGGCAGAACGAAAACGCTGGTTAGCAC
CGCAGGTGTAGAGAAGGCACTTAGCCTGGGGGTAACTAAACTGGTCGAGC
GATGGATTTCCGTCTCTGGTGTAGCTGATGATCCGAATAACTACCTGTTT
TGCCGGGTCAGAAAAAATGGTGTTGCCGCGCCATCTGCCACCAGCCAGCT
ATCAACTCGCGCCCTGGAAGGGATTTTTGAAGCAACTCATCGATTGATTT
ACGGCGCTAAGGATGACTCTGGTCAGAGATACCTGGCCTGGTCTGGACAC
AGTGCCCGTGTCGGAGCCGCGCGAGATATGGCCCGCGCTGGAGTTTCAAT
ACCGGAGATCATGCAAGCTGGTGGCTGGACCAATGTAAATATTGTCATGA
ACTATATCCGTAACCTGGATAGTGAAACAGGGGCAATGGTGCGCCTGCTG
GAAGATGGCGATTAGGAGCTCGCATCACACGCAAAAAGGAAATTGGAATA
AATGCGAAATTTGAGATGTTAATTAAAGACCTTTTTGAGGTCTTTTTTTC
```

-continued

```
TTAGATTTTTGGGGTTATTTAGGGGAGAAAACATAGGGGGGTACTACGAC
CTCCCCCCTAGGTGTCCATTGTCCATTGTCCAAACAAATAAATAAATATT
GGGTTTTTAATGTTAAAAGGTTGTTTTTTATGTTAAAGTGAAAAAAACAG
ATGTTGGGAGGTACAGTGATAGTTGTAGATAGAAAAGAAGAGAAAAAAGT
TGCTGTTACTTTAAGACTTACAACAGAAGAAAATGAGATATTAAATAGAA
TCAAAGAAAAATATAATATTAGCAAATCAGATGCAACCGGTATTCTAATA
AAAAAATATGCAAAGGAGGAATACGGTGCATTTTAAACAAAAAAAGATAG
ACAGCACTGGCATGCTGCCTATCTATGACTAAATTTTGTTAAGTGTATTA
GCACCGTTATTATATCATGAGCGAAAATGTAATAAAAGAAACTGAAAACA
AGAAAAATTCAAGAGGACGTAATTGGACATTTGTTTTATATCCAGAATCA
GCAAAAGCCGAGTGGTTAGAGTATTTAAAAGAGTTACACATTCAATTTGT
AGTGTCTCCATTACATGATAGGGATACTGATACAGAAGGTAGGATGAAAA
AAGAGCATTATCATATTCTAGTGATGTATGAGGGTAATAAATCTTATGAA
CAGATAAAAATAATTAACAGAAGAATTGAATGCGACTATTCCGCAGATTG
CAGGAAGTGTGAAAGGTCTTGTGAGATATATGCTTCACATGGACGATCCT
AATAAATTTAAATATCAAAAAGAAGATATGATAGTTTATGGCGGTGTAGA
TGTTGATGAATTATTAAAGAAAACAACAACAGATAGATATAAATTAATTA
AAGAAATGATTGAGTTTATTGATGAACAAGGAATCGTAGAATTTAAGAGT
TTAATGGATTATGCAATGAAGTTTAAATTTGATGATTGGTTCCCGCTTTT
ATGTGATAACTCGGCGTATGTTATTCAAGAATATATAAAATCAAATCGGT
ATAAATCTGACCGATAGATTTTGAATTTAGGTGTCACAAGACACTCTTTT
TTCGCACCAGCGAAAACTGGTTTAAGCCGACTGGAGCTCCTGCACTGGAT
GGTGGCGCTGGATGGTAAGCCGCTGGCAAGCGGTGAAGTGCCTCTGGATG
TCGCTCCACAAGGTAAACAGTTGATTGAACTGCCTGAACTACCGCAGCCG
GAGAGCGCCGGGCAACTCTGGCTCACAGTACGCGTAGTGCAACCGAACGC
GACCGCATGGTCAGAAGCCGGGCACATCAGCGCCTGGCAGCAGTGGCGTC
TGGCGGAAAACCTCAGTGTGACGCTCCCCGCCGCGTCCCACGCCATCCCG
CATCTGACCACCAGCGAAATGGATTTTTGCATCGAGCTGGGTAATAAGCG
TTGGCAATTTAACCGCCAGTCAGGCTTTCTTTCACAGATGTGGATTGGCG
ATAAAAAACAACTGCTGACGCCGCTGCGCGATCAGTTCACCCGTGCACCG
CTGGATAACGACATTGGCGTAAGTGAAGCGACCCGCATTGACCCTAACGC
CTGGGTCGAACGCTGGAAGGCGGCGGGCCATTACCAGGCCGAAGCAGCGT
TGTTGCAGTGCACGGCAGATACACTTGCTGATGCGGTGCTGATTACGACC
GCTCACGCGTGGCAGCATCAGGGGAAAACCTTATTTATCAGCCGGAAAAC
CTACCGGATTGATGGTAGTGGTCAAATGGCGATTACCGTTGATGTTGAAG
TGGCGAGCGATACACCGCATCCGGCGCGGATTGGCCTGAACTGCCAGCTG
GCGCAGGTAGCAGAGCGGGTAAACTGGCTCGGATTAGGGCCGCAAGAAAA
CTATCCCGACCGCCTTACTGCCGCCTGTTTTGACCGCTGGGATCTGCCAT
TGTCAGACATGTATACCCCGTACGTCTTCCCGAGCGAAAACGGTCTGCGC
TGCGGGACGCGCGAATTGAATTATGGCCCACACCAGTGGCGCGGCGACTT
```

-continued

CCAGTTCAACATCAGCCGCTACAGTCAACAGCAACTGATGGAAACCAGCC

ATCGCCATCTGCTGCACGCGGAAGAAGGCACATGGCTGAATATCGACGGT

TTCCATATGGGGATTGGTGGCGACGACTCCTGGAGCCCGTCAGTATCGGC

GGAATTCCAGCTGAGCGCCGGTCGCTACCATTACCAGTTGGTCTGGTGTC

AAAAATAATAATAACCGGGCAGGCCATGTCTGCCCGTATTTCGCGTAAGG

AAATCCATTATGTACTATTTCAAGCTAATTCCGGTGGAAACGAGGTCATC

ATTTCCTTCCGAAAAAACGGTTGCATTTAAATCTTACATATGTAATACTT

TCAAAGACTACATTTGTAAGATTTGATGTTTGAGTCGGCTGAAAGATCGT

ACGTACCAATTATTGTTTCGTGATTGTTCAAGCCATAACACTGTAGGGAT

AGTGGAAAGAGTGCTTCATCTGGTTACGATCAATCAAATATTCAAACGGA

GGGAGACGATTTTGATGAAACCAGTAACGTTATACGATGTCGCAGAGTAT

GCCGGTGTCTCTTATCAGACCGTTTCCCGCGTGGTGAACCAGGCCAGCCA

CGTTTCTGCGAAAACGCGGGAAAAAGTGGAAGCGGCGATGGCGGAGCTGA

ATTACATTCCCAACCGCGTGGCACAACAACTGGCGGGCAAACAGTCGTTG

CTGATTGGCGTTGCCACCTCCAGTCTGGCCCTGCACGCGCCGTCGCAAAT

TGTCGCGGCGATTAAATCTCGCGCCGATCAACTGGGTGCCAGCGTGGTGG

TGTCGATGGTAGAACGAAGCGGCGTCGAAGCCTGTAAAGCGGCGGTGCAC

AATCTTCTCGCGCAACGCGTCAGTGGGCTGATCATTAACTATCCGCTGGA

TGACCAGGATGCCATTGCTGTGGAAGCTGCCTGCACTAATGTTCCGGCGT

TATTTCTTGATGTCTCTGACCAGACACCCATCAACAGTATTATTTTCTCC

CATGAAGACGGTACGCGACTGGGCGTGGAGCATCTGGTCGCATTGGGTCA

CCAGCAAATCGCGCTGTTAGCGGGCCCATTAAGTTCTGTCTCGGCGCGTC

TGCGTCTGGCTGGCTGGCATAAATATCTCACTCGCAATCAAATTCAGCCG

ATAGCGGAACGGGAAGGCGACTGGAGTGCCATGTCCGGTTTTCAACAAAC

CATGCAAATGCTGAATGAGGGCATCGTTCCCACTGCGATGCTGGTTGCCA

ACGATCAGATGGCGCTGGGCGCAATGCGCGCCATTACCGAGTCCGGGCTG

CGCGTTGGTGCGGATATCTCGGTAGTGGGATACGACGATACCGAAGACAG

CTCATGTTATATCCCGCCGTCAACCACCATCAAACAGGATTTTCGCCTGC

TGGGGCAAACCAGCGTGGACCGCTTGCTGCAACTCTCTCAGGGCCAGGCG

GTGAAGGGCAATCAGCTGTTGCCCGTCTCACTGGTGAAAAGAAAAACCAC

CCTGGCGCCCAATACGCAAACCGCCTCTCCCCGCGCGTTGGCCGATTCAT

TAATGCAGCTGGCACGACAGGTTTCCCGACTGGAAAGCGGGCAGTGAGCG

CAACGCAATTAATGTGAGTTAGGCATCGCATCCTGCCTCGCGCGTTTCGG

TGATGACGGTGAAAACCTCTGACACATGCAGCTCCCGGAGACGGTCACAG

CTTGTCTGTAAGCGGATGCCGGGAGCAGACAAGCCCGTCAGGGCGCGTCA

GCGGGTGTTGGCGGGTGTCGGGGCGCAGCCATGACCCAGTCACGTAGCGA

TAGCGGAGTGTATACTGGCTTAACTATGCGGCATCAGAGCAGATTGTACT

GAGAGTGCACCATATGCGGTGTGAAATACCGCACAGATGCGTAAGGAGAA

AATACCGCATCAGGCGCTCTTCCGCTTCCTCGCTCACTGACTCGCTGCGC

TCGGTCGTTCGGCTGCGGCGAGCGGTATCAGCTCACTCAAAGGCGGTAAT

ACGGTTATCCACAGAATCAGGGGATAACGCAGGAAAGAACATGTGAGCAA

-continued

AAGGCCAGCAAAAGGCCAGGAACCGTAAAAAGGCCGCGTTGCTGGCGTTT

TTCCATAGGCTCCGCCCCCCTGACGAGCATCACAAAAATCGACGCTCAAG

TCAGAGGTGGCGAAACCCGACAGGACTATAAAGATACCAGGCGTTTCCCC

CTGGAAGCTCCCTCGTGCGCTCTCCTGTTCCGACCCTGCCGCTTACCGGA

TACCTGTCCGCCTTTCTCCCTTCGGGAAGCGTGGCGCTTTCTCAATGCTC

ACGCTGTAGGTATCTCAGTTCGGTGTAGGTCGTTCGCTCCAAGCTGGGCT

GTGTGCACGAACCCCCCGTTCAGCCCGACCGCTGCGCCTTATCCGGTAAC

TATCGTCTTGAGTCCAACCCGGTAAGACACGACTTATCGCCACTGGCAGC

AGCCACTGGTAACAGGATTAGCAGAGCGAGGTATGTAGGCGGTGCTACAG

AGTTCTTGAAGTGGTGGCCTAACTACGGCTACACTAGAAGGACAGTATTT

GGTATCTGCGCTCTGCTGAAGCCAGTTACCTTCGGAAAAAGAGTTGGTAG

CTCTTGATCCGGCAAACAAACCACCGCTGGTAGCGGTGGTTTTTTTGTTT

GCAAGCAGCAGATTACGCGCAGAAAAAAAGGATCTCAAGAAGATCCTTTG

ATCTTTTCTACGGGGTCTGACGCTCAGTGGAACGAAAACTCACGTTAAGG

GATTTTGGTCATGAGATTATCAAAAAGGATCTTCACCTAGATCCTTTTAA

ATTAAAAATGAAGTTTTAAATCAATCTAAAGTATATATGAGTAAACTTGG

TCTGACAGTTACCAATGCTTAATCAGTGAGGCACCTATCTCAGCGATCTG

TCTATTTCGTTCATCCATAGTTGCCTGACTCCCCGTCGTGTAGATAACTA

CGATACGGGAGGGCTTACCATCTGGCCCCAGTGCTGCAATGATACCGCGA

GACCCACGCTCACCGGCTCCAGATTTATCAGCAATAAACCAGCCAGCCGG

AAGGGCCGAGCGCAGAAGTGGTCCTGCAACTTTATCCGCCTCCATCCAGT

CTATTAATTGTTGCCGGGAAGCTAGAGTAAGTAGTTCGCCAGTTAATAGT

TTGCGCAACGTTGTTGCCATTGCTACAGGCATCGTGGTGTCACGCTCGTC

GTTTGGTATGGCTTCATTCAGCTCCGGTTCCCAACGATCAAGGCGAGTTA

CATGATCCCCCATGTTGTGCAAAAAAGCGGTTAGCTCCTTCGGTCCTCCG

ATCGTTGTCAGAAGTAAGTTGGCCGCAGTGTTATCACTCATGGTTATGGC

AGCACTGCATAATTCTCTTACTGTCATGCCATCCGTAAGATGCTTTTCTG

TGACTGGTGAGTACTCAACCAAGTCATTCTGAGAATAGTGTATGCGGCGA

CCGAGTTGCTCTTGCCCGGCGTCAACACGGGATAATACCGCGCCACATAG

CAGAACTTTAAAAGTGCTCATCATTGGAAAACGTTCTTCGGGGCGAAAAC

TCTCAAGGATCTTACCGCTGTTGAGATCCAGTTCGATGTAACCCACTCGT

GCACCCAACTGATCTTCAGCATCTTTTACTTTCACCAGCGTTTCTGGGTG

AGCAAAAACAGGAAGGCAAAATGCCGCAAAAAAGGGAATAAGGGCGACAC

GGAAATGTTGAATACTCATACTCTTCCTTTTTCAATATTATTGAAGCATT

TATCAGGGTTATTGTCTCATGAGCGGATACATATTTGAATGTATTTAGAA

AAATAAACAAATAGGGGTTCCGCGCACATTTCCCCGAAAAGTGCCACCTG

ACGTCCAATAGACCAGTTGCAATCCAAACGAGAGTCTAATAGAATGAGGT

CGAAAAGTAAATCGCGTAATAAGGTAATAGATTTACATTAGAAAATGAAA

GGGGATTTTATGCGTGAGAATGTTACAGTCTATCCCGGCATTGCCAGTCG

GGGATATTAAAAAGAGTATAGGTTTTTATTGCGATAAACTAGGTTTCACT

-continued

```
TTGGTTCACCATGAAGATGGATTCGCAGTTCTAATGTGTAATGAGGTTCG

GATTCATCTATGGGAGGCAAGTGATGAAGGCTGGCGCTCTCGTAGTAATG

ATTCACCGGTTTGTACAGGTGCGGAGTCGTTTATTGCTGGTACTGCTAGT

TGCCGCATTGAAGTAGAGGGAATTGATGAATTATATCAACATATTAAGCC

TTTGGGCATTTTGCACCCCAATACATCATTAAAAGATCAGTGGTGGGATG

AACGAGACTTTGCAGTAATTGATCCCGACAACAATTTGATTACAAATAAA

AAGCTAAAATCTATTATTAATCTGTTCCTGCAGGAGAGACCG
```

E. Transcriptome DNA Array Methods

In addition to the above methods, transcriptome DNA array methods were used in the development of mutants of the present invention. First, target RNA was harvested from a *Bacillus* strain by guanidinium acid phenol extraction as known in the art (See e.g., Farrell, *RNA Methodologies*, (2nd Ed.). Academic Press, San Diego, at pp. 81] and time-point was reverse-transcribed into biotin-labeled cDNA by a method adopted from deSaizieu et al. (deSaizieu et al., J. Bacteriol., 182: 4696-4703 [2000]) and described herein. Total RNA (25 mg) was incubated 37° C. overnight in a 100-mL reaction: 1×GIBCO first-strand buffer (50 mM Tris-HCl pH 8.3, 75 mM KCl, 3 mM $MgCl_2$); 10 mM DTT; 40 mM random hexamer; 0.3 mM each dCTP, dGTP and dTTP; 0.12 mM dATP; 0.3 mM biotin-dATP (NEN0; 2500 units SuperScript II reverse-transcriptase (Roche). To remove RNA, the reaction was brought to 0.25 M NaOH and incubated at 65° C. for 30 minutes. The reaction was neutralized with HCl and the nucleic acid precipitated at −20° C. in ethanol with 2.5 M ammonium-acetate. The pellet was washed, air-dried, resuspended in water, and quantitated by UV spectroscopy. The reaction yield was approximately 20-25 mg biotin-labeled cDNA.

Twelve mg of this cDNA were fragmented in 33 mL 1× One-Phor-All buffer (Amersham-Pharmacia #27-0901-02) with 3.75 milliunits of DNaseI I at 37° C. for 10 minutes. After heat-killing the DNase, fragmentation was validated by running 2 mg of the fragmented cDNA on a 3% agarose gel. Biotin-containing cDNA routinely ranged in size from 25 to 125 nucleotides. The remaining 10 mg of cDNA were hybridized to an Affymetrix *Bacillus* GeneChip array.

Hybridizations were performed as described in the Affymetrix Expression Analysis Technical Manual (Affymetrix) using reagent suppliers as suggested. Briefly, 10 mg of fragmented biotin-labeled cDNA were added to a 220-mL hybridization cocktail containing: 100 mM MES (N-morpholinoethanesufonic acid), 1M $Na^+$, 20 mM EDTA, 0.01% Tween 20; 5 mg/mL total yeast RNA; 0.5 mg/mL BSA; 0.1 mg/mL herring-sperm DNA; 50 pM control oligonucleotide (AFFX-B1). The cocktails were heated to 95° C. for 5 minutes, cooled to 40° C. for 5 minutes, briefly centrifuged to remove particulates, and 200 mL was injected into each pre-warmed pre-rinsed (1×MES buffer+5 mg/ml yeast RNA) GeneChip cartridge. The arrays were rotated at 40° C. overnight.

The samples were removed and the arrays were filled with non-stringent wash buffer (6×SSPE, 0.01% Tween 20) and washed on the Affymetrix fluidics station with protocol Euk-GE-WS2, using non-stringent and stringent (0.1 M MES, 0.1 M [$Na^+$], 0.01% Tween 20) wash buffers. Arrays were stained in three steps: (1) streptavidin; (2) anti-streptavidin antibody tagged with biotin; (3) streptavidin-phycoerythrin conjugate.

The signals in the arrays were detected with the Hewlett-Packard Gene Array Scanner using 570 nm laser light with 3-mm pixel resolution. The signal intensities of the 4351 ORF probe sets were scaled and normalized across all time points comprising a time course experiment. These signals were then compared to deduce the relative expression levels of genes under investigation. The threonine biosynthetic and degradative genes were simultaneous transcribed, indicating inefficient threonine utilization. Deletion of the degradative threonine pathway improved expression of the desired product (See, FIG. 7). The present invention provides means to modify pathways with transcription profiles that are similar to threonine biosynthetic and degradative profiles. Thus, the present invention also finds use in the modification of pathways with transcription profiles similar to threonine in order to optimize *Bacillus* strains. In some preferred embodiments, at least one gene selected from the group consisting of rocA, ycgN, ycgM rocF and rocD is deleted or otherwise modified. Using the present invention as described herein resulted in the surprising discovery that the sigD regulon was transcribed. Deletion of this gene resulted in better expression of the desired product (See, FIG. 7). It was also surprising to find the transcription of gapB and pckA. Deletion of pckA did not result in improvement or detriment. However, the present invention provides means to improve strain protein production through the combination of pckA deletion or modification and deletion or modification of gapB and/or fbp. In addition, during the development of the present invention, it was observed that the tryptophan biosynthetic pathway genes showed unbalanced transcription. Thus, it is contemplated that the present invention will find use in producing strains that exhibit increased transcription of genes such as those selected from the group consisting of trpA, trpB, trpC, trpD, trpE, and/or trpF, such that the improved strains provide improved expression of the desired product, as compared to the parental (i.e., wild-type and/or originating strain). Indeed, it is contemplated that modifications of these genes in any combination will lead to improved expression of the desired product.

F. Fermentations

Analysis of the strains produced using the above constructs were conducted following fermentation. Cultures at 14 L scale were conducted in Biolafitte® fermenters. Media components per 7 liters are listed in Table 9.

TABLE 9

| Media Components per 7 L Fermentation | | |
|---|---|---|
| NaH2PO4—H2O | 0.8% | 56 g |
| KH2PO4 | 0.8% | 56 g |
| MgSO4—7H2O | 0.28% | 19.6 g |
| antifoam | 0.1% | 7 g |
| CaCl2—2H2O | 0.01% | 0.7 g |
| ferrous sulfate—7H2O | 0.03% | 2.1 g |
| MnCl2—4H2O | 0.02% | 1.4 g |
| trace metals 100 × stock* | 1% | 70 g |
| H2SO4 | 0.16% | 11.2 g |
| 60% glucose | 1.29% | 90 |

*See, Harwood and Cutting, supra, at p. 549

The tanks were stirred at 750 rpm and airflow was adjusted to 11 Liters per minute, the temperature was 37° C., and the pH was maintained at 6.8 using $NH_4OH$. A 60% glucose solution was fed starting at about 14 hours in a linear ramp from 0.5 to 2.1 grams per minute to the end of the fermentation. Off-gasses were monitored by mass spectrometry. Carbon balance and efficiency were calculated from glucose fed, yield of protein product, cell mass yield, other carbon in broth, and $CO_2$ evolved. A mutant strain was compared to parent strain to judge improvements. Although this mutant pckA strain did not show improvement under these conditions, it is contemplated that improvements will be produced under modified culture conditions (i.e., as known to those in the art), and/or incorporation of additional genes. In some preferred embodiments, these additional genes are selected from the group consisting of gapB, alsD, and/or fbp Example 4

Host Cell Transformation to Obtain an Altered *Bacillus* Strain

Once the DNA construct was created by Method 1 or 2 as described above, it was transformed into a suitable *Bacillus subtilis* lab strain (e.g., BG2036 or BG2097; any competent *Bacillus* immediate host cell may be used in the methods of the present invention). The cells were plated on a selective media of 0.5 ppm phleomycin or 100 ppm spectinomycin as appropriate (Ferrari and Miller, *Bacillus Expression: A Gram-Positive Model* in *Gene Expression Systems: Using Nature for the Art of Expression*, pgs 65-94 [1999]). The laboratory strains were used as a source of chromosomal DNA carrying the deletion that was transformed into a *Bacillus subtilis* production host strain twice or BG3594 and then MDT 98-113 once. Transformants were streaked to isolate a single colony, picked and grown overnight in 5 mL of LB plus the appropriate antimicrobial. Chromosomal DNA was isolated as known in the art (See e.g., Hardwood et al., supra).

Figure 4:
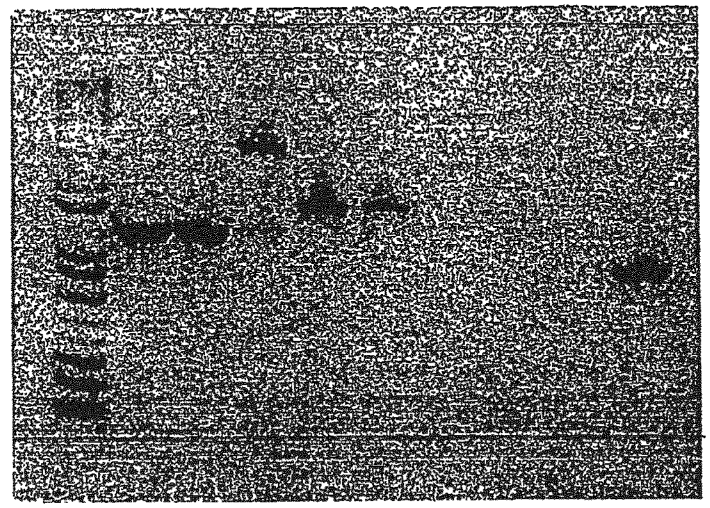
FIG. 4 provides an electrophoresis gel of *Bacillus* DHB deletion clones. Lanes 1 and 2 depict two strains carrying the DHB deletion amplified with primers 1 and 11, and illustrate a 1.2 kb band amplified from upstream of the inactivating chromosomal segments into the phleomycin marker. Lane 3 depicts the wild-type control for this reaction. Only non-specific amplification is observed. Lanes 4 and 5 depict the DHB deleted strains amplified with primers 9 and 12. This 2 kb band amplifies through the antibiotic region to below the downstream section of the inactivated chromosomal segment. Lane 6 is the negative control for this reaction and a band is not illustrated. Lanes 7 and 8 depict the deletion strains amplified with primers 1 and 4 and the illustration confirms that the DHB region is missing. Lane 9 is the wild-type control.

The presence of the integrated DNA construct was confirmed by three PCR reactions, with components and conditions as described above. For example, two reactions were designed to amplify a region from outside the deletion cassette into the antimicrobial gene in one case (primers 1 and 11) and through the entire insert in another (primers 1 and 12). A third check amplified a region from outside the deletion cassette into the deleted region (primers 1 and 4). FIG. 4 shows that a correct clone showed a band in the first two cases but not the third. Wild-type *Bacillus subtilis* chromosomal DNA was used as a negative control in all reactions, and should only amplify a band with the third primer set.

Example 5

Shake Flask Assays—Measurement of Protease Activity

Figure 7:
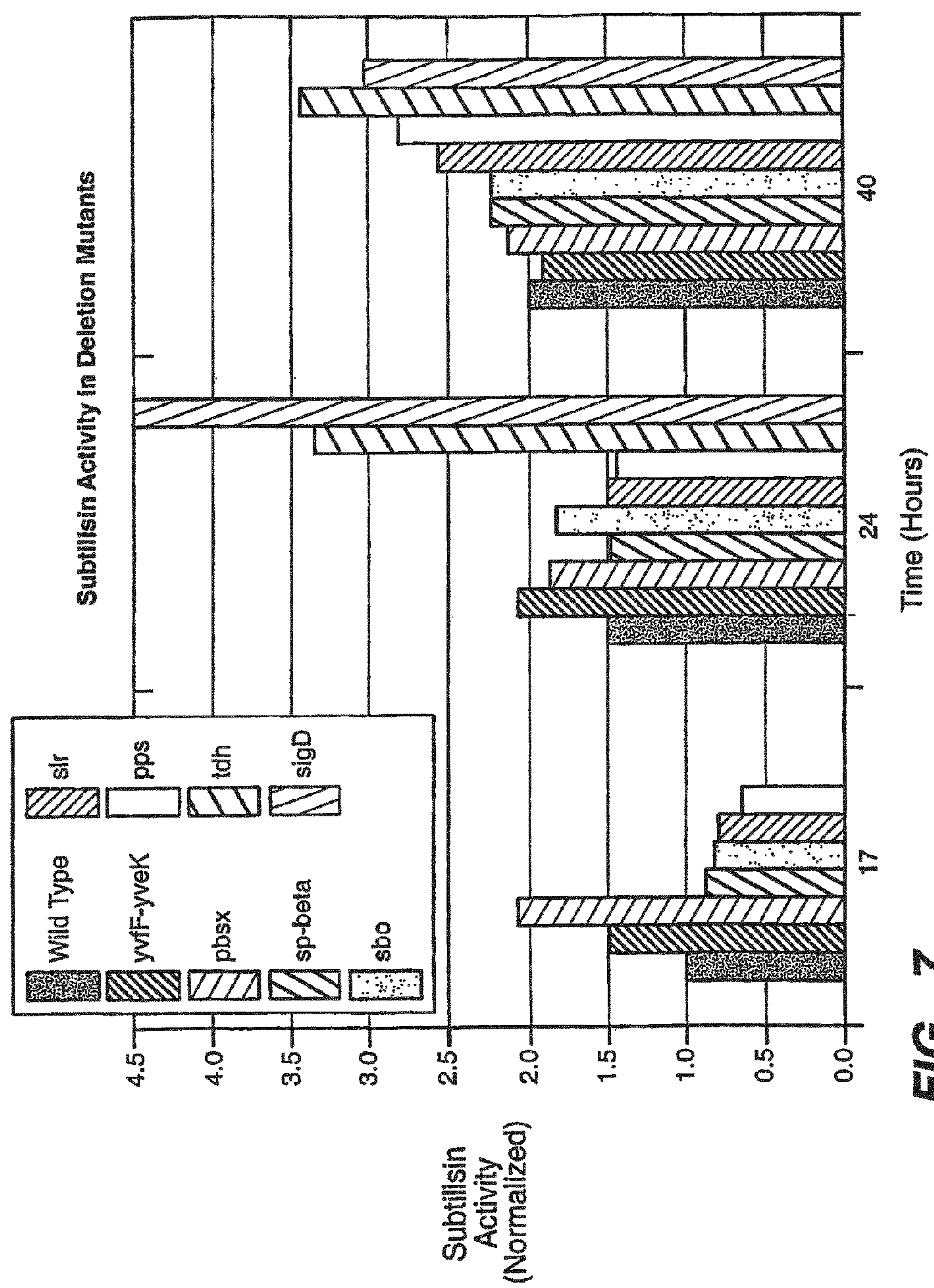
FIG. 7 provides a bar graph showing improved subtilisin secretion measured from shake flask cultures with *Bacillus subtilis* wild-type strain (unaltered) and corresponding altered *Bacillus subtilis* strains having various deletions. Protease activity (g/L) was measured after 17, 24 and 40 hours or was measured at 24 and 40 hours.
Figure 8:
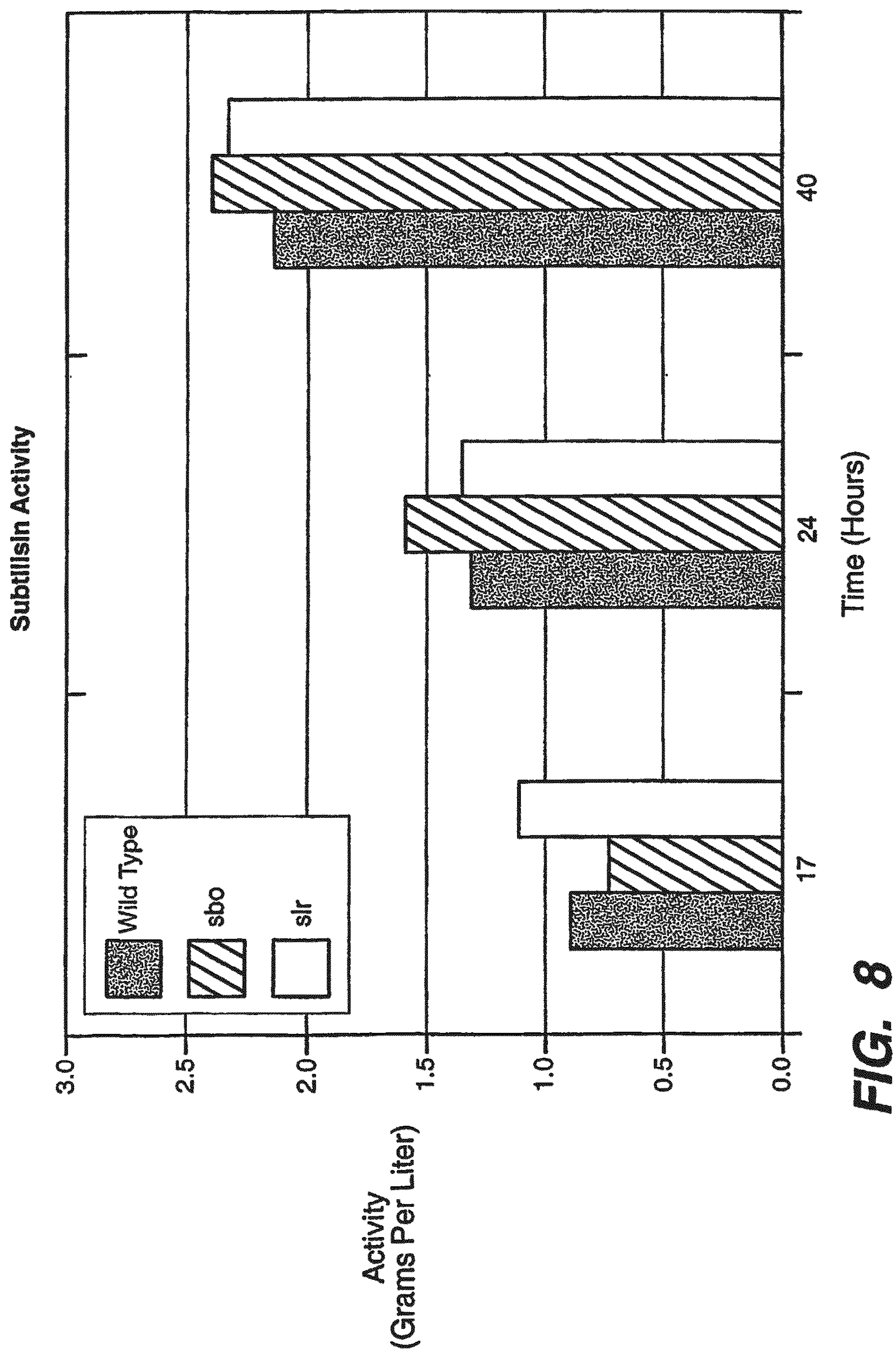
FIG. 8 provides a bar graph showing improved protease secretion as measured from shake flask cultures in *Bacillus subtilis* wild-type strain (unaltered) and corresponding altered deletion strains (-sbo) and (-sir). Protease activity (g/L) was measured after 17, 24 and 40 hours.

Once the DNA construct was stably integrated into a competent *Bacillus subtilis* strain, the subtilisin activity was measured by shake flask assays and the activity was compared to wild type levels. Assays were performed in 250 ml baffled flasks containing 50 mL of growth media suitable for subtilisin production as known in the art (See, Christianson et al., Anal. Biochem., 223:119-129 [1994]; and Hsia et al., Anal. Biochem. 242:221-227 [1996]). The media were inoculated with 50 μL of an 8 hour 5 mL culture and grown for 40 hours at 37° C. with shaking at 250 RPM. Then, 1 mL samples were taken at 17, 24 and 40 hours for protease activity assays. Protease activity was measured at 405 nM using the Monarch Automatic Analyser. Samples in duplicate were diluted 1:11 (3.131 g/L) in buffer. As a control to ensure correct machine calibration one sample was diluted 1:6 (5.585 g/L), 1:12 (2.793 g/L and 1:18 (1.862 g/L). FIG. 7 illustrates the protease activity in various altered *Bacillus subtilis* clones. FIG. 8 provides a graph showing improved protease secretion as measured from shake flask cultures in *Bacillus subtilis* wild-type strain (unaltered) and corresponding altered deletion strains (-sbo) and (-slr). Protease activity (g/L) was measured after 17, 24 and 40 hours.

Cell density was also determined using spectrophotometric measurement at an OD of 600. No significant differences were observed for the samples at the measured time (data not shown).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as should not be unduly limited to such specific embodiments. Indeed, various modifications of the described modes for carrying out the invention that are obvious to those skilled in the art and/or related fields are intended to be within the scope of the present invention.

The invention claimed is:

1. A method for enhancing the expression of a protein of interest in *Bacillus* comprising:

(a) introducing a DNA construct including a selective marker and an inactivating chromosomal segment into a *Bacillus* host strain, wherein said DNA construct is integrated into the chromosome of said *Bacillus* host strain, resulting in the deletion of an indigenous chromosomal region or fragment thereof from said *Bacillus* host cell to produce an altered *Bacillus* strain, wherein said indigenous chromosomal region is the PPS region; and (b) growing the altered *Bacillus* strain under suitable conditions, wherein expression of a protein of interest is greater in the altered *Bacillus* strain compared to the expression of the protein of interest in a *Bacillus* host cell that has not been altered.

2. The method of claim 1, further comprising recovering said protein of interest.

3. The method of claim 1, further comprising the step of excising said selective marker from the altered *Bacillus* strain.

4. The method of claim 1, wherein the altered *Bacillus* strain comprises a deletion of at least a second indigenous chromosomal region or fragment thereof.

5. The method of claim 1, wherein the protein of interest is an enzyme.

6. The method of claim 1, wherein the *Bacillus* host strain is selected from the group consisting of *B. licheniformis, B. lentus, B. subtilis, B. amyloliquefaciens, B. brevis, B. stearothermophilus, B. clausii, B. alkalophilus, B. coagulans, B. circulans, B. pumilus and B. thuringiensis.*

7. A method for obtaining a protein of interest from a *Bacillus* strain comprising:

(a) transforming a *Bacillus* host cell with a DNA construct comprising a selective marker and an inactivating chromosomal segment, wherein the DNA construct is integrated into the chromosome of the *Bacillus* strain resulting in deletion of an indigenous chromosomal region or fragment thereof, to produce an altered *Bacillus* strain, wherein the indigenous chromosomal region is the PPS region, (b) culturing the altered *Bacillus* strain under suitable growth conditions to allow the expression of the protein of interest, and (c) recovering the protein of interest.

8. The method of claim 7, wherein the protein of interest is an enzyme.

9. The method of claim 7, wherein the *Bacillus* host comprises a heterologous gene encoding a protein of interest.

10. The method of claim 7, wherein the *Bacillus* host cell is selected from the group consisting of *B. licheniformis, B. lentus, B. subtilis, B. amyloliquefaciens B. brevis, B. stearothermophilus, B. clausii, B. alkalophilus, B. coagulans, B. circulans, B. pumilus and B. thuringiensis.*

11. The method of claim 7, wherein the altered *Bacillus* strain further comprises at least one mutation in a gene selected from the group consisting of degU, degQ, degS, sco4, spollE and oppA.

12. The method of claim 7, wherein the protein of interest is an enzyme selected from the group consisting of proteases, cellulases, amylases, carbohydrases, lipases, isomerases, transferases, kinases, and phosphatases.

13. The method of claim 12, wherein the enzyme is a protease.

14. The method of claim 7, wherein the altered *Bacillus* strain comprises deletion of at least a second indigenous chromosomal region or fragment thereof.

15. The method of claim 14, wherein the at least second indigenous chromosomal region or fragment thereof is selected from the group consisting of: PBSX, SKIN, prophage 7, SP-β, prophage 1, prophage 2, prophage 3, prophage 4, prophage 5, prophage 6, PKS, YVFF-YVEK, DHB, and combinations thereof.

* * * * *